US007989416B2

(12) United States Patent
Boakes et al.

(10) Patent No.: US 7,989,416 B2
(45) Date of Patent: Aug. 2, 2011

(54) LANTIBIOTIC BIOSYNTHETIC GENE CLUSTERS FROM *A. GARBADINENSIS* AND *A. LIGURIAE*

(75) Inventors: Steven Boakes, Hertfordshire (GB); Jesus Cortes Bargallo, Hertfordshire (GB); Michael John Dawson, Hertfordshire (GB)

(73) Assignee: Novacta Biosystems Limited, Hertfordshire (GB)

( * ) Notice: Subject to any disclaimer, the term of this patent is extended or adjusted under 35 U.S.C. 154(b) by 245 days.

(21) Appl. No.: 12/161,221

(22) PCT Filed: Jan. 17, 2007

(86) PCT No.: PCT/GB2007/000138
§ 371 (c)(1), (2), (4) Date: Sep. 11, 2008

(87) PCT Pub. No.: WO2007/083112
PCT Pub. Date: Jul. 26, 2007

(65) Prior Publication Data
US 2010/0048459 A1 Feb. 25, 2010

(51) Int. Cl.
*A61K 38/12* (2006.01)
*C07K 7/64* (2006.01)

(52) U.S. Cl. ............ 514/2.3; 514/1.1; 514/2.4; 514/2.6; 514/2.7; 530/317

(58) Field of Classification Search .................. None
See application file for complete search history.

(56) References Cited

U.S. PATENT DOCUMENTS

| | | | |
|---|---|---|---|
| 3,710,795 | A | 1/1973 | Higuchi et al. |
| 5,112,806 | A | 5/1992 | Chatterjee et al. |
| 5,304,540 | A | 4/1994 | Blackburn et al. |
| 5,667,991 | A | 9/1997 | Koller et al. |
| 5,683,675 | A | 11/1997 | Vedia et al. |
| 5,763,395 | A | 6/1998 | Blackburn et al. |
| 5,958,873 | A | 9/1999 | Sakr et al. |
| 5,985,823 | A | 11/1999 | Goldstein |
| 6,022,851 | A | 2/2000 | Vertesy et al. |
| 6,569,830 | B1 | 5/2003 | Climo et al. |
| 7,122,514 | B2 | 10/2006 | Climo et al. |
| 2010/0168410 | A1 | 7/2010 | Cade et al. |

FOREIGN PATENT DOCUMENTS

| | | |
|---|---|---|
| DE | 197 45 583 | 4/1999 |
| EP | 0195359 | 9/1986 |
| EP | 0572942 | 12/1993 |
| EP | 0700998 | 3/1996 |
| EP | 1646646 | 3/2007 |
| WO | WO 91/07949 | 6/1991 |
| WO | WO 91/11172 | 8/1991 |
| WO | WO 94/02518 | 2/1994 |
| WO | WO 97/00694 | 1/1997 |
| WO | WO 98/55148 | 12/1998 |
| WO | WO 02/00196 | 1/2002 |
| WO | WO 02/088367 | 11/2002 |
| WO | WO 02/103010 | 12/2002 |
| WO | WO 03/099862 | 12/2003 |
| WO | WO 2004/033706 | 4/2004 |
| WO | WO 2005/093069 | 10/2005 |
| WO | WO 2006/080920 | 8/2006 |
| WO | WO 2007/036706 | 4/2007 |
| WO | WO 2007/083112 | 7/2007 |
| WO | WO 2008/151434 | 12/2008 |
| WO | WO 2009/010763 | 1/2009 |
| WO | WO 2009/010765 | 1/2009 |
| WO | WO 2010/058238 | 5/2010 |
| WO | WO 2010/082018 | 7/2010 |
| WO | WO 2010/082019 | 7/2010 |
| WO | WO 2010/092019 | 7/2010 |
| WO | WO 2010/089544 | 8/2010 |

OTHER PUBLICATIONS

Definition of moiety, from http://dictionary.reference.com/browse/moiety, pp. 1-3. Accessed Aug. 26, 2010.*
Rudinger J, "Characteristics of the amino acids as components of a peptide hormone sequence," Peptide Hormones, JA Parsons Edition, University Park Press, Jun. 1976, pp. 1-7.*
"Designing Custom Peptides," from SIGMA Genosys, pp. 1-2. Accessed Dec. 16, 2004.*
Schinzel R, Drueckes P, "The phosphate recognition site of *Escherichia coli* maltodextrin phosphorylase," FEBS, Jul. 1991, 286(1,2): 125-128.*
Berendsen HCJ, "A Glimpse of the Holy Grail?" Science, 1998, 282: 642-643.*
Voet D, Voet JG, Biochemistry, Second Edition, John Wiley & Sons, Inc., 1995, pp. 235-241.*
Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.*
Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.*
European Search Report issued in European Patent Application No. EP 10 00 0424 (Apr. 1, 2010).
European Examination issued in European Patent Application No. 07 704 921.1 (Apr. 4, 2010).
International Search Report and Written Opinion in PCT/GB2010/000043 (Mar. 29, 2010).
Widdick et al., "Cloning and engineering of the cinnamycin biosynthetic gene cluster from *Streptomyces cinnamoneus cinnamoneus* DSM 40005", PNAS, 100(7):4316-4321 (Apr. 1, 2003).
Arioli et al. "Gardimycin, a new anitbiotic from *Actinoplanes*: III. Biological properties" The Journal of Antibiotics 29(5):511-515 (1976).
Berge et al. "Pharmaceutical salts" Journal of Pharmaceutical Sciences 66(1):1-19 (1977).

(Continued)

*Primary Examiner* — Julie Ha
(74) *Attorney, Agent, or Firm* — Morgan, Lewis & Bockius LLP

(57) ABSTRACT

Characterization of the biosynthetic gene cluster for the lantibiotic actagardine, identification of a novel variant of actagardine and its biosynthetic cluster, and methods of production and use of actagardine are described.

15 Claims, 4 Drawing Sheets

OTHER PUBLICATIONS

Bierbaum et al. "Cloning, sequencing and production of the lantibiotic mersacidin" FEMS Microbiology Letters 127:121-126 (1995).

Bierman et al. "Plasmid cloning vectors for the conjugal transfer of DNA from *Escherichia coli* to *Streptomyces* spp." Gene 116(1): 43-49 (1992).

Britton et al. "Genome-Wide Analysis of the Stationary-Phase Sigma Factor (Sigma-H) Regulon of *Bacillus subtilis*" Journal of Bacteriology 184(17):4881-4890 (2002).

Castiglione et al. "A novel lantibiotic acting on bacterial cell wall synthesis produced by uncommon actinomycete *Planomonospora* sp." Biochemistry 46:5884-5895 (2007).

Chatterjee et al. "Biosynthesis and Mode of Action of Lantibiotics" Chem. Rev. 105:633-683 (2005).

Coronelli et al. "Gardimycin, A New Antibiotic From Actinoplanes: II. Isolation and preliminary characterization" Journal of Antibiotics 29(5):507-510 (1976).

Cotter et al. "Bacterial lantibiotics: strategies to improve therapeutic potential" Current Protein Peptide Science 6(1):61-75 (2005).

Dabard et al. "Ruminococcin A, a new lantibiotic produced by a *Ruminococcus gnavus* strain isolated from human feces" Appl. Environ. Microbiol. 67:4111-4118 (2001).

Dawson "Lantibiotics as antimicrobial agents" Expert Opinion on Therapeutic Patents, Informa Healthcare, GB, 17(4):365-369 (2007).

Dower et al. "High efficiency transformation of *E. coli* by high voltage electroporation" Nucleic Acids Research 16(13):6127-6145 (1988).

Fleisher et al. "Improved oral drug delivery: solubility limitations overcome by the use of prodrugs" Advanced Drug Delivery Reviews 19(2):115-130 (1996).

Flett et al. "High efficiency intergeneric conjugal transfer of plasmid DNA from *Escherichia coli* to methyl DNA-restricting Streptomycetes" FEMS Microbiology Letters 155(2): 223-229 (1997).

Fukase et al. "Synthetic study of peptide antibiotic nisin. V. Total synthesis of nisin" Bull. Chem. Soc. Jpn. 65:2227-2240 (1992).

Fumi et al. "Rifaximin treatment for symptoms of irritable bowel syndrome" The Annals of Pharmacotherapy 42:408-412 (2008).

Gardiner et al. "Fate of the Two-Component Lantibiotic Lacticin 3147 in the Gastrointestinal Tract" Applied and Environmental Microbiology 73(21):7103-7109 (2007).

Gravesen et al. "pbp2229-Mediated nisin resistance mechanism in *Listeria monocytogenes* confers cross-protection to class IIa bacteriocins and affects virulence gene expression" Applied and Environmental Microbiology 70(3): 1669-1679 (2004).

Guder et al. "Role of the single regulator MrsR1 and the two-component system MrsR2/K2 in the regulation of mersacidin production and immunity" Applied and Environmental Microbiology 68(1):106-113 (2002).

Guiotto et al. "PEGylation of the antimicrobial peptide nisin A: problems and perspectives" I1 Farmaco 58(1):45-50 (2003).

Gust et al. "PCR-targeted Streptomyces gene replacement identifies a protein domain needed for biosynthesis of the sesquiterpene soil odor geosmin" PNAS 100(4): 1541-1546 (2003).

Gust et al. "λ Red-mediated genetic manipulation of antibiotic-producing Streptomyces" Advances in Applied Microbiology 54:107-128 (2004).

Heinzelmann et al. "A glutamate mutase is involved in the biosynthesis of the lipopeptide antibiotic friulimicin in *Actinoplanes friuliensis*" Antimicrobial Agents and Chemotherapy 47(2): 447-457 (2003).

Hilger et al. "Differential binding of IgG and IgA antibodies to antigenic determinants of bovine serum albumin" Clin. Exp. Immunol. 123:387-394 (2001).

Holtsmark, et al. "Purification, Characterization, and Gene Sequence of Michiganin A, an Actagardine-Like Lantibiotic Produced by the Tomato Pathogen *Clavibacter michiganensis* subsp. *michiganensis*" Applied and Environmental Microbiology 72(9):5814-5821 (2006).

Kettenring et al. "Sequence determination of actagardine, a novel lantibiotic, by homonuclear 2D NMR spectroscopy" J. Antibiot. 43(9):1082-1088 (1990).

Lonetto et al. "The sigma 70 family: sequence conservation and evolutionary relationships" Journal of Bacteriology 174(12): 3843-3849 (1992).

Louie et al. "A phase 2 study of the toxin binding polymer tolevamer in patients with *C. difficile* associated diarrhoea" Proceedings of 14th European Congress of Clinical Microbiology and Infectious Diseases, Prague Congress Centre, Prague, Czech Republic, p. 548 (May 1-4, 2004).

Louie et al. "Tolemaver (GT160-246) binds Clostridium cytotoxins A/B and is associated with restoration of components of the anaerobic intestinal microflora during treatment of *C. difficile* associated diarrhoea" Proceedings of 14th European Congress of Clinical Microbiology and Infectious Diseases, Prague Congress Centre, Prague, Czech Republic, p. 855 (May 1-4, 2004).

Malabarba et al. "Physico-chemical and biological properties of actagardine and some acid hydrolysis products" The Journal of Antibiotics 38(11):1506-1511 (1985).

Malabarba et al. "Synthesis and biological activity of some amide derivatives of the lantibiotic actagardine" The Journal of Antibiotics 43(9):1089-1097 (1990).

Marahiel et al. "Regulation of peptide antibiotic production in *Bacillus*" Molecular Microbiology 7(5):631-636 (1993).

McClerren et al. "Discovery and in vitro biosynthesis of haloduracin, a two-component lantibiotic" PNAS 103(46):17243-17248 (2006).

Miner et al. "Steroid-refractory ulcerative colitis treated with corticosteroids, metronidazole and vancomycin: a case report" BMC Gastroenterology 5:3 (2005).

O'Sullivan et al. "High- and low-copy-number *Lactococcus* shuttle cloning vectors with features for clone screening" Gene 137:227-231 (1993).

Parenti et al. "Gardimycin, a new antibiotic from Actinoplanes. I. Description of the producer strain and fermentation studies" The Journal of Antibiotics 29(5):501-506 (1976).

Rea et al. "Antimicrobial activity of lacticin 3147 against clinical *Clostridium difficile* strains" Journal of Medical Microbiology 56:940-946 (2007).

Rey et al. "Complete genome sequence of the industrial bacterium *Bacillus licheniformis* and comparisons with closely related *Bacillus* species" Genome Biology 5(10):R77 (2004).

Sahl et al. "Lantibiotics: Biosynthesis and biological activities of uniquely modified peptides from gram-positive bacteria" Ann. Rev. Microbiology 52:41-79 (1998).

Somma et al. "Gardimycin, a new antibiotic inhibiting peptidoglycan synthesis" Antimicrobial Agents and Chemotherapy 11(3):396-401 (1977).

Szekat et al. "Construction of an expression system for site-directed mutagenesis of the lantibiotic mersacidin" Applied and Environmental Microbiology 69(7):3777-3783 (2003).

"Treatment of *Clostridium difficile*-Associated Disease (CDAD)" Obstetrics and Gynecology 109(4):993-995 (2007).

Turner et al. "Solution structure of plantaricin C, a novel lantibiotic" Eur. J. Biochem. 264:833-839 (1999).

Turtell et al. "The use of nisin in cheesemaking. Chapter 5: International acceptance of nisin as a food preservative" Bulletin of the Int. Dairy Fed. 329:20-23 (1988).

Ugurlu et al. "Colonic delivery of compression coated nisin tablets using pectin/HPMC polymer mixture" Eur. J. Pharm. Biopharm. 67:202-210 (2007).

van Kraaij et al. "Lantibiotics: biosynthesis, mode of action and applications" Nat. Prod. Rep. 16:575-587 (1999).

Zimmermann et al. "The three-dimensional solution structure of the lantibiotic murein-biosynthesis-inhibitor actagardine determined by NMR" Eur. J. Biochem. 246:809-819 (1997).

Altena, Karsten, et al., "Biosynthesis of the lantibiotic mersacidin: organization of a type B lantibiotic gene cluster," Applied and Environmental Microbiology, Jun. 2000, pp. 2565-2571, vol. 66, No. 6.

Zimmerman, Norbert, et al., "The tetracyclic lantibiotic actagardine H-NMR and C-NMR assignments and revised primary structure," European Journal of Biochemistry, Mar. 15, 1995, pp. 786-797, vol. 228, No. 3.

Vertesy, Laszlo, et al., "Ala(0)-actagardine, a new lantibiotic from cultures of *Actinoplanes liguriae* ATCC 31048," Journal of Antibiotics, Japan Antibiotics Research Association, Aug. 1999, pp. 730-741, vol. 52, No. 8.

De Vos, Willem M., et al., "Maturation pathway of nisin and other lantibiotics: post-translationally modified antimicrobial peptides exported by gram-positive bacteria," Molecular Biology, 1995, pp. 427-437, vol. 17, No. 3.

Jack, Ralph, et al., "The genetics of lantibiotic biosynthesis," Bioessays, 1995, pp. 793-802, vol. 17, No. 9.

Written Opinion of the International Preliminary Examining Authority in PCT/GB2010/000043, dated Feb. 1, 2011.

Wikipedia, the free encyclopedia, "Lanthionine", http://en.wikipedia.org/wiki/Lanthionine, Nov. 2, 2011.

Examination Report in New Zealand Patent Application No. 569486 dated Mar. 10, 2011.

International Preliminary Report on Patentability in PCT/GB2010/000043 dated Apr. 14, 2011.

International Preliminary Report on Patentability in PCT/GB2010/000042 dated Apr. 19, 2011.

International Preliminary Report on Patentability in PCT/GB2010/000188 dated Apr. 19, 2011.

Boakes et al., "Organization of the biosynthetic genes encoding deoxyactagardine B (DAB), a new lantibiotic produced by *Actinoplanes liguariae* NCIMB41362", The Journal of Antibiotics, 63:351-358 (2010).

Appleyard et al. "NVB302 : Gastrointestinal Stability and in vivo Activity in the Hamster Cecitis Model for *Clostridium difficile* Infection," Poster F1-1520, 49th ICAAC, Sep. 12-15, 2009, San Francisco, USA Appleyard et al. "NVB302: A Narrow Spectrum Antibiotic under Development for the Treatment of *Clostridium difficile* Infection," Poster F1-1517, 49th ICAAC, Sep. 12-15, 2009, San Francisco, USA.

Boakes et al., "Organization of the genes encoding the biosynthesis of actagardine and engineering of a variant generation system," Molecular Microbiology, 2009, 72(5), pp. 1126-1136.

European Examination for European Patent Application No. 07704921.1 dated Aug. 30, 2010.

International Search Report and Written Opinion for PCT/GB2010/000042 dated May 20, 2010.

International Search Report and Written Opinion for PCT/GB2010/000188 dated May 20, 2010.

New Zealand Examination Report for New Zealand Patent Application 569486 dated Apr. 27, 2010.

Translation of Israeli Examination Report for Israeli Patent Application No. 192446 dated Apr. 22, 2010.

Wadman et al. "NVB302: In vitro Activity Against *Clostridium difficile* and Intestinal Strains of Anaerobic Bacteria," Poster F1-1518, 49th ICAAC, Sep. 12-15, 2009, San Francisco, USA.

* cited by examiner

SEQUENCE LISTING

<160> NUMBER OF SEQ ID NOS: 318

<210> SEQ ID NO 1
<211> LENGTH: 19
<212> TYPE: PRT
<213> ORGANISM: Actinoplanes liguriae

<400> SEQUENCE: 1

Ser Ser Gly Trp Val Cys Thr Leu Thr Ile Glu Cys Gly Thr Leu Val
1               5                   10                  15

Cys Ala Cys

<210> SEQ ID NO 2
<211> LENGTH: 19
<212> TYPE: PRT
<213> ORGANISM: Artificial sequence
<220> FEATURE:
<223> OTHER INFORMATION: Synthetic sequence: Primary polypeptide
      sequence of Actagardine B variant V V

<400> SEQUENCE: 2

Ser Ser Gly Trp Val Cys Thr Leu Thr Ile Glu Cys Gly Thr Val Val
1               5                   10                  15

Cys Ala Cys

<210> SEQ ID NO 3
<211> LENGTH: 19
<212> TYPE: PRT
<213> ORGANISM: Artificial sequence
<220> FEATURE:
<223> OTHER INFORMATION: Synthetic sequence: Primary polypeptide
      sequence of Actagardine B variant L I

<400> SEQUENCE: 3

Ser Ser Gly Trp Val Cys Thr Leu Thr Ile Glu Cys Gly Thr Leu Ile
1               5                   10                  15

Cys Ala Cys

<210> SEQ ID NO 4
<211> LENGTH: 19
<212> TYPE: PRT
<213> ORGANISM: Actinoplanes garbadinensis

<400> SEQUENCE: 4

Ser Ser Gly Trp Val Cys Thr Leu Thr Ile Glu Cys Gly Thr Val Ile
1               5                   10                  15

Cys Ala Cys

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10

<400> SEQUENCE: 10

000

<210> SEQ ID NO 11
<211> LENGTH: 20
<212> TYPE: PRT
<213> ORGANISM: Actinoplanes liguriae

<400> SEQUENCE: 11

```
Ala Ser Ser Gly Trp Val Cys Thr Leu Thr Ile Glu Cys Gly Thr Leu
1               5                   10                  15

Val Cys Ala Cys
            20
```

<210> SEQ ID NO 12
<211> LENGTH: 20
<212> TYPE: PRT
<213> ORGANISM: Artificial sequence
<220> FEATURE:
<223> OTHER INFORMATION: Synthetic sequence: Primary polypeptide
      sequence of Ala-Actagardine B variant V V

<400> SEQUENCE: 12

```
Ala Ser Ser Gly Trp Val Cys Thr Leu Thr Ile Glu Cys Gly Thr Val
1               5                   10                  15

Val Cys Ala Cys
            20
```

<210> SEQ ID NO 13
<211> LENGTH: 20
<212> TYPE: PRT
<213> ORGANISM: Artificial sequence
<220> FEATURE:
<223> OTHER INFORMATION: Synthetic sequence: Primary polypeptide
      sequence of Actagardine B variant L I

<400> SEQUENCE: 13

```
Ala Ser Ser Gly Trp Val Cys Thr Leu Thr Ile Glu Cys Gly Thr Leu
1               5                   10                  15

Ile Cys Ala Cys
            20
```

<210> SEQ ID NO 14
<211> LENGTH: 20
<212> TYPE: PRT
<213> ORGANISM: Actinoplanes garbadinensis

<400> SEQUENCE: 14

```
Ala Ser Ser Gly Trp Val Cys Thr Leu Thr Ile Glu Cys Gly Thr Val
1               5                   10                  15

Ile Cys Ala Cys
            20
```

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20

<400> SEQUENCE: 20

000

<210> SEQ ID NO 21

<400> SEQUENCE: 21

000

<210> SEQ ID NO 22
<211> LENGTH: 64
<212> TYPE: PRT
<213> ORGANISM: Artificial sequence
<220> FEATURE:
<223> OTHER INFORMATION: Synthetic sequence: Primary polypeptide
      sequence of pre-pro-Actagardine B variant V V

<400> SEQUENCE: 22

```
Met Ser Ala Ile Thr Val Glu Thr Thr Trp Lys Asn Thr Asp Leu Arg
1               5                   10                  15

Glu Asp Leu Thr Ala His Pro Ala Gly Leu Gly Phe Gly Glu Leu Ser
            20                  25                  30

Phe Glu Asp Leu Arg Glu Asp Arg Thr Ile Tyr Ala Ala Ser Ser Gly
        35                  40                  45

Trp Val Cys Thr Leu Thr Ile Glu Cys Gly Thr Val Val Cys Ala Cys
    50                  55                  60
```

<210> SEQ ID NO 23

```
<211> LENGTH: 64
<212> TYPE: PRT
<213> ORGANISM: Artificial sequence
<220> FEATURE:
<223> OTHER INFORMATION: Synthetic sequence: Primary polypeptide
      sequence of pre-pro-Actagardine B variant L I

<400> SEQUENCE: 23

Met Ser Ala Leu Ala Ile Glu Lys Ser Trp Lys Asp Val Asp Leu Arg
1               5                   10                  15

Asp Gly Ala Thr Ser His Pro Ala Gly Leu Gly Phe Gly Glu Leu Thr
                20                  25                  30

Phe Glu Asp Leu Arg Glu Asp Arg Thr Ile Tyr Ala Ala Ser Ser Gly
            35                  40                  45

Trp Val Cys Thr Leu Thr Ile Glu Cys Gly Thr Leu Ile Cys Ala Cys
    50                  55                  60

<210> SEQ ID NO 24

<400> SEQUENCE: 24

000

<210> SEQ ID NO 25

<400> SEQUENCE: 25

000

<210> SEQ ID NO 26

<400> SEQUENCE: 26

000

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

<210> SEQ ID NO 31

<400> SEQUENCE: 31

000

<210> SEQ ID NO 32
```

```
<400> SEQUENCE: 32
000

<210> SEQ ID NO 33
<400> SEQUENCE: 33
000

<210> SEQ ID NO 34
<400> SEQUENCE: 34
000

<210> SEQ ID NO 35
<400> SEQUENCE: 35
000

<210> SEQ ID NO 36
<400> SEQUENCE: 36
000

<210> SEQ ID NO 37
<400> SEQUENCE: 37
000

<210> SEQ ID NO 38
<400> SEQUENCE: 38
000

<210> SEQ ID NO 39
<400> SEQUENCE: 39
000

<210> SEQ ID NO 40
<400> SEQUENCE: 40
000

<210> SEQ ID NO 41
<400> SEQUENCE: 41
000

<210> SEQ ID NO 42
<400> SEQUENCE: 42
000

<210> SEQ ID NO 43
<400> SEQUENCE: 43
000
```

```
<210> SEQ ID NO 44
<400> SEQUENCE: 44
000

<210> SEQ ID NO 45
<400> SEQUENCE: 45
000

<210> SEQ ID NO 46
<400> SEQUENCE: 46
000

<210> SEQ ID NO 47
<400> SEQUENCE: 47
000

<210> SEQ ID NO 48
<400> SEQUENCE: 48
000

<210> SEQ ID NO 49
<400> SEQUENCE: 49
000

<210> SEQ ID NO 50
<400> SEQUENCE: 50
000

<210> SEQ ID NO 51
<400> SEQUENCE: 51
000

<210> SEQ ID NO 52
<400> SEQUENCE: 52
000

<210> SEQ ID NO 53
<400> SEQUENCE: 53
000

<210> SEQ ID NO 54
<400> SEQUENCE: 54
000

<210> SEQ ID NO 55
```

-continued

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60

<400> SEQUENCE: 60

000

<210> SEQ ID NO 61

<400> SEQUENCE: 61

000

<210> SEQ ID NO 62

<400> SEQUENCE: 62

000

<210> SEQ ID NO 63

<400> SEQUENCE: 63

000

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

-continued

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100
<211> LENGTH: 38168
<212> TYPE: DNA
<213> ORGANISM: Actinoplanes garbadinensis

<400> SEQUENCE: 100

```
gatcggccgc cgtcagctgg agaagcgctg gctggcgcgg ctcacccgca acggccaccc      60
gcatccgacc cgggcgctgg cgctgcggat gggcgcggtg gagttcgcgg ggcagctggc     120
gctgcagctc gccgacatgc gcaagccgg cacgccgtca gcgacctgac ccgctgctcg     180
acgcagctcg ctcgccggtc ccgcgccgcg ccgatcaact ccggcagcac ggcgcgagct     240
tcaatcagcc ggcccggcgc acccctacg ccggtgcgac gaggcatgcc cgagaccagc     300
gcggccgcag agggccggtc ggcgccggac cggtcagcgc gcccgcaatc aggccggcag     360
gcccgcccgg agccggaccg gtcggcgcgc ccgcaatcag gccgacaggc cgcccgggg     420 tcaggctggt cggctgcgcc gggccggcag gccggcgagc agcgcgtcga gcgtctcggc     480
atccgcccag ccgttgactg acactgcgcc tgccgccgtg accgtgacct caaggcggtc     540
cggtgtcacc gccacgtcga tcggcgcgtc ctcgatgcgg tcgctcaagc ggatgaactg     600
ctggttcgtc gagccgaccc agggccgctc gtggtccagc aggtcctgcc ggaaggggcc     660
ggccaccagc aggtccgtgg cgtcgagcag tgcggcgacg tcggcccggc cgtccgcggc     720
gagagcgcgc agacgggcgt actcgtagcc ggtgaacgtc atgaccgagc gacccgcctg     780
ccgcaccccg gcgccaccg cggcgagacc ggccgcctgc tcgaacggct cgccgccgag     840
cagggtgaca cccgtggtgc ccgtggcgag cactcggtcc accaactcgg cgggtgcggc     900 cggcaccca ccgcgtacgc cgaacaaatg cggattgaag catccggcgc accggatggt     960
gcaaccctgc acccagatcg cggtccgctc gcccggtcct tcggcggtgg tccggtcgag    1020
gaaccgggcc accgcacga gcggcggctc agacatcgac tatccgaccg aaaggcgtct    1080
ggttcgcttg cggcggcggc tcgcacgaca gccggtcccg gaccgcgacg aactcgtgtg    1140
gtgcgagccc ggccacggcc gcgaactcgc cgagactggc gaatccgccc cgcgcctgcc    1200
gcgccgccac gacgtccgcc acccgctgcg gggtgagacc gggcacggcg ccaactgtt    1260 gcgcgtccgc ggtgttgaca tcgagccgct cgggcgccgg ctccagcagc gagcccggca    1320
cacccccagc cggcgagccc agcgcgggct ccagcgggcc gggcgcgggc ccagcgggcc    1380
aggccgctgt gggctcagcc tgccggccgg ctgcgggctc agcctgccag cccgctgccg    1440
gctcagcctg ccagcccgct gccggctcag cctgccagcc cgctgccggc tcagcgggcc    1500
ggcccgccgc cggctcagcc agcgggcccc tcgcgggctc aggcccggga gtccctccgt    1560
agaactcttg cggcgaagga acgacaccct gtagttgcgg cggcagcgga gtcgccacgg    1620
gagcgggcgc gttcgcccac ggcgcctgct ggggctgcgc ataccacggc acgtgagcgg    1680
cacgccagcg cagccaggag gcgttgatga cgaacgcgtg cgcgacgctg atcggccaca    1740
ccatgaacat gatcgagaac gcgaggttct gctggagcga gtcctcggcg ccctcactgc    1800
cgagaaagaa gcagaagttg gccacgacgg tgtagaggat cccggcgatc caccacaccg    1860
gccgccgggc gcggatgccg acgtagagga accgaccgc ggagaaacag ctgaagggca    1920
ccatcggcgc gatcacccag gcgctgtgcg cgaggcgcca cgacagccgc gccggccgg    1980 tccgcttgcc cggctcgtga cctggatgcg gcggatagga cggatacggc tgctggtgag    2040 caggcggaa cggcggcagc ggctgctgac cggaagcagg cgggaacggc ggcagcggct    2100
gcttgccgaa cgacggcggg tacgccggct gcgaggcggg atacgggtcc tggcccgggt    2160
taggcggtgt ccacgtcacg gttcacgatc cgttccgcg cggtgtgcgc ctgacgcgtg    2220
taatccgcgg tgtacgcact gtgccgcacc tgcccgccga cgagatcctc cagaacggcc    2280
acgtagtcca ggcagcgctc gccgagaatg tccacggtct cggcactgac ctggccgtcg    2340
ggaccgaccg tgacgacgat ccgaggattc tccgtcatgc ccgctccctc tccacctcga    2400
```

```
agaccaggcg cacactggcg tcctggccga ccgactccga ctccagccgc agcccggcct    2460
cgggcgcctg cgcgcgcagc cgctccagga cggcctgctg gacccgccgc ccgtacgcgg    2520
tgtcgacggt cgtcatcaac tcgacagccc ctggctgatc gacgccggtg acgtgcgcgg    2580
cccagatgcc gtccgcgccg cgggtgaacg tcgcggcgct ctgcgtccag gtcgccgaga    2640
tcgtgtcgcc ggcggccgtc acggtggctc cggtgtcgcg cagcgccgca tcgagcaggg    2700
tgacatcgcg catgcgggtc tgcacctggc agatcagccg gccgtcgtcc atccggcccg    2760
cggcggcctg aaccgcggcc gcgccaacgg caccagcagc agtgaaacgc    2820
tcaccatgcc ccccgttctc gctgtggcca cacctatcg gcagggtgcg acaaatcatc    2880
ggttggtgag gtcccagtcg tcggtgccgg tggccgacac ggcgcgattg cgggcccagc    2940
cgcgcagggc gtcgacccgc tcggcctgcg tcacgctgag cggcacgatg ctcatcaccg    3000
cgcgtacgag atcgtcgcgc cgcagtgggc ggcgttcgga gaacgcgtcg aacagtcccg    3060
caatgaccgc ctgctctatc tccgcgcgg agtagccctc ggtcagcccg ccagctcgg    3120 tgagcagctc ggcatcgacc cgcagctcgc cggcggcacg ccggtgccgc agcgcccgcc    3180
cgaggtgcac ccgccacacc gcgacccgct cggaccggct cggcagatcc acgaagaacg    3240
tctcgtcgaa gcgtcccttg cgcaacagct ccggcggcag cccgtcgaag tcgttggccg    3300
tcgcgatcac gaagaccgga gtccgcttct cctgcatcca ggtgaggaag gtgccgaaga    3360
cccgggcacc ggtgccggaa tcacccccgg tgccgccggc gaagcccttc tcgatctcgt    3420
cgacccacag gacgcacggg gcgaccgcct ccgccgtacg caatgcggtg cgcatgttgt    3480
gctcgctgga accgaccagg ccggagaaga cacggccgat gtcgaagcgc agcagaggca    3540
ggttccaggc ggtcgcgacc gccttggcgg tcagcgactt gccgcagccc ggcacgccgg    3600
tgatcagtac gccgcgcggc gcgggcaggc cgtacccggc cgcctcgtcc agccaggatc    3660
cgttgcgttt gaccagccag gccttgaggt tctccaggcc gccgacgtcg tcgagcacgg    3720
ttccggcggc catgaactcc agcacgcccg atttgcgtac ggtctggcgc ttctcctcgt    3780
gcacgatctc caggtcggcc agatcgagca cggcgtcgtt caccatggcc cgggcgtacg    3840
cgttctccgc ctcctgcatg gtcaggccgg ccgcggccgt gacgaaccgc tcccggctct    3900
gctcgtcgag ctccacccgc agccgcccgg acgcggtgtt cccgcgcacc atggcgtcga    3960
gcagagcgcg caactccagc tggccgggca gcgggaagtc gacgatcgtg acgtccttgc    4020
tcagctcgac cggcaggtcc agtaccggcg agagcagcac gagtgtccgc gggctgcggc    4080
cggcccggaa cgcctgggcg atgtcgcgca ccagccggac gacctccggg ctctgcgcga    4140
acagcgggtg caggtcgcgg aagacgaaga cagccggttc gtcgatgcgc tgcaccgccc    4200
tgagcgcgtc ggtggcccgc tgcgcgcccg agcgggcctc gccgttcggc tggaccagac    4260
cggcggtcag cgaccaggtc cagacggcac gtggcacgcg gacgaggtcg gcgtcgccgg    4320
cgatgccggc gaggtggtgc agcgcccgct gctcctcgta cgtctcgagg tggagcaccg    4380
ggaaccgggc cttcaacagc tgcgcgaacg tctccgcgaa cgacctctcc accggcgcat    4440
cctacgcccg cgccggccgg cgtgtcagag cccggacggg gtgccggtgg cgtcgcgtgc    4500
cgtccggtcc ttcccgcgct cgacgggttc gttgggttga tcggtcatgg catcctcctg    4560
ctcagtccgg gcggtagacg gcggtgtccc cggacacggc gccggggtcg taccccgagc    4620
ggccggtttc ctccgtggtg tcctgctcgt cagcgccggc gcctgtcgac tcgccgggtt    4680
tgcgcagtga cgccgcgtat gccggggttc cgtccggctc gtccgtggga tgccgctgga    4740
gttgttctcg gtcatcggtc atgaacggcg gacttccctg caagagcgcg gacaaacgtg    4800
```

```
gtcgtttatc ccgcagccgg gcgggcagtc gtccaccatg gaacccatcg gtgaccctga    4860
cgagcagacc ggcgacttcg ccgaagagca cgaactgacc gaggtgacag ccgaggagga    4920
cgacgacggc gagccggaga gcccggatcg ctggaccggc ggcatggact ccgacggtcc    4980
cccgtgacct gcggctacga tccctcacag gtgcccgccc cgccgacgac ccgaggttcg    5040
tagccgttgt cctccatcac ccgagctgacc gagtccgtgc gtgccttcgc gcgcgagcgc    5100
aactgggagc agttccacac gccgaagaac ctcgcgatgg ccctggccgg cgaggtcggt    5160
gagcttctgg ccgagttcca gtggctgacg ccggaacaat cagccgcggt catgcgcgat    5220
cccgatctcg gcccgcgggt ccgggccgag atcgagacg tcacgatcta tctcgtacgc    5280
ctggcggacg tgctcggcat cgacctggtc gaggcggcca ccgacaagtt ggcggaagcc    5340
ggccgccgct acaccgtcga agccgcccgc gactcggccg ccaagatcga tcagctgtag    5400
ttcagcgaga agttgttgac cgtgaagttg gactgaccgg cggtgccgct gatctcgaag    5460
ccgaactgcg cctcgccgac cgtcacgtca ccccaccagc cgttggtgcg cagccagttc    5520
aggatcgcca ggatgtcgac ggtgccggag ttcgtgttgg tacggatgaa cgagaagacc    5580
gcgttggcgc cgttcgaccc gcggtagacg ttccaggtgt gcccgccgac ggacaggttg    5640
cggacgttcg gcaccgcgcc gttggcgtcg tactgttcgg cgatcggccc gaccgcgccc    5700
tgctggttgg tccagatcat gacctcgtag gcgtggttgt tcgcccagat gtcgtaggtc    5760
gtcgagtagt cgccgctgga cggcaccgac acgttgaagg agctcgtcag agaattgagc    5820
gagctcagcg tacggttgag ggtctttccg gtgttggggt aggacttgac cccgctggtg    5880
cgcgggtgat tcgcgacgac gccccagttg gtgccgctgc gcgcccagat ggtctgggtg    5940
ccggcgcccg agcccagat gttgttgtga ggatgtatcc gttgttggtc cagttcgccc    6000
actgtcccga gtcgacccag acggcgtcgc tcggtacgcc gttggtgggc ggctgcgagc    6060
tcgggctggt ggggccagcc gatccggtgc aggcggtccc gttgagcgtg aacgtgcccg    6120
gtgccggggt ggcggcgccg gagccgttga atccgaacga cacggtcgcg ttggtgccga    6180
cggatccgtt gtagccggcg ttgcgggcgg tgacctgcga tccgctctgg gtcaggctgg    6240
tgttccaggc ctgggtgacg gtctgcccgc cggagtagga ccagaccaac gtccagttcg    6300
tgagcggatc acccaggttg gtgatggtga cgttggcgcc gaagccgccg ggccactggc    6360
tgctcacggt gtaggcgacg cggcagccgg ccgcggcgga cgccgggagc gcggtgacga    6420
cgccggcacc ggcgatgagg gccgccgagg cggccaggga gagcgcgaga gtacgtctgc    6480
gcatgccgtt ccaatctcgg aggggaaca cacgacgctc gtcgaagcgc ttcgataatg    6540
aaggctgggg atctacgagt gtcgatgcgg gatgaggccg atgttacgac ccgccgccgc    6600
ggcgaggcaa ccgctacctt gggcgcatga cgatcaccga gaccgatctc gcccacctgc    6660
gccgatgcgt cgacctggcc cgcgaggccc tcgacgacgg cgacgagccg ttcggttccg    6720
tcctggtctc cgccgacggc aaggtgctgt tcgaggacca caaccgggtg aggcacggcg    6780
acgccaccca gcaccggag ttcgcgatct cccgctgggc ggccgagcac ctgaccccgc    6840
gggagcgcgc cagcgcgacg gtctacacct cgggcgagca ctgcccgatg tgctcagcga    6900
gccacggctg ggtccgcctg ggcgcatcg tgtacgcggc gtcgagcgcc cagctgaccg    6960
cctggtacaa ggagtgggga atcccggcgg gcccggtcgc cccgctaccg atcaccacag    7020
tggtccccgg cgccgtcgtg gagggcccgg tcccagcctt cgaggccgag ctgcgggagc    7080
tacatcgcgc ccgcttcacc ccagcgcagt agccgccgga cgaaacccga cccttctcgc    7140
caatgaaccg gacctgcgag cgtgtctgga ttgaccgcgg aggcccgcaa cgccacaggc    7200
```

```
tcgatctccg tcaccgtcgg acctcagggg caggtcgagg atctgcgcct tgacgaccga    7260
gtgcatgacc tcccatccca ggaactgagc cagcagatcc tgacagtgat gcgaaaggct    7320
cagtaccagc tcaccgagta cgtctcggcg cacatccgtg acaccgtggg catggattcg    7380
gagaccggtc gcaatgtgct cgacgcgttc gcacagcgct tcccgctgcc ggagatgacc    7440
gatgagcgtt gagcaggtac agctgccgat cgacgtaatc aaccggcaca ccactaccat    7500
cgccgcaacc gccgatgccg tacggcaggc ccgcgccgcg gcaggtcagg cagccatgga    7560
ctcgcaagcg tacggccagt tgtgtcagtt cctgccgacc gcgttcagcg tcgtgttcga    7620
gagtgcgatc gtcgccatga ccggcagcgc cgaagcgttg caggaaacca ccttcaacct    7680
gcaggatgcc gtcacgacgt tcagatacac cgacgagtcg gccgctcgca ccatcgcctc    7740
cgcaggttcg ccgccgtgac cacaccactt gtcgcccaag ccggggactc caccacggga    7800
ttgaccggtc tggggctcgt ggaggacgcc caccagatcg cagaagccat ccgcgggaac    7860
agttgggtcg acggcgtcct cggcggagtc ggggccagcc tcgacggtct ggcgctggcg    7920
atcgacccgc tcggcaccct tgccgcctgg ggcgtcgcct ggctcatcga gcacgtccaa    7980
ccgctacaag acgccctgga ctggctggcc ggcgacgtcg acgagatagc cgcccaagcc    8040
gccacctggc gcaacgtcgc cgccttcacc gacagcgccc agcaggatta cgccgatcgg    8100
ctccgcaccg aggtcgccgg ctggttcggc gcctccggcg acgcataccg ggcccatgcc    8160
agcgaacact tggccgcact gaaaggcatc agcaccgcag ccggcggcat ttcgtccgcc    8220
gtcgaaggcg ccggcctgct cgtcagcctg gtgcgcggaa ttgtccgcga cctgatcgcc    8280
cagttcgtcg ccactctggc cgttcggctg ccacaatggc tcgccgccga aggactcact    8340
ctgggcctcg ccaccccgt tgtcgcgagc caagttgccg ccctcgtcgc ccgcggggtc    8400
aacaagatcc agcacttcat acgggcgctg ctcaacagcc ttcgacggct gatgcccatg    8460
atcgaccggc tgggtgaagt cctggagcgg ctccgcatgc tcaccgaccg gctcgcaagg    8520
tccagcccct ccaccgccc ggagccgaca cccggcccg ctactcacgc cggaaccgag    8580
aacgcatcgg gaaacaagcc cgagggcgac ctcgaaccga acgaaccgcg cccggccgag    8640
gctgacgcca gagacagtac gcctcaggcg ttcgtggacg aggtcgtcag caaccccgg    8700 tcagtcgcgg gacactccgc gcagtccatc gcggaccagt tcaacgccgc cggatactct    8760
gcggtcgtcg agcagagcac caggagcggc acctcgggga acgccatcca ggtacgcatt    8820 cacgccacc cggatatcac caacatccag gtgcatccgg gaggaggacg gcacacgccg    8880
gaggggtccc cgtattggaa aatttcgacg aatacggtcg ggaagatctg gatcatcccc    8940
gaaaatttcc ggggcgccga tgaactgcgt gggaatgtgg tgcgctatga caaataagat    9000
catcaaagtg gatcgggtgg gatccgcggg ggaagctgcc acgctcgtcg ccctgggcgt    9060
cgacatcgtc ggggtcgatc ttcgtcctga tccgcgattc gttgatgatc gcacgctgga    9120
cgccgaacag gttcgccaca tccgcgaagc gctgccgcac acgacgctgg ccgtcaccat    9180
ggacaccggc accgagccgg accatgtcgt cgaactcgca aggcgaatcg gcgcggatct    9240
ggtccagtcg atcaacggtg tcatcccgcc gctcccagta cgccgtcgcc tgcgcaaggc    9300
cgacatcgcg attgtctatg cgggcacaga gatctcccac gacgacgatc ccggctgggt    9360
cttcagcgcg tacgacgaca ctccggacct gaacgccgcc ctgtttcaag tggaggtgct    9420
tccggagtac ctcgattcct gggagttttct gcgtgaccgc tccccggaat atgccgacga    9480
gttccagatc gaagatctcg acgacctcgg acgcgctcgc cccttggttg ccggcctgaa    9540
tctcacggct cagaacctcg acgagatcag ggcacggctt ccccacgtcc gcggtctggc    9600
```

```
gctcaccctc gcgcacgagg ccgcgaggag cgacgcgcgg ttcttcatgt ttccccacgt   9660
agtggacatc ctttcgggag actcgtccgg gtgaccggca tcgcgcggga gggggctggt   9720
gtcgcagagt caggctgacg gcattccggc gggcctgacg ggaggaacct catgaccggg   9780
ctgttcacca tgcgcaagca cgaggagggc gccggggagg ttcggatcgt cgtgagcggc   9840
gagatcgacg gcgatgtcag cgcggcgctc accctgttca tcgccaacgc cgccgagcag   9900
gacggtgtcc gatcggtgct ggtggatctg gagccggtgc tgctgctggc cgcagccggg   9960
atccggtgcc tgctgagcgg ccgtgaggcg gctctgctgc agggctgctc ctacgagctg  10020
gtcaacgtcc ggcacgaggt cgcggattca ctgcacgccg ccggcgtggc agatctgctg  10080
ctcaccctgc cggtccgctg agccggctca gctcggcgtcg tcgaagccct cgtcggcgcg  10140
ttcgcggcgc aggtgtgcct cggcccggcg cgcctggtca cccttctccg ctgccagccc  10200
ggcgtacatg gcctgcacct tctcgtacgg ctggccgggc ggcagcagcg ggatcgccgg  10260
atcgaccacg gcctcgatca gcgtcgggcg gtccgcggac agcgccgcct cccacgcgcc  10320
ggtcaggtcg gacgggtcgg tgatccgcac tccgcgcagg ccgagcagct cggcgtagcg  10380
ccgtacggg acgtcgggca gttcctgcga cgtgacgaag cgcggctcgc cctcggtctc  10440
gcgctgctcc cagctgacct cggccaggtc ccggttgttc agcacgcaca ccacgaagcg  10500
cgggtccgcc cagtcgcgcc agcgggcggc caccgtgatc agttccgcca tgcccgccat  10560
ctgcatcgcg ccgtcgccgg ccagcaccac gaccgggcgt tgcggcgccg ccagcttggc  10620
ggcgagaccg tacggcaacc cgcacccat cgacgccagc gtgctggaca gatgcgccgg  10680
gacaccgcgg ggcagccgca ggtgccgggc gtaccagtag acgaccgagc cgacgtcgac  10740
ccgcgacctgc gcgtccgcgg gcaggtggtc ggagagggag cgaatcacgt gctgcgggtt  10800
gaccggttcg gcgggcgccg cggcccgggc cgcgctgatc aggcgccagc gctgcaccca  10860
ttcctccacg cgggcgcccc aggcgccgct gccccggctg ggcagcagtc cgagcagctc  10920
acgcaaggtt tccacggcgt cgcccaggag cgggacctca accggatacc gtacgcccag  10980
acggcgcccg tccacgtcga tctgtacggc ccgcgcctgc cccggccggg gatagaactc  11040
ggtccacggg tcgttcgtgc cgatcagcag cagcgtgtcg cagtgccgca tcagctcggc  11100
gctggccgtg gtgcccaggt gccccatgac gccggtgtgg aacggcaggt tctcgtcgag  11160
gaccggcttg ccgagcagcg aggtggtcac gccggcaccg agccgctgcg ccagctcgac  11220
gatctcgcgc tccgcgccgt acgctccctg ccccaccatg atcgccaccc gctcgccgga  11280
gcggagcacc tcggccgcct cgcgcaggtc ttccgggcgg ggcaccaccc gggcggggcg  11340
cagccccgcg ctcgtcgcca gcacaccgtg ctcatgcgcc tgcgggtcgg gcgccggggc  11400
cgtctgtacg tcgtgcggca ggaccacgca ggtcgggctg cgggtcgcga gcgcggtgcg  11460
gaacgcgcgg tcgaggagca tcggcacctg ctcgctcgtg tgcgcggcct gcacgaactg  11520
ggcgcacacg tcgccgaaga gccgcaccag gtcgatctcc tgctggtacg cgctgccgag  11580
caccgtcgag acctgctggc cgacgatcgc gacgaccggt ttggagtcga gtttcgcgtc  11640
gtagaggccg ttgagcaggt gcaccgcgcc gggaccctgg gtggcgaggc agactccggc  11700
accaccggtg tacttggcgt ggccgacggc catgaacgcc gcgccctcct cgtgccgggc  11760
ctgcacgaag gtgggccggc cggccgcgcg cagcgctccg atcacgccgt cgatgccgtc  11820
cccggagtac ccgaagaccc gttccacgtc ccacgcggtc agacgctcca cgaccacgtc  11880
cgacacggtc cgctccgtca ccgctgcctc ctcacgtcac accgggggct acccgctcag  11940
ccgcgcggta ctcgccttgc gcgaaatgcg actcgcgtgc acctcacggg ccgggcggac  12000
```

-continued

```
gcggcacgga tctgagctgg ttcccgcccg gttctgatcc cctgtgatcg gggtacacac   12060
gtgcggtgag cagggacaag acgtaccggc cggtccgtcc cgacgggatc cggaccacct   12120
tccacgacgg tgtactcggg cgcatgcgga tccggtgcct gggcgagccg cgtccgggcg   12180
taccggagat cgtgatgatc cagggtatga ccgtgagtga ctatctgctg ccgggtctgg   12240
gcgcgctcag cgcctggacc cgggtgcacc tggtggagct gccggaggc agcggcagcg   12300 gccggccgcc gcacgatctc acggtcgagg agtacgcgcg ggccgcggcc gactggctgt   12360
gcgcccagcg cctgggccgg atcgtgctgg ccggccattc gagcggcacg caggtggcgg   12420
cggagaccgc gctgttgtgc ccggacgagg tggccggagt ggtgctggcc ggcccggcga   12480
tcgacccggt ggcccgcggc ggcctgcggg tcttcgcgcg ctggtggatc gaccggcgcg   12540
gcgacccgaa gagcctggac gaggtgcaca acccgaacg cgagcaggtc gggttccggc   12600
ggctgttcca ggtgctgcgc gcccacctgc gtcacgacct ggagaagccg gtggtcgggc   12660
tctgcgtgcc ggtgctggtc atccgcgcca gcgaggaccg gctcggcacc cgcgcggtggg   12720 cccggcggct cgccgatctg gctgccgtgg gcggccggta cgtcgaggtg ccgggcaccc   12780
actcgttctg ctggcgttac ccgcaggcct ggtccgcgcc gatccgtgaa ttcgccggat   12840
ggtcggtatc ggtctccggc acctgaacgg acgtttcggt ggcatcgccg ccaccgcggg   12900
ccggcgcatc cgcatccaca gtccggggtg agggtcagcg ccgttcggag gcggagtgtc   12960
gatgatcggt caattgacgt gcttccatga gccgccctac ggtccgacag agaaatcgtt   13020
atccggacca ccatcgacat ccgaatcggt ggccccggag ccgatcatcg accgaccccg   13080
ggccaccccc gctcttgcca gagggggcga ggcacatgac ggaagctgat catcgtccga   13140
ccgttctcag gagaatccta cggctgtgcg ccgtgcttct catggtgctc ggagtgggcc   13200
tggtcggcgc cccgacgtcg cacgccggcg gcaagccgac catctccaag gaggcgttcg   13260
gcagcgtcgg cggcaaggcc gtcgaccggt acaccctcac caacgggcgc ctgcaggtgc   13320
ggatcctcac ctacggaggc atcctgcaga ccatcacgtt ccccgaccac cgcggccgca   13380
gggccaacgt gacgctcgga ttcaggaccc tcgacgagta cgtgacgacg aagaacccgg   13440
cgtacttcgg cgccatcatc ggccgctacg gcaaccggat tgccgacggc cggttcaccc   13500
tggacggcac gacctaccag ctggcgacca caacgaccc gaaccacctg cacggcgggg   13560
tcgtcggctt cgacaagcgg gtgtgggacg ccacgccgat ccgcgacggc gacagcgtcg   13620
ggctgcgcct gacctacacc agcccgcacg gcgaggagaa ctaccccgga acctgcgcg   13680 tgacgatgac ctacaccgtc acccggcaga tgggtatccg gatggactac cgggcgacga   13740
ccgacagacc gacgatcgtc aacctgacca accacgcgta ctggaacctc ggcggcgagg   13800
gcaccgggac catcgacgac cacctgctga agctcaacgc caaccgctac acgccggtcg   13860
acgccacgct gatcccgacg ggggcgatcg acgcggtcgc cggcacaccg atggacttcc   13920
gccggcccac gccgatcggc gcgcgcaacc gcgacccgtt ccagcaactg gtgtacgggc   13980
gcggctacga ccacaactgg ggtgctgaacc gcgaggacgg ccagttccgg cgtctcgagt   14040
tcgcggcccg ggcggtcgac ccggacagcg ggcggcagct caccatctac accaccgagc   14100
cgggcatcca gttctacggc ggcaacttcc tcgacggcac cctgtacggc accagcggcc   14160
gggcctaccg tcagggagac ggtttcgccc tggagacaca gcacttcccg gattctccga   14220
accacgcgaa cttcccgtcg accgtccttc gaccgggaca gacctacaac tcgacgacca   14280
tctaccagtt cggtaccgcc gactgatcgc ctcaggccgg ccgccgcggg acggcgcgcc   14340
gcggccggcc gcacggcagt cagcggcggc gactggaggc acacatgcca cgcatccatc   14400
```

```
cgaaagtcga ggaggccgtc tctacgctcg acctgaaccg gacgacacga cgccggctgt   14460
tgtccggaac cggggttgttc agcgcctcgc tcgccgcggg cgcgctgctg agcgcatgca   14520
gcgaccagaa cgacgccag aaccagaccg agggcgccgg taacttcccg gacaccccg    14580 agtggcggtt cacattcgtc aaccacgtga ccaccaaccc gttcttcacc ccgacgcagt   14640
acgggatgga ggacgccgcg acgctgctcg gcatcgccaa gccgcagtgg accggctcgc   14700
agaactcgat cgtggccgaa atggtgaacg cgacgaacac cgcggtcagc gcaaaggtgg   14760
acggaatcgc catcgccgtg gtcgacaagg acgcgttccg ggggccggtc gaccaggctc   14820
tcaacgcggg gataccggtg gtgtcgtaca acgccgacga gcccggggc gcgccgggca   14880 cgaaccggct ggcctatatc ggacagggcc tgtacgagtc cgggtacgcg ctgggccagc   14940
gggcgttgca ggtgctggac tccggcgagg tggccgcctt catcgccacc ccgggcgcgc   15000
tgaacatcca gccgcgcatc gacggcgcgc aacaggcgtt caaggactcc ggcaagccga   15060
tcacgttcac cgccggtcgcc acgaacgccg acgtgacacg cggtctgtcc atcatcgacg   15120
cgtacgccca ggggcacgcc aacctggccg gcatgctggc ggtggacgcc ggatcgacgt   15180
cgtcggtggg tcagaccgtc aagaagtaca acatgcgcgg caaggggctc aaggtggccg   15240
gcgggttcga cctgatcccg gagacgctga ccgggatcca ggagggcagc ctcgactaca   15300
ccatcgacca gcagccttat ctgcagggat tcctgcccgt gctggcgctg tacttctaca   15360
aggtgtccgg cgggctgatc gcgccgagtg agacgaacac cgggctgttg ttcgtcacca   15420
aggacaacgt cgccccgtac cagagcacga agagccggta cgagggctcc acgaccgaca   15480
aggttctcgt acctcgcagc gggccgatcg cccatggatg accggatctc gcctgcgccc   15540
gcgcaggcgc cttccctcga ggtcgagcaa cgccgtggcc ggtggcagcc ggtcacggcg   15600
gccggccgga aggtcctcga cgccttcctg cggcggcgtg aggccagcgt gctgctcgtc   15660 gcgatcgggcc tgatgatcta ctttcgggcg tccagcccgg tcttcctgag ccgcgacaac   15720
ctggtcaaca tcgcccaggc gaccgcgccc gtcgcgatca tcgcggtcgg catcgtgctg   15780
ctgctggtca gcggcgagat cgacctgtcc gtcggtatcg tggccgcgct ggcgccgttc   15840
ctgttccact tcgggatcaa cttctactcg ctgccggtgg tgcccgcctt cgtggtggcg   15900
ctggcgatcg cggccggaat cggcctggtg aacgggctga tcgtcacgca gctgcacgtg   15960
ccctcgttcg tgacgacgct gggcacgttc ttcgccgtgc agggcatcct gctgatcacg   16020
tcgcacgcct atccggtgcc gatcccgac gcggccaagg gcacgttcca aacctggctc   16080
ggcgccgggc cgtgggccag catcacctgg gcgctgatca tcgtcgcgat cttccacacg   16140
gtgctgaccc tgaccggtg gggcctgcac accatctcgg tcggcggcaa cccggtcggc   16200
gccaccgagg ccggcatccg cgcctcccgc atcaagatcg gcaacttcgt gatcaccagc   16260
acgctgggtg ggctggtcgg catcatggag gcgttccgga tcaacaccat cgacccgaac   16320 atcgcggcg gcacgacgct gaccttctac gccatctcgg cggcggtcat cggcggcacc   16380
gcgctcgccg gcggctccgg caccatcgtc ggcgccttcc tgggcgccct cgtgctggcc   16440
gagctgcaga cgggttcaa cctcatcggc tacagcgcca caccatcatt cctcatcctg   16500
ggcctggcca tcctcgtctc gatgatcgcc aaccagtacc tctcccgact gcgccgggca   16560
ggccgatcat gaccgcggaa accgtgtccg acgcgctgcg cgtacagaac atcgccaaga   16620
gattcggcgc tctcaccgcg ctgcaggacg tgaccctgcg cgtcgccgaa ggcgaggtgc   16680
tgggcctgat cggcgacaac ggcgccggca agtcgaccct catcaaaatc atctgcgggt   16740
accaccggcc ggacgccggg cgcatcttcg tcggcggcga ggaggtcacg ctgcgcagcg   16800
```

```
tcgaccacgc ccgctcggtc ggcatcgacg ccgtctatca ggacctggcc ctggtcaacg   16860
agctgtccgt ctaccacaac atgttcctca accgggagct cgtacggtgg ccgctgctga   16920
acaaccgggc gatgcgccgc cgtgccgagg agcacctgcg cgacatggga gtgaacctgc   16980
cggacgtcgg cgtcgaggtg gccaagctct ccggcggcca gcgccaggcg atcgcggtgg   17040
cccgctgcgt ctactccgac gcccgcatcc tgctgctgga cgagccgcta gccgcgatgg   17100
gcgcgaagga gggcacgatg atcctcgacc tgatccgcga cctgaaggcg cgcggcaacg   17160
tgtcgatcat catcatcgcg cacaactacg cgcaggtgct cgacgtgtgc gaccgggtga   17220
acctgctgca gcacggccgg atcaccttcg acaagaggtc ggcggacacg tcgctggccg   17280
aactgaccga gctggtggtc gccgagtacc gcaccggccg cgggcggtga cgcctcagcg   17340
cttgcggccg actccgctgt actggctcgc gccggtcgtc tcgtcgccgg ggtcgggatg   17400
ccactgcggg ctcggcacga cgcccggcgg gaccaggtcc agtccctcga agaagccggc   17460
gatctcgtcg ggcgtatgca tcaggtaggg caccgcaccg gaggagttgt aggcgtcctg   17520
ggcctggttg agcgcctcct ccccggcgac gcgcacaccg tcgttgatcg acaggtagct   17580
gccgggcggc agcccggcca tcagctgccg gacgatgtcg cggacctccg cggtgctggg   17640
gatgtggccg agcacgccgt tgaggatcag cgccaccggc cggcccatgt cgagctcgcg   17700
ggcggcgacc gccaggatgt ccgccggttt ctgcaggtca ccctcgaggt agacgtcgga   17760
cgacccggcc agcagctcac ggccgtgctc caccgcgtac gggtccttgt cgacgtagag   17820
gacccgggcg tcaggggcga cccgctgcgc gatctggtgg gtgttgtcga cggtgggcag   17880
gcccgcgccg acgtcgagga actggcgcac gccggcctcg ccggcgaggt agcgcacggc   17940
acgcgacagg taccgccggg actcgcgggc gatctcgtcg atgccgggga acacggcacg   18000
gtactcgtcg ccggcagcgc ggtcgaccgg gaggttgtcg gtgccgccga gccagtagtt   18060
ccagatgcgg gccgactggg gcaccgaggc gccggactcc atagtcacgg atcgatagcc   18120
tagcccttgc gcgcctgggt ggcgacgccc tcgacgaagt agcgctggca caggaagaac   18180
gcgatgatca tcggcaccgt ggtgatcacc gcgccggcca ggacgatctc ccagcgggcc   18240
tcgcccgcct ggccgaactg gtcgaggatc gccttcatgc cgcgcggcat ggtgaacagc   18300
gccggatccc gcagatagat cagcggcttg agcaggtcgg accagctggc ccgcagctcg   18360
aacacgaacg ccacgatcag cgccggccgg cacagcggca ccgcgatgcg ccagaacagc   18420
cgccagtacc cggcgccgtc gacgcgggcc gcctcgaaca gctcacgggg cacgccgagg   18480
aagaactgcc ggatcaggaa gatgtagaag gcgctgccga acaggttgcc ggcccagagc   18540
ggcacctgcg tggcggccag gccgagctcg ttccagatca ggtacgtggg gatcatggtg   18600
accgcgccgg gcagcatcat cgtgccgacg accagggcga caacacgtt  gcgcccgggg   18660 aagcggaagt aggcgaagcc gaacgccacg accgcgctgg agatcgtgac cgcggccgcg   18720
gcggcgagtg ccaccacgac gctgttgaac atccaggtca gcacgggcgc ggcgtcccag   18780
atggcggtgt agttccccgg cgcccactcg gcggggagca gccggttgtc gaagacgtcg   18840
gggcggggct tgagggaggc gctgaccagc cagacgaacg ggtacacgaa gatcaccgcg   18900
gcggcggcca gggcggtcca gagcacccag ggatgcgggc cgcgcgaggt gcgcggtggc   18960
atggtcctgt cctcagccac agccacggcc tcactcgctc tcgtagtaga cgaatcgccg   19020
gctgagccgg acctgcacga ccgtgatgat cacgatgatc aggaacagca gccaggccag   19080
cgccgaggcg taccccatgt gcaggaactg gaaggcctgc tggaacaggt agaccacata   19140
gaacagggcg gcgtcgttgc cgtacgtctg ctggttggca ctgccgtaga aggcggtgta   19200
```

```
gacctcgtcg aaggtctgca gcgaggcgat cgtgttgatg atcagcgtga agaagagcgc   19260
gccgctgatc atcggcacgg tgaccgcgcg gaaccgcgcc cacgccgacg cgccgtccat   19320
ctcggcggcc tcgtagaggt cgcggggcac gttctgcagc gccgccaggt agatgatgac   19380
cgtgctgccg aggctccagg cgccgatcag caccaggccg ggcttgatcc acgggccgtc   19440
gacggtccag ttcggcccgt cgatgccgac cgtgcccagc gcctcgttca cgatgccgac   19500
ctggccgttg aacagcagca ggaacagcac gcccacggcc accttggggg tgatcgtcgg   19560
caggtagaag atcgtgcgga agaacccggc ggagcggcgc ccgacccggg ccagcagcat   19620
cgccagggcc agggacacga tcatggtgac cggcacgtgc agcgccgtgt agatcagcgt   19680
gttggcgatg ctcgtacgca cccgcgggtc ggcgagcatc tgccggtagt tctcgccgcc   19740
gacgaagtcg gtgctggtga gcacgtcgta gtcggtgaac gacaggacga ggctggccac   19800
catcggcccc gccatgaaga ccgtgaagcc gatgagccac ggcgacagga aaccgaaggc   19860
ggccagggtc tcccgccgcc gcacggcggc actcatcgtc agcgtccgct gttggccttg   19920
tccagcgcgg cctgagcctg ctgctgggcc tcggccatgg cctgggcggg tttctgcttg   19980
ccttccagga cccggttgac cgcgttctgc caggcggcct tgaattcctc accggcggcg   20040
agcgccggct ccgagaagcc ggactcctgg gtctgcagga cgatctgcac gttggcgtcg   20100
ggtttcacga cgtctctgaa gatcacttcg tcggccttct tgttgccggt gtagacgccg   20160
gcgaagggtt tgttctcctt cttgcgcagc tcggcacggg ccctcgcggc ggcgatccag   20220
gtctcgctcg cggtcatcgt cttgatccac ttacaggcct gcccagggtg cgcgctgttc   20280
gccgggatgg cccaggcgtt gcccgtgatc cagtcgatcg gctgcccgtc gacgccgcgg   20340
aacgcgccca cggtcacctt gaccttcggc gagttgtcgg cgagcacgtt gaggtagaag   20400
tcctccatcg ggaaggcgcc gagctggttg ctggcgaact ggttcttggc gccgaagaag   20460
tcccacgagt cgcggaacga cttgaagttc gaccagccgc cctgcgcgtt gatcaggccg   20520
acggcgtatt cgagggcctc gaccaccttc gggttgttca gctgggcggt gcgaccgtcg   20580
tcgctgacca gggcggcgcc gttcgcgcgc gcccagacgg gcaggaactc gggcagcttc   20640
gggtcgaacc cgatccgctg gagcttgccg ccgctcatcc tggtgagccg ggccgtggcc   20700
gtcgacagcg cctgccagtc ccccgtgtcg aacccggcgg gatccaagtt gacctcggcg   20760
aacgcggcgt cgttgagcat caggacgcgg ttgttgtaga agtccggcag gccgtacagc   20820
tgcccgttca gggtcgcctc ggtgaccgcg gcctcgcgga actggctcat gtcgatcttc   20880
tcccgttcga cgcagtcgcc gagcggagtg agcgccttct tggccgcgta ggtgccgagc   20940
agccgccgtt ccatgtacac caggtccggc ggggtcctgg aggccaccgc ggacaggaac   21000
gcctgggcgt cgaagctgcc ctcggacgcc ttcgccaggc tgggcgcgat cacggcgttg   21060
gccgcgtcga agcgggtctt ggcgatctcg tcgccggtgc cgaaacccat catggtcagc   21120
gtcaccgcgg cgttgctgtc ggagtccgaa tcggatccgc ccacgccacc gcagcccgcc   21180
gccaatgtca gaaccagggc accacccacc acaaaccgga tcgatcggat gaacatcgtt   21240
gttctcccat tttcacttgt tcccgtgggc gaagcataag ttcacttcga tgcccgcgca   21300
ctcggagcgg ctgctgtcaa ccgccgaccg gttggcggat caccacgatc gggtggtgcg   21360
gccgctgccg ggccgcgctc ctgctcccgc cgccacgcgc gtgggcagat accgatcggc   21420
gtcgctctaa tcgatggcag ggataccgac ggtgacaccg tttcctcccg ccgcttcatc   21480
ccgacgtaat cgcgggcatg gcgccgtggc cgcgtttcgt cgaaatcgcc gggctattcg   21540
cccgggaagt ccaccgaaag gaagacacac catgtctgct ctcgccatcg agaagtcctg   21600
```

```
gaaggacgtc gacctccgtg acggggcgac cagccacccg gccggcctcg gcttcggcga   21660
gctcaccttc gaggaccttc gcgaggaccg caccatctac gccgccagca gcggctgggt   21720
gtgcaccctg acgatcgagt gcggcaccgt gatctgcgcc tgctgatcga cgatcgtttc   21780
cggcccgggg cgggcatcgc ccgccccggg ccatccattt cgcgcgggga gcagccatgt   21840
caccggttcc ttcactcaat tccacctcgg tacgcgacag cgcgtatctg cacgaacgaa   21900
cggtgaccgg agaagaccag ccggcaccgg ccgcgcaggc gcggatagcg tcctggcgcg   21960
attcggcgtt cctcgacgac cgggttctcg acatccggct acgtcaatgg ggaatcgacc   22020
gtgccacctt cggccggctg ctcaccgacg acgacttcac cgttcccggc cggctgctcg   22080
cctgggcgga cgagctggcc acggtgctgg ccaccgacac gacaccggtc accggactcg   22140
agttgtccac caaactgtgg tcacagggat tcgaccggct gctcttcgcc ggcctgcttc   22200
acccgttcct cgcccactac gaacagcggc tgcacgagcg cgtgccccgg ccgatcgccg   22260
gcagcctgcg ccgccgctg ctggagtcgc tggccaaccg gctgctcgcc gtcgcggcac   22320
gcaccctgct gctggagctc aacgtggccc gtgtgcacgg gcggctgacc ggcgacaccc   22380
cgcagcagcg ctacgacgac tacgaccggc ggctgctcac cgaccccgcc tacctggccg   22440
ccctcttcga ggaatacccg gtgctcggcc gttgcctggt cgaatgcggc cggcgttggg   22500
tggaccacgc cgccgagctg ttcaaccggc tccacgacga cgagcccgaa ctgcgcgcgg   22560
ccggtctgct gccgccgtcg gcggaagcgc tgcgcagcgt acggctggac ctcggggacc   22620
cgcacaacgg cggccggtcg gtggtgcagc tgaccttcga cgacggcacc gacctggtct   22680
acaagccgcg gccggtcgga tccgaacgcg cctacgccga gacgatggcc gcgctggccc   22740
gccacgggct gccggtgccg gtgaccgccc cgcgcgtgct ggaccgtggc gggcacggct   22800
ggtgcgagtt cgtccggccc gcgccctgcg ccgacgccgc cgagctgtcc cgcttctacc   22860
ggcgcgccga atcggtgctg gcggccatgc tgctgctcgg tggcgtcgac atgcacatgg   22920
agaacgtcat cgccgcgggg tcgtcgttca ccccgatcga cctggagacc gtgctgcagt   22980
ccggagagct cggcgacggc gccaccgacg cgtacgggcg ggccctcgac ctgctcaacc   23040
gcagcgtgct ggcgatcggc atcctgcccg cccgcgcgtt cggtggccgg cagcgaaaga   23100
gtgtcgacgt cagcgccctc ggcggcggcg aaccgcagac cgcgccccgg ccggtgccac   23160
gcatcgtcga cgcgtacacc gacacggcac ggctggaagc ggtcgaggcc accatggccg   23220
gcgcccagaa ccggccgagc ctgccggcg ccgaggtccg cccgtgggag cacaccgctg   23280
acgtggtcgc cgggttcacc gacgcctacg acatcatgct ggcccaccgc gccgacttcg   23340
accggctgct gcgcggcttc cacgacgtgg aggtgcgcta cctgccccgg cccacccgtc   23400
gttacagcat cttcctgacc gagagctacc accccgacta cctgcgcgac gccagcgacc   23460
gggaccggct gctcgacaag ctgtggaccg ccgcggacgc ccgccccgag ctgattccga   23520
tcatcgagtc ggagaagcga caactgctcg ccggtgacat cccgtgcttc cgcagcgtcg   23580
cgggaagccg gcagatccgc accgcctccg gcccgctgca cccggagttc ttcaccgcgc   23640
cggccgtcac cgtactgacc cgccggctcg gcgagttcgg accggtgcac cgcgccgccc   23700
aggtacgcat catccgcgac tcgatggcca cgatgcccgg ccccggcccc gccgcccagc   23760
cgtcccccga ccgggcggcg ggccccggcc cccgcgtcac cggcgccgac ccggcacgc   23820 tcgccgaccg catcgcccgc aggctcgccg acgaggcgat cctcggcgac cgcgacgtgt   23880
cctggatcgc cgtcagcatc gaaggcgtcg cccaggagac ctacagctac aagccgatgg   23940
cgaccggcct gtacgacggc gtggccggcc tggcgctcac cttcgcgtac gcggcccgca   24000
```

```
ccctcggcga cgaccgctac ctggacctgg cacaccgagc ggcccgcccc gtcgccggct   24060
acctgcgcta cctcgccgag caccgcatcg tcgagaccgt cggcgcctac agcggcaccg   24120
ccgggctgct ctacgccctg gaccacgtgg cccacgccac cggcgacgac tcctacctcg   24180
acgcggtctc ggaggcggtg ccgtggctgc gcgaatgcgc cacccgcgag gagtgccccg   24240
acctgatcgc cgggctggcc ggctgcgccc tgatcagcct ggacctgcac gggcgccacc   24300
ggatcgacgg gctgcgcgag gtggcggcca tctgcgccga acggctcgcc gccctcgccg   24360
tcgacgtcga cggcgccgcc ggatggccgg ccactccgga cggaccgctg ctcggcgggt   24420
tctcccacgg cgcggccggc atcgcctggc cgctgcaccg gctcgccacc gaactcggcg   24480
acccctcgct gcgcgagctc gcccgccgcg cggtccagtt cgaccgcgac ctgtacgtgc   24540
ccgccgcggg cgcctggcgt gacctgcgcc cggagatggc cggcaccgac tcctaccccg   24600
cgctgtggtg ccacggggcc gccggcatcg gcctgtcccg gctgctcatc gcgcagcacg   24660
accaggacac gcgactggcc gcggaggcca ccgccgccct cgacctggtc ggcgcgcacg   24720
gcttcggcca caaccacagc atctgccacg gcgacttcgg cgccctcgcc ctgttcgacc   24780
tggcggcacg aaccggcttc gaccccgggc gccacgacgc ggccgccgcg gccgtgaccg   24840
ccgacatcgc cgccaacgga gcccgttgtg gcctggtcgg cgacatccac atgccgggac   24900
tcatgctcgg cgccgccggc atctgcctga gcctgctgcg catcgcccac cccgcgcagg   24960
tgcccgcggt ggcctggctg cagccgccgc tgacctgagg aggagcccat gccggaagag   25020
atcgtgctca gcgtgctgga ccaggtgccg gtgttccgtg acggcagccc ggcggaggcg   25080
gtgcgcgacg cggtcgcgct ggcccgcagc gccgaacagt acggctacca ccgcttctgg   25140
atcgccgagc accacggcag cgcggccaac gcgtgcgccg ccccgaggt ggtgacggcc   25200
gcggtggccg ccgccacgag ccggatccgg gtgggcagcg gcggcgtgct gctgccgcac   25260
tacagcccgc tgaaggtggc cgagacgttc cgggtgctgg cggcgctgta tccgggccgc   25320
atcgacctcg gtttcggccg ggctcctggt gggccgccgg cgatggccga gctgctcaac   25380
ccgtacgcgg tccgcaccga cgaggcgttc ctggagcaga tcggccggct gctgggtttc   25440
ctcggcgaca cccgtacggt cagccgcgtg tcggtgacgc cgcaggtgga agagccccg   25500
gtgccgtgga tgctcggcgc cgggaccggc agcgcccgga tggccggcat gctgggttg   25560
ccgttctgtt tcgcccagtt catcgcgacc gaggagtgcc cggaggcgat cgaggcgtac   25620
cgggatgcgt tccggccgtc gccctggctg gagcgacccc agccgatgct cgccttgcgg   25680
gtgctgtgcg ccgactcgga cgcggaggcc gaggaactgg ccacgtgttt ctggatgtcg   25740
tgcacgaccg gctggcgtgc gcaggtgcag ctcaccgacg actaccgtgg gggcgcgccc   25800
aatctcgacg acgcacgccg gtaccggctg accgcggagg acctcgcgct gcgggagagc   25860
cggccgttcc tgcagatctc cgggacgccg gcgcggtgg gcaaggagat ccgcaggttg   25920
caggcggtgt acggggtatc cgaggtggtg ctcaccacga actgccccgg cctgccggcg   25980
cggcgccgct cctacgaact gctcgccggc gagttcgcat ccccggcggc ctgacggcct   26040
caggtccgcg gtagctccgc gtaggtcccg cgcaatgccg cggacctgac ggccgtcagg   26100
acaggcagac gtcgtcgctg gacagacccg acgcatacgc caggacggcg gcctgcacgc   26160
ggttggccac gccgagcttg ctcaggatca cgctgacgtg ctccttcacc gtggcggcgc   26220
tgaggaacag ctgccggctg atctccgcgt tcgtgaggcc ggcgccgagc aggcgcagaa   26280
tgctctgctc ccggtcggac agctgttga cccgctcgca ggccggtgac ccggcccccg   26340
cggcagatcc ccgtgagccc gcacgcacga ccaccgacga cgcctcgggc gccagcacga   26400
```

```
tgctgccctc ggccagcgcc cgcacggcgg cgaccagctg ttcgggctgg ctgtcgcgca    26460
acaggaagcc gcaggcccca ccccgcagcg agtcgagcac cagctcgggt ggggcgagag    26520
tggtcagcat cgccgatcgcc ggcgggctgc tcagagcccg cagctgatcg agcacctcca    26580
gcccgtcgct ctgggcactg tggccgtcga gcagcaccac ggcaggccgg tgctgctcga    26640
cggccgatct caggttctcc cggtccgtcg tggcgaccgc gaagccgccg gtgctctcca    26700
ggatcatctt gatgccgatg ctgaccagtg cttcgccgtc cacgaccagt acgtccgtca    26760
cgatcggtcc cccgcgagcc gccgaacgca tgcaacttgc atccgcattc gtgacattac    26820
ttcacttata tggtcgaatc aatcgatttt tcgcgtatag tcattaacaa cacacagcgc    26880
gtcgtcagcg ggtcagaccc tcggccgggg cgacccgcgc cgcccgccgc gccggcgcca    26940
gactggccac caccccggtc agcaccgcca ccaccagcac ggcggccagc tggccccacg    27000
gcaggcggat caccggatcg gcggtacgcc ccacggccgc cgccaccgcg ccagccccca    27060
ccgggacacc gaccacgagg ccggccaccg tgccgagcag cgtgatcacg accgcctcga    27120
ccgcgagcat cgcccgcagc cgcgcccggc gtgtgcccag cgcccgcaac agcgccatct    27180
cgcgtacccg ctcgacgacc gacaggccca gcagattcgc gatgccgagc agtgcgatca    27240
ccaccgtgac cgccagcatc gccagcgaca gtcccaacag gatcgacagc acgttcgcga    27300
tgtcaccgcc ctcggtgacc ccgccaccga cctgcaccag cgcgtcgcgg gcggccaccg    27360
cgccgacggc ggccgacagc gcctcccggt cgaagccggg gtcagcgacg ccccacaccg    27420
ttgtcggcac cgcctcgatc cggttcgccg ccagggtccg cgcgctcacc acgcccagca    27480 gctgccggt ggtgtccgcc agccgcgacg cccgggcgat caggttcacc cggcgctcgc    27540
cgacctcgac gacgatcggg gcgctgtccg gcaggcccca ctcggccaga taggtcgccg    27600
gcaccagcac caccggctcc ccggcgagct ccggtgccac ccgggccgcc agttcgtcgc    27660
cgggcgcggc cagcagccgc ggcgtcgcct tgccgccgtc cgggaaacgg gccgcgaccg    27720
tgccgaccgt gccactggcc gacagctgtg gcaccgcggc gaaggccccg gcggtggcac    27780
cgctgatcgg ctcgccgtcg gtgcgcaggc ccgccgccac cgggtagcgc gcctccaggt    27840
cggcgttcac cgtggcccgc ccgctggtcg ccgccaccgc caggcaggtg atcagcgccg    27900
cgccgaccac caccgccatc gccgccgaag ccgtccggcg cgcgttctgg ctcaggctgg    27960
tcccggccag gccggcggcc acgccgaaac gctccagcag ccgcgccgcc ggcgccaggg    28020
acaacgcgat cagccgcggc aacgccgcca gcaaccccgc cgccagcaga agcccgccca    28080
gcagcgccag gggcagcgac gcgccgatcg ccgccaccgc gagcgcggcg cgcccacca    28140 cggtcaccac ggtgcccacg acgagccggc gaccgccgcg gaccgtgccg gccggcggct    28200
cgtcggccgc ctgcaacgcc cgcaccgggg cgatcctggt ggcacgccgg gccggcgccc    28260
aggcggccac cagcgtggcc agcaccccgg ccagcacaca gccggccagg gcgaacggat    28320
tgacccgcag cccgccgccg ctgatgtcga gcaggtcggc gccgagataa cccagccca    28380 caccgccgc cgcgccgacc aggccgccgg ctgttccggc gatcgccgcc tcggccagca    28440
cgacccggct cacctgggca cgatgaccgc cgaccagccg cagcagggcg atctgccga    28500 tccgctggac gatcaccacg tggaaggtgt tcgcgatgac cagcaccgcc gcgagcaggg    28560
cgacagccgc gaacgccagc atgatcacga ccagctggcc gttgccgccg gcgaacctcg    28620
cggcggcctg atccgcagcc gccgaggcgt cggtcgccga gatgccgggg cccatgctgc    28680
gccgcaacgc gtcaacggtg ccggtcagcg aggcgtcgtc ggcgacagtc agcagcgcgg    28740
ccggcggcac gtcaccggcg aagaacgacg cgtcggcgta gaaccggaag tccgagccgg    28800
```

```
tcagcggccg gaaacccagg tcggcggcac cggtcacggt gaccggctgc ggcgccgcct   28860
caccgtggcg taccgtcagc gtggcccga cgtcgatgcc gaggtcgtcg agggtgcgct    28920
ggtcggcgac gagctgtccg ggcccggtgg gccacgcgcc ccggtccaag gtgaaccagc   28980
ggacctgcgg ggtggccgcg atgctctgca cgttggccga gccgcgccgc gatccgccga   29040
acacgctgac cgtgcgcgcg tactgcgcgt ccaccgagcg caccccggc accgcggccg    29100 cggcctcgta ccaggccggg tcgcggaccg tgtcgtcggc gtcgagcacg atgtcggcgg   29160
tggtcaacgg cgcggcggcg gtacgccgca ggccctcacc cgaggtggcc gcgaaggtcg   29220
cggtcgcggc caggaaaccg gtcgccagca tcaccgccgc gacgatcgcg aacagccggg   29280
ccgggtaggc gcgcagctgg gaccaggcaa gcgcgaagat catcgtcaca ccgccaccga   29340
cgccatcgcc gcgaggatct gatcgcggcc gggactgcgc agttcctcac ggatccggcc   29400
gtcggccatc accaggaccc ggtcggcgta cgtcgcggcg cccggatcgt gggtgaccat   29460
gatgatcgtc tggccggagc ggcgtgccgc gtcgcgcagc ccgcccagca gcgcgcggcc   29520
ggtggcgatg tccagcgcgc cggtcggctc gtcggcgaag accaccgacg gcttggccag   29580 cagcgccccgc gccaccgcca cccgctgctg ctggccgccg gacagctcgg acggacgatg   29640
ccccagccgg tcggtgatct gcagtgaatc ggtgatcttc gcagctcgc ccggatccac    29700 ccggcggccg gcgagccgta gcggcagcac gatgttctgc tccgccgtca gcgtcggcag   29760
caggttgaac gcctggaaga cgaagccgat ccggtcgcgg cgcaggtcgg tcagggcccg   29820
gtcgtccaga ccgccaatg accgccggc caggctgacc gtgcccgccg tcggtgtgtc     29880
caatccggcc agcaggtgca tcagcgtcgt cttcccggaa ccggacgggc ccatgatcgc   29940
ggtgaactgg ccccgcggaga agcccgcgga caccccgtcg acggctgtca cggcagccgg   30000
ccctgttccg tacgtcttgc tgacgtcccg gcaactgacc atctcggcgt gtgtcgtctg   30060
cgttgtcacc gcacccacgc tagaaatccg cgcggaccgg cacatcccac cacgggatcc   30120
cggtcgggcg gtggaccgat accttcgtat gacccgccgg tatcgacctc gggcgccgtg   30180
ttcccgcaat cgatgatgtc tgcttaggct gggaccgtgg tgcgagggaa ccgggtgctc   30240
aggatcgacg ccctcgtcgc cgccgcggtg gtcatcggct gtctgctcct cgggctcgcc   30300
gggctgtccg agtggtactg gtcggccgcg gtggccgtac cgttgcttct ccggcgcagc   30360
gctccgcgct gcttcctggc gctggtcgcc ggcgtctccg gcctgcacct gctggcctcg   30420
cacagcttca tgttccccgg cgatctggtc gctctggtcg cggtgcacgc cgccgcggcg   30480
cacgcgccgg gccgtgcccg ccacgccgga ctgctgctcg gcgccgccgg agctctcgtg   30540
gtggccgccc aggccctgca ggaccagcgc ctcggctcgg cgctgcccgc ggtgctgatc   30600
gtcgcgagca cgatggccgc ctggtcgatc gggctgatgc agcgccagca gcgcagcgcc   30660
gtgctcgacg ccgagcaccg ccgccggctg gccgaacagg acagcgccat gcgcgcgcag   30720
ctggccgtgc acgaggagcg cacccggatc agccaggaga tgcacgacat catcgcccac   30780
tcgctggcct cgatcatcgc ccaggccgaa ggcggccggg tcgccgcccg cgccgacgcg   30840
cggatcgccg ggcggtgtt cgaccggatc gcggcctcg gccgtcaagc cctcaccgac     30900
gtgaaacggc tgctcaccgt cgtggaccac gacgacgaat ggcacgacga cggactggag   30960
cggctgccgg tgctgctcgc cggagtcacc gaggccgggc tggacgtgac cgtggacagc   31020
agcggggcgc cgcagccgct cgccgccggg atggacctcg ccgtgtaccg ggtgatccag   31080
gagtcgctga ccaacgtgct caagcacgcg ccggcgcgcc gggcctgcct gcggatgcgg   31140
tggacgcccg cgctgctcac ggtcacggtg agcagcccgc ttcccggtgg ccgcggcgcc   31200
```

```
ggcctggtcg aggggcgcgg cctgtccggg atccggcagc gctgctcact gttcaacggc   31260
gactgcaccg tcaccgcgac cacggaactc accgtcacca ccacctggcc cctcaccccg   31320
gaaggagcgc gcgcatgacg cggccaccga tcgccgtgct gatcgccgac gatcaggagc   31380
tggtacgcac cggtttcgcg atggtcgtcg acgcggcgcc ggacatgcgg gtcgtggcca   31440
tcgccgcgag cggcgcggag gcgatcgagc tggccgccga acaccggccg gacgtcatcc   31500
tgatggacat ccgcatgccg ggcaccgacg ggatcaccgc gaccagcgcg atcctggccg   31560
ccggcggcga gcggccaccg aagatcatcg cgctgacgac gtacgacagc agcgactacg   31620
cgacgcggat cctcaccgcc ggggccagcg gctatctgct gaaggacgcg accgccgagg   31680
gcctgacggc ggcgatccgc agcgcgtacc acggcgggtc ggtgatcgcc cgacgacga   31740 cccggaacct ggtcgcggcc cgcgccgagc caccgccgcc ggctcgcgac ccggcgccgc   31800
tggacacgtt caccgcccgg gaacgcgacg tgttcgacct gatcgtggcg ggcgccaaca   31860
acgcggagat cgcggcccgg ctgcacctgg ccgaggtgac ggtgaagacg cacgtcggcc   31920
gggtgctggc caagctcggg gtacgcgacc ggctcaacgt agtcgtctgg gcgtaccgca   31980
acggcgctgt cggctgatcc gcaccctcag gcccttgaca cggtgccacg gtggcacggt   32040
gtgatagacc cgggtcgttt cgcctcacac tggtggtggt gcggtgagtt cctgggtacg   32100
ccggcgcgat cacaacgtct tcgtcaacgc gttcaacatg ctcatatgcg gcctcatcgc   32160
cggcgtcgtc gtggccgctg ccgcgttccc gttcgccgcg atgtccggcc tggccgccaa   32220
ggccggccag cagacgttcg cgagcctgcc cagcgagctg aaggcgttcc ggtcaccgca   32280
gatcagccgg atctacgccg ccgacaacag gacccaggtc gcccagttct acgacgagtt   32340
ccgcagtgac gtcccgctca aggagatgtc gccgttcatg cgcgacgcca tggtcgcggc   32400
cgaggaccgg cagttctacc agcaccacgg cgtggacctg aaaggcgcgg cgcgtgcgct   32460
ggtcaacaac cgcaacggcg ggcagaaaca gggcgcgtcg acgatcacca tgcagtgggt   32520
acggatctcg ctggcctact cggcgaccaa gccgcaggac gtcatcgacg ccaccgagga   32580
cgccccgaag cgcaaggtcg ccgagatgaa gtacgcgctc gaggtggaga agcagctcag   32640
caaggaccag atcctggagc ggtacctgaa catcgtgccg ttcggcaagc agacgtacgg   32700
catctacgcg gccagccggg tctacttcaa caagaagccc aaggacctca cgatcggcga   32760
ggccgcgctg ctggccgcca tcgtgaaggc gccgtccgcg tacgacccca ccgacccgga   32820
cggttacgag ctcatccggc agcggcgcaa cgcctatgtc atcccgggca tggtggagat   32880
gggcgccatc acccgggcgc aggccgacgc ggcgctcaag gaggccatcc cgcgcaaggt   32940
acgcccgatg agcaacggct gcgtgtcggt ggccaagaac aactgggget tcttctgcga   33000 ctacttctac cgctggtgga tggagcgcaa ggagttcggg cccacgccgt acgaccggga   33060
gcgccggctg aagagcggcg gctaccggat caccacgaca ctcgacgtca aggcgcagaa   33120
gcaggcccgg gatcggatcg gcgacctgat ctccgagaag aacaagaacg cgctgctgct   33180
ggcagccgtc gagcccggca ccggcaaggt acgcatgctc gccgccaacc gccggtacaa   33240
gctggacgat ccggatgatc cgcagaacgc gatctcctcc gacccgagaa aggcgcgcaa   33300
gggcatccgt ggctcgtacc cgaacacgac gaatcccctg ctgaccggcg gcggcgacat   33360
caccggctac caggccggct cggtgatgaa gatgttcacc atcgtcgccg cgctggagca   33420
gggctacccg ctcgcctaca cgatcaggac gcagagccgg taccgctccc gctacatcat   33480
cgagagcagc aacgacgcgg cctgcccegg aacgcacttc tggtgtccca gcaacgccgg   33540
tggcggcggc gagggtgtct tcaacatgtg gaccggcctg ggcaggtcga tcaacacgta   33600
```

```
cttcgtgccg ctggaggaac gcgtcggcgc ggagaaggtg gtcagcgccg cgaaacgctt   33660
cggcatccag ttccgggagc cggacgacgc actgctggcc gaaccgggca acgcacacca   33720
gtggggcgcc ttcaccctgg gcgtctcggc caccacccg ctggacatgg ccaacgccta    33780
cgccaccctg gccgccgacg ggatgtactg cccgccgacc ccgatcgagc ggatcgccac   33840
ccgtgacggc gaccagctgg acgtcggccg gtccccgtgc gtacgggcga ccgccaagga   33900
cgtcgcccgc gccgccctcg acgcggcccg ctgcccggtg ggcgactccg cgcagctcgg   33960
ccggtgcggg ggaagcaccg ccggcatcac ccggtcggtg gtcgggcatc cggtgttcgg   34020
caagaccggc accaccgacc gcgaccggac cgcctcgctg atcgccggca ccaccgcgct   34080
ggtggtcgcc ggttacctgg tcaaccccga ctaccagaac caccgcgacc ggctcgacca   34140
cgaccaggtc aacccggccg tctaccgcac gctcgccgac tacatggagg gcaggccacg   34200
ggagtcgttc aagcggccgt cgagcgggcg gatcgcgttc ggtgaccagc gctcgatccc   34260
ggacgtcgag tgcgacccga tgccccgcgc ccgcgaccgt ctggaggatg ccggcttcga   34320
cgtctggcga ggccaggaag tggagtcgga ctgtcccgcg ggcaccgcgg ccggcaccga   34380
gccgagcggc cggaccgtca agaacggcgt ggtggtgatc caggtgagca agggccgccg   34440
gggcgcgtca ccgccgatct tcccgccgat cgggccaccc cgctgaccgg ctgacggcgt   34500
agacgtcgcc ggcgttcgcc tcgtgcggca gcccggccag gtgcgcgagc atctcgtcgc   34560
gggcggccca ccggccgaag gtgcgggcca tggtctcgcc cagggagacg tcgaagccgt   34620
cgaagcccag ctcgccggca cggtcgaggc agcgccgggc cacgtcccgg gcgatcgtcg   34680
tgaactcgaa cgacaacgcc cggacaccgc ggctcagacc ggcgagcacc gcgtcctcgt   34740
acccttcgac gtcgatcttg atgaaggccg gcaggccgaa tcgctggacg agcgtgtcca   34800
gggtgaccgc agggacggtg atctgctggt cccagacctc gttctcccag ccgcgcgagc   34860
cggtcgccgg ggtcaggaag cgcaccgagt tcgtggagac cgtcgggttc gccgagttga   34920
tgtagagcgg cacgctcccg ccggcgggcc cgcacgcggc ctcgacgagc gccacccggt   34980
cgtcgtgggc gtagagcgcg cgcagcgccc gcatgcacag cggctgcggt tcgacggcga   35040
ccacgcgggc gccgagccgc cggaagcagg cgacccggtc accgacgtgc gcgccgatgt   35100
cgaagacgac gtcacccggc cggacgaaac gccggtacat cgcgtccatc gcggcctccc   35160
ggccggcgtc accgtagtag taacgcagcg accgggtcag cggcgccatg gccgggtcga   35220
ctctcagttt gcgcaggtca tcggtcacgg cgggggcatt ccccgatca ggcgatccat    35280 gcatcgccgg cgcgtgcgca ggtaggcggc gatcgcccgg gcggaacgca cgcccgaggt   35340
ggtcatgacg ttgtgcgcgg cggccgggac ggtcaccgac acgccgccgg tcatcgccgc   35400
cacctcggca cgccagcgca gcggcgccac cggatcaagc gacccgccga gcaccagcgg   35460
gggtacgggc aaccgcgcca gatcctcctc gatcgcgttg cgtaccgagt ggccgaccgt   35520
ggccagaacc cgccacggct tggcgtcggc gatgtcgcgg accagcaccg cgcctgcca    35580 cggcgcctcg atccacaggt ccaccgccca ccggccgatc agcgcccgcc gggaccgggc   35640
cgccgggtcg gtggtcgggc tggccagcac gacggcggcg accaggtccg gccgcagcac   35700
cgcgagacgg gccgccacct cggcgccgaa cgagtgcccg gcgatgcagg cccggggcac   35760
gccgagcacg tccagccagg ccgcgaggtg ttcggcgtgc cggcccacgt cgtacgcgcg   35820
gcgcggcttg tcgctgaacc cgaacccggg aaggtccgga acgaggaccg gatggcggcc   35880
cgccagcgcg tgggcggtgg gcatcaggta gcggtgcgag acggcgagcc cgtgtaccag   35940
caccaccgga aggccgccgg cgtggcacgc gtgccggtcg tgcgtacgca ctccaccgac   36000
```

```
cgtcaccagg cggctgtcga atcggggcac cgcggagatg tacccgtcc ttccgcaatc    36060 tttccgcgc ggttagtttc gagttgtgtc gccgccttc cggctcgacg aggcggtcgc     36120
cgacgtctac ggcgacctgc gcctggcgcc cgtgctgcgg cggctgctgc ggcacagcgg    36180
ccgcctgacc ggctcggtgg ccggcagcgt gtcgctgatc gacgcggacc gcggctgcta    36240
cgtcaaggcc gccgagtacg gcgcgaactg ccagctcgga cgctcttttcc cgctcgacga   36300 gggcgccacc ggccgcgcct tcggcagccg ccggcccgtg gtgatcccgg actacggtca    36360
gctgcgggcc ggtcatctcg cggcggcgca tccggcacgg aagggcccgg ccgtcgctgt    36420
gccgatctgg tggcgcggcg acgtgatcgc ggtgaacgtc gccttcgcgc cggccttctc    36480
cctgggtggt gtcgacgaac tggaggcgct gacccagtcc gcggccgccg cgatcgtccg    36540
cagccggggt gtgcgggtcc gcgccgaccc gccgtacgcg gctccggccg caccgttcac    36600
cccgcgcgag gccgaggtcc tcgatctgct ccggcagggt ctgaccgacc gcgagatggc    36660
ccgccggctc ggcctgtccg cgaagaccgt ggagaagcac gtcggcgcga tcaggcgcaa    36720
gaccgggacc tccaaccgta cggcggcggt cgtcacggcc ctggacaacg actgggtggg    36780
gaatcttccc cataccgcgg agcacaccac cgggtcttga ctggcggcat gcccgtcgtc    36840
tccatgaagg acatcctcga ccgtgcgctg gccgagcggt acggtgtggc cgccttcaac    36900
atcgtcaacg acctgaccgt cgaggccgtg ctcgccgccg cggcggagga acgcgccccg    36960
gtcatcctgc agacctcggt caagacggtc cggatgtacg gccgccccg gctgtacgag    37020 atcgtccacg ccttcgccca cgacgcgccc gtcccggtga ccctgcacct ggaccactgc    37080
cccgagcggt cggtcatctc cgactgcctc gccggcggct ggaactccgt gctcttcgac    37140
gcgcacgagc tcgacgtggc cgacaacctg cgccagacca ccgaggtggt ggccgaggcc    37200
cgtcgcgccg gcgcccacgt cgagggcgag atcgagggca tccagggtgt cgaggacgac    37260
gtcggcaacg actacgcccc gatggtgcag agcctggagg tggcggtcga cttcatcaaa    37320
cgcaccggcg tcgactgttt cgcgccggcc atcggcaacg cgcacggcca gtacaagcag    37380
gcgcccgtgc tcaacacccg ccgggtcagc gacctcgttg cggccaccgg catcccgatg    37440
gccctgcacg gcggcaccgg cctctccgac gagcagttca ccgacctcat cgcccgtggc    37500
tgcgcgaagt caacatctc cacggcgctc aaggagtcgt tcatgaaatc cggcctggag    37560
ttcctgcgcg aggccgatga gcgcggcaaa tgggatccgc cgtcgctgtt ccggcatcag    37620 cgggcggcg tcgtagagat ggcccggcag cacatccggc tcttcggcgg atcggggcgc    37680
gcgtggtgaa cgccctggtc ttcgactgcg acggcgtgct ggccgacacc gaacggcacg    37740
gccacctgcc cgcgttcaac gccacgttcg agcagttcgg gctgcccgtg cggtggagcg    37800
aggaggaata cggcgagaag ctgcgcatcg gcggcggcaa ggagcggatg gcgtcgctgt    37860
tcgccgatcc cgccttcgcc gcggcggccg gcgacaccga ccgtacggaa ctgctgcgaa    37920
cctggcaccg cgccaagacc gcggctttca cgaagctggt cgccgagggc cggattccgg    37980
cccgtccggg cacagcccgg atcatcagcg aggcactccg ggcaggatgg acggtcgcgg    38040
tcgcttccac gtcggccgag gattcggtac gcgcagtgct cgtcaacgcc gtgggagcga    38100
cgactgccga gcggatcccg gtgttcgccg gagacgtcgt gcccgcgaag aaacccgacc    38160
cggcgatc                                                             38168
```

<210> SEQ ID NO 101
<211> LENGTH: 146
<212> TYPE: PRT
<213> ORGANISM: Actinoplanes garbadinensis

<400> SEQUENCE: 101

Met Pro Arg Arg Ser Thr Arg Cys Ser Pro Ala Cys Arg Pro Gly Ala
1               5                   10                  15

Ala Asp Gln Pro Asp Pro Gly Arg Ala Cys Arg Pro Asp Cys Gly Arg
            20                  25                  30

Ala Asp Arg Ser Gly Ser Gly Arg Ala Cys Arg Pro Asp Cys Gly Arg
        35                  40                  45

Ala Asp Arg Ser Gly Ala Asp Arg Pro Ser Ala Ala Ala Leu Val Ser
    50                  55                  60

Gly Met Pro Arg Arg Thr Gly Val Gly Ala Pro Gly Arg Leu Ile
65              70                  75                  80

Glu Ala Arg Ala Val Leu Pro Glu Leu Ile Gly Ala Ala Arg Asp Arg
                85                  90                  95

Arg Ala Ser Cys Val Glu Gln Arg Val Arg Ser Leu Thr Ala Cys Arg
            100                 105                 110

Ala Cys Ala Cys Arg Arg Ala Ala Ala Pro Ala Ala Pro Arg Thr Pro
        115                 120                 125

Pro Arg Pro Ser Ala Ala Pro Ala Pro Gly Ser Asp Ala Gly Gly Arg
    130                 135                 140

Cys Gly
145

<210> SEQ ID NO 102
<211> LENGTH: 149
<212> TYPE: PRT
<213> ORGANISM: Actinoplanes garbadinensis

<400> SEQUENCE: 102

Val Ser Val Ser Leu Leu Val Pro Leu Ala Met Ala Gly Ala Ala
1               5                   10                  15

Ala Val Gln Ala Ala Ala Gly Arg Met Asp Asp Gly Arg Leu Ile Cys
            20                  25                  30

Gln Val Gln Thr Arg Met Arg Asp Val Thr Leu Leu Asp Ala Ala Leu
        35                  40                  45

Arg Asp Thr Gly Ala Thr Val Thr Ala Ala Gly Asp Thr Ile Ser Ala
    50                  55                  60

Thr Trp Thr Gln Ser Ala Ala Thr Phe Thr Arg Gly Ala Asp Gly Ile
65              70                  75                  80

Trp Ala Ala His Val Thr Gly Val Asp Gln Pro Gly Ala Val Glu Leu
                85                  90                  95

Met Thr Thr Val Asp Thr Ala Tyr Gly Arg Arg Val Gln Gln Ala Val
            100                 105                 110

Leu Glu Arg Leu Arg Ala Gln Ala Pro Glu Ala Gly Leu Arg Leu Glu
        115                 120                 125

Ser Glu Ser Val Gly Gln Asp Ala Ser Val Arg Leu Val Phe Glu Val
    130                 135                 140

Glu Arg Glu Arg Ala
145

<210> SEQ ID NO 103
<211> LENGTH: 518
<212> TYPE: PRT
<213> ORGANISM: Actinoplanes garbadinensis

<400> SEQUENCE: 103

Val Glu Arg Ser Phe Ala Glu Thr Phe Ala Gln Leu Leu Lys Ala Arg

-continued

```
1               5                   10                  15
Phe Pro Val Leu His Leu Glu Thr Tyr Glu Glu Gln Arg Ala Leu His
                20                  25                  30

His Leu Ala Gly Ile Ala Gly Asp Ala Asp Leu Val Arg Val Pro Arg
                35                  40                  45

Ala Val Trp Thr Trp Ser Leu Thr Ala Gly Leu Val Gln Pro Asn Gly
 50                  55                  60

Glu Ala Arg Ser Gly Ala Gln Arg Ala Thr Asp Ala Leu Arg Ala Val
 65                  70                  75                  80

Gln Arg Ile Asp Glu Pro Ala Val Phe Val Arg Asp Leu His Pro
                85                  90                  95

Leu Phe Ala Gln Ser Pro Glu Val Val Arg Leu Val Arg Asp Ile Ala
                100                 105                 110

Gln Ala Phe Arg Ala Gly Arg Ser Pro Arg Thr Leu Val Leu Leu Ser
                115                 120                 125

Pro Val Leu Asp Leu Pro Val Glu Leu Ser Lys Asp Val Thr Ile Val
                130                 135                 140

Asp Phe Pro Leu Pro Gly Gln Leu Glu Leu Arg Ala Leu Leu Asp Ala
145                 150                 155                 160

Met Val Arg Gly Asn Thr Ala Ser Gly Arg Leu Arg Val Glu Leu Asp
                165                 170                 175

Glu Gln Ser Arg Glu Arg Phe Val Thr Ala Ala Ala Gly Leu Thr Met
                180                 185                 190

Gln Glu Ala Glu Asn Ala Tyr Ala Arg Ala Met Val Asn Asp Ala Val
                195                 200                 205

Leu Asp Leu Ala Asp Leu Glu Ile Val His Glu Glu Lys Arg Gln Thr
                210                 215                 220

Val Arg Lys Ser Gly Val Leu Glu Phe Met Ala Ala Gly Thr Val Leu
225                 230                 235                 240

Asp Asp Val Gly Gly Leu Glu Asn Leu Lys Ala Trp Leu Val Lys Arg
                245                 250                 255

Asn Gly Ser Trp Leu Asp Glu Ala Ala Gly Tyr Gly Leu Pro Ala Pro
                260                 265                 270

Arg Gly Val Leu Ile Thr Gly Val Pro Gly Cys Gly Lys Ser Leu Thr
                275                 280                 285

Ala Lys Ala Val Ala Thr Ala Trp Asn Leu Pro Leu Leu Arg Phe Asp
                290                 295                 300

Ile Gly Arg Val Phe Ser Gly Leu Val Gly Ser Ser Glu His Asn Met
305                 310                 315                 320

Arg Thr Ala Leu Arg Thr Ala Glu Ala Val Ala Pro Cys Val Leu Trp
                325                 330                 335

Val Asp Glu Ile Glu Lys Gly Phe Ala Gly Thr Gly Gly Asp Ser
                340                 345                 350

Gly Thr Gly Ala Arg Val Phe Gly Thr Phe Leu Thr Trp Met Gln Glu
                355                 360                 365

Lys Arg Thr Pro Val Phe Val Ile Ala Thr Ala Asn Asp Phe Asp Gly
                370                 375                 380

Leu Pro Pro Glu Leu Leu Arg Lys Gly Arg Phe Asp Glu Thr Phe Phe
385                 390                 395                 400

Val Asp Leu Pro Ser Arg Ser Glu Arg Val Ala Val Trp Arg Val His
                405                 410                 415

Leu Gly Arg Ala Leu Arg His Arg Ala Ala Gly Leu Arg Val
                420                 425                 430
```

```
Asp Ala Glu Leu Leu Thr Glu Leu Ala Gly Leu Thr Glu Gly Tyr Ser
        435                 440                 445

Gly Ala Glu Ile Glu Gln Ala Val Ile Ala Gly Leu Phe Asp Ala Phe
    450                 455                 460

Ser Glu Arg Arg Pro Leu Arg Arg Asp Asp Leu Val Arg Ala Val Met
465                 470                 475                 480

Ser Ile Val Pro Leu Ser Val Thr Gln Ala Glu Arg Val Asp Ala Leu
                485                 490                 495

Arg Gly Trp Ala Arg Asn Arg Ala Val Ser Ala Thr Gly Thr Asp Asp
            500                 505                 510

Trp Asp Leu Thr Asn Arg
        515

<210> SEQ ID NO 104
<211> LENGTH: 203
<212> TYPE: PRT
<213> ORGANISM: Actinoplanes garbadinensis

<400> SEQUENCE: 104

Val Gly Glu Leu Asp Gln Gln Arg Ile His Pro His Asn Asn Ile Trp
1               5                   10                  15

Gly Ser Gly Ala Gly Thr Gln Thr Ile Trp Ala Arg Ser Gly Thr Asn
            20                  25                  30

Trp Gly Val Val Ala Asn His Pro Arg Thr Ser Gly Val Lys Ser Tyr
        35                  40                  45

Pro Asn Thr Gly Lys Thr Leu Asn Arg Thr Leu Ser Ser Leu Asn Ser
    50                  55                  60

Leu Thr Ser Ser Phe Asn Val Ser Val Pro Ser Ser Gly Asp Tyr Ser
65                  70                  75                  80

Thr Thr Tyr Asp Ile Trp Ala Asn Asn His Ala Tyr Glu Val Met Ile
                85                  90                  95

Trp Thr Asn Gln Gln Gly Ala Val Gly Pro Ile Ala Glu Gln Tyr Asp
            100                 105                 110

Ala Asn Gly Ala Val Pro Asn Val Arg Asn Leu Ser Val Gly Gly His
        115                 120                 125

Thr Trp Asn Val Tyr Arg Gly Ser Asn Gly Ala Asn Ala Val Phe Ser
    130                 135                 140

Phe Ile Arg Thr Asn Thr Asn Ser Gly Thr Val Asp Ile Leu Ala Ile
145                 150                 155                 160

Leu Asn Trp Leu Arg Thr Asn Gly Trp Trp Gly Asp Val Thr Val Gly
                165                 170                 175

Glu Ala Gln Phe Gly Phe Glu Ile Ser Gly Thr Ala Gly Gln Ser Asn
            180                 185                 190

Phe Thr Val Asn Asn Phe Ser Leu Asn Tyr Ser
        195                 200

<210> SEQ ID NO 105
<211> LENGTH: 219
<212> TYPE: PRT
<213> ORGANISM: Actinoplanes garbadinensis

<400> SEQUENCE: 105

Met Arg Arg Arg Thr Leu Ala Leu Ser Leu Ala Ser Ala Ala Leu
1               5                   10                  15

Ile Ala Gly Ala Gly Val Val Thr Ala Leu Pro Ala Ser Ala Ala Ala
            20                  25                  30

Gly Cys Arg Val Ala Tyr Thr Val Ser Ser Gln Trp Pro Gly Gly Phe
```

```
                35                  40                  45
Gly Ala Asn Val Thr Ile Thr Asn Leu Gly Asp Pro Leu Thr Asn Trp
 50                  55                  60

Thr Leu Val Trp Ser Tyr Ser Gly Gly Gln Thr Val Thr Gln Ala Trp
 65                  70                  75                  80

Asn Thr Ser Leu Thr Gln Ser Gly Ser Gln Val Thr Ala Arg Asn Ala
                 85                  90                  95

Gly Tyr Asn Gly Ser Val Gly Thr Asn Ala Thr Val Ser Phe Gly Phe
                100                 105                 110

Asn Gly Ser Gly Ala Ala Thr Pro Ala Pro Gly Thr Phe Thr Leu Asn
                115                 120                 125

Gly Thr Ala Cys Thr Gly Ser Ala Gly Pro Thr Ser Pro Ser Ser Gln
130                 135                 140

Pro Pro Thr Asn Gly Val Pro Ser Asp Ala Val Trp Val Asp Ser Gly
145                 150                 155                 160

Gln Trp Ala Asn Trp Thr Asn Asn Gly Tyr Ile Leu Thr Thr Thr Ser
                165                 170                 175

Gly Ala Arg Ala Pro Ala Pro Arg Pro Ser Gly Arg Ala Ala Ala Pro
                180                 185                 190

Thr Gly Ala Ser Ser Arg Ile Thr Arg Ala Pro Ala Gly Ser Ser Pro
                195                 200                 205

Thr Pro Thr Pro Glu Arg Pro Ser Thr Val Arg
    210                 215

<210> SEQ ID NO 106
<211> LENGTH: 161
<212> TYPE: PRT
<213> ORGANISM: Actinoplanes garbadinensis

<400> SEQUENCE: 106

Met Thr Ile Thr Glu Thr Asp Leu Ala His Leu Arg Arg Cys Val Asp
 1               5                  10                  15

Leu Ala Arg Glu Ala Leu Asp Asp Gly Asp Glu Pro Phe Gly Ser Val
                 20                  25                  30

Leu Val Ser Ala Asp Gly Lys Val Leu Phe Glu Asp Arg Asn Arg Val
                 35                  40                  45

Arg His Gly Asp Ala Thr Gln His Pro Glu Phe Ala Ile Ser Arg Trp
 50                  55                  60

Ala Ala Glu His Leu Thr Pro Arg Glu Arg Ala Ser Ala Thr Val Tyr
 65                  70                  75                  80

Thr Ser Gly Glu His Cys Pro Met Cys Ser Ala Ser His Gly Trp Val
                 85                  90                  95

Arg Leu Gly Arg Ile Val Tyr Ala Ala Ser Ser Ala Gln Leu Thr Ala
                100                 105                 110

Trp Tyr Lys Glu Trp Gly Ile Pro Ala Gly Pro Val Ala Pro Leu Pro
                115                 120                 125

Ile Thr Thr Val Val Pro Gly Ala Val Val Glu Gly Pro Val Pro Ala
                130                 135                 140

Phe Glu Ala Glu Leu Arg Glu Leu His Arg Ala Arg Phe Thr Pro Ala
145                 150                 155                 160

Gln

<210> SEQ ID NO 107
<211> LENGTH: 413
<212> TYPE: PRT
<213> ORGANISM: Actinoplanes garbadinensis
```

<400> SEQUENCE: 107

```
Val Thr Thr Pro Leu Val Ala Gln Ala Gly Asp Ser Thr Thr Gly Leu
 1               5                  10                  15
Thr Gly Leu Gly Leu Val Glu Asp Ala His Gln Ile Ala Glu Ala Ile
             20                  25                  30
Arg Gly Asn Ser Trp Val Asp Gly Val Leu Gly Gly Val Gly Ala Ser
         35                  40                  45
Leu Asp Gly Leu Ala Leu Ala Ile Asp Pro Leu Gly Thr Leu Ala Ala
 50                  55                  60
Trp Gly Val Ala Trp Leu Ile Glu His Val Gln Pro Leu Gln Asp Ala
 65                  70                  75                  80
Leu Asp Trp Leu Ala Gly Asp Val Asp Glu Ile Ala Ala Gln Ala Ala
             85                  90                  95
Thr Trp Arg Asn Val Ala Ala Phe Thr Asp Ser Ala Gln Gln Asp Tyr
        100                 105                 110
Ala Asp Arg Leu Arg Thr Glu Val Ala Gly Trp Phe Gly Ala Ser Gly
            115                 120                 125
Asp Ala Tyr Arg Ala His Ala Ser Glu His Leu Ala Ala Leu Lys Gly
130                 135                 140
Ile Ser Thr Ala Ala Gly Gly Ile Ser Ser Ala Val Glu Gly Ala Gly
145                 150                 155                 160
Leu Leu Val Ser Leu Val Arg Gly Ile Val Arg Asp Leu Ile Ala Gln
                165                 170                 175
Phe Val Ala Thr Leu Ala Val Arg Leu Pro Gln Trp Leu Ala Ala Glu
            180                 185                 190
Gly Leu Thr Leu Gly Leu Ala Thr Pro Val Val Ala Ser Gln Val Ala
        195                 200                 205
Ala Leu Val Ala Arg Gly Val Asn Lys Ile Gln His Phe Ile Arg Ala
210                 215                 220
Leu Leu Asn Ser Leu Arg Arg Leu Met Pro Met Ile Asp Arg Leu Gly
225                 230                 235                 240
Glu Val Leu Glu Arg Leu Arg Met Leu Thr Asp Arg Leu Ala Arg Ser
                245                 250                 255
Ser Pro Ser Thr Arg Pro Glu Pro Thr Pro Gly Pro Ala Thr His Ala
            260                 265                 270
Gly Thr Glu Asn Ala Ser Gly Asn Lys Pro Glu Gly Asp Leu Glu Pro
        275                 280                 285
Asn Glu Pro Arg Pro Ala Glu Ala Pro Ala Arg Asp Ser Thr Pro Gln
290                 295                 300
Ala Phe Val Asp Glu Val Val Ser Asn Pro Arg Ser Val Ala Gly His
305                 310                 315                 320
Ser Ala Gln Ser Ile Ala Asp Gln Phe Asn Ala Ala Gly Tyr Ser Ala
                325                 330                 335
Val Val Glu Gln Ser Thr Arg Ser Gly Thr Ser Gly Asn Ala Ile Gln
            340                 345                 350
Val Arg Ile His Gly His Pro Asp Ile Thr Asn Ile Gln Val His Pro
        355                 360                 365
Gly Gly Gly Arg His Thr Pro Glu Gly Ser Pro Tyr Trp Lys Ile Ser
370                 375                 380
Thr Asn Thr Val Gly Lys Ile Trp Ile Pro Glu Asn Phe Arg Gly
385                 390                 395                 400
Ala Asp Glu Leu Arg Gly Asn Val Val Arg Tyr Asp Lys
            405                 410
```

<210> SEQ ID NO 108
<211> LENGTH: 217
<212> TYPE: PRT
<213> ORGANISM: Actinoplanes garbadinensis

<400> SEQUENCE: 108

```
Val Gly Lys Pro Cys Pro Asp Leu Val Glu Val Leu Ser Arg Glu Ile
1               5                   10                  15

Gln Ala Gly Asn Gln Gly Ala Ser Ala Ser Glu Val Val Glu Ile Phe
            20                  25                  30

Asp Leu Glu Leu Val Gly Ile Phe Arg Gly Ala Val Thr Gln Lys Leu
        35                  40                  45

Pro Gly Ile Glu Val Leu Arg Lys His Leu His Leu Lys Gln Gly Gly
    50                  55                  60

Val Gln Val Arg Ser Val Val Arg Ala Glu Asp Pro Ala Gly Ile
65                  70                  75                  80

Val Val Val Gly Asp Leu Cys Ala Arg Ile Asp Asn Arg Asp Val Gly
                85                  90                  95

Leu Ala Gln Gly Asp Ala Tyr Trp Glu Arg Arg Asp Asp Thr Val Asp
            100                 105                 110

Arg Leu Asp Gln Ile Arg Ala Asp Ser Pro Cys Glu Phe Asp Asp Met
        115                 120                 125

Val Arg Leu Gly Ala Gly Val His Gly Asp Gly Gln Arg Arg Val Arg
    130                 135                 140

Gln Arg Phe Ala Asp Val Ala Asn Leu Phe Gly Val Gln Arg Ala Ile
145                 150                 155                 160

Ile Asn Glu Ser Arg Ile Arg Thr Lys Ile Asp Pro Asp Asp Val Asp
                165                 170                 175

Ala Gln Gly Asp Glu Arg Gly Ser Phe Pro Arg Gly Ser His Pro Ile
            180                 185                 190

His Phe Asp Asp Leu Ile Cys His Ser Ala Pro His Ser His Ala Val
        195                 200                 205

His Arg Arg Pro Gly Asn Phe Arg Gly
    210                 215
```

<210> SEQ ID NO 109
<211> LENGTH: 592
<212> TYPE: PRT
<213> ORGANISM: Actinoplanes garbadinensis

<400> SEQUENCE: 109

```
Val Ser Asp Val Val Glu Arg Leu Thr Ala Trp Asp Val Glu Arg
1               5                   10                  15

Val Phe Gly Tyr Ser Gly Asp Gly Ile Asp Gly Val Ile Gly Ala Leu
            20                  25                  30

Arg Arg Ala Gly Arg Pro Thr Phe Val Gln Ala Arg His Glu Glu Gly
        35                  40                  45

Ala Ala Phe Met Ala Val Gly His Ala Lys Tyr Thr Gly Gly Ala Gly
    50                  55                  60

Val Cys Leu Ala Thr Gln Gly Pro Gly Ala Val His Leu Leu Asn Gly
65                  70                  75                  80

Leu Tyr Asp Ala Lys Leu Asp Ser Lys Pro Val Val Ala Ile Val Gly
                85                  90                  95

Gln Gln Val Ser Thr Val Leu Gly Ser Ala Tyr Gln Gln Glu Ile Asp
            100                 105                 110
```

```
Leu Val Arg Leu Phe Gly Asp Val Cys Ala Gln Phe Val Gln Ala Ala
            115                 120                 125
His Thr Ser Glu Gln Val Pro Met Leu Leu Asp Arg Ala Phe Arg Thr
        130                 135                 140
Ala Leu Ala Thr Arg Ser Pro Thr Cys Val Val Leu Pro His Asp Val
145                 150                 155                 160
Gln Thr Ala Pro Ala Pro Asp Pro Gln Ala His Glu His Gly Val Leu
                165                 170                 175
Ala Thr Ser Ala Gly Leu Arg Pro Ala Arg Val Val Pro Arg Pro Glu
            180                 185                 190
Asp Leu Arg Glu Ala Ala Glu Val Leu Arg Ser Gly Glu Arg Val Ala
        195                 200                 205
Ile Met Val Gly Gln Gly Ala Tyr Gly Ala Glu Arg Glu Ile Val Glu
210                 215                 220
Leu Ala Gln Arg Leu Gly Ala Gly Val Thr Thr Ser Leu Leu Gly Lys
225                 230                 235                 240
Pro Val Leu Asp Glu Asn Leu Pro Phe His Thr Gly Val Met Gly His
                245                 250                 255
Leu Gly Thr Thr Ala Ser Ala Glu Leu Met Arg His Cys Asp Thr Leu
            260                 265                 270
Leu Leu Ile Gly Thr Asn Asp Pro Trp Thr Glu Phe Tyr Pro Arg Pro
        275                 280                 285
Gly Gln Ala Arg Ala Val Gln Ile Asp Val Asp Gly Arg Arg Leu Gly
290                 295                 300
Val Arg Tyr Pro Val Glu Val Pro Leu Leu Gly Asp Ala Val Glu Thr
305                 310                 315                 320
Leu Arg Glu Leu Leu Gly Leu Leu Pro Ser Arg Ala Ser Gly Ala Trp
                325                 330                 335
Gly Ala Arg Val Glu Glu Trp Val Gln Arg Trp Arg Leu Ile Ser Ala
            340                 345                 350
Ala Arg Ala Ala Ala Pro Ala Glu Pro Val Asn Pro Gln His Val Ile
        355                 360                 365
Arg Ser Leu Ser Asp His Leu Pro Ala Asp Ala Gln Val Ala Val Asp
370                 375                 380
Val Gly Ser Val Val Tyr Trp Tyr Ala Arg His Leu Arg Leu Pro Arg
385                 390                 395                 400
Gly Val Pro Ala His Leu Ser Ser Thr Leu Ala Ser Met Gly Cys Gly
                405                 410                 415
Leu Pro Tyr Gly Leu Ala Ala Lys Leu Ala Ala Pro Gln Arg Pro Val
            420                 425                 430
Val Val Leu Ala Gly Asp Gly Ala Met Gln Met Ala Gly Met Ala Glu
        435                 440                 445
Leu Ile Thr Val Ala Ala Arg Trp Arg Asp Trp Ala Asp Pro Arg Phe
450                 455                 460
Val Val Cys Val Leu Asn Asn Arg Asp Leu Ala Glu Val Ser Trp Glu
465                 470                 475                 480
Gln Arg Glu Thr Glu Gly Glu Pro Arg Phe Val Thr Ser Gln Glu Leu
                485                 490                 495
Pro Asp Val Pro Tyr Ala Arg Tyr Ala Glu Leu Leu Gly Leu Arg Gly
            500                 505                 510
Val Arg Ile Thr Asp Pro Ser Asp Leu Thr Gly Ala Trp Glu Ala Ala
        515                 520                 525
Leu Ser Ala Asp Arg Pro Thr Leu Ile Glu Ala Val Val Asp Pro Ala
530                 535                 540
```

```
Ile Pro Leu Leu Pro Pro Gly Gln Pro Tyr Glu Lys Val Gln Ala Met
545                 550                 555                 560

Tyr Ala Gly Leu Ala Ala Glu Lys Gly Asp Gln Ala Arg Arg Ala Glu
                565                 570                 575

Ala His Leu Arg Arg Glu Arg Ala Asp Glu Gly Phe Asp Asp Pro Ser
            580                 585                 590

<210> SEQ ID NO 110
<211> LENGTH: 266
<212> TYPE: PRT
<213> ORGANISM: Actinoplanes garbadinensis

<400> SEQUENCE: 110

Val Ser Arg Asp Lys Thr Tyr Arg Pro Val Arg Pro Asp Gly Ile Arg
1               5                   10                  15

Thr Thr Phe His Asp Gly Val Leu Gly Arg Met Arg Ile Arg Cys Leu
                20                  25                  30

Gly Glu Pro Arg Pro Gly Val Pro Glu Ile Val Met Ile Gln Gly Met
            35                  40                  45

Thr Val Ser Asp Tyr Leu Leu Pro Gly Leu Gly Ala Leu Ser Ala Trp
50                  55                  60

Thr Arg Val His Leu Val Glu Leu Pro Gly Gly Ser Gly Ser Gly Arg
65                  70                  75                  80

Pro Pro His Asp Leu Thr Val Glu Glu Tyr Ala Arg Ala Ala Ala Asp
                85                  90                  95

Trp Leu Cys Ala Gln Arg Leu Gly Arg Ile Val Leu Ala Gly His Ser
            100                 105                 110

Ser Gly Thr Gln Val Ala Ala Glu Thr Ala Leu Leu Cys Pro Asp Glu
        115                 120                 125

Val Ala Gly Val Val Leu Ala Gly Pro Ala Ile Asp Pro Val Ala Arg
    130                 135                 140

Gly Gly Leu Arg Val Phe Ala Arg Trp Trp Ile Asp Arg Arg Gly Asp
145                 150                 155                 160

Pro Lys Ser Leu Asp Glu Val His Lys Pro Glu Arg Glu Gln Val Gly
                165                 170                 175

Phe Arg Arg Leu Phe Gln Val Leu Arg Ala His Leu Arg His Asp Leu
            180                 185                 190

Glu Lys Pro Val Val Gly Leu Cys Val Pro Leu Val Ile Arg Gly
        195                 200                 205

Ser Glu Asp Arg Leu Gly Thr Ala Arg Trp Ala Arg Arg Leu Ala Asp
    210                 215                 220

Leu Ala Ala Val Gly Gly Arg Tyr Val Glu Val Pro Gly Thr His Ser
225                 230                 235                 240

Phe Cys Trp Arg Tyr Pro Gln Ala Trp Ser Ala Pro Ile Arg Glu Phe
                245                 250                 255

Ala Gly Trp Ser Val Ser Val Ser Gly Thr
            260                 265

<210> SEQ ID NO 111
<211> LENGTH: 396
<212> TYPE: PRT
<213> ORGANISM: Actinoplanes garbadinensis

<400> SEQUENCE: 111

Met Thr Glu Ala Asp His Arg Pro Thr Val Leu Arg Arg Ile Leu Arg
1               5                   10                  15
```

```
Leu Cys Ala Val Leu Leu Met Val Leu Gly Val Gly Leu Val Gly Ala
        20                  25                  30

Pro Thr Ser His Ala Gly Gly Lys Pro Thr Ile Ser Lys Glu Ala Phe
            35                  40                  45

Gly Ser Val Gly Gly Lys Ala Val Asp Arg Tyr Thr Leu Thr Asn Gly
 50                  55                  60

Arg Leu Gln Val Arg Ile Leu Thr Tyr Gly Gly Ile Leu Gln Thr Ile
 65                  70                  75                  80

Thr Phe Pro Asp His Arg Gly Arg Arg Ala Asn Val Thr Leu Gly Phe
                85                  90                  95

Arg Thr Leu Asp Glu Tyr Val Thr Thr Lys Asn Pro Ala Tyr Phe Gly
            100                 105                 110

Ala Ile Ile Gly Arg Tyr Gly Asn Arg Ile Ala Asp Gly Arg Phe Thr
        115                 120                 125

Leu Asp Gly Thr Thr Tyr Gln Leu Ala Thr Asn Asn Asp Pro Asn His
    130                 135                 140

Leu His Gly Gly Val Val Gly Phe Asp Lys Arg Val Trp Asp Ala Thr
145                 150                 155                 160

Pro Ile Arg Asp Gly Asp Ser Val Gly Leu Arg Leu Thr Tyr Thr Ser
                165                 170                 175

Pro His Gly Glu Glu Asn Tyr Pro Gly Thr Leu Arg Val Thr Met Thr
            180                 185                 190

Tyr Thr Val Thr Arg Gln Met Gly Ile Arg Met Asp Tyr Arg Ala Thr
        195                 200                 205

Thr Asp Arg Pro Thr Ile Val Asn Leu Thr Asn His Ala Tyr Trp Asn
    210                 215                 220

Leu Gly Gly Glu Gly Thr Gly Thr Ile Asp Asp His Leu Leu Lys Leu
225                 230                 235                 240

Asn Ala Asn Arg Tyr Thr Pro Val Asp Ala Thr Leu Ile Pro Thr Gly
                245                 250                 255

Ala Ile Asp Ala Val Ala Gly Thr Pro Met Asp Phe Arg Arg Pro Thr
            260                 265                 270

Pro Ile Gly Ala Arg Asn Arg Asp Pro Phe Gln Gln Leu Val Tyr Gly
        275                 280                 285

Arg Gly Tyr Asp His Asn Trp Val Leu Asn Arg Glu Asp Gly Gln Phe
    290                 295                 300

Arg Arg Leu Glu Phe Ala Ala Arg Ala Val Asp Pro Asp Ser Gly Arg
305                 310                 315                 320

Gln Leu Thr Ile Tyr Thr Thr Glu Pro Gly Ile Gln Phe Tyr Gly Gly
                325                 330                 335

Asn Phe Leu Asp Gly Thr Leu Tyr Gly Thr Ser Gly Arg Ala Tyr Arg
            340                 345                 350

Gln Gly Asp Gly Phe Ala Leu Glu Thr Gln His Phe Pro Asp Ser Pro
        355                 360                 365

Asn His Ala Asn Phe Pro Ser Thr Val Leu Arg Pro Gly Gln Thr Tyr
    370                 375                 380

Asn Ser Thr Thr Ile Tyr Gln Phe Gly Thr Ala Asp
385                 390                 395

<210> SEQ ID NO 112
<211> LENGTH: 378
<212> TYPE: PRT
<213> ORGANISM: Actinoplanes garbadinensis

<400> SEQUENCE: 112
```

```
Met Pro Arg Ile His Pro Lys Val Glu Glu Ala Val Ser Thr Leu Asp
1               5                   10                  15

Leu Asn Arg Thr Thr Arg Arg Leu Leu Ser Gly Thr Gly Leu Phe
            20                  25                  30

Ser Ala Ser Leu Ala Ala Gly Ala Leu Leu Ser Ala Cys Ser Asp Gln
        35                  40                  45

Asn Asp Gly Gln Asn Gln Thr Glu Gly Ala Gly Asn Phe Pro Asp Thr
    50                  55                  60

Pro Glu Trp Arg Phe Thr Phe Val Asn His Val Thr Thr Asn Pro Phe
65              70                  75                  80

Phe Thr Pro Thr Gln Tyr Gly Met Glu Asp Ala Ala Thr Leu Leu Gly
                85                  90                  95

Ile Ala Lys Pro Gln Trp Thr Gly Ser Gln Asn Ser Ile Val Ala Glu
                100                 105                 110

Met Val Asn Ala Thr Asn Thr Ala Val Ser Ala Lys Val Asp Gly Ile
            115                 120                 125

Ala Ile Ala Val Val Asp Lys Asp Ala Phe Arg Gly Pro Val Asp Gln
        130                 135                 140

Ala Leu Asn Ala Gly Ile Pro Val Val Ser Tyr Asn Ala Asp Gly Ala
145                 150                 155                 160

Arg Gly Ala Pro Gly Thr Asn Arg Leu Ala Tyr Ile Gly Gln Gly Leu
                165                 170                 175

Tyr Glu Ser Gly Tyr Ala Leu Gly Gln Arg Ala Leu Gln Val Leu Asp
                180                 185                 190

Ser Gly Glu Val Ala Ala Phe Ile Ala Thr Pro Gly Ala Leu Asn Ile
            195                 200                 205

Gln Pro Arg Ile Asp Gly Ala Gln Gln Ala Phe Lys Asp Ser Gly Lys
        210                 215                 220

Pro Ile Thr Phe Thr Ala Val Ala Thr Asn Ala Asp Val Thr Arg Gly
225                 230                 235                 240

Leu Ser Ile Ile Asp Ala Tyr Ala Gln Gly His Ala Asn Leu Ala Gly
                245                 250                 255

Met Leu Ala Val Asp Ala Gly Ser Thr Ser Ser Val Gly Gln Thr Val
            260                 265                 270

Lys Lys Tyr Asn Met Arg Gly Lys Gly Leu Lys Val Ala Gly Gly Phe
        275                 280                 285

Asp Leu Ile Pro Glu Thr Leu Thr Gly Ile Gln Glu Gly Ser Leu Asp
290                 295                 300

Tyr Thr Ile Asp Gln Gln Pro Tyr Leu Gln Gly Phe Leu Pro Val Leu
305                 310                 315                 320

Ala Leu Tyr Phe Tyr Lys Val Ser Gly Gly Leu Ile Ala Pro Ser Glu
                325                 330                 335

Thr Asn Thr Gly Leu Leu Phe Val Thr Lys Asp Asn Val Ala Pro Tyr
            340                 345                 350

Gln Ser Thr Lys Ser Arg Tyr Glu Gly Ser Thr Thr Asp Lys Val Leu
        355                 360                 365

Val Pro Arg Ser Gly Pro Ile Ala His Gly
370                 375

<210> SEQ ID NO 113
<211> LENGTH: 352
<212> TYPE: PRT
<213> ORGANISM: Actinoplanes garbadinensis

<400> SEQUENCE: 113
```

```
Met Asp Asp Arg Ile Ser Pro Ala Pro Ala Gln Ala Pro Ser Leu Glu
1               5                   10                  15

Val Glu Gln Arg Arg Gly Arg Trp Gln Pro Val Thr Ala Ala Gly Arg
            20                  25                  30

Lys Val Leu Asp Ala Phe Leu Arg Arg Glu Ala Ser Val Leu Leu
        35                  40                  45

Val Ala Ile Gly Leu Met Ile Tyr Phe Arg Ala Ser Ser Pro Val Phe
    50                  55                  60

Leu Ser Arg Asp Asn Leu Val Asn Ile Ala Gln Ala Thr Ala Pro Val
65                  70                  75                  80

Ala Ile Ile Ala Val Gly Ile Val Leu Leu Val Ser Gly Glu Ile
                85                  90                  95

Asp Leu Ser Val Gly Ile Val Ala Ala Leu Ala Pro Phe Leu Phe His
                100                 105                 110

Phe Gly Ile Asn Phe Tyr Ser Leu Pro Val Val Pro Ala Phe Val Val
            115                 120                 125

Ala Leu Ala Ile Ala Ala Gly Ile Gly Leu Val Asn Gly Leu Ile Val
        130                 135                 140

Thr Gln Leu His Val Pro Ser Phe Val Thr Thr Leu Gly Thr Phe Phe
145                 150                 155                 160

Ala Val Gln Gly Ile Leu Leu Ile Thr Ser His Ala Tyr Pro Val Pro
                165                 170                 175

Ile Pro Asp Ala Ala Lys Gly Thr Phe Gln Thr Trp Leu Gly Ala Gly
            180                 185                 190

Pro Trp Ala Ser Ile Thr Trp Ala Leu Ile Ile Val Ala Ile Phe His
        195                 200                 205

Thr Val Leu Thr Leu Thr Arg Trp Gly Leu His Thr Ile Ser Val Gly
210                 215                 220

Gly Asn Pro Val Gly Ala Thr Glu Ala Gly Ile Arg Ala Ser Arg Ile
225                 230                 235                 240

Lys Ile Gly Asn Phe Val Ile Thr Ser Thr Leu Gly Gly Leu Val Gly
                245                 250                 255

Ile Met Glu Ala Phe Arg Ile Asn Thr Ile Asp Pro Asn Ile Gly Gly
            260                 265                 270

Gly Thr Thr Leu Thr Phe Tyr Ala Ile Ser Ala Ala Val Ile Gly Gly
        275                 280                 285

Thr Ala Leu Ala Gly Gly Ser Gly Thr Ile Val Gly Ala Phe Leu Gly
290                 295                 300

Ala Leu Val Leu Ala Glu Leu Gln Asn Gly Phe Asn Leu Ile Gly Tyr
305                 310                 315                 320

Ser Ala Asn Thr Ile Phe Leu Ile Leu Gly Leu Ala Ile Leu Val Ser
                325                 330                 335

Met Ile Ala Asn Gln Tyr Leu Ser Arg Leu Arg Arg Ala Gly Arg Ser
            340                 345                 350

<210> SEQ ID NO 114
<211> LENGTH: 253
<212> TYPE: PRT
<213> ORGANISM: Actinoplanes garbadinensis

<400> SEQUENCE: 114

Met Thr Ala Glu Thr Val Ser Asp Ala Leu Arg Val Gln Asn Ile Ala
1               5                   10                  15

Lys Arg Phe Gly Ala Leu Thr Ala Leu Gln Asp Val Thr Leu Arg Val
            20                  25                  30
```

```
Ala Glu Gly Glu Val Leu Gly Leu Ile Gly Asp Asn Gly Ala Gly Lys
            35                  40                  45

Ser Thr Leu Ile Lys Ile Ile Cys Gly Tyr His Arg Pro Asp Ala Gly
    50                  55                  60

Arg Ile Phe Val Gly Gly Glu Val Thr Leu Arg Ser Val Asp His
65                  70                  75                  80

Ala Arg Ser Val Gly Ile Asp Ala Val Tyr Gln Asp Leu Ala Leu Val
                85                  90                  95

Asn Glu Leu Ser Val Tyr His Asn Met Phe Leu Asn Arg Glu Leu Val
            100                 105                 110

Arg Trp Pro Leu Leu Asn Asn Arg Ala Met Arg Arg Ala Glu Glu
        115                 120                 125

His Leu Arg Asp Met Gly Val Asn Leu Pro Asp Val Gly Val Glu Val
130                 135                 140

Ala Lys Leu Ser Gly Gly Gln Arg Gln Ala Ile Ala Val Ala Arg Cys
145                 150                 155                 160

Val Tyr Ser Asp Ala Arg Ile Leu Leu Asp Glu Pro Leu Ala Ala
                165                 170                 175

Met Gly Ala Lys Glu Gly Thr Met Ile Leu Asp Leu Ile Arg Asp Leu
            180                 185                 190

Lys Ala Arg Gly Asn Val Ser Ile Ile Ile Ala His Asn Tyr Ala
        195                 200                 205

Gln Val Leu Asp Val Cys Asp Arg Val Asn Leu Leu Gln His Gly Arg
210                 215                 220

Ile Thr Phe Asp Lys Arg Ser Ala Asp Thr Ser Leu Ala Glu Leu Thr
225                 230                 235                 240

Glu Leu Val Val Ala Glu Tyr Arg Thr Gly Arg Gly Arg
                245                 250

<210> SEQ ID NO 115
<211> LENGTH: 255
<212> TYPE: PRT
<213> ORGANISM: Actinoplanes garbadinensis

<400> SEQUENCE: 115

Met Glu Ser Gly Ala Ser Val Pro Gln Ser Ala Arg Ile Trp Asn Tyr
1               5                   10                  15

Trp Leu Gly Gly Thr Asp Asn Leu Pro Val Asp Arg Ala Ala Gly Asp
            20                  25                  30

Glu Tyr Arg Ala Val Phe Pro Gly Ile Asp Glu Ile Ala Arg Glu Ser
        35                  40                  45

Arg Arg Tyr Leu Ser Arg Ala Val Arg Tyr Leu Ala Gly Glu Ala Gly
    50                  55                  60

Val Arg Gln Phe Leu Asp Val Gly Ala Gly Leu Pro Thr Val Asp Asn
65                  70                  75                  80

Thr His Gln Ile Ala Gln Arg Val Ala Pro Ala Arg Val Leu Tyr
                85                  90                  95

Val Asp Lys Asp Pro Tyr Ala Val Glu His Gly Arg Glu Leu Leu Ala
            100                 105                 110

Gly Ser Ser Asp Val Tyr Leu Glu Gly Asp Leu Gln Lys Pro Ala Asp
        115                 120                 125

Ile Leu Ala Val Ala Ala Arg Glu Leu Asp Met Gly Arg Pro Val Ala
    130                 135                 140

Leu Ile Leu Asn Gly Val Leu Gly His Ile Pro Ser Thr Ala Glu Val
145                 150                 155                 160
```

```
Arg Asp Ile Val Arg Gln Leu Met Ala Gly Leu Pro Pro Gly Ser Tyr
            165                 170                 175

Leu Ser Ile Asn Asp Gly Val Arg Val Ala Gly Glu Glu Ala Leu Asn
            180                 185                 190

Gln Ala Gln Asp Ala Tyr Asn Ser Ser Gly Ala Val Pro Tyr Leu Met
            195                 200                 205

His Thr Pro Asp Glu Ile Ala Gly Phe Phe Glu Gly Leu Asp Leu Val
        210                 215                 220

Pro Pro Gly Val Val Pro Ser Pro Gln Trp His Pro Asp Pro Gly Asp
225                 230                 235                 240

Glu Thr Thr Gly Ala Ser Gln Tyr Ser Gly Val Gly Arg Lys Arg
                245                 250                 255

<210> SEQ ID NO 116
<211> LENGTH: 280
<212> TYPE: PRT
<213> ORGANISM: Actinoplanes garbadinensis

<400> SEQUENCE: 116

Met Pro Pro Arg Thr Ser Arg Gly Pro His Pro Trp Val Leu Trp Thr
1               5                   10                  15

Ala Leu Ala Ala Ala Val Ile Phe Val Tyr Pro Phe Val Trp Leu
            20                  25                  30

Val Ser Ala Ser Leu Lys Pro Arg Pro Asp Val Phe Asp Asn Arg Leu
            35                  40                  45

Leu Pro Ala Glu Trp Ala Pro Gly Asn Tyr Thr Ala Ile Trp Asp Ala
        50                  55                  60

Ala Pro Val Leu Thr Trp Met Phe Asn Ser Val Val Ala Leu Ala
65                  70                  75                  80

Ala Ala Ala Val Thr Ile Ser Ser Ala Val Val Ala Phe Gly Phe
                85                  90                  95

Ala Tyr Phe Arg Phe Pro Gly Arg Asn Val Leu Phe Ala Leu Val Val
            100                 105                 110

Gly Thr Met Met Leu Pro Gly Ala Val Thr Met Ile Pro Thr Tyr Leu
            115                 120                 125

Ile Trp Asn Glu Leu Gly Leu Ala Ala Thr Gln Val Pro Leu Trp Ala
        130                 135                 140

Gly Asn Leu Phe Gly Ser Ala Phe Tyr Ile Phe Leu Ile Arg Gln Phe
145                 150                 155                 160

Phe Leu Gly Val Pro Arg Glu Leu Phe Glu Ala Ala Arg Val Asp Gly
                165                 170                 175

Ala Gly Tyr Trp Arg Leu Phe Trp Arg Ile Ala Val Pro Leu Cys Arg
            180                 185                 190

Pro Ala Leu Ile Val Ala Phe Val Phe Glu Leu Arg Ala Ser Trp Ser
        195                 200                 205

Asp Leu Leu Lys Pro Leu Ile Tyr Leu Arg Asp Pro Ala Leu Phe Thr
210                 215                 220

Met Pro Arg Gly Met Lys Ala Ile Leu Asp Gln Phe Gly Gln Ala Gly
225                 230                 235                 240

Glu Ala Arg Trp Glu Ile Val Leu Ala Gly Ala Val Ile Thr Thr Val
                245                 250                 255

Pro Met Ile Ile Ala Phe Phe Leu Cys Gln Arg Tyr Phe Val Glu Gly
            260                 265                 270

Val Ala Thr Gln Ala Arg Lys Gly
        275                 280
```

<210> SEQ ID NO 117
<211> LENGTH: 301
<212> TYPE: PRT
<213> ORGANISM: Actinoplanes garbadinensis

<400> SEQUENCE: 117

Met Ser Ala Ala Val Arg Arg Glu Thr Leu Ala Ala Phe Gly Phe
1               5                   10                  15

Leu Ser Pro Trp Leu Ile Gly Phe Thr Val Phe Met Ala Gly Pro Met
            20                  25                  30

Val Ala Ser Leu Val Leu Ser Phe Thr Asp Tyr Asp Val Leu Thr Ser
        35                  40                  45

Thr Asp Phe Val Gly Gly Glu Asn Tyr Arg Gln Met Leu Ala Asp Pro
    50                  55                  60

Arg Val Arg Thr Ser Ile Ala Asn Thr Leu Ile Tyr Thr Ala Leu His
65                  70                  75                  80

Val Pro Val Thr Met Ile Val Ser Leu Ala Leu Ala Met Leu Leu Ala
                85                  90                  95

Arg Val Gly Arg Arg Ser Ala Gly Phe Phe Arg Thr Ile Phe Tyr Leu
            100                 105                 110

Pro Thr Ile Thr Pro Lys Val Ala Val Gly Val Leu Phe Leu Leu Leu
        115                 120                 125

Phe Asn Gly Gln Val Gly Ile Val Asn Glu Ala Leu Gly Thr Val Gly
130                 135                 140

Ile Asp Gly Pro Asn Trp Thr Val Asp Gly Pro Trp Ile Lys Pro Gly
145                 150                 155                 160

Leu Val Leu Ile Gly Ala Trp Ser Leu Gly Ser Thr Val Ile Ile Tyr
                165                 170                 175

Leu Ala Ala Leu Gln Asn Val Pro Arg Asp Leu Tyr Glu Ala Ala Glu
            180                 185                 190

Met Asp Gly Ala Ser Ala Trp Ala Arg Phe Arg Ala Val Thr Val Pro
        195                 200                 205

Met Ile Ser Gly Ala Leu Phe Phe Thr Leu Ile Ile Asn Thr Ile Ala
210                 215                 220

Ser Leu Gln Thr Phe Asp Glu Val Tyr Thr Ala Phe Tyr Gly Ser Ala
225                 230                 235                 240

Asn Gln Gln Thr Tyr Gly Asn Asp Ala Ala Leu Phe Tyr Val Val Tyr
                245                 250                 255

Leu Phe Gln Gln Ala Phe Gln Leu His Met Gly Tyr Ala Ser Ala
            260                 265                 270

Leu Ala Trp Leu Leu Phe Leu Ile Ile Val Ile Thr Val Val Gln
        275                 280                 285

Val Arg Leu Ser Arg Arg Phe Val Tyr Tyr Glu Ser Glu
290                 295                 300

<210> SEQ ID NO 118
<211> LENGTH: 445
<212> TYPE: PRT
<213> ORGANISM: Actinoplanes garbadinensis

<400> SEQUENCE: 118

Met Phe Ile Arg Ser Ile Arg Phe Val Val Gly Gly Ala Leu Val Leu
1               5                   10                  15

Thr Leu Ala Ala Gly Cys Gly Val Gly Gly Ser Asp Ser Asp Ser
            20                  25                  30

Asp Ser Asn Ala Ala Val Thr Leu Thr Met Met Gly Phe Gly Thr Gly

```
            35                  40                  45
Asp Glu Ile Ala Lys Thr Arg Phe Asp Ala Ala Asn Ala Val Ile Ala
 50                  55                  60
Pro Ser Leu Ala Lys Ala Ser Glu Gly Ser Phe Asp Ala Gln Ala Phe
 65                  70                  75                  80
Leu Ser Ala Val Ala Ser Arg Thr Pro Pro Asp Leu Val Tyr Met Glu
                     85                  90                  95
Arg Arg Leu Leu Gly Thr Tyr Ala Ala Lys Lys Ala Leu Thr Pro Leu
                100                 105                 110
Gly Asp Cys Val Glu Arg Glu Lys Ile Asp Met Ser Gln Phe Arg Glu
            115                 120                 125
Ala Ala Val Thr Glu Ala Thr Leu Asn Gly Gln Leu Tyr Gly Leu Pro
        130                 135                 140
Asp Phe Tyr Asn Asn Arg Val Leu Met Leu Asn Asp Ala Ala Phe Ala
145                 150                 155                 160
Glu Val Asn Leu Asp Pro Ala Gly Phe Asp Thr Gly Asp Trp Gln Ala
                165                 170                 175
Leu Ser Thr Ala Thr Ala Arg Leu Thr Arg Met Ser Gly Gly Lys Leu
            180                 185                 190
Gln Arg Ile Gly Phe Asp Pro Lys Leu Pro Glu Phe Leu Pro Val Trp
        195                 200                 205
Ala Arg Ala Asn Gly Ala Ala Leu Val Ser Asp Gly Arg Thr Ala
210                 215                 220
Gln Leu Asn Asn Pro Lys Val Val Glu Ala Leu Glu Tyr Ala Val Gly
225                 230                 235                 240
Leu Ile Asn Ala Gln Gly Gly Trp Ser Asn Phe Lys Ser Phe Arg Asp
                245                 250                 255
Ser Trp Asp Phe Phe Gly Ala Lys Asn Gln Phe Ala Ser Asn Gln Leu
            260                 265                 270
Gly Ala Phe Pro Met Glu Asp Phe Tyr Leu Asn Val Leu Ala Asp Asn
        275                 280                 285
Ser Pro Lys Val Lys Val Thr Val Ala Pro Phe Arg Gly Val Asp Gly
290                 295                 300
Gln Pro Ile Asp Trp Ile Thr Gly Asn Ala Trp Ala Ile Pro Ala Asn
305                 310                 315                 320
Ser Ala His Pro Gly Gln Ala Cys Lys Trp Ile Lys Thr Met Thr Ala
                325                 330                 335
Ser Glu Thr Trp Ile Ala Ala Ala Arg Ala Arg Ala Glu Leu Arg Lys
            340                 345                 350
Lys Glu Asn Lys Pro Phe Ala Gly Val Tyr Thr Gly Asn Lys Lys Ala
        355                 360                 365
Asp Glu Val Ile Phe Arg Asp Val Val Lys Pro Asp Ala Asn Val Gln
        370                 375                 380
Ile Val Leu Gln Thr Gln Glu Ser Gly Phe Ser Glu Pro Ala Leu Ala
385                 390                 395                 400
Ala Gly Glu Glu Phe Lys Ala Ala Trp Gln Asn Ala Val Asn Arg Val
                405                 410                 415
Leu Glu Gly Lys Gln Lys Pro Ala Gln Ala Met Ala Glu Ala Gln Gln
            420                 425                 430
Gln Ala Gln Ala Ala Leu Asp Lys Ala Asn Ser Gly Arg
        435                 440                 445

<210> SEQ ID NO 119
<211> LENGTH: 64
```

```
<212> TYPE: PRT
<213> ORGANISM: Actinoplanes garbadinensis

<400> SEQUENCE: 119

Met Ser Ala Leu Ala Ile Glu Lys Ser Trp Lys Asp Val Asp Leu Arg
1               5                   10                  15

Asp Gly Ala Thr Ser His Pro Ala Gly Leu Gly Phe Gly Glu Leu Thr
            20                  25                  30

Phe Glu Asp Leu Arg Glu Asp Arg Thr Ile Tyr Ala Ala Ser Ser Gly
        35                  40                  45

Trp Val Cys Thr Leu Thr Ile Glu Cys Gly Thr Val Ile Cys Ala Cys
    50                  55                  60

<210> SEQ ID NO 120
<211> LENGTH: 1053
<212> TYPE: PRT
<213> ORGANISM: Actinoplanes garbadinensis

<400> SEQUENCE: 120

Met Ser Pro Val Pro Ser Leu Asn Ser Thr Ser Val Arg Asp Ser Ala
1               5                   10                  15

Tyr Leu His Glu Arg Thr Val Thr Gly Glu Asp Gln Pro Ala Pro Ala
            20                  25                  30

Ala Gln Ala Arg Ile Ala Ser Trp Arg Asp Ser Ala Phe Leu Asp Asp
        35                  40                  45

Arg Val Leu Asp Ile Arg Leu Arg Gln Trp Gly Ile Asp Arg Ala Thr
    50                  55                  60

Phe Gly Arg Leu Leu Thr Asp Asp Phe Thr Val Pro Gly Arg Leu
65                  70                  75                  80

Leu Ala Trp Ala Asp Glu Leu Ala Thr Val Leu Ala Thr Asp Thr Thr
                85                  90                  95

Pro Val Thr Gly Leu Glu Leu Ser Thr Lys Leu Trp Ser Gln Gly Phe
            100                 105                 110

Asp Arg Leu Leu Phe Ala Gly Leu Leu His Pro Phe Leu Ala His Tyr
        115                 120                 125

Glu Gln Arg Leu His Glu Arg Val Pro Arg Pro Ile Ala Gly Ser Leu
    130                 135                 140

Arg Arg Pro Leu Leu Glu Ser Leu Ala Asn Arg Leu Leu Ala Val Ala
145                 150                 155                 160

Ala Arg Thr Leu Leu Leu Glu Leu Asn Val Ala Arg Val His Gly Arg
                165                 170                 175

Leu Thr Gly Asp Thr Pro Gln Gln Arg Tyr Asp Asp Tyr Asp Arg Arg
            180                 185                 190

Leu Leu Thr Asp Pro Ala Tyr Leu Ala Ala Leu Phe Glu Glu Tyr Pro
        195                 200                 205

Val Leu Gly Arg Cys Leu Val Glu Cys Gly Arg Arg Trp Val Asp His
    210                 215                 220

Ala Ala Glu Leu Phe Asn Arg Leu His Asp Asp Glu Pro Glu Leu Arg
225                 230                 235                 240

Ala Ala Gly Leu Leu Pro Pro Ser Ala Glu Ala Leu Arg Ser Val Arg
                245                 250                 255

Leu Asp Leu Gly Asp Pro His Asn Gly Gly Arg Ser Val Val Gln Leu
            260                 265                 270

Thr Phe Asp Asp Gly Thr Asp Leu Val Tyr Lys Pro Arg Pro Val Gly
        275                 280                 285

Ser Glu Arg Ala Tyr Ala Glu Thr Met Ala Ala Leu Ala Arg His Gly
```

```
              290                 295                 300
Leu Pro Val Pro Val Thr Ala Pro Arg Val Leu Asp Arg Gly His
305                 310                 315                 320

Gly Trp Cys Glu Phe Val Arg Pro Ala Pro Cys Ala Asp Ala Glu
                325                 330                 335

Leu Ser Arg Phe Tyr Arg Arg Ala Gly Ser Val Leu Ala Ala Met Leu
                340                 345                 350

Leu Leu Gly Gly Val Asp Met His Met Glu Asn Val Ile Ala Ala Gly
            355                 360                 365

Ser Ser Phe Thr Pro Ile Asp Leu Glu Thr Val Leu Gln Ser Gly Glu
        370                 375                 380

Leu Gly Asp Gly Ala Thr Asp Ala Tyr Gly Arg Ala Leu Asp Leu Leu
385                 390                 395                 400

Asn Arg Ser Val Leu Ala Ile Gly Ile Leu Pro Ala Arg Ala Phe Gly
                405                 410                 415

Gly Arg Gln Arg Lys Ser Val Asp Val Ser Ala Leu Gly Gly Gly Glu
                420                 425                 430

Pro Gln Thr Ala Pro Arg Pro Val Pro Arg Ile Val Asp Ala Tyr Thr
            435                 440                 445

Asp Thr Ala Arg Leu Glu Ala Val Glu Ala Thr Met Ala Gly Ala Gln
        450                 455                 460

Asn Arg Pro Ser Leu Pro Gly Ala Glu Val Arg Pro Trp Glu His Thr
465                 470                 475                 480

Ala Asp Val Val Ala Gly Phe Thr Asp Ala Tyr Asp Ile Met Leu Ala
                485                 490                 495

His Arg Ala Asp Phe Asp Arg Leu Leu Arg Gly Phe His Asp Val Glu
                500                 505                 510

Val Arg Tyr Leu Pro Arg Pro Thr Arg Arg Tyr Ser Ile Phe Leu Thr
            515                 520                 525

Glu Ser Tyr His Pro Asp Tyr Leu Arg Asp Ala Ser Asp Arg Asp Arg
        530                 535                 540

Leu Leu Asp Lys Leu Trp Thr Ala Ala Asp Ala Arg Pro Glu Leu Ile
545                 550                 555                 560

Pro Ile Ile Glu Ser Glu Lys Arg Gln Leu Leu Ala Gly Asp Ile Pro
                565                 570                 575

Cys Phe Arg Ser Val Ala Gly Ser Arg Gln Ile Arg Thr Ala Ser Gly
                580                 585                 590

Pro Leu His Pro Glu Phe Phe Thr Ala Pro Ala Val Thr Val Leu Thr
            595                 600                 605

Arg Arg Leu Gly Glu Phe Gly Pro Val His Arg Ala Ala Gln Val Arg
        610                 615                 620

Ile Ile Arg Asp Ser Met Ala Thr Met Pro Gly Pro Arg Pro Ala Ala
625                 630                 635                 640

Gln Pro Ser Pro Asp Arg Ala Ala Gly Pro Arg Pro Arg Val Thr Gly
                645                 650                 655

Ala Asp Pro Ala Thr Leu Ala Asp Arg Ile Ala Arg Arg Leu Ala Asp
                660                 665                 670

Glu Ala Ile Leu Gly Asp Arg Asp Val Ser Trp Ile Gly Val Ser Ile
            675                 680                 685

Glu Gly Val Ala Gln Glu Thr Tyr Ser Tyr Lys Pro Met Ala Thr Gly
        690                 695                 700

Leu Tyr Asp Gly Val Ala Gly Leu Ala Leu Thr Phe Ala Tyr Ala Ala
705                 710                 715                 720
```

```
Arg Thr Leu Gly Asp Asp Arg Tyr Leu Asp Leu Ala His Arg Ala Ala
            725                 730                 735

Arg Pro Val Ala Gly Tyr Leu Arg Tyr Leu Ala Glu His Arg Ile Val
            740                 745                 750

Glu Thr Val Gly Ala Tyr Ser Gly Thr Ala Gly Leu Leu Tyr Ala Leu
            755                 760                 765

Asp His Val Ala His Ala Thr Gly Asp Asp Ser Tyr Leu Asp Ala Val
            770                 775                 780

Ser Glu Ala Val Pro Trp Leu Arg Glu Cys Ala Thr Arg Glu Glu Cys
785                 790                 795                 800

Pro Asp Leu Ile Ala Gly Leu Ala Gly Cys Ala Leu Ile Ser Leu Asp
            805                 810                 815

Leu His Gly Arg His Arg Ile Asp Gly Leu Arg Glu Val Ala Ala Ile
            820                 825                 830

Cys Ala Glu Arg Leu Ala Ala Leu Ala Val Asp Val Asp Gly Ala Ala
            835                 840                 845

Gly Trp Pro Ala Thr Pro Asp Gly Pro Leu Leu Gly Gly Phe Ser His
850                 855                 860

Gly Ala Gly Ile Ala Trp Pro Leu His Arg Leu Ala Thr Glu Leu
865                 870                 875                 880

Gly Asp Pro Ser Leu Arg Glu Leu Ala Arg Arg Ala Val Gln Phe Asp
            885                 890                 895

Arg Asp Leu Tyr Val Pro Ala Ala Gly Ala Trp Arg Asp Leu Arg Pro
            900                 905                 910

Glu Met Ala Gly Thr Asp Ser Tyr Pro Ala Leu Trp Cys His Gly Ala
            915                 920                 925

Ala Gly Ile Gly Leu Ser Arg Leu Leu Ile Ala Gln His Asp Gln Asp
            930                 935                 940

Thr Arg Leu Ala Ala Glu Ala Thr Ala Leu Asp Leu Val Gly Ala
945                 950                 955                 960

His Gly Phe Gly His Asn His Ser Ile Cys His Gly Asp Phe Gly Ala
            965                 970                 975

Leu Ala Leu Phe Asp Leu Ala Ala Arg Thr Gly Phe Ala Pro Gly Arg
            980                 985                 990

His Asp Ala Ala Ala Ala Val  Thr Ala Asp Ile Ala  Ala Asn Gly
            995                 1000                1005

Ala Arg Cys Gly Leu Val Gly  Asp Ile His Met Pro  Gly Leu Met
            1010                1015                1020

Leu Gly Ala Ala Gly Ile Cys  Leu Ser Leu Leu Arg  Ile Ala His
            1025                1030                1035

Pro Ala Gln Val Pro Ala Val  Ala Trp Leu Gln Pro  Pro Leu Thr
            1040                1045                1050

<210> SEQ ID NO 121
<211> LENGTH: 341
<212> TYPE: PRT
<213> ORGANISM: Actinoplanes garbadinensis

<400> SEQUENCE: 121

Met Pro Glu Glu Ile Val Leu Ser Val Leu Asp Gln Val Pro Val Phe
1               5                   10                  15

Arg Asp Gly Ser Pro Ala Glu Ala Val Arg Asp Ala Val Ala Leu Ala
            20                  25                  30

Arg Ser Ala Glu Gln Tyr Gly Tyr His Arg Phe Trp Ile Ala Glu His
            35                  40                  45
```

His Gly Ser Ala Ala Asn Ala Cys Ala Ala Pro Glu Val Val Thr Ala
 50                  55                  60

Ala Val Ala Ala Ala Thr Ser Arg Ile Arg Val Gly Ser Gly Gly Val
 65                  70                  75                  80

Leu Leu Pro His Tyr Ser Pro Leu Lys Val Ala Glu Thr Phe Arg Val
                 85                  90                  95

Leu Ala Ala Leu Tyr Pro Gly Arg Ile Asp Leu Gly Phe Gly Arg Ala
                100                 105                 110

Pro Gly Gly Pro Pro Ala Met Ala Glu Leu Leu Asn Pro Tyr Ala Val
            115                 120                 125

Arg Thr Asp Glu Ala Phe Leu Glu Gln Ile Gly Arg Leu Leu Gly Phe
        130                 135                 140

Leu Gly Asp Thr Arg Thr Val Ser Arg Val Ser Val Thr Pro Gln Val
145                 150                 155                 160

Glu Glu Pro Pro Val Pro Trp Met Leu Gly Ala Gly Thr Gly Ser Ala
                165                 170                 175

Arg Met Ala Gly Met Leu Gly Leu Pro Phe Cys Phe Ala Gln Phe Ile
            180                 185                 190

Ala Thr Glu Glu Cys Pro Glu Ala Ile Glu Ala Tyr Arg Asp Ala Phe
        195                 200                 205

Arg Pro Ser Pro Trp Leu Glu Arg Pro Gln Pro Met Leu Ala Leu Arg
    210                 215                 220

Val Leu Cys Ala Asp Ser Asp Ala Glu Ala Glu Leu Ala Thr Cys
225                 230                 235                 240

Phe Trp Met Ser Cys Thr Thr Gly Trp Arg Ala Gln Val Gln Leu Thr
                245                 250                 255

Asp Asp Tyr Arg Gly Gly Ala Pro Asn Leu Asp Asp Ala Arg Arg Tyr
            260                 265                 270

Arg Leu Thr Ala Glu Asp Leu Ala Leu Arg Glu Ser Arg Pro Phe Leu
        275                 280                 285

Gln Ile Ser Gly Thr Pro Ala Ala Val Gly Lys Glu Ile Arg Arg Leu
    290                 295                 300

Gln Ala Val Tyr Gly Val Ser Glu Val Val Leu Thr Thr Asn Cys Pro
305                 310                 315                 320

Gly Leu Pro Ala Arg Arg Ser Tyr Glu Leu Leu Ala Gly Glu Phe
                325                 330                 335

Ala Ser Pro Ala Ala
            340

<210> SEQ ID NO 122
<211> LENGTH: 231
<212> TYPE: PRT
<213> ORGANISM: Actinoplanes garbadinensis

<400> SEQUENCE: 122

Met Arg Ser Ala Ala Arg Gly Gly Pro Ile Val Thr Asp Val Leu Val
  1               5                  10                  15

Val Asp Gly Glu Ala Leu Val Ser Ile Gly Ile Lys Met Ile Leu Glu
                 20                  25                  30

Ser Thr Gly Gly Phe Ala Val Ala Thr Thr Asp Arg Glu Asn Leu Arg
             35                  40                  45

Ser Ala Val Glu Gln His Arg Pro Ala Val Val Leu Leu Asp Gly His
         50                  55                  60

Ser Ala Gln Ser Asp Gly Leu Glu Val Leu Asp Gln Leu Arg Ala Leu
 65                  70                  75                  80

```
Ser Ser Pro Pro Ala Ile Ala Met Leu Thr Thr Leu Ala Pro Pro Glu
            85                  90                  95

Leu Val Leu Asp Ser Leu Arg Gly Gly Ala Cys Gly Phe Leu Leu Arg
            100                 105                 110

Asp Ser Gln Pro Glu Gln Leu Val Ala Ala Val Arg Ala Leu Ala Glu
            115                 120                 125

Gly Ser Ile Val Leu Ala Pro Glu Ala Ser Ser Val Val Arg Ala
            130                 135                 140

Gly Ser Arg Gly Ser Ala Ala Gly Ala Gly Ser Pro Ala Cys Glu Arg
145                 150                 155                 160

Val Lys Gln Leu Ser Asp Arg Glu Gln Ser Ile Leu Arg Leu Leu Gly
            165                 170                 175

Ala Gly Leu Thr Asn Ala Glu Ile Ser Arg Gln Leu Phe Leu Ser Ala
            180                 185                 190

Ala Thr Val Lys Glu His Val Ser Val Ile Leu Ser Lys Leu Gly Val
            195                 200                 205

Ala Asn Arg Val Gln Ala Ala Val Leu Ala Tyr Ala Ser Gly Leu Ser
            210                 215                 220

Ser Asp Asp Val Cys Leu Ser
225                 230

<210> SEQ ID NO 123
<211> LENGTH: 812
<212> TYPE: PRT
<213> ORGANISM: Actinoplanes garbadinensis

<400> SEQUENCE: 123

Met Ile Phe Ala Leu Ala Trp Ser Gln Leu Arg Ala Tyr Pro Ala Arg
1               5                   10                  15

Leu Phe Ala Ile Val Ala Ala Val Met Leu Ala Thr Gly Phe Leu Ala
            20                  25                  30

Ala Thr Ala Thr Phe Ala Ala Thr Ser Gly Glu Gly Leu Arg Arg Thr
            35                  40                  45

Ala Ala Ala Pro Leu Thr Thr Ala Asp Ile Val Leu Asp Ala Asp Asp
            50                  55                  60

Thr Val Arg Asp Pro Ala Trp Tyr Glu Ala Ala Ala Val Pro Gly
65                  70                  75                  80

Val Arg Ser Val Asp Ala Gln Tyr Ala Arg Thr Val Ser Val Phe Gly
            85                  90                  95

Gly Ser Arg Arg Gly Ser Ala Asn Val Gln Ser Ile Ala Ala Thr Pro
            100                 105                 110

Gln Val Arg Trp Phe Thr Leu Asp Arg Gly Ala Trp Pro Thr Gly Pro
            115                 120                 125

Gly Gln Leu Val Ala Asp Gln Arg Thr Leu Asp Leu Gly Ile Asp
            130                 135                 140

Val Gly Ala Thr Leu Thr Val Arg His Gly Glu Ala Ala Pro Gln Pro
145                 150                 155                 160

Val Thr Val Thr Gly Ala Ala Asp Leu Gly Phe Arg Pro Leu Thr Gly
            165                 170                 175

Ser Asp Phe Arg Phe Tyr Ala Asp Ala Ser Phe Phe Ala Gly Asp Val
            180                 185                 190

Pro Pro Ala Ala Leu Leu Thr Val Ala Asp Asp Ala Ser Leu Thr Gly
            195                 200                 205

Thr Val Asp Ala Leu Arg Arg Ser Met Gly Pro Gly Ile Ser Ala Thr
            210                 215                 220
```

```
Asp Ala Ser Ala Ala Ala Asp Gln Ala Ala Arg Phe Ala Gly Gly
225                 230                 235                 240

Asn Gly Gln Leu Val Val Ile Met Leu Ala Phe Ala Ala Val Ala Leu
            245                 250                 255

Leu Ala Ala Val Leu Val Ile Ala Asn Thr Phe His Val Ile Val
        260                 265                 270

Gln Arg Ile Arg Gln Ile Ala Leu Leu Arg Leu Val Gly Gly His Arg
    275                 280                 285

Ala Gln Val Ser Arg Val Val Leu Ala Glu Ala Ala Ile Ala Gly Thr
    290                 295                 300

Ala Gly Gly Leu Val Gly Ala Ala Gly Val Gly Leu Gly Tyr Leu
305                 310                 315                 320

Gly Ala Asp Leu Leu Asp Ile Ser Gly Gly Leu Arg Val Asn Pro
            325                 330                 335

Phe Ala Leu Ala Gly Cys Val Leu Ala Gly Val Leu Ala Thr Leu Val
            340                 345                 350

Ala Ala Trp Ala Pro Ala Arg Arg Ala Thr Arg Ile Ala Pro Val Arg
        355                 360                 365

Ala Leu Gln Ala Ala Asp Glu Pro Pro Ala Gly Thr Val Arg Gly Gly
    370                 375                 380

Arg Arg Leu Val Val Gly Thr Val Val Thr Val Val Gly Ala Ala Ala
385                 390                 395                 400

Leu Ala Val Ala Ala Ile Gly Ala Ser Leu Pro Leu Ala Leu Leu Gly
                405                 410                 415

Gly Leu Leu Leu Ala Ala Gly Leu Leu Ala Ala Leu Pro Arg Leu Ile
            420                 425                 430

Ala Leu Ser Leu Ala Pro Ala Ala Arg Leu Leu Glu Arg Phe Gly Val
        435                 440                 445

Ala Ala Gly Leu Ala Gly Thr Ser Leu Ser Gln Asn Ala Arg Arg Thr
    450                 455                 460

Ala Ser Ala Ala Met Ala Val Val Val Gly Ala Ala Leu Ile Thr Cys
465                 470                 475                 480

Leu Ala Val Ala Ala Thr Ser Gly Arg Ala Thr Val Asn Ala Asp Leu
                485                 490                 495

Glu Ala Arg Tyr Pro Val Ala Ala Gly Leu Arg Thr Asp Gly Glu Pro
            500                 505                 510

Ile Ser Gly Ala Thr Ala Gly Ala Phe Ala Ala Val Pro Gln Leu Ser
    515                 520                 525

Ala Ser Gly Thr Val Gly Thr Val Ala Ala Arg Phe Pro Asp Gly Gly
    530                 535                 540

Lys Ala Thr Pro Arg Leu Leu Ala Ala Pro Gly Asp Glu Leu Ala Ala
545                 550                 555                 560

Arg Val Ala Pro Glu Leu Ala Gly Glu Pro Val Val Leu Val Pro Ala
                565                 570                 575

Thr Tyr Leu Ala Glu Leu Gly Leu Pro Asp Ser Ala Pro Ile Val Val
            580                 585                 590

Glu Val Gly Glu Arg Arg Val Asn Leu Ile Ala Arg Ala Ser Arg Leu
        595                 600                 605

Ala Asp Thr Thr Gly Gln Leu Leu Gly Val Val Ser Ala Arg Thr Leu
    610                 615                 620

Ala Ala Asn Arg Ile Glu Ala Val Pro Thr Thr Val Trp Gly Val Ala
625                 630                 635                 640

Asp Pro Gly Phe Asp Arg Glu Ala Leu Ser Ala Ala Val Gly Ala Val
                645                 650                 655
```

```
Ala Ala Arg Asp Ala Leu Val Gln Val Gly Gly Gly Val Thr Glu Gly
            660                 665                 670

Gly Asp Ile Ala Asn Val Leu Ser Ile Leu Gly Leu Ser Leu Ala
    675                 680                 685

Met Leu Ala Val Thr Val Val Ile Ala Leu Leu Gly Ile Ala Asn Leu
690                 695                 700

Leu Gly Leu Ser Val Val Glu Arg Val Arg Glu Met Ala Leu Leu Arg
705                 710                 715                 720

Ala Leu Gly Thr Arg Arg Ala Arg Leu Arg Ala Met Leu Ala Val Glu
            725                 730                 735

Ala Val Val Ile Thr Leu Leu Gly Thr Val Ala Gly Leu Val Val Gly
            740                 745                 750

Val Pro Val Gly Leu Ala Ala Val Ala Ala Ala Val Gly Arg Thr Ala
            755                 760                 765

Asp Pro Val Ile Arg Leu Pro Trp Gly Gln Leu Ala Ala Val Leu Val
    770                 775                 780

Val Ala Val Leu Thr Gly Val Val Ala Ser Leu Ala Pro Ala Arg Arg
785                 790                 795                 800

Ala Ala Arg Val Ala Pro Ala Glu Gly Leu Thr Arg
            805                 810

<210> SEQ ID NO 124
<211> LENGTH: 244
<212> TYPE: PRT
<213> ORGANISM: Actinoplanes garbadinensis

<400> SEQUENCE: 124

Met Ile Val Trp Pro Glu Arg Arg Ala Ala Ser Arg Ser Pro Pro Ser
1               5                   10                  15

Ser Ala Arg Pro Val Ala Met Ser Ser Ala Pro Val Gly Ser Ser Ala
            20                  25                  30

Lys Thr Thr Asp Gly Leu Ala Ser Ser Ala Arg Ala Thr Ala Thr Arg
        35                  40                  45

Cys Cys Trp Pro Pro Asp Ser Ser Asp Gly Arg Cys Pro Ser Arg Ser
    50                  55                  60

Val Ile Cys Ser Glu Ser Val Ile Phe Arg Ser Ser Pro Gly Ser Thr
65                  70                  75                  80

Arg Arg Pro Ala Ser Arg Ser Gly Ser Thr Met Phe Cys Ser Ala Val
                85                  90                  95

Ser Val Gly Ser Arg Leu Asn Ala Trp Lys Thr Lys Pro Ile Arg Ser
            100                 105                 110

Arg Arg Arg Ser Val Arg Ala Arg Ser Ser Arg Pro Ala Asn Asp Arg
        115                 120                 125

Pro Ala Arg Leu Thr Val Pro Ala Val Gly Val Ser Asn Pro Ala Ser
    130                 135                 140

Arg Cys Ile Ser Val Val Phe Pro Glu Pro Asp Gly Pro Met Ile Ala
145                 150                 155                 160

Val Asn Trp Pro Ala Glu Lys Pro Ala Asp Thr Pro Ser Thr Ala Val
                165                 170                 175

Thr Ala Ala Gly Pro Val Pro Tyr Val Leu Leu Thr Ser Arg Gln Leu
            180                 185                 190

Thr Ile Ser Ala Cys Val Val Cys Val Val Thr Ala Pro Thr Leu Glu
        195                 200                 205

Ile Arg Ala Asp Arg His Ile Pro Pro Arg Asp Pro Gly Arg Ala Val
    210                 215                 220
```

Asp Arg Tyr Leu Arg Met Thr Arg Arg Tyr Arg Pro Arg Ala Pro Cys
225                 230                 235                 240

Ser Arg Asn Arg

<210> SEQ ID NO 125
<211> LENGTH: 367
<212> TYPE: PRT
<213> ORGANISM: Actinoplanes garbadinensis

<400> SEQUENCE: 125

Val Leu Arg Ile Asp Ala Leu Val Ala Ala Val Val Ile Gly Cys
1               5                   10                  15

Leu Leu Leu Gly Leu Ala Gly Leu Ser Glu Trp Tyr Trp Ser Ala Ala
                20                  25                  30

Val Ala Val Pro Leu Leu Arg Ser Ala Pro Arg Cys Phe Leu
            35              40                  45

Ala Leu Val Ala Gly Val Ser Gly Leu His Leu Ala Ser His Ser
    50                  55                  60

Phe Met Phe Pro Gly Asp Leu Val Ala Leu Val Ala Val His Ala Ala
65              70                  75                  80

Ala Ala His Ala Pro Gly Arg Ala Arg His Ala Gly Leu Leu Gly
                85                  90                  95

Ala Ala Gly Ala Leu Val Val Ala Ala Gln Ala Leu Gln Asp Gln Arg
            100                 105                 110

Leu Gly Ser Ala Leu Pro Ala Val Leu Ile Val Ala Ser Thr Met Ala
            115                 120                 125

Ala Trp Ser Ile Gly Leu Met Gln Arg Gln Gln Arg Ser Ala Val Leu
    130                 135                 140

Asp Ala Glu His Arg Arg Leu Ala Glu Gln Asp Ser Ala Met Arg
145                 150                 155                 160

Ala Gln Leu Ala Val His Glu Glu Arg Thr Arg Ile Ser Gln Glu Met
                165                 170                 175

His Asp Ile Ile Ala His Ser Leu Ala Ser Ile Ile Ala Gln Ala Glu
                180                 185                 190

Gly Gly Arg Val Ala Ala Arg Ala Asp Ala Arg Ile Ala Gly Pro Val
            195                 200                 205

Phe Asp Arg Ile Ala Gly Leu Gly Arg Gln Ala Leu Thr Asp Val Lys
210                 215                 220

Arg Leu Leu Thr Val Val Asp His Asp Glu Trp His Asp Gly
225                 230                 235                 240

Leu Glu Arg Leu Pro Val Leu Leu Ala Gly Val Thr Glu Ala Gly Leu
                245                 250                 255

Asp Val Thr Val Asp Ser Ser Gly Ala Pro Gln Pro Leu Ala Ala Gly
            260                 265                 270

Met Asp Leu Ala Val Tyr Arg Val Ile Gln Glu Ser Leu Thr Asn Val
        275                 280                 285

Leu Lys His Ala Pro Ala Arg Arg Ala Cys Leu Arg Met Arg Trp Thr
    290                 295                 300

Pro Ala Leu Leu Thr Val Thr Val Ser Ser Pro Leu Pro Gly Gly Arg
305                 310                 315                 320

Gly Ala Gly Leu Val Glu Gly Arg Gly Leu Ser Gly Ile Arg Gln Arg
                325                 330                 335

Cys Ser Leu Phe Asn Gly Asp Cys Thr Val Thr Ala Thr Glu Leu
                340                 345                 350

```
Thr Val Thr Thr Thr Trp Pro Leu Thr Pro Glu Gly Ala Arg Ala
        355                 360                 365
```

<210> SEQ ID NO 126
<211> LENGTH: 220
<212> TYPE: PRT
<213> ORGANISM: Actinoplanes garbadinensis

<400> SEQUENCE: 126

```
Met Thr Arg Pro Pro Ile Ala Val Leu Ile Ala Asp Asp Gln Glu Leu
1               5                   10                  15

Val Arg Thr Gly Phe Ala Met Val Asp Ala Ala Pro Asp Met Arg
            20                  25                  30

Val Val Ala Ile Ala Ala Ser Gly Ala Glu Ile Glu Leu Ala Ala
        35                  40                  45

Glu His Arg Pro Asp Val Ile Leu Met Asp Ile Arg Met Pro Gly Thr
    50                  55                  60

Asp Gly Ile Thr Ala Thr Ser Ala Ile Leu Ala Ala Gly Gly Glu Arg
65                  70                  75                  80

Pro Pro Lys Ile Ile Ala Leu Thr Thr Tyr Asp Ser Ser Asp Tyr Ala
                85                  90                  95

Thr Arg Ile Leu Thr Ala Gly Ala Ser Gly Tyr Leu Leu Lys Asp Ala
            100                 105                 110

Thr Ala Glu Gly Leu Thr Ala Ala Ile Arg Ser Ala Tyr His Gly Gly
        115                 120                 125

Ser Val Ile Ala Pro Thr Thr Thr Arg Asn Leu Val Ala Ala Arg Ala
    130                 135                 140

Glu Pro Pro Pro Pro Ala Arg Asp Pro Ala Pro Leu Asp Thr Phe Thr
145                 150                 155                 160

Ala Arg Glu Arg Asp Val Phe Asp Leu Ile Val Ala Gly Ala Asn Asn
                165                 170                 175

Ala Glu Ile Ala Ala Arg Leu His Leu Ala Glu Val Thr Val Lys Thr
            180                 185                 190

His Val Gly Arg Val Leu Ala Lys Leu Gly Val Arg Asp Arg Leu Asn
        195                 200                 205

Val Val Val Trp Ala Tyr Arg Asn Gly Ala Val Gly
    210                 215                 220
```

<210> SEQ ID NO 127
<211> LENGTH: 782
<212> TYPE: PRT
<213> ORGANISM: Actinoplanes garbadinensis

<400> SEQUENCE: 127

```
Met Leu Ile Cys Gly Leu Ile Ala Gly Val Val Ala Ala Ala Ala
1               5                   10                  15

Phe Pro Phe Ala Ala Met Ser Gly Leu Ala Ala Lys Ala Gly Gln Gln
            20                  25                  30

Thr Phe Ala Ser Leu Pro Ser Glu Leu Lys Ala Phe Arg Ser Pro Gln
        35                  40                  45

Ile Ser Arg Ile Tyr Ala Ala Asp Asn Arg Thr Gln Val Ala Gln Phe
    50                  55                  60

Tyr Asp Glu Phe Arg Ser Asp Val Pro Leu Lys Glu Met Ser Pro Phe
65                  70                  75                  80

Met Arg Asp Ala Met Val Ala Ala Glu Asp Arg Gln Phe Tyr Gln His
                85                  90                  95

His Gly Val Asp Leu Lys Gly Ala Ala Arg Ala Leu Val Asn Asn Arg
```

```
                    100                 105                 110
Asn Gly Gly Gln Lys Gln Gly Ala Ser Thr Ile Thr Met Gln Trp Val
            115                 120                 125
Arg Ile Ser Leu Ala Tyr Ser Ala Thr Lys Pro Gln Asp Val Ile Asp
            130                 135                 140
Ala Thr Glu Asp Ala Pro Lys Arg Lys Val Ala Glu Met Lys Tyr Ala
145                 150                 155                 160
Leu Glu Val Glu Lys Gln Leu Ser Lys Asp Gln Ile Leu Glu Arg Tyr
            165                 170                 175
Leu Asn Ile Val Pro Phe Gly Lys Gln Thr Tyr Gly Ile Tyr Ala Ala
            180                 185                 190
Ser Arg Val Tyr Phe Asn Lys Lys Pro Lys Asp Leu Thr Ile Gly Glu
            195                 200                 205
Ala Ala Leu Leu Ala Ala Ile Val Lys Ala Pro Ser Ala Tyr Asp Pro
            210                 215                 220
Thr Asp Pro Asp Gly Tyr Glu Leu Ile Arg Gln Arg Asn Ala Tyr
225                 230                 235                 240
Val Ile Pro Gly Met Val Glu Met Gly Ala Ile Thr Arg Ala Gln Ala
            245                 250                 255
Asp Ala Ala Leu Lys Glu Ala Ile Pro Arg Lys Val Arg Pro Met Ser
            260                 265                 270
Asn Gly Cys Val Ser Val Ala Lys Asn Asn Trp Gly Phe Phe Cys Asp
            275                 280                 285
Tyr Phe Tyr Arg Trp Trp Met Glu Arg Lys Glu Phe Gly Pro Thr Pro
            290                 295                 300
Tyr Asp Arg Glu Arg Arg Leu Lys Ser Gly Gly Tyr Arg Ile Thr Thr
305                 310                 315                 320
Thr Leu Asp Val Lys Ala Gln Lys Gln Ala Arg Asp Arg Ile Gly Asp
            325                 330                 335
Leu Ile Ser Glu Lys Asn Lys Asn Ala Leu Leu Leu Ala Ala Val Glu
            340                 345                 350
Pro Gly Thr Gly Lys Val Arg Met Leu Ala Ala Asn Arg Arg Tyr Lys
            355                 360                 365
Leu Asp Asp Pro Asp Asp Pro Gln Asn Ala Ile Ser Ser Asp Pro Arg
            370                 375                 380
Lys Ala Arg Lys Gly Ile Arg Gly Ser Tyr Pro Asn Thr Thr Asn Pro
385                 390                 395                 400
Leu Leu Thr Gly Gly Gly Asp Ile Thr Gly Tyr Gln Ala Gly Ser Val
            405                 410                 415
Met Lys Met Phe Thr Ile Val Ala Ala Leu Glu Gln Gly Tyr Pro Leu
            420                 425                 430
Ala Tyr Thr Ile Arg Thr Gln Ser Arg Tyr Arg Ser Arg Tyr Ile Ile
            435                 440                 445
Glu Ser Ser Asn Asp Ala Ala Cys Pro Gly Thr His Phe Trp Cys Pro
            450                 455                 460
Ser Asn Ala Gly Gly Gly Gly Glu Gly Val Phe Asn Met Trp Thr Gly
465                 470                 475                 480
Leu Gly Arg Ser Ile Asn Thr Tyr Phe Val Pro Leu Glu Glu Arg Val
            485                 490                 495
Gly Ala Glu Lys Val Val Ser Ala Ala Lys Arg Phe Gly Ile Gln Phe
            500                 505                 510
Arg Glu Pro Asp Asp Ala Leu Leu Ala Glu Pro Gly Asn Ala His Gln
            515                 520                 525
```

```
Trp Gly Ala Phe Thr Leu Gly Val Ser Ala Thr Thr Pro Leu Asp Met
            530                 535                 540

Ala Asn Ala Tyr Ala Thr Leu Ala Ala Asp Gly Met Tyr Cys Pro Pro
545                 550                 555                 560

Thr Pro Ile Glu Arg Ile Ala Thr Arg Asp Gly Asp Gln Leu Asp Val
                565                 570                 575

Gly Arg Ser Pro Cys Val Arg Ala Thr Ala Lys Asp Val Ala Arg Ala
            580                 585                 590

Ala Leu Asp Ala Ala Arg Cys Pro Val Gly Asp Ser Ala Gln Leu Gly
            595                 600                 605

Arg Cys Gly Gly Ser Thr Ala Gly Ile Thr Arg Ser Val Val Gly His
610                 615                 620

Pro Val Phe Gly Lys Thr Gly Thr Thr Asp Arg Asp Arg Thr Ala Ser
625                 630                 635                 640

Leu Ile Ala Gly Thr Thr Ala Leu Val Val Ala Gly Tyr Leu Val Asn
                645                 650                 655

Pro Asp Tyr Gln Asn His Arg Asp Arg Leu Asp His Asp Gln Val Asn
                660                 665                 670

Pro Ala Val Tyr Arg Thr Leu Ala Asp Tyr Met Glu Gly Arg Pro Arg
                675                 680                 685

Glu Ser Phe Lys Arg Pro Ser Ser Gly Arg Ile Ala Phe Gly Asp Gln
            690                 695                 700

Arg Ser Ile Pro Asp Val Glu Cys Asp Pro Met Pro Arg Ala Arg Asp
705                 710                 715                 720

Arg Leu Glu Asp Ala Gly Phe Asp Val Trp Arg Gly Gln Glu Val Glu
                725                 730                 735

Ser Asp Cys Pro Ala Gly Thr Ala Gly Thr Glu Pro Ser Gly Arg
            740                 745                 750

Thr Val Lys Asn Gly Val Val Val Ile Gln Val Ser Lys Gly Arg Arg
            755                 760                 765

Gly Ala Ser Pro Pro Ile Phe Pro Pro Ile Gly Pro Pro Arg
            770                 775                 780
```

<210> SEQ ID NO 128
<211> LENGTH: 253
<212> TYPE: PRT
<213> ORGANISM: Actinoplanes garbadinensis

<400> SEQUENCE: 128

```
Met Ala Pro Leu Thr Arg Ser Leu Arg Tyr Tyr Tyr Gly Asp Ala Gly
1               5                   10                  15

Arg Glu Ala Ala Met Asp Ala Met Tyr Arg Arg Phe Val Arg Pro Gly
            20                  25                  30

Asp Val Val Phe Asp Ile Gly Ala His Val Gly Asp Arg Val Ala Cys
        35                  40                  45

Phe Arg Arg Leu Gly Ala Arg Val Val Ala Val Glu Pro Gln Pro Leu
    50                  55                  60

Cys Met Arg Ala Leu Arg Ala Leu Tyr Ala His Asp Asp Arg Val Ala
65                  70                  75                  80

Leu Val Glu Ala Ala Cys Gly Pro Ala Gly Gly Ser Val Pro Leu Tyr
                85                  90                  95

Ile Asn Ser Ala Asn Pro Thr Val Ser Thr Asn Ser Val Arg Phe Leu
            100                 105                 110

Thr Ala Ala Thr Gly Ser Arg Gly Trp Glu Asn Glu Val Trp Asp Gln
        115                 120                 125
```

```
Gln Ile Thr Val Pro Ala Val Thr Leu Asp Thr Leu Val Gln Arg Phe
        130                 135                 140

Gly Leu Pro Ala Phe Ile Lys Ile Asp Val Glu Gly Tyr Glu Asp Ala
145                 150                 155                 160

Val Leu Ala Gly Leu Ser Arg Gly Val Arg Ala Leu Ser Phe Glu Phe
                165                 170                 175

Thr Thr Ile Ala Arg Asp Val Ala Arg Arg Cys Leu Asp Arg Ala Gly
                180                 185                 190

Glu Leu Gly Phe Asp Gly Phe Asp Val Ser Leu Gly Glu Thr Met Ala
            195                 200                 205

Arg Thr Phe Gly Arg Trp Ala Arg Asp Glu Met Leu Ala His Leu
        210                 215                 220

Ala Gly Leu Pro His Glu Ala Asn Ala Gly Asp Val Tyr Ala Val Ser
225                 230                 235                 240

Arg Ser Ala Gly Trp Pro Asp Arg Arg Glu Asp Arg Arg
                245                 250

<210> SEQ ID NO 129
<211> LENGTH: 261
<212> TYPE: PRT
<213> ORGANISM: Actinoplanes garbadinensis

<400> SEQUENCE: 129

Val Pro Arg Phe Asp Ser Arg Leu Val Thr Val Gly Gly Val Arg Thr
1               5                   10                  15

His Asp Arg His Ala Cys His Ala Gly Gly Leu Pro Val Leu Val
            20                  25                  30

His Gly Leu Ala Val Ser His Arg Tyr Leu Met Pro Thr Ala His Ala
            35                  40                  45

Leu Ala Gly Arg His Pro Val Leu Val Pro Asp Leu Pro Gly Phe Gly
    50                  55                  60

Phe Ser Asp Lys Pro Arg Arg Ala Tyr Asp Val Gly Arg His Ala Glu
65                  70                  75                  80

His Leu Ala Ala Trp Leu Asp Val Leu Gly Val Pro Arg Ala Cys Ile
                85                  90                  95

Ala Gly His Ser Phe Gly Ala Glu Val Ala Ala Arg Leu Ala Val Leu
            100                 105                 110

Arg Pro Asp Leu Val Ala Ala Val Leu Ala Ser Pro Thr Thr Asp
        115                 120                 125

Pro Ala Ala Arg Ser Arg Arg Ala Leu Ile Gly Arg Trp Ala Val Asp
        130                 135                 140

Leu Trp Ile Glu Ala Pro Trp Gln Ala Pro Val Leu Val Arg Asp Ile
145                 150                 155                 160

Ala Asp Ala Lys Pro Trp Arg Val Leu Ala Thr Val Gly His Ser Val
                165                 170                 175

Arg Asn Ala Ile Glu Glu Asp Leu Arg Arg Leu Pro Val Pro Pro Leu
            180                 185                 190

Val Leu Gly Gly Ser Leu Asp Pro Val Ala Pro Leu Arg Trp Arg Ala
        195                 200                 205

Glu Val Ala Ala Met Thr Gly Gly Val Ser Val Thr Val Pro Ala Ala
    210                 215                 220

Ala His Asn Val Met Thr Thr Ser Gly Val Arg Ser Ala Arg Ala Ile
225                 230                 235                 240

Ala Ala Tyr Leu Arg Thr Arg Arg Cys Met Asp Arg Leu Ile Gly
                245                 250                 255
```

```
Gly Met Pro Pro Pro
            260

<210> SEQ ID NO 130
<211> LENGTH: 244
<212> TYPE: PRT
<213> ORGANISM: Actinoplanes garbadinensis

<400> SEQUENCE: 130

Val Ser Pro Pro Phe Arg Leu Asp Glu Ala Val Ala Asp Val Tyr Gly
1               5                   10                  15

Asp Leu Arg Leu Ala Pro Val Leu Arg Arg Leu Leu Arg His Ser Gly
            20                  25                  30

Arg Leu Thr Gly Ser Val Ala Gly Ser Val Ser Leu Ile Asp Ala Asp
        35                  40                  45

Arg Gly Cys Tyr Val Lys Ala Ala Glu Tyr Gly Ala Asn Cys Gln Leu
    50                  55                  60

Gly Arg Ser Phe Pro Leu Asp Glu Gly Ala Thr Gly Arg Ala Phe Gly
65                  70                  75                  80

Ser Arg Arg Pro Val Val Ile Pro Asp Tyr Gly Gln Leu Arg Ala Gly
                85                  90                  95

His Leu Ala Ala Ala His Pro Ala Arg Lys Gly Pro Ala Val Ala Val
            100                 105                 110

Pro Ile Trp Trp Arg Gly Asp Val Ile Ala Val Asn Val Ala Phe Ala
        115                 120                 125

Pro Ala Phe Ser Leu Gly Gly Val Asp Glu Leu Glu Ala Leu Thr Gln
    130                 135                 140

Ser Ala Ala Ala Ile Val Arg Ser Arg Gly Val Arg Val Arg Ala
145                 150                 155                 160

Asp Pro Pro Tyr Ala Ala Pro Ala Ala Pro Phe Thr Pro Arg Glu Ala
                165                 170                 175

Glu Val Leu Asp Leu Leu Arg Gln Gly Leu Thr Asp Arg Glu Met Ala
            180                 185                 190

Arg Arg Leu Gly Leu Ser Ala Lys Thr Val Glu Lys His Val Gly Ala
        195                 200                 205

Ile Arg Arg Lys Thr Gly Thr Ser Asn Arg Thr Ala Ala Val Val Thr
    210                 215                 220

Ala Leu Asp Asn Asp Trp Val Gly Asn Leu Pro His Thr Ala Glu His
225                 230                 235                 240

Thr Thr Gly Ser

<210> SEQ ID NO 131
<211> LENGTH: 281
<212> TYPE: PRT
<213> ORGANISM: Actinoplanes garbadinensis

<400> SEQUENCE: 131

Met Lys Asp Ile Leu Asp Arg Ala Leu Ala Glu Arg Tyr Gly Val Ala
1               5                   10                  15

Ala Phe Asn Ile Val Asn Asp Leu Thr Val Glu Ala Val Leu Ala Ala
            20                  25                  30

Ala Ala Glu Glu Arg Ala Pro Val Ile Leu Gln Thr Ser Val Lys Thr
        35                  40                  45

Val Arg Met Tyr Gly Arg Pro Arg Leu Tyr Glu Ile Val His Ala Phe
    50                  55                  60

Ala His Asp Ala Pro Val Pro Val Thr Leu His Leu Asp His Cys Pro
65                  70                  75                  80
```

Glu Arg Ser Val Ile Ser Asp Cys Leu Ala Gly Gly Trp Asn Ser Val
            85                  90                  95

Leu Phe Asp Ala His Glu Leu Asp Val Ala Asp Asn Leu Arg Gln Thr
            100                 105                 110

Thr Glu Val Val Ala Glu Ala Arg Arg Ala Gly Ala His Val Glu Gly
            115                 120                 125

Glu Ile Glu Gly Ile Gln Gly Val Glu Asp Val Gly Asn Asp Tyr
130                 135                 140

Ala Pro Met Val Gln Ser Leu Glu Val Ala Val Asp Phe Ile Lys Arg
145                 150                 155                 160

Thr Gly Val Asp Cys Phe Ala Pro Ala Ile Gly Asn Ala His Gly Gln
                    165                 170                 175

Tyr Lys Gln Ala Pro Val Leu Asn Thr Arg Arg Val Ser Asp Leu Val
                    180                 185                 190

Ala Ala Thr Gly Ile Pro Met Ala Leu His Gly Gly Thr Gly Leu Ser
                    195                 200                 205

Asp Glu Gln Phe Thr Asp Leu Ile Ala Arg Gly Cys Ala Lys Val Asn
210                 215                 220

Ile Ser Thr Ala Leu Lys Glu Ser Phe Met Lys Ser Gly Leu Glu Phe
225                 230                 235                 240

Leu Arg Glu Ala Asp Glu Arg Gly Lys Trp Asp Pro Pro Ser Leu Phe
                    245                 250                 255

Arg His Gln Arg Ala Ala Val Val Glu Met Ala Arg Gln His Ile Arg
                    260                 265                 270

Leu Phe Gly Gly Ser Gly Arg Ala Trp
                    275                 280

<210> SEQ ID NO 132
<211> LENGTH: 192
<212> TYPE: PRT
<213> ORGANISM: Actinoplanes garbadinensis

<400> SEQUENCE: 132

Met Gly Ser Ala Val Ala Val Pro Ala Ser Ala Gly Gly Gly Arg Arg
1               5                   10                  15

Asp Gly Pro Ala Ala His Pro Ala Leu Arg Arg Ile Gly Ala Arg Val
                20                  25                  30

Val Asn Ala Leu Val Phe Asp Cys Asp Gly Val Leu Ala Asp Thr Glu
            35                  40                  45

Arg His Gly His Leu Pro Ala Phe Asn Ala Thr Phe Glu Gln Phe Gly
        50                  55                  60

Leu Pro Val Arg Trp Ser Glu Glu Tyr Gly Glu Lys Leu Arg Ile
65                  70                  75                  80

Gly Gly Gly Lys Glu Arg Met Ala Ser Leu Phe Ala Asp Pro Ala Phe
                85                  90                  95

Ala Ala Ala Ala Gly Asp Thr Asp Arg Thr Glu Leu Leu Arg Thr Trp
                100                 105                 110

His Arg Ala Lys Thr Ala Ala Phe Thr Lys Leu Val Ala Glu Gly Arg
            115                 120                 125

Ile Pro Ala Arg Pro Gly Thr Ala Arg Ile Ile Ser Glu Ala Leu Arg
        130                 135                 140

Ala Gly Trp Thr Val Ala Val Ala Ser Thr Ser Ala Glu Asp Ser Val
145                 150                 155                 160

Arg Ala Val Leu Val Asn Ala Val Gly Ala Thr Thr Ala Glu Arg Ile
                165                 170                 175

```
Pro Val Phe Ala Gly Asp Val Val Pro Ala Lys Lys Pro Asp Pro Ala
        180                 185                 190
```

<210> SEQ ID NO 133

<400> SEQUENCE: 133

000

<210> SEQ ID NO 134

<400> SEQUENCE: 134

000

<210> SEQ ID NO 135

<400> SEQUENCE: 135

000

<210> SEQ ID NO 136

<400> SEQUENCE: 136

000

<210> SEQ ID NO 137

<400> SEQUENCE: 137

000

<210> SEQ ID NO 138

<400> SEQUENCE: 138

000

<210> SEQ ID NO 139

<400> SEQUENCE: 139

000

<210> SEQ ID NO 140

<400> SEQUENCE: 140

000

<210> SEQ ID NO 141

<400> SEQUENCE: 141

000

<210> SEQ ID NO 142

<400> SEQUENCE: 142

000

<210> SEQ ID NO 143

<400> SEQUENCE: 143

000

<210> SEQ ID NO 144

<400> SEQUENCE: 144

000

<210> SEQ ID NO 145

<400> SEQUENCE: 145

000

<210> SEQ ID NO 146

<400> SEQUENCE: 146

000

<210> SEQ ID NO 147

<400> SEQUENCE: 147

000

<210> SEQ ID NO 148

<400> SEQUENCE: 148

000

<210> SEQ ID NO 149

<400> SEQUENCE: 149

000

<210> SEQ ID NO 150

<400> SEQUENCE: 150

000

<210> SEQ ID NO 151

<400> SEQUENCE: 151

000

<210> SEQ ID NO 152

<400> SEQUENCE: 152

000

<210> SEQ ID NO 153

<400> SEQUENCE: 153

000

<210> SEQ ID NO 154

<400> SEQUENCE: 154

000

<210> SEQ ID NO 155

<400> SEQUENCE: 155

000

<210> SEQ ID NO 156

<400> SEQUENCE: 156

000

<210> SEQ ID NO 157

<400> SEQUENCE: 157

000

<210> SEQ ID NO 158

<400> SEQUENCE: 158

000

<210> SEQ ID NO 159

<400> SEQUENCE: 159

000

<210> SEQ ID NO 160

<400> SEQUENCE: 160

000

<210> SEQ ID NO 161

<400> SEQUENCE: 161

000

<210> SEQ ID NO 162

<400> SEQUENCE: 162

000

<210> SEQ ID NO 163

<400> SEQUENCE: 163

000

<210> SEQ ID NO 164

<400> SEQUENCE: 164

000

<210> SEQ ID NO 165

<400> SEQUENCE: 165

000

<210> SEQ ID NO 166

<400> SEQUENCE: 166

000

<210> SEQ ID NO 167

<400> SEQUENCE: 167

000

<210> SEQ ID NO 168

<400> SEQUENCE: 168

000

<210> SEQ ID NO 169

<400> SEQUENCE: 169

000

<210> SEQ ID NO 170

<400> SEQUENCE: 170

000

<210> SEQ ID NO 171

<400> SEQUENCE: 171

000

<210> SEQ ID NO 172

<400> SEQUENCE: 172

000

<210> SEQ ID NO 173

<400> SEQUENCE: 173

000

<210> SEQ ID NO 174

<400> SEQUENCE: 174

000

<210> SEQ ID NO 175

<400> SEQUENCE: 175

000

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190

<400> SEQUENCE: 190

000

<210> SEQ ID NO 191

<400> SEQUENCE: 191

000

<210> SEQ ID NO 192

<400> SEQUENCE: 192

000

<210> SEQ ID NO 193

<400> SEQUENCE: 193

000

<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000

<210> SEQ ID NO 198

<400> SEQUENCE: 198

000

<210> SEQ ID NO 199

<400> SEQUENCE: 199

000

<210> SEQ ID NO 200
<211> LENGTH: 40402
<212> TYPE: DNA
<213> ORGANISM: Actinoplanes liguriae

<400> SEQUENCE: 200

```
gatcaggtcg accgcggagc tgatctggtc acggatcgcg cggatcggca ggtccatgcc      60
ggccatcagc accatcgtct ccagccggga cagcgcgtcc cgcggcgtgt tcgcgtgcag     120
ggtggtcagc gagccgtcgt ggccggtgtt catcgcctgc agcatgtcga gcgcggcggc     180
gtcacggacc tcgccgacga cgatccggtc cgggcgcatc cgcagcgcgt tgcggaccag     240
gtcgcgggtg gtgatcgtgc cccggccctc ggagttcggc ggccgggact ccaggcgcac     300
cacgtggtcc tggaccagtt gcagctcggc ggcgtcctcg atggtcacga tgcgctcgtc     360
ggccgggacg aagctggaga ggacgttcag gatcgtggtc ttgccggagc cggtgccgcc     420
gctgaccagg atggtgcgcc ggccgcgcac gcacgcgtcc aggaactcgg cggcctgccg     480
ggtgagcgtg ccgtactgca gcaggtcacc gacggtgagc gggaccgcgg cgaacttgcg     540
gatggtcagc gtcgagccgt ccagcgcgat cggcgggacc acggcgttga cccggctccc     600
gtccggcagc cgggcgtcga cggtcgggct ggcctcgtcc acgcggcggc cgacccgcga     660
gcagatccgg tcgatgatcc ggcgcaggtg ctgctcgtcg tcgaactcgg cggcgacctt     720
ctcgaggcgg ccgaaccgct cgacgtagac cgagtacggc ccgttcacca tcacctcggt     780
caccgacggg tcgcgcagca gcgactcgat cggtccgtgg ccgagcacct cgtcggtcac     840
ctcgcgggtg atccgggccc ggtccgcgcc ggagagcggg gtctcctccc gggcgagcag     900
gtcgtggagc gcgtcccgga cccgggcgtc caggtcctcg ctctggccgg tggtgtagag     960
cgtcggcccg agctcgtcgg cgagccgccg ctggatccgc agccgcacct cgccgacctg    1020
gtcctgcggc gggcggccgg cggcccggta gcggtcgccg ccgcgtggct cggtgggcgg    1080
tggtgggggc gtgccggcgc cgctcaggcg gctggagagg ctcacgggaa caacctcccg    1140
aggaacccgc ggcgccgctg gggtgtggtg ccgacgccgg cgatccggtc accgagctcc    1200
cggatcgccc ggctgaccgg gtgcagcggg tcggtgacgg cgatcggctc gccgtggttg    1260
accgagaccg tcacgtcccg gctggccggc acctgcaccg cgaacggcat gccggccgcg    1320
acctccacct cggacgggct caggccgacc tgggcgccgg cccggttgaa gaccagcagc    1380
cgcttgtcct tggggtagtc gagcaggtcg aacatctccg cggtgagccg gaccgacttg    1440
agcgccggaa gatccggggt gacgatcggg atgaaccagt cggacatgtc cagcgcggcc    1500
agcacctggt cggtgaccac ggacggggtg tccaccacga tgaagtcgta gagcgggcgg    1560
gccacgtcca gcagctcgac gacgaactcc cggcggacct gctcgccctc ggccgggctg    1620
gccggcgcca ggagggcgtc gagactttgc cggtacgtcg tgacgatcga ccgcagcccg    1680
ggctcgtcca gccgaccggc catctgcagg cccccggcga tgttgcgttc cggggacagc    1740
ttcatcatga tcgccacgtc gccgaactgc aggtccaggt ccatcagcag cacccggcgt    1800
ccggcaccgg ccagcgcgac ggccaggttc accgccacca cgctgcgccc gcagccgccc    1860
ttgccggcga agaccgtgac cacactggcg tacgggcgt tgtcgccggt cccgcgcatg    1920
gtggtgctca gcgccttgga caggtcgacc gaccggaccg tcgcgctgcg gatgccctcc    1980
tcgtcctcct cggcgaccag gtccggatc ccggactgca ggcagcgcag caccacgccg    2040
gcctcgatcg cgtggcggat cagcaccacc ccgatcaccg ggcgctgcaa ccgctggtac    2100
gccgtgaaca tcagcgcctc gtccaggtcc acgaccgcgc cgatcaccac gagcagcgtc    2160
tccgggtagc gggggagata cgactccagc tcgctcatgt tcttgagcat cgtgccgccg    2220
atcgcccgga agtcgttgcc ccagtgcgtg cggcgctcgt cgtcgggctc gacgtacaca    2280
tagaggctca tcgcacgacc cagctcgtgt cgatcgccgg gccggtgctc gcggtggcgt    2340
tcgggccgag cagcgccagg tagagcgatc cgctctgggc ggcgtgcacg agtcgcaggg    2400
```

```
cgtcggtgtc gccgacggcc agggtcacga cgtaccgctg gatctccttg accgcggcgg    2460
tgctgtcgcc ggccgaggcg gacggaccgg gggtgggcga gggcgacggc gtcacggggg    2520
cctgacccgg ttccgcctcc ccgatggtga tcacccgtgc cttcggcagc aggagctcgg    2580
tcatcgggat ggtctcgtgg tcctccgcca tcaggacctt cgcctggtac gtgtaataga    2640
ccgcgacctg gtcgccgggc gtgatgttgc cggctacctg cggggcgacg ttgagcgcca    2700
ccgagaccgc gagcgaccta cggggcaccg ggatccgccc ggtgtgcgac ggcgccggtg    2760
acgccgggac gaacagcgtc cgcatgagga gctgccgggg ctgcaggtcc ccgccgagcc    2820
ggagcgggtc gagcgcgctg tcccaggtgg tcagcgcccc ggcgggcacg gtgacggtgg    2880
ggaccaggag ccgctcggtc aggccccggg cgcggatctc ggcgccgctg gtcccggacg    2940
ggatgtgctg cccggcgacc aggatccagg tgccctcccg gccgctgagc gcgcgccggt    3000
cggccgaccg ggcgtaggac aggacggccg ccccgctgat cccggccagc accagcgcgg    3060
ccagcaggat caggatgcgg cggcgcatga cttcaccttc tcaggcaccg gtcatcccgt    3120
acggccgatc accatcgcgc cgtaataccg cgaggtggcg aaccgcgtcg gtacgtggtc    3180
cgtgaccagc gctctggtga agtagccgta gaggcaggac tgcgccgcgc acagcgctct    3240
ctgcgccccc ggcacgagcg aggggaccgc ggatccgggt gacaccgggc cgctgaccgg    3300
gctctcgtag ccggtgagga cgagcggcgc gaagccggcg atccggtagt acgacggcag    3360
cgtgccgatc accgccacct gcctgtcgaa gatcggcacc agcaccggct gccccgaggt    3420
gatcaggacg ttcagccggt cgaggcaggc cgtggcggcg gaggcgttgc cggggccgat    3480
ggtgaatccg ccgacccagc tgtccgccgg cccgtcggtc gccgggatgc cggtcagctc    3540
gcaggaggcg tccggtgcgc tgaccggcag caggcccggc agcgccggcg ggccgtccgg    3600
ctgcccgagc cacgtgtaac cggcgacggt ctcgccggcg tcggccgggc aggacgtggc    3660
gaggatgccg tcgctgatcg ggatgtagcc ggccgtcggg tcggagaggc cgagcagcgg    3720
gtggacgccg gtctgcgggt tcgggccggt gggcggcggc ggggcgaaga acctcgtgta    3780
gtcgccggtc agccgcagga agtcgcaccg ggagacgccg agcgcgagga cgtcggtgac    3840
cgccggagct ccccaggcga cccggccgca ggcgcccatc ttcgcccgt ggtacgccga    3900 cccggccaga ccgcgcccga acagcggcgg caccaccgag gtgttgtcgc gtttgcgggt    3960
ggacgtccgg acctcgacgt accggtacgg cccggaggcg ctcggcggcg cggggcacgt    4020
gaccggggtg ttccaggagc tcgggcagcc ggcgtcggcg gtggtgacgc cggcggcgga    4080
gacggtggtg atgcagaact ggacgtccga gacgaggtcc ttggcgttcc ggtcggcgta    4140
ccgctgcgcg ttgtcccgct gcgcggcgac ggtgcaggtg gcggacgtca ggtcccggcc    4200
ggccgtgccg gcgcaggcct gcgcgacctt ccacgacgcc gcgtcggccc cgctctgcaa    4260
ctgctcccgc tcggcgtaga gcgcgccgat gtcgatcacc agcgccgcca tcccgagcag    4320
gacgccggcg ccggccagga cggcgaccag cgcggtgatc acgccgtgct cgccgcgggg    4380
cgggaacagg gcgtggatca gccgacgcat gacatcacgc cggtcgcgct catcgtgatc    4440
gtgcccatgg tctgccgcc gaccagcctg accagcgcca ccatcggcgt gatcggctgg    4500
taccggcggg tcagcacgac ctcgcgtcg gcgccggcga gcgaggtggc cgaacaggtc    4560
gtgacggtct gggtcaccga cggcgccccg gtggcgccga cgatgccgtt gaccttggcg    4620
tgcaccgccg cggccgtgcc gttcagggcg ccgagccggg cgccctcccg ggccgcctcg    4680
gtgagctgga tgtactgctg gagcagccgg cccatgtcga tgatcccgaa caggatcagc    4740
agcagcaccg gcatcacgat ggcggtctcc agcgccgcgg cgccccggtc ccggttatcg    4800
```

```
tgcggagctc tccgctccct gggcgagaac cgtacgcaac atcccggcca gccggtccgc    4860
cgtatacggc ttcgccacga atggcgaccc ggcacggatc agccctttct tgatggcgat    4920
ctcctccggg accccggaga cgtagacgat cttcatgccc ggccggacct cggaggccga    4980
gcgggccagc tccccgccgg agactcccgg caggcccagg tcggtgagca gcacgtcgat    5040
cgctccgctg tgcacccggc acgtcatgat ggcgctgacc gggtcttccg ccacgaggac    5100
gacgaacccg cgcatctcca gcatctgtgc ggcgagctca cgcaggtcct cgtcgtcctc    5160
caccaggaga acgaccggcc cctgccgctc ggttgctttc cacatcattc ctctcccggt    5220
gcacgaggaa tccggcgacg actcttcccg tcgctgcctc tgctcacgct atccaccggc    5280
ctgcctggcc cggtggcatt cgcggaaatg tcgatgccct caaatcagca tttgtccggc    5340
ggcactgtcc gtgttaacgc tcactacgtt gcgctgacgt cacgtttcgt cccggtaaca    5400
gttcggggtc ttgacagatc acgagcgtcg atgggtgaat gtgttcaatc ctgatcggac    5460
gagtgcagga taaacaacgt ttgcgtgtga agccgtttgg ctttgagggg gctccatgtt    5520
caattacgtc agtttcgtgc gccctaaaac ctttgccgcc accttcgcgg cagccgccct    5580
gctgctcggc tcgggcgcct gcgcgaagag cgaggactcc ggggacaccg tggcggcggg    5640
tcccgccccg tcggcggcgc aggtggtcca gtccgcctcg gccggctccg cgacctgtgc    5700
cttggatcag tacggcgcgt ccaagctcga cctgaagacc gcctccgtcg gcttctccca    5760
gtcggagaag gaggcgaacc cgttccggat cgccgagacg aagtccatca aggacgaggc    5820
cgcgaagctg ggcatcacca acctcaagac ctcgaacgcg aactcacaat tcaacaagca    5880
gatcgccgac gtcgagcaga tgatcgatgc gggcgtgcag ctgctggtga tcgcgccgct    5940
caactcggac ggctgggact cggtgttcgc caaggcgacg gcgaagcaca tcccgatcat    6000
cacgatcgac cggaagatca acgcgaccgc ctgcaaggac tacctgacct tcatcggctc    6060
cgacttcgcc gagcagggca gcggggccgc cgacgcgctg gccaagtcgc tgggcaacaa    6120
gggcgaggtg gcgatcctgc tgggcgctcc cggcaacaac gtcaccacgc tgcggaccag    6180
cggcttcaag gacgagatcg ccaaggtcgc gccggacatc aagatcacgt tcgagcagac    6240
cggcaacttc tcccgggagg acgggcagaa ggtcgccgag cagctgctgc agtccaagcc    6300
gaacatcaac ggcatctacg gcgagaacga cgagatggcg ctcggcgcga tcaccgcgct    6360
caagggcgcc ggcaagaagg ccggcgacgt caagatcgtc tcgatcgacg gcaccaaggg    6420
cgcggtgcag ggcatcgtgg acggctgggt ctccgcggtg atcgagtcca cccgcgctt    6480 cgggccgctg gccttcgaca ccgcgacgaa gttcttcggc ggcgagccgg tcggccagga    6540
catcgtcatc caggaccgtg cctacgacga gtcgaacgcc aagaccgaca tcggcagcgc    6600
gtactagaga gcgctcccaa tcgggtgtcc ggggatgaac cgggcacccg ccggcacgga    6660
ggagggcggc tcatgctgct ggaagtctcc ggcgtctcca agaccttccc cggcgtacgc    6720
gccctggacg gggtgtcctt caccctgaac ccggcgagg tgcacgcgct ggtggggag    6780 aacggcgccg gcaagtcgac gttgatcaaa gtgctcaccg gggtctacca gccggacagt    6840
ggcgagctgc gctaccgcgg cgagccggcc cggttcgcca ccccgctgga cgcccagcgg    6900
gccggtatct cgaccatcta tcaggaggtc aacctcgtcc cgctgatgag cgtggcgcac    6960
aacctgttcc tcgccgggga gccgcgcaac cggttcgggc tgctgacga ggcccggatg    7020 gtcgccgagg ccaccgagat cctggccggt tacggcgtac gcaccgatgt ccgccgccgc    7080
ctcggcaccc tggccctggg cgcgcagcag atggtcgcgc tcgcccgggc cgtcatggtc    7140
gacgcccggg tcgtggtgat ggacgagccc acctcgtcgc tggagccgcg cgaggtggag    7200
```

```
accctgttcg gggtgatccg cgagctgcac accgcgggca tcggcatcgt ctacgtctcg    7260
caccggctgg acgagctcta ccgggtgtgc gacgcggtca cgatcctgcg cgacggcaag    7320
ctcgtgcaca ccggccggat ggccgatctc gaccggcgca cgctggtctc gctgatgctc    7380
ggccgcgagt tcggggcgga cttcaccagc ttctccgagt caccgcagag caccccggag    7440
ggcgagccgg tcctgcgggt gtccggcctg accagccgcc cccggctcga cgacatcagc    7500
ttcgacgtgc gccccggcga ggtggtcggc ctgggcggcc tgctcggcgc cggccgcagc    7560
gagacgatca aggcgatcgg cggggcgtac ccgatcgact ccggcgtgat cgaggtcggc    7620
ggcgtccggc tcggcaggcc cagcacggta cgggcggtcc gcgcgggcgt ggccacccag    7680
ccggaggacc gcaaggccga ggggatcgtc cccggcctgt cgatccggga caacatcgcg    7740
ctcgcgatcc tgccgcggat ggcccgtttc ggactggtca gcgacaagcg gatcgacagc    7800
atcgtcgcca cgtacatgag ccggctgcgg atcaaggcgt ccggtccgga ccaggcggtc    7860
ggcgatctct ccggtggcaa ccagcagaag gtgctgctcg cgcggctgct cgccaccggc    7920
ccgaaggtgc tgctgctcga cgagccgacc cggggcatcg atgtcggcgc caaggccgag    7980
gtgcaggcgc tgatcgacga gctggcgaag gaggggctcg gtgtcgtgct ggtctcctcg    8040
gacgccgagg aactggtcga gggcgcggac cgggtggtgg tgctgcgcga cggcgcggtc    8100
gtcggcaccc tcaccggcga ccgggtgacc accgaggccc tgatggccac gatcgcggag    8160
gccgcggatg agcactgaga ccctgacccg cccgcggatg acgttcaacc cggcgtgggc    8220
ggcacgctac ggcgtctacg cggcgatcgt tctgctgatc gtcgtcaaca tcgccttcac    8280
gccgtacttc ctgacccctga gcaatctgcg gatccagctg atccaggcgg cgccggtggt    8340
gatcgtcgcg ctcggcatgg ccctggtcat cggcaccgag gggatcgacc tctcggtggg    8400
ttcggtcatg gcgctcgccg cggccttcat accctctat ctggggtacg gcgtgacagc    8460
cgcgatcctc gtctcgctcc tcgcgggtgt ggcggtcggg ctgatcaacg gtgtcctggt    8520
cgcgaaggcc ggcctgcagc cgatcgtggc gacgctggcc ctgttcgtcg gcggtcgcgg    8580
gctggccgtg gtgatctccg gtggacagct caaggacgtg cgcaacgccg acctgctcta    8640
cctgggctcc ggtgacctgc tcggcgtgcc ggtcctggtc tggatcgcgg cgctgctggt    8700
gctcgtggtg gcgttcgtgg tccggcgtac cgtcttcggc cggcgcctgc tggccgtcgg    8760
cggcaaccgg cccgccgccg agctcgccgg cctcccggtc aagcgggtgc tgatcggcgt    8820
ctacgtcttc tgcgcggtgc tcgcctcgat cgccggcctg ctctcggtcg cgcgcatcca    8880
gtccagcgac gcgtccgcgg tcggcctgct gatcgagctc tccgcgatca ccgcggtggt    8940
cgtcggcggc accccgctca ccggcggccg ggtccgggtg ctcggcaccg tggccggggc    9000
cctgctcatg caactggtgg tcgccaccat gatcaaacac gatctcccgc cgtccaccac    9060
cgagatggtg caggccgtga tcatcctggt cgcggtctac gtggcccggg agaggaggac    9120
ccggtgacca tgtcgatccc cgtgcccgct ttccggaacg gcggcttcgt gcagcgccag    9180 ggccgcgctcg cggtgctggt caccgtggtg gcgatcagcc tggccgcgtt ccccggcttc    9240
cgcagcgcgg acaacgccgg cacgatcctg gtcgccgcgg cgccaccgat gctgatcgcg    9300
ctcggcatga ccttcgtgat catcacgggg gggatcgacc tctcggtcgg ctcgctctac    9360
gtgctcggcg ggtggtcgc cgcctgggcg tcgcagtggg gagtcgtcgc ggcgctggcc    9420
gcgccgttgc tcctgtgcgg ggccatcggc gtactgaacg ggatcctgat ctcgagaacc    9480
gggatggcgc ccttcatcgt cacctcgcc gcgctgctcg gcgcccgtgg cctcatgcgc    9540
agcatcagcg atgagggctc gacgacgtac ctggtcagga gcgacgtctt ccacgagctg    9600
```

```
ggcacgggat ccctgctcgg cgtcggtctg ccggtctggc tggccgcggt tctggtcggc   9660
gccgggatcc tggtgctgaa ccggacccgg ttcgggcacg ccgtgcacgc catcggcggg   9720
agcgaggacg ccgccgcgct gatggggctg cccgtacggc gaataaaggt ctgggtctat   9780
ctcctctccg ggctgctcgc gggactcgcc ggtgcgatca acgcggccaa gctcggctcc   9840
ggggtcaccg tgctcggcag tggcatggag ctcgacgcca tcgccgccgt cgtgatcggt   9900
ggcacgctgc tcaccggcgg ctccgggtcg atcgccggca cggtcgcggg ggtgctgctg   9960
ctcggcgtga tccagaacct gatcaaccag gtcggcaacg tcaacagcaa ctggcagcag  10020
gtgatcagcg gtgggttcct cgccgctgtg gtcgtggcgc agacaactct cgtacgcgca  10080
agaagatctt gacgtggagg cccgcccggg gaccctgccg cgggcgggca ggcgtaggtt  10140
gcccgcatga cggagcatcg ggtctccccg gccgggcggg cgctcgcgtg gctgatgctg  10200
gtctccgggt tcgccgcggt cgtcgggtcg ttcctgccgt gggcctgggt cgacttcccg  10260
gagcagggca gcagccaggt gtccgggagc ctcgtgtcca acctgttcac cgcgttcttc  10320
ggggtcgtgc tcgccgggta cgcggtgccc gccgtgcgcg gcgagcgcct gcccggcctc  10380
gagacgttct tctcggtcgg cgccgggctg gtgctgttca cgctcggggc ctgggacagc  10440
cggcacctga cctcgatgac cgccgccctg gtcgcggccg acaccggcac gaccatcggg  10500
cccggtctct ggctgtgcat gatcggcggc ctgctgggcg cgctcgcggc ggcggccctc  10560
gccgtccggg gacgccggcc ggtcgtcagc tcccgggtgt gaccacccag tccgggtggt  10620
tcggcatcgg aggggtcgtg acgccgagga gccaggaggc caggaacggc cgcagatcct  10680
ggcgggcgac ccgcgaggcg agcgtgatga agtcaccggt cgaggcggag cggccgcggt  10740
acgtcgtcag ccaggcgcgt tcgacccgct ggaacgtcgc cgcgccgatc ttctgccgga  10800
gcgcgtagag gaccagcgcg ccgccggcgt agacgttcgg gttgaagacg tcccacgtgg  10860
tcgccgcgtc gagcggggcg gcgaccggac cgtacctggc gcggaagatg tcgccggcgg  10920
cgtagacggc cttgaagaac gcctcgcggt cggccaggcc ggtgtactgc gggaacccgc  10980
cggtctcctc cgaccagagc atctcgtacc aggtggcgtg gccctcgttg agccagacgt  11040
cgctccacga gaacggcgag acgctgtcgc cgaaccactg gtgggccagc tcgtgggtca  11100
tcgacgggcc gcgggtggtc tcggggccgg tgaacagggc ggcgccgtac agcgaaaggg  11160
tctgggtctc cagggcgtag cccaggtcgt cgtcgatcac cagggagccg tagtcctcga  11220
acggataggg cccggcctgc ttctccatcc aggcgagctg ctcgcgttcc ccggcgatcg  11280
cgggcagcag cgtgccggcg aggcgtcgcg gcaccacgtc gcggatcggg gtgccgccgg  11340
ccgccgggcg gcgctcgacc acgaagtcgc cgacggccgt ctgcaccagc tcggtggcca  11400
tcggggcgga ctcgcggtag accgagctga cgtggccgtc gtgctcggtc gtgctcacca  11460
gcgtgccgtt ggccgtcccg gtccagccgg ccggcacggt gagcgtgatc gtgaaggtcg  11520
ccttgtcccg tggatggtcg ttgccgggga acagcaggtg cgccgagccg ggctgggcag  11580
cgagcaccgt cccgtccggc gtcgccacga gagcggccgg ggcggcggtg aagttcgcga  11640
ccgtgacccg gaacagccgc ccccggggaa ggggcgccgc cgggatgacg gtcagctcgt  11700
cgccgtcccg ggcggcccgc gcgggctgcc cgtcgaccga acgcgcccg atcgaggcgc  11760 cgccgaagtc gaggtcgaag cgggacaggc tctgcccggc gacggcggtg atcgtcacat  11820
cgccggatac gacctgcttc gggtccttct ccgggtagcg caggcggagg tcgtagtcga  11880
gcacgtcgta gccgccgttg ccgagcagcg ggtagaggcg gtcgccgagg ccggcggacc  11940
cgggtgacgg cgagggcccg gcctgcgccg gtgcggcggc tgcggccagg gcgaggacga  12000
```

```
cggtggcgcc gacggtgagg acgcgggtgc ccgcggacgt tcgcatggct tccgacgcta   12060
ggcgacacca ccggaagcca tcgacccatg ggcatgtatg aaatcccaca atctccgatg   12120
tggacggacg gatggtgcgc agtatgcaac ttgcagattt cgggacattc cctagcccgg   12180
cggttgccgt gtgcacccgt tcgaccactg tccggaaccg cgtggtgagc agggtgaacg   12240
ttcatgcggc ccgggccgcc ggaggtcccg tgaccgttcg cattgccgtg cgccggtgaa   12300
tcactccgct ttacgacttc gcgacaagtg gttaatgtcg gcgaagcgat atatcgtcca   12360
gttattcggg ggactgcggt gcatgagcaa aaaatcactc cggcgattgc cagcggatca   12420
ccgcaaattg aattgctgcc cgtcaattcc ctgcgagtga tggattcgcc gcgactgaac   12480
ggtgaggacc cgcggcacac cgaggtgctc gccggcttcg gggcggagct cccgccgatc   12540
gtcgtgcacc gggcgaccat gcgggtcatc gacggcgcgc accggctgag cgcggcccgg   12600
ctgcgcggcg acgaccggat cagggcggtg ctgttcgacg gcaccgagca ggaggcctac   12660
gtgctgagcg tcaaggccaa cgtgacgcac gggctgccgc tgtccgccgc cgagcgcacc   12720
cgtgcggcgg agcgcatcat cacgatgcat cctgactggt cggaccggat gatcgcggcg   12780
tccagcgggc tgggcgcgcg gaccgtcggc ggcctccgcc ggcggcgcgc ggcctccggc   12840
gagagcccgg cgggcctccg ctcgcgcgcc ggccgggaca gccgcgtccg gccggccggc   12900
agcaccgcgg gccggctgaa agcggtcgac tacctccagg accggccgga cgcctcactg   12960
cgggagatcg cccggcacgc cggcgtctct ccgtcgaccg cccgtgacgt ccgggaccgg   13020
ctgcaccgcg gcgaggaccc gatccccgcc acgcaacgcg cggcggcacg ccccggaaac   13080
gattccccgc cgctgcggtc gctggtccag ggcttggcga gcgacccgtc gttgcgattc   13140
agcgagtccg ggcgcgatct gctgcgctgg ttgattgccc acgccgttca ggacggcgaa   13200
tggaaagggc tggtcgacac tattccggcg cattccgcgc aggcgctggc gaaaatcgcg   13260
cgccattgtt cgcgggaatg gcgtgagttc gcggacatcc tggagaagga cgccgcgtag   13320
gccaccggca tttcttccgg cacccggtcc gccctccgtc acgcacaggt cagagtactg   13380
atggcggctg tcaacccgcc gatctgcggg taggtgccga cgtccttccg ccgaccgtct   13440
gccgaacgca tccggtcggt gcccgatgtg cgggtaggca ttcaccgatc agggttgctc   13500
caatgtctct cgtcgatacc gcggctgata cctccgcggt actcggcaga acactccgtg   13560
gctatggcgc cgtggtcccg gagccttccc tgaagtactt cggacgtacc tgtccggagt   13620
cccccacaga aggagacatc atgtcggcca tcaccgtgga aaccacctgg aagaacaccg   13680
acctccggga ggacctcacc gctcacccgg ccggcctcgg cttcggcgag ctgagcttcg   13740
aggacctgcg tgaggaccgc accatctacg cggccagcag cggctgggtc tgcaccctga   13800
ccatcgagtg cggcacgctc gtctgcgcct gctgaccaac ggtcatcgca ctgccgggac   13860
cggggctgac cccggtcccg gcaccctctc cccggcagga gcctgcatgt catcctttgc   13920
gatcgccgct tcgccggcca gcgcgtacct gcacgagcgc tccgccggcc ccggcggcga   13980
ccccgtggcg gagcacgagc gggtcgagtc gtggcgcgag tccgcgttcc tggacgaccc   14040
ggtcctggac atccgcctgc gcgagctcgg actcagccgg gccgagttcg gccggctgct   14100
gaccgacggc gcgtacgacg ccgggagcac ggccctcgac tgggccggcg agctggccgc   14160
cgtgctggcc accgggaccg gcgcggtcac cggactcgcc cggtcgacca agctgtgggc   14220
gcagggcttc gaccggctgc cgttcgccgg gctgatcgag aggttcctcg cgtactacga   14280
gccgcgggtg ccgcgcaccg ccgggaccgt ccgggtgtcc ctgctggaga gcctcgcgaa   14340
ccgcctgctc acggtcgcga cccggaccct gctgctggaa ctgaacgtgg cccgggtgca   14400
```

```
cggccgcctg accggcgcca cccccgggga acgctacgac cactacgacc gggtcctgct   14460
gaccgacccg gactacctgc gctcgctctt cggcgagtac ccggtgctcg gccgggccat   14520
ggtcgagtgc ggccgccgct gggcgtcggc gatggccgag ctgttccagc gcctggacgc   14580
cgaccgtccc gccctgcacg ccgccgggct gctgccggcc ggcgcgggcg aggtcaccgc   14640
gctccggccc gacctcggag acccgcacaa cagcggccgc gcggtcgcga tcctgacctt   14700
ccggtccggt gcccagctgg tgtacaagcc ccggccggtc gggccggagc gcgcgtacgc   14760
cgagaccgcc gcggccctga accggcacgg cctgagcctg ccgctgaccg ccgtggacgt   14820
gctcgaccgc ggcgcctacg gctggtgcga gctggtccgg cacgagccgt gcgccgaccg   14880
cgccgacctg gaccgcttct accggcgtac cggcgcggtc ctggccacca ctctgctgct   14940
cggcgccgtc gacgtgcaca tggagaacgt catcgcggcc ggctcgtcct gcatgccat   15000 cgacctggag acgctgctgc agcccggggt cccgtccggt gacgcgacgg acgcctacac   15060
ccgggcgctc gacctgctca accagagcgt gctggcgatc gggatcctgc ccgcccgggc   15120
gttcggcggc cgggagcgca agagcgtcga cgtcagcgcg atcggcggcg gcgaggcaca   15180
gaccgcgccc cggccggtgc cgatggtcgt ggagccgttc accgacgtgg cccggatcga   15240
ggcggtggaa gcgaccatgc tgggcgcgca gaaccggccg gtgctggtcg gcgccgaggt   15300
gcggcccgag gagcacaccg aggcggtggt ggccggcttc accgaggcgt acgacctgat   15360
cgtccggcac cgcgaggact cgccgacct gctggccggc ttcggtgacg tcgaggtgcg   15420
ctacctgccc cgcccgaccc gccggtacag catgttcctg accgagagct accacccgga   15480
ctacctgcgc gacgcgcgtg accgcgaccg gctgctcgac aagctgtgga ccgccgcggg   15540
cgcccgtccc gacctgatcc ccatcatcga gtcggagaag cgccagctgc tggccggcga   15600
catcccgtgc ttccgcgcgc tggccggcga ccgggcgatc cgcaccgcgt ccgccccggt   15660
ggcgccggac ttcttcgacg cccccggcat cgaggtgctg gccggccgcc tgcggcagtt   15720
cgggccggtg caccgggctg cccagctgcg gatcatccgc gagtcgatgg gaaccatgcc   15780
cgcgcccggc ccgatcgccg ggacacccgc gccatcctcc gagcggcgtg gcggcctcga   15840 ccccgtgag gccgccacgc tcggggaccg gctcgtgcgg gagctcgcgg acgaggcgat   15900
cctcggggcc gacgacgccg gctggatcgg agtcagcatc gagggcctcg accaggagac   15960
gttcagctac aagccgatgg cgaccgggct gtacgacggc atcgcgggaa tggcgctgac   16020
gtacgcgtac gccgcccgca cgctcggcga cgagcgctac ctcgacctga cccgccgtac   16080
cgtcaagctg gtctccggct atctgcggta cctcgccgag caccggatcg tggagacggt   16140
cggggcgtac agcgggatgg ccggcctgct ctacacgctg gatcacgtcg cccatgccac   16200
cggcgacgcg tcgctgctgg gcgagatcga ggccgcgctg ccctggctgc gggagtgcgc   16260
tacccgcgag gagtgcccgg acctgatcgc cggcctggcc ggttgcgccg tcgtcgcgct   16320
gtcgctgtac cggcggcacg gcatcgccgg ttaccgcgag gtcgcggaga tctgcggccg   16380
gcgactggcc ggcaccgcgg tcgacgtcga gggcgccgcg ggctgggccg cgacccggac   16440
cggcgtgatc ctcggcggtt tctcgcacgg ctcggccggg atcgcctggg ccctgcacga   16500
gctcgccgcc gagttcggtg accgggacct gcgcgagctg gccgaccggg cggtcgagtt   16560
cgaccggcgg ctgtacgttc cggccgcgg cgcctggcgc gacctgcggc ccgagatggc   16620
cggcaccgac ggttacccgg cgctctggtg tcacggcgcc gccggcatcg gcctgtcccg   16680
gctgctgatc caccggatcc ggccggacga gcggctcgcc gaggaggccc gcgccgcggt   16740
ggcgctggtc cggcggcacg gcttcggcca caatcacagc ctctgccacg gcgacttcgg   16800
```

```
cgcgctggcc ctgctcggcc tggccgaccg cgcgtggccc gggtcgggcg gccacgacga   16860
gcgtgccggc gcggtcgtgc gggacatcgg cgagaccggt ctgcgctgcg ggctgggcaa   16920
cggcatccgg atgccgggtc tgatgctcgg cgccgcgggc gccggactga gcctgctccg   16980
gctggccgcg cccgccgacg tgcccgcggt cacctggctg gaaccgccgc ggggcacgca   17040
tgtctgagac ggccgggctg ctgcggcgga gcctgctcga tcaccggggc aagctcgccg   17100
ccgtggccgg tctcgccgtc gccggggtcg gctgccagct gggccagccg ttcctcatcc   17160
ggcgcgtgct cacggcggtg cagtccgcac agccgtaccg ccaattggct ctcgccgttc   17220
tggcggtcat ggtcgtcggc gcggcgctgg gcgccgtcca gcagttcctg ctgcagcgca   17280
ccggggaggc gatggtcttc acggtgcgcc gcacgctcgt cgcgcacctg ctgcggctgc   17340
cggtcgcggc ctacgacgag cggcagtccg gcgatctggt gtcccgggtc ggcgccgaca   17400
ccgcccaggt gcgctcggtg atcacgtccg gggtggtcga cctggccggg ggcgtcctgc   17460
tcgtcggcgg ctcgatcgcc ggcatgatca tcattgatcc ggtcctgctc ggcgtcagcc   17520
tggcgccggt gctgtgcggc gccgccgggg tccggctggt cggccgtcgg ctgcgcccgc   17580
tcagctcggg ggtccaggag tcgatcgcg cgctcaccgc ctcgaccacc cgggccctcg   17640
gcgcgatccg cacgatccgg gtcgccggcg ccaccgagcg cgagaccgcc ctgatcgtcg   17700
ccgaggccga ccgcgcccgg gcggcgggcg tccggctcgc cctggtcgcg gcccaggccg   17760
gcccgatcgt ccggctcgcc ctgcagggcg cgttcgtcgc ggtgatcggc ttcggcggct   17820
accgggtcgc gaacgcgcg gtgtcggtcg gcgacctggt cgcgttcacg ctgctgctgt   17880
tcacgctggc gctgccctg gcccagctcg ccgaggcggc cacccggatc cagaccgggc   17940
tgggcgcgct gacccggatc gaggagatcc tggccctgcc ggacgaggac agcgcgctcg   18000
gcgtccgtgc gaggacgccc gccacggtcc ggcacgatcc ggtgctgctg gagttcgatc   18060
acgtgtcgtt ccgctatccc accggcgggg agatcctgcg cgacgtcagc ttccgggtgc   18120
cggccggcag caccaccgcg ctcgtcgggc cgtccggggc cggcaagtcg acgatcctgg   18180
cactgatcgc ccggctctac gaggtccacg gtggccggat cctgctgcac ggccgcgaca   18240
tccgcgacta cccgctcgcc gagctgcggg ccgccctcgg ctacgtcgag caggaggccc   18300
cggtgctggc cggcaccgtc cgggacaacc tgacactggc cgcgccggac gtcgcggaac   18360
acgcgatccg ccacgtcacc gcatcggtca acctcgacga cctgctcgcc cgtgacccgg   18420
ccggcctgga cgcgcggtc ggggacggcg gcgtgctgtt ctccggcggt gaacggcaac   18480
ggctcgccgt cgcccggacc ctgctcgccc cgggcgaact gctgctcttc gacgagccga   18540
ccgcccacct ggacgccgc aacgagcagg cgctgcagca cggcctgacc gcgcacgccg   18600
ccggccggac gctggtggtg gtcgcgcacc gcctggcgac cgtcgcgcac gccgaccaga   18660
tcctggtgat cgacgacggt cgttcggtcg ccgccgggcg gcacgaggag ctgctcgtcc   18720
gcgacccgac ctaccgcgag ttcgccaccc gtcaactgct gacctgaatc ccgaggtgta   18780
cgccatgctc agtgtcctgg accaggtgcc cgtgttccgt ggcgacgacc ccgccgaggc   18840
ggtccgcgag gccgtcgggc tcgcccgggc cgccagtcg ctcggctatc accggttctg   18900
gatcgccgag catcacggca gcgccgccaa cgcgtcgcgc gcgccggaga tcgtggcggc   18960
ggccgtcgcc ggagccaccg aacgatccg ggtgggcacc ggggagtgc tgctgccgta   19020 ctacagcccg ctcaaggtgg cggaggcctt ccgggtgctg gcggcgctgt atccggggcg   19080
gatcgacctc gggttcgggc ggggcagggg cgggccggcg gtgatggccg agctgctcaa   19140
cccgtacgcg atcgcgaccg aggaggcgta cgccgagcag gtcggccggc ttctcgcgtt   19200
```

```
cctgggcgac gcgcggaccg tcagccgggt gtcggtcacg ccggcggtgc aggacccgcc   19260
gttgccgtgg ctgctcggct ccggcgtcgg cagcgcccgc ctcgccggga tgctcggcgt   19320
gccgttctgc ttcgcgcagt tcatcgcgac cgaggagtgc ccggaggcga tcgcggcgta   19380
ccaggagtcg ttccggagct cgccgtggct ggacgagccg caggcgatgc tggcgttgcg   19440
ggtgctcgcg gccggcaccg ccgaggacgc cgaggagctg gccaccggct tctggatgtc   19500
gtgcaccacc ggatggcggg cccaggtccg gccggacgac gactaccggg gtggcgtgcc   19560
gaacctggcg gacgcccagc ggtacacgct gaccgaggag gacctggcga tgcgcgcgag   19620
ccggccgtac ctgcagatct ccggcacggc ggagacggtc ggcgaggaga tccggcgact   19680
gcgcaaggtg tacgacgtgg ccgaggtcat gctcaccacg aactgtcccg ggcggccgc   19740 cccggcgccg gtcctacgag ctgctggccg ccgagctcgg gctgaccgcg ccggcgtgac   19800
ccgggtcagg ccagctcgtc ggtggtgagg ccggcggcgt acgccagcac ggcggcctgc   19860
acccggttgg ccacaccgag cttgcgcagg atgacgctga cgtactcctt gaccgtggag   19920
tcgctgatga acaggcgccc ggcgatctcc gcgttggtca gccctgccc gatcaacccc   19980 agaacggcct gttcccggtc ggagagctgt ttgacctcgt cgaccgcgtt ctcggcggcc   20040
ggagtgcccc ggcaggccgc gcccagcatg atcgacgagg cctccggcgc cagcacggtc   20100
accccggacg ccagcgcgcg gaccgccgcg accagttgct ccggctgact gtccttgagc   20160
aggaagccgc aggcgccacc gcgcagcgac tccagcacgg tgctggacgc cgccagcgtg   20220
gccagcaccg ccagcgccgg cccggactcc aggtcgcgca gccgggtcag cagcggcacg   20280
ctctccggca gggtcgcgtg cgcgtccagc aggacgaccg cgggccggtg ctcgctgacc   20340
gcggcgagcg cgctgtcgcg gtcagcggcg acgacggaga agccacccat cgtctccagg   20400
atcatcttga tgccgatcga gaccagggcc tcctcggcca ccaccagtac gtccgccatg   20460
cctcccccgg gcaatgtagc cgtacgagat ttgatagtgc acaaaaacca tcgaattact   20520
gctctttcga atcatacatg tatttatgca aatttctggt caggaaacgg ggacgatccg   20580
agacgcccgg gccggcgtct cggatcgtcc ttcaccgcgc acggctatcg cacgagccct   20640
tccgcggggg cgatccgcgt ggctcgccga gccggcgcca ggctggccag cacaccggtg   20700
accgcggcgg ccaccagcac gagacccagc tgcggccacg ccagcatgat caccggttcg   20760
gcctgccggc ccacggccgc gatcacgccg accagcccga ccggcacccc gatgacgatg   20820
ccggccaccg tgccgaccag cgtgatcgtg accgcctcga cggcgaccat cgcgcgcagc   20880
cggctccggc gggtgccgag cgcccgcagc agggccatct cccgggttcg ttcgatcacc   20940
gagaggccga gcaggttggc gatgccgagc agcgcgatca ccacggtgac cgccagcatg   21000
cccagcgaca gtccgagcag gatggacagg acgttcatga tgtcgccgcc ctcggtgaca   21060
ccgccgccga cctccacacc ggcgtcgcgt gccgccaccg cgttgacgtc ggcggccagc   21120
gtctcccggt cgaagccgcc cggcgcggtg ccccagaccg tggtcggcac ggtccggacc   21180
ccggcggcgg tcaggacgtc accggtggtg acgccgagca gctgcccggt cgtgtcggcc   21240
agccgcgagc cccgggcggt gaaccgcagg tcccgcccgc cggccgtgac cgtgagcgga   21300
gcaccgtccg tcagcccgcg cgccgtcagg taggaggccg gcaccagcag caccgggtcc   21360
ccggtggacg cgctcagctc cggcgcgagg cgcccggcca cgtcggtggg gagcgccgcg   21420
atccgggccg gcgtgggttt gccgcggcc gggaacgtcg ccgcgctcgt cgccacggtg   21480
gccgtggtca gccggtgat cccggacagc gcccggaccg tgcggtcgtc gatcgccgcg   21540
ccgtcggtgt gcacgctgac cgccaccgga tagcgcgcct ccaggtcggc ctccaccgtg   21600
```

```
gcccgcccgc tcgccgaggc cacggccagg ccggtgatca gcgcggcccc gacgaccacg   21660
gccatcgtcg ccgacgccgt ccggcgcgcg ttctgccgga ggttgctgcc ggccaggctc   21720
gccgccaccc cgaaccgttc caggccgcgc gccgccggcg gcaacagcag ggcgatgccc   21780
agcggcagcg cggtcagcag cccggcggcg agcagcaccc cgccgaccag cgccgagcggc  21840 agggaggtgc cgatcgcggc gagacccagc acgcccacgg ccaggccgat caggatcagc   21900
ccggcgacca ggcggcgccc gccgcggacc tgtgcgggaa gagcgtccgg cacctcctgc   21960
agcgcgcgca ccggggggaac ccgggtcgca cggcgggccg gcgcccaggc cgcgacgacc  22020
gtggcgccca ccccggtgag cacacacagc gccagcacga tcgggttgac cgccaggccg   22080
ccgccgttga tgtcgagcag gccggccccg agatagccga gcccgacacc ggcgaccgcg   22140
ccgatcaccg cgccgatgct cccggcgatc gccgcctccg ccagcaccac ccggctcacc   22200
tggcggcggt gccgccgac cagccgcagc aacgcgacct ggcggacccg ctgggagacg    22260
atcacctgga aggtgttcgc gatgaccagg atcgacgcga gcagcgccac cgcggcgaac   22320
gccagcatca gcacgaccag ctgggtgttg ccaccggcga accggccggc ggccgcgtcg   22380
gcggccgccg acgcgtcggt cgcggtcgcc cccggcggca gggcccggcc gaccgcgtcg   22440
acggtctcgg ccagccggtc ccggtccgtg acggtgagca gcgcggccgg cggcgtgtcc   22500
ccggcgaaga acgacgcggc ggcgtagaac cggtagtccg agccggtcag cgggcggaag   22560
ccgagatcgg ccgagccgac cacggtcacc ggcaccgggg cggccgtgcc ctgccggaag   22620
tcgaggtggg cgccgacccc gacgccgagg tcggtgaggg tccgccggtc ggcgacgacc   22680
tgcccggccg cgctcggcca ggtgccctcg tcgacggtga accagcgcac cgacgcggtc   22740
gccgggatgc tctgcacgtt ggccgagccg cgccggtcgc cgccgaagac gctgaccgtc   22800
cgtgcgtact gcgggtcgac gctccgcacg ccccgcaccc cggcggccgc ctggtaccac   22860
tgcgggtcgt gcaccgtgtc gtcggcgtcg agcacgatgt ccgccgtggt caacggggcc   22920
gcggcggtga gccgcagacc ctcgtccgag gtgctcgcga acgtggccgt ggcggccagg   22980
aagccggtgg ccagcacgac cgcggcgacg atcgcgagca gccggccggg gtgcgaccgg   23040
acctgcgacc aggccagcgt gaagatcatg acgtcaccgt caccgacgcc atgaccgaca   23100
tgatcgactc cagtgtgggc gctcggagct cgtcccagag ccgcccgtcg gccatgatca   23160
agacccgatc ggcgtacgtc gcggcggcag cgtcatgcgt caccatgatg atcgtctggc   23220
tggcctgccg ggcggcgttc tgcagcccgg cgagcagcgc ccggccggtg gcgatgtcca   23280
gcgcgccggt cggctcgtcg gcgaacacca ccgacggctc ggtgagcagc gcgcgtgcca   23340
ccgcgacccg ctgctgctgg ccaccggaca gctcggcggg ccgatggccg agccggtcgc   23400
cgatctgcag cgacgcggcg atgcgctgca gccggtcgcg gtccaccgga cggccggcca   23460
gccgcagcgg cagcacgatg ttctgctcgg cggtcagcgt gggcagcagg ttgaacgcct   23520
ggaagatgaa gccgacccgg tcccggcgca ggtcggtgag cgcgcggtcg tccagcccgg   23580
cgagcgcggt gccggccagg ctgacctcgc cctcggtcgg tgtgtccagc ccggcgagca   23640
ggtgcatcag cgtggtcttg ccggagccgg aggggcccat gatcgcggtg aactcgccgg   23700
ccgcgaagga ggtcgacacc ccgtcgacgg cgaccaccgc ggcgtccccg gttccgtacc   23760
gtttacgcag gttgcggcaa ctgaccatgg agctgctctt cgtctgcatc atcacggttg   23820
cgacgttagg gaagtggcgg gccgcccaca tccgtccggg gcatcgccgc gaccgatacc   23880
aaggtatcga cctggcgtgc ggatggtgcc gcgagcgctc gcggtcccta ctctgagagc   23940
gtgggaagct gggacaggag aacgctgacg gtcgatacgg tgatcgccgg cgccgcggtc   24000
```

```
atggtgtgcc tgctgctcgg gttggccggt ctggacgagt ggtactggtc ggccgcgctc   24060
tgcgtccccc tggtgatccg gcgctcggct ccggtggtct tcctcgcgct ggtcgcggtg   24120
ctctccggca tccacatgat ctactccggc agcttcgcgt tccccggtga cctggtcgat   24180
ctggtcgccg tgcacgccgt cgccggttac ggcccggccc gggtccggca cctgggcctg   24240
ctgctcggcg tggccggcag cctggtggtg accgccgggc gctgcacgca cgggctgccg   24300
tcgtccgcga cgctgcccgc cgcgctgatc gtcgccgcga ccctggccgc ctggtcgacc   24360
ggcctgatgc aacgccggca gcgggccgac gtgatcgagg ccgatcaccg ccgccggctc   24420
gccgagcagg acagcgcgat gcgtgcccgg ctcgcggcga tcgaggagcg cacccggatc   24480
agtcaggaga tgcacgacat catcgcccac tcgctggcct cggtgatcgc ccaggccgag   24540
ggcggccggg tcgccgcgcg cgccgacgcg gtcgtcgccg gcccgctgtt cgaccgcatc   24600
gcgcagatcg gccgggaggc cctcaacgac gtgaagcggc tgctgaactc gatcgacggc   24660
gacacgccgg acgacttcgc gcagggcctg cccgacctgc cgggcctgct ggccggggtc   24720
tccgccgccg gcctcgacgt gacgttcgag gtggccggcc cggagcagcc gctcgcgtcc   24780
ggcatggacc tggcggtgta ccgggtgatc caggagtcac tgaccaacgt gctcaaacac   24840
gccacgcagc ggcaggcccg gctcagcctg gtgtggacgc cggcgtggct cgaggtcagc   24900
gtgaccagcc cgctgacctt cgccggccgc ctccgcgagg tcgcgggct gtccggcatc   24960 cggcagcggt gctcgttgtt caacggcgac tgcgagatcg tggccgggca gaccttcagc   25020
gtgatcaccc gctggccgct cgcccgtccg gaggttgccg tcccatgacc gagccgcaga   25080
tcgacgtggt gatcgccgac gatcaggacc tcgtccggac gggcttcgcc ctggtcgtcg   25140
actcggcccc ggacatgcgg gtggtcgcga ccgcggcgga cggcgccgag gtggtgcggc   25200
tggccgcgga gttccgcccc gacgtggtgc tgatggacat ccggatgccc cgggtcgacg   25260
gcatcaccgc ggcccgggcg atcctggagg caacgctca ccgccgaag atcgtcgcgc   25320 tgaccaccta cgacaacgat gagtacgcca gccggatcct ggccgccggc gccagtgggt   25380
acctgttgaa ggacaccacc gccgagggcc tgaccgcggc gatccggacg gtgcaccgcg   25440
gcggctcggt gctggcccg tccaccaccc accgcctggt gaccgcgcac cgtcagcatc   25500
cggcacgccc gtccgcgctg ctggattcct tcaccacccg ggagcgcgag gtcttcgacc   25560
tgatcgtggc cggcgccagc aacgcggaga tcgccgaccg cctgaacctg gcggaggtca   25620
cgatcaagac ccacgtcggc cgggtgctgg ccaagatcgg cgtccgcgac cgggtgaacg   25680
tcgtgatctg ggcctaccgg aacggcgccg ggccgagctg agcaggggcc aggccgcgct   25740
cgcactcggc cgaatcccga aaagcggcta ggggaagcgg atctcggcgg ccagcggcag   25800
gtggtcactg ccggtccggg ggagggccgt cagccgcgtg accgtcatcg atcgcgccag   25860
cacctggtcg atccgggcga ccggcgtccg cgccggccag gtgaacgcga agtccgcggg   25920
cgaatcgatc atcacttgcc ggatcggccg cagcccgcgg tcgtccaccg acgtgttcag   25980
gtccccgatc acgaccagcc gcggaaccgg gtcggcggcg agcagcgcgc cgagcttccg   26040
ggcgctctcg tcccgccgtg ccgaggtgag tcccgccgcg gtgacccgca ccgacggcag   26100
atgcgcgacg tacaccgcgg tgtccccgcc cggcgtccgg gccaccgccc gcagcccccg   26160
gttccagtcc tcgcccaggt catgcggccg gatgtcgatc gcctccgcgc cggtcagcgg   26220
atagcgcgac cacagcgcca cggtcccctg cacggtgtgg aacggaagct ccgcgtcgag   26280
cacaccccgg taggcggcca ccgcctccgg cagcacctcc tccagcccga ccaggtccgg   26340
atgtgccgcg agcagcgccc gggcggtccc cgccgggtcc gggttctcgt cgctcacgtt   26400
```

-continued

```
gtgctgcacg acgatcagat ccggcgtgcc ggtgtcccgg tcgaccacgt agccgccgaa    26460
atggatcagc cacgcgccca gcggcagcag caccgcggcg aggccggtca gcgatcgccg    26520
catcagcgcc agcaggagca ggaccggcac ggccagcccg aaccacggca aaaacgcctc    26580
gatcaggctg cccgcgttgc cgaccgcgtt ggggaccaga cggtgaccga gaatgaccgc    26640
cccggccaga acagcggtcc acaagatcgg catcgggaga tgttatctta tttcgcatgc    26700
gaaataatga gacggtacgg atcccggtag cgaccggcgg cgccgtcacg gccacgctgt    26760
tcgcgcccga gtccgcgcgt gccgtgctgg tcgtgcaccc ggcgaccgcg actccgcagg    26820
gcttctacgc gtcgttcgcc acctacctgg cggagaacgg gatcgccacg gtcacctacg    26880
actaccgtgg caccgccgt tccggctccc cgcgcgacca ccgtgacctg gcatgcgcg     26940 actggatcgg cgccgacgcc ccggccgtcg cggcgtgggc cgccgaccgc ttcccgggcc    27000
tgccccggct cgccgccggt cacagcctcg gcgggcacgt gatcgcgctc ggcgcggccg    27060
gcccggatct ggccgcctcg gtgatcgtcg cctcgcacat cgccgcgctg cgcaccatcc    27120
cgagccggct ggagcggttc cgcgtgcgaa tcatgcttca catcctgggt ccggccctcg    27180
ggcggctgct gggctacgtg ccggccagaa gtctgggcct cggcgaggac ctgccggccg    27240
ccgcgatgtt ggagtggggc ggctgggcgc gcagggacaa ctacttcttc gacgacccgt    27300
cgatgcgcgc cgccgagcgc gccgccaccc tgaccggccc ggtcctggcc gtcggcacca    27360
cggacgaccc gtggtccacg ccgcgccaga tggacgccct caccgtgcac ctgaccagcg    27420
catccgtgga gcgcgaacc tactcaccgg ccgccgccgg ggtcccggtg atcgggcacc    27480
acggcctgtt ccggcgcgcc gtgcgcgaca ccgtctggcc ggaactgctg gcctggttgc    27540
acgcccactc ggagaaggcg tcaagatgac cgcgtgcgcc tgcctcgcct gatcttcctg    27600
ctcttcaacg ccgaccgcgc ggtccggcgc tggatcgacg cccgttccgg tgacaccggg    27660 atcgcgcgt ccggcgccgg cgtgctgttc tacctcgccg gtcacgagaa cgccctcatc    27720
ggcgacgtga ccgcggccct gggtgcgtca ccatccggca tgagcggcct ggtgaaccgc    27780
ctggagcgtg gcggttgcct gaccgcctcg caggacccgg ccgacgcccg cgcggtgcgg    27840
ctcgccctga ccccgcgcgg acaccaggtg gtgatccacg cccgcgggct ggtcgacgac    27900
ctgaacgagc agctcacggc cggtttcgac gacgccgaga tagcggtcgt ccaacgctgg    27960
ctggagcacg tgacccgggt gtccgtgcaa cgtgaggagc gactcggtta gcgtccggtg    28020
atcagctaaa cctccgggac gggccgccga agtgaggtgt cgcaaggcac caccgcttcc    28080
gatccgccct tgaggagacc catggctgac tccgtcgtct tcgaccagat ccccgtcgtc    28140
cgcgccatcg gccgaggcac cacctcgctg agcgccttcc acgacgcgct ggtgaccatg    28200
gagtgcggtt tctacaacct tgtccggctc tccagcgtca tcccgccggg caccgccgtc    28260
gaccccagcg gcaaggctcc ggtcccggtc ggggcgtggg cgacaagct gtactgcgtc    28320 tacgccgagc agcacgccag ccagccgggc gaggaggcgt gggccggcat cggctgggtg    28380
cagcgccgcg acggccaggg cggcctgttc gtcgagcacg agggcaccag cgagtcgttc    28440
gtccgcgagg cgatcaaggc cagcctccgc gacctggtca agggccacga ggacgacttc    28500
gacggcccgg acttcgtcgt ccacggcgtg gtctccgacg gcgagccggt ctgcgcgatg    28560
gtgctcgccc cctacgagac cgccccgtgg cgcggcgtcc gtgccaccga cccgccggc     28620 atgaactgac ctgtcaccac gagagcctcg cctcgcacgt cggggcgagg ctttcggcat    28680 tcgctttta cttcgacaac cccctcccgta ccgaagaaat cgaagatcaa attcttcatt    28740
gcctatctcc gctgtggtcc agatcgtcgc tcccgcgggg acccttccgg tctgagcagg    28800
```

```
gccgtaaccg gcccagaacg ctcagcccga aagggcgacc tccgtggcgg ggcacggtca   28860
gggcaaaatt ccgtcgccgg tcgccaggga ttcgccgccg gttgctgcgg gtggggtgcg   28920
gcggtccgcc ggaggtatgg gttgccgcta cgctcggcta gctttcgacc accggtaacg   28980
tgtaattccc cttcggtcca cctacgcccg ttgtgatctc cttatggtgg gctcgcttat   29040
cctcgtcctg tgcatctggg ccgcatcggc cgcgatgttc ttccggctgt cctctccggc   29100
ccggacgccg ggcacccgtg cctggcgttt cgccccgatc ctgaccgccg gtttcgcgat   29160
tccgctcgcc gccgcctacg gtcggcagga ctggtccacc ttcgggtcgc tgctggtcgc   29220
cggcctggcc gccttcgcgg tcctgctcta cctgctccgt cccgtccgcc tctgatccat   29280
actcggtcgt tgtgacgacc cggatgcccc gcctcgagat cgaatactgc acacagtgcc   29340
gctggctgct ccgcgccgcg tggctggcgc aggagctgct caccacattc ccccgcgatc   29400
tcggcgaggt tgccctggtc cccgggatcg gcggcgtctt cgaggtccgc ctcgacggcg   29460
agatcctctg gaaccgcaag ccggacggct tccccgacct cgcccagctc aagcgcctgg   29520
tccgcgaccg ggtcgccccg ggccgcgacc tcggccactc cgaccgcgcc gccaccgact   29580
cctagcccac acgtcctcct ccaccgctcc ggccgcggga cgcgtctacg cgtacaggat   29640
ccggtcgatc gtctcgcggg ggagcagcgt gcgggcccgc ccaccgcaga cggcgaccac   29700
cgccggccgc ccgacataga catcgcgccg ctggtggtac gccccggtac cggacagcgc   29760
caccagatca ccggccgcca tgtcacccgg cagctccgcc accgccaccg tcgcgtcccc   29820
gcagcgaacc gtgatcgacc ggcccggcgc cggcgacgcc cggccgatca gcgctgccgt   29880
gtgcaggccg gcgcagtccg ccccggggcag gcagtccggg acgtccccgt ccagctcgat   29940
cacgccgtcc ccggcggcca ccactcggtg caccgtgatc ccggcacgac ccagcagcgc   30000
acgcccgggc gacacgtgca cctcgggcgg ctcaatgccg taccccctcgg aagtgacctg   30060 cgcgaccgcc cgcaacctgg cagcgaaaat gcccaccggg agatcggcgg catggccgcc   30120
gccgaggttg agcacgggca ccgtcgtccg cagtcgcgcg acgaacccga tcgcctcacg   30180
caggcaactc tcgtaggtgc cgaagcggtt cagccggtgc ccgagcgagc agtccagccc   30240
ggccagcacc agcctccgcg accgggtcac cgtggcgacg gcggcgagcg cggccgagct   30300
gttcagccgc accccgtagc cgcgctgtgc gctgccggc cggaccctca gcaggacgcg   30360
ctgccccggc cgggaccgcg ccgcgaccac ttccgcctcg gaggccgagc cgatcacgac   30420
ggcggcgccg caggacagtg ccgcctccag atccgccacg gacttcccgc tcccgaacag   30480
cgccagcgac tccgggcgga tccccgcgtc gagcgccgtc cgcagttcgg cggccgagcg   30540
gcagtagcag cccagcccgt cccgcgcgat ccaccgcgcg gcacccctga gcaggccgcc   30600
cttggcgctg cagcacaccg cgcccggccc gaacgccgcg acgtactccg cgcagcgact   30660
gtgcacatcg gtctcgtcga tcacgtgcac cggagtgccg tgggccgcgg cgatccgggt   30720
caccggcacc ccgccgacgg tgaggtcacc gggctcggtc cagcgtgcgg tgagcggcca   30780
gttcgcgggg tcgaggcgcg gcggagcga cgcgcccagt gagggcagaa tctcggacaa   30840
cgtcataccg cgagcctgct cgccggcccg tgcccgagaa gatccggata cgccacgttg   30900
acgatcgacg tgccgttgtt gacgtgtcgc ctacaggtcg gggctgtcgg cgggagccat   30960
gatccgcagc gcgttcgggt cgatcgcgat ccgcatcggc gtcgtgcccc gaggctcgcc   31020
gtcgacctcg acggccaccg gccgatccgt ctccagccag agttcccgga ccgcgatgaa   31080
agggcgttca tgcagggtac ggcgatgccc ggtggccgcg ttccgggccg tctcgcgcag   31140
cagctcccgc cggctcgccc cgcccaccgg ataggcgacc agcagccggt cgtcggcgtg   31200
```

```
cgcgtccgcg gtgatcggcc ggccggcgtg gaaaccgccg ttcgcgacgt acacctgatg   31260
ggtgtggaac cgcagctccc gccccctcggc ccggatcacc gcgcggaccg gccggtgccg   31320
ggcgagcagc ccgagcgcgg tcatcggata cgccagccgc cccacggccc gtttcaaccg   31380
cggcggcgcg ctgatcatca cctcgccgga gagcccgatc ccgacgtggt tggtgaacgg   31440
cacgtccccg gcgacgccca ggtccacgtc gatgactttg ccgtccacca gggtcgcgat   31500
ggcggcttcg aggtccggct cgatccgcac ggtccgggcg aagttgttgg tggtgccgag   31560
cggcagcacc ccgagcgcca cgtcccggtg tgccagcatc cgccccgcgg tgctgatcgt   31620
cccgtccccg cccccggcga tcagcaggtc gggctctttc ctgagcgctt cggagatcag   31680
cccgtccagc ccgccggact gctccagcgc atacgtcccg agcagctcga acccggcctc   31740
gacaagccgc cgccgcgcct cttcgtagag gagccgcccc cgccgggacc gcgtgttgac   31800
aacaagaacc gcccgccgcc ctcgccggat gtcagcactg tgctcccgct tactacgcac   31860
ccgccgaccc tatccgcccc aacccaccca acgcccacgc ctcgttcccg cccgcccggt   31920
cccgagccgt gatcaccagc cgcaaggcct cagctggcgt tgacggctga tttcggcccg   31980
gttttgcgcc gtaggcgcca gccgcgaggt gtcggctggc gttcagggct ggattcggct   32040
cggttttgag ccgtgggtgc cagctggggg ctgcggccgg aaggggggtgg atgtggggat   32100 gccccggggc cgtaggcctc ggggcaccga aaaagcgaac cagctcagct gttggcgatg   32160
aacgccggat gcgacagcag gaacgtgtcg atctggtcct tcttgatcga cttcagcagg   32220
tccatgctgt cgtcgctcag gagctcgacg ctgccggagc ccggcacgtt ctccgagttc   32280
agcttgccgg cgttggtctt gatggtgagg agcttgtccg gcttgaggct gcgcatcgcg   32340
agcgcccagt cggccaggtc gatgccaccg tcgtcgaccg tcatcgcctt gccgaacgcg   32400
ctgagcagct tcggcagctt ggtcggcgag tcgaggccgt ccttcagcgc ctggttgatg   32460
atcgccttga agaactgctg ctggtgccgc tggcgaccgt agtcgagcga gttgtcggcg   32520
agcaggtcac gctggcggac gaagtcgagc gcctggccgg gggtgaagca gtggtcgccc   32580
ttggtgtacg tgttcggcgt cacgcccgag atcttgctct tcagcgtgcc gtccgggttg   32640
atcacgaacg gcttggcggt cttgccgttc tggtccttgc ccaggtggat cgacttggtc   32700
gtggtgtcca cgtacatgca gaccttgccg agcacgttca ccacgtcgcg gaagccctgg   32760
aagtcgatga tcgccccggc gtccggcgtg atgccggtca gttccttgac ggtcatggtg   32820
agcaactcga agccgtgctg cagcgcctcg ttgcccttga gccgcgggt gccgaacgcg   32880 aacgcggcgt tgatcttcgt cttgccgccg gcccacttct gcttcccgtt gtcgtacgcc   32940
gggatgtaga cgtagctgtc ccgggggagc gagatcatgt aaccgctgct gtggtccttg   33000
ttgatgtgca gcaggatgat cgagtccgac cggaggggct cgccgttggt ctgcgtgggc   33060
cgctggtcga tgccgacgag caggagattc ttcgccccgt cgaggttcgc gttcttcttc   33120
tcctcggcgg gtttcgccga ccgagcagc gactcctgcc cgaccgagga ggtggccgcg   33180
gccaccgtcg cgttcagccc gatcgcgcca ccgccaccgc cgaccagcag cagtgagccg   33240
aagaccacgg tccagaaagc ccagcggggt gtgcggcgtc ggcgcttgct ggtcctacgc   33300 aaggggctc ctctaatcgg ggcggtcgtt ccgccccagg acaatctagg acggtcgttc   33360
cacccatgaa gacgggcgcc gcgagcgaaa agattgcctg cggaacattg aattttcctg   33420
agcgtcaggt agctacaagc tgaacgtcgc gctcgtgccc cgtggcgtcg cggaacgttg   33480
cttccctgtt actccccaac gcgacgtctg tgttaacca tcgcaccacc aaggcgacct   33540
aggttctgca cggccccggg cccccgaggt tccgacaaag ttgcccaaag cgagtcgcca   33600
```

```
tgccctcaga gccggatgtc agtgtcgtca ttccgacgtg taaccggccg gagttggccg    33660
tccgcgcggt gcgcagcgcc ctcgggcaga cgcaccggaa cctcgaggtg atcgtcgtcg    33720
tcgacggtcc cgacgaggcg accgtgacgg cgctgggcga ggtcggtgac ccgcgactca    33780
gcgtgatcgt gctgccggag cgtggcaagg ccccgaacgc gcggaacact ggcgcccggg    33840
ccgcccgcgg ccgctggacg gcgatgctcg acgacgacga cgagtggctg cccaccaaga    33900
tcgaacggca gctggagacg gccgcggcgg cgaccgtgga gcgcccggtg gtggcctgcc    33960
ggatgatcag ccggacgccg cgggccgaca cgatcatgcc gcgccggctg cccgagccgg    34020
gtgagccgat cagtgaatac ctgctggtcc gccgcggtct gttctacggc gacggcttcg    34080
tgcagacgtc ctgcatcatg gcgccgaccg agctgtggcg gaaggtgccg ttcaccgtcg    34140
gcctgcgccg cgcgcaggag ctggactgga cgctgcgggc gatgcgcgag ccgggcaccg    34200
cgctgatcta cgccgaggag ccgctggtcc tctggcacca ggacgagaac cgtgaccgga    34260
tcagcctgca gaacccgtgg cgcgagcaac tggagtggct gcgcggcaac cgggagctgt    34320
tcacgccgcg tgcctacgcc gcgttcacgc tgagtgtgct gagctcgatg gccgcgccga    34380
cccgggacac cgggctcttc cgtgagctgc tcgccgaggc ccgcacgcac ggcgaccggg    34440
gcaccgtcga ctaccttacg cacatgcaga tctgggccct cccgccgagc gtccggcacc    34500
gcctgcgtga cgtcgtggtg ggccgcggca agacgagcag caatgccggc tgagcgccgg    34560
gtcgcgatct ggcgcagttc gatgctgccc ggctccgaga cgttcgtccg caatcaggcc    34620
gacgcgctga cccgctggac cccggcctat gtcggcgcgg tccggcacga gtcggtgctg    34680
tcccgccccg acgacgtgat cgccttcccg ggcggcaagg ggttcctgcg actgcggctg    34740
accggggcgt ctccccagct gcagaagacg atttccgccg tacggccgaa tctggttcat    34800
gcccatttcg gtggtgacgg atggctggtg agccactccg cccagcagct gggggtgccg    34860
ctggccgtca ccgtgcacgg gcacgacgtg accgtcagc cgtccagccc gggcgcgaag    34920
ggcgtgcgct accgccgcaa cctgcagacc gttttcacgc gggcgtcgct ggtcatcgcg    34980
gtctcggagg tgatccgcgg ccaggcgatc aggtggggcg ccgacccggc gaaggtgaag    35040
gtgcactaca ccggcatcgc ggttcccccg gagcagccgg aggaggtgcc gaagcggtgg    35100
gacgtggtgt tcatcggccg tttcgtcgcc aagaagggcg tcgacgacct gctcaccgcg    35160
ctcgccgcgg tcgagtcgcg cccgcgcgcg ctgctcatcg gcgacggcga gctgatgacg    35220
gcgatgcgtg cccgtgccga gcagctgggc gtggacgtca cgttcgccgg cagcggacc    35280 cccgagcagg tgcggcgcca cctgctggag tcgcggctgc tggcctgccc gtcgaagacc    35340
gcgccggacg gggacaccga gggcctgccg accacgatcc tggaggcggc cgcgctcggc    35400
ctgccggtgg tcgcaacccg gcacagcggc atcccggagg ccgtgatcga cggtgagacc    35460
ggcctgctca gcccggaggc ggacccggcg gcgctggcgg tgtcgctgac ccggctgctc    35520
ggtgacgagg atctccagcg ccggctcggt gcgcgggcg ggcggcacgt cacggcacac    35580
ttcgatctcg tggagcagac caggcggctg gaggacctgt atgacgaggt cgtggcgggc    35640
gctagggtct aggcctgcct gtccggcttc ctggggggaaa tcatgatctg cacgcactgc    35700
ggctcaccgg cggcgccgac cgtcggcccg tgcccgggct gcggccgtcc ggtctccgcc    35760
ccggccgggg tgttcccgga cccgctggcc gcgccggccg agcggtcgct ccccacgtcg    35820
gcgtacagcg tgccggtcga tccgtacacc ggcccgacca ccggtgaccc gttcgccggc    35880
gactcgttcc acaccccgcc gccggcgtcc ccgatgccgc cgccggtgac cgagccgatc    35940
acgccgacgc cgccccgcc ggcctacgcc ccgccccgc agtacagccc gccgccgtat    36000
```

```
gcggggcgc  ccggtcagcc  ctatccgggt  cagccttacc  caggtcagcc  ctacccggga   36060
cagccctacc  ccgggcagca  gccgtatccc  ggccagcagc  cctacccgg   atacggccag   36120 tcgaacagcc  aggccctgac  catcgtcgcc  tacgtcctcg  gcggcttcgg  tctcctgacc   36180 atgacccgc   tcatcggcgt  cgtcggcctg  gtcctggcga  acttcgcgaa  gcgccgtcac   36240
gagcgcaatg  cctcgatcgc  ggtcaagatc  gtcgccggcc  tggtgatcgc  cgctttggtg   36300
ctgagcatcg  tggaccgcat  cgtttaaggc  ctgccctgcc  gatcactcag  ggcggcgact   36360
tctgggcggc  ggggtgtgctc ccctcgccgg  aaaggatgtc  cggttcccgg  gatggtcagt   36420
actgtcggct  catgggcgaa  catttcgatc  ttgtcgtgct  gggcgccggt  ccgggtggat   36480
atgtcgcggc  gatccgcggc  gctcaactgg  gcctgaccac  cgcgatcgtc  gaggacaagt   36540 actgggcgg   cgtctgcctc  aacgtcggct  gcatcccgtc  gaaagcgctg  ctgcgcaacg   36600
cggagctggc  gcacatcttc  caccaccagg  cgcagacctt  cggcatcgag  gggaaggtca   36660
ccttcgactt  cgccgtcgcc  caccagcgca  gccgcagcgt  cgccgacggc  cgcgtcaagg   36720
gcgtgcactt  cctgatgaag  aagaacggga  tcaccgagat  ccaggggcgt  ggcgagttca   36780
ccgacgcgca  cacgctgcgg  gtcggcgacc  ggacggtcac  gttcgacaac  tgcatcctgg   36840
cgaccggcgc  gagcacccgg  atgattcccg  gcacgagcgt  ctcgaagcgg  gtcgtgacgt   36900
acgaggagca  gatcctcgac  cccgacctgc  cggacagcat  cgtgatcgtc  ggcgccggcg   36960
cgatcggcgt  cgagttcgcg  tatgtgctgc  gcaactacgg  cgtcgacgtg  accatcgtgg   37020
agttcctcga  ccgatgctg   ccgctggagg  acgaggaggt  ctccaaggag  ctgctccggc   37080
agtaccgcaa  gctcggcgtc  gacgtgcggg  tcggcacccg  ggtggagggc  atcgaggagg   37140
gcgccgactc  ggtccgcgtc  accgtctcca  agaacgggaa  gaccgaggtc  ctcgaggccg   37200
acaaggtgat  gcaggcgatc  ggcttcaagc  ccaacgtgga  gggctacggg  ctggagacca   37260
ccggcgtcac  ggtgtccgac  cgcggcgcgg  tcgagatcga  cgacttctgc  cgtacgaacg   37320
tgcccggcat  ctacgccatc  ggcgacgtca  ccgcgaagct  gatgctggcg  cacgccgccg   37380
aggcgatggg  catcgtggcg  gccgagacga  tcgccggcgc  cgagacgatg  gccctcgact   37440
accggatgat  cccgcgcgcg  actttctgcc  agccgcaggt  cgccagcttc  gggtggaccg   37500
aggcgcaggc  ccgcgagcag  ggcttcgacg  tcaaggtggc  caagttcccg  ttcaccgcga   37560
acggcaaggc  gcacggcctc  ggcgacgcga  ccgggttcgt  gaagatcctc  agtgacgcga   37620
agtacgggga  gctgctcggc  gcgcaccga   tcgggccgga  cgtgaccgag  ctgctacccg   37680
agctgaccct  ggcccagcag  tgggacctga  ccgtccacga  ggtcgggcgc  aacgtgcacg   37740
cgcatccgac  gctcgccgag  gcggtcaagg  aggcgatcca  cggcctggcc  ggccacatga   37800
tcaacttctg  agtccgccgc  tcggccgacg  ggtccgccgc  tcggccgacg  ggtccgccgc   37860
tcggccgacg  ggtccgctgt  ccggccgacg  agtccgccgc  ccggctgacg  cccggggag    37920 tagccggagc  cgcccgtacc  gcgcctgcgg  tagcccgaat  acctacgcgg  ggatgacgac   37980
tccgccccgc  cggtcgggaa  cgctgagcct  tgtgaccctg  accgtcgagc  ctccgatcgc   38040
cccggcgccg  cccgccgccc  cggggcgatc  ccggcggcgc  aggctgggct  atctggcgtt   38100
cgtgctggtc  gcggtggtgg  cggtggtgac  gctgcgcgac  cggctgccgg  atccggggga   38160
gttcctcgac  gcgctgcgag  cggccgactg  gcggtgggcg  gcgctcgcgg  tggggccgga   38220
ggtgctgtcc  cagatcgcgt  acgccgagca  gcagcgccgg  cttctcgccg  cgttcggagt   38280
gcgcgtgccg  gcccggcggg  cgatcgcgat  gacgtacgtc  cggtcggcgc  tgagcatggc   38340
gctgccggcc  gggtcggcgg  cctccgcggc  gtacgccttc  caggtctatc  gtcgccacgg   38400
```

```
cgccaccgcg gcgatctccg cgacggcgac cctgatctcg acggtcgtga ccgtgatgtc    38460
gctgggcctg ctctacgccg cgacctggtc gctgaccgcc accgtcgtgg ccggcctggc    38520
cgttctcctg ctgtggatct accggaccgt gcggggcccg gtccccgcgc gtgccggcgt    38580
gccgcgccgt ctgagggtcg ccccgatcgc ccgcctgctc cagcggcccg ccgtggccca    38640
ggcgctccgg ggtgcacggt ccgtcccggc cggacgtgg ctcacggtga ccctggccgg    38700
cgtgatcaac tggctgctgg acatggcctg cctgctcctc gcggccgacg cgctgcacgc    38760
cgggctcggc tggagccggc tcgcgctgat ctacctggcc gtccaggtgg tccggcagat    38820
cccgctcacc cccggcggca tcggcctgat cgagaccagc atgctcgccg gcctgatcgc    38880
cgcgggcgcc ccgcaggtca ccgccgccgg gatcgtcctg atctaccggc tgatctcgtt    38940
ctggctgatc ctgcccagcg ggctggccgc ccacctgacc ctgcgccggg ggaccgtgcc    39000
gccggtgact ccgggctgac cgccggggct caggcgcggt cgaactgctg gaggacggcg    39060
ccgaggccga gcgtcagggc cgggccgggc agtcgtgagt ccagcccgta ccgccggccg    39120
gggttctccc gatcgaccag gtcctgccag agcccggtca ccggatcgcc cagccccggc    39180
aggtcgtgcc cggccgcccg gagcagctcg gccaggtcgt tctgctggcg cagccgctgc    39240
tcctcgaaga tctggctcca ctgcatcagc gagatcgacg cctccagtgt gtccggcacc    39300
gtctcgtcca gcatcggcag cggtcgcgcc gcggcccacg ccgcgagctg cgccccggtc    39360
accgtgccgg gatcgtcgtc gcggctgcgc gccagcgcgt acgacagcag cgccgtggtc    39420
tccaccagca ggtgctgcac cgggacgcgc gccggcgggt ccagccacca gtggtccgcc    39480
tcgagcaggg ccgcggcgtg ccgggtcgcc gcccgccacc agccgtcgtc gccgccggcc    39540
agggcgtcgg tgtaggacca caggaaggtc acccttccgt gcctaccagc ggcacttgac    39600
acgagtcaat cacgcgaacg cgtggcgacg accgcgatcg cttcgacgga gatcagcagc    39660
ccgtgcggga gaaccacgcc ggcgggcgcg gaccggggcg gcgggcgggtc gggcatgtgc    39720
cgcgccagca cctggttgat caccgggaag tcctcgacgt gcgtgtagaa gacggtcagc    39780
ttcaccagcc cgtccagccc gtccagcccg gagccggccg ccgccagcac cgccccgagg    39840
ttgcacagcg cctgctcggt ctgcgcctcg atgccgtcca ccggcttccc ggtcgcgggg    39900
tcgatcccgg gcatcccgga gcagaacacg aacccgccgg cgacgatcgc ctggctgtag    39960
ggccccagcg ccgtgggggc ccgctcactc gtcaccgcga tgcgatccat cgggcgagtc    40020
tcccgcaccg ggcatcgatg gtctttcggc tttatgacac gggtgggagc ttgacagccg    40080
tacatcgttt atcgattatc aatatatcga aaaacgataa gggggtacgt cgtgaagacc    40140
gactggttga cggagttcca ccaggtgctg ctggtcgccg cgctgggcgc cggggccgcc    40200
gccgtcctcg ggaccgtcgg gctcgtggtg caggacgagg tcgtcgtccc gggcggcacg    40260
tcggctccgg cgagcgtggt cagcgaccgg agcgtcaccc agctcctgct cgccgtggcg    40320
gccgccgtgc cgacgtacct gctggcgacc gccatgctgg tgctgctgta ccggttggtc    40380
ggcgccgcgc gtcgcgggga tc                                             40402
```

<210> SEQ ID NO 201
<211> LENGTH: 334
<212> TYPE: PRT
<213> ORGANISM: Actinoplanes liguriae

<400> SEQUENCE: 201

Val Arg Leu Arg Ile Gln Arg Arg Leu Ala Asp Glu Leu Gly Pro Thr
1               5                   10                  15

Leu Tyr Thr Thr Gly Gln Ser Glu Asp Leu Asp Ala Arg Val Arg Asp
            20                  25                  30

Ala Leu His Asp Leu Leu Ala Arg Glu Glu Thr Pro Leu Ser Gly Ala
        35                  40                  45

Asp Arg Ala Arg Ile Thr Arg Glu Val Thr Asp Glu Val Leu Gly His
 50                  55                  60

Gly Pro Ile Glu Ser Leu Leu Arg Asp Pro Ser Val Thr Glu Val Met
 65                  70                  75                  80

Val Asn Gly Pro Tyr Ser Val Tyr Val Glu Arg Phe Gly Arg Leu Glu
                85                  90                  95

Lys Val Ala Ala Glu Phe Asp Asp Glu Gln His Leu Arg Ile Ile
            100                 105                 110

Asp Arg Ile Cys Ser Arg Val Gly Arg Arg Val Asp Glu Ala Ser Pro
        115                 120                 125

Thr Val Asp Ala Arg Leu Pro Asp Gly Ser Arg Val Asn Ala Val Val
130                 135                 140

Pro Pro Ile Ala Leu Asp Gly Ser Thr Leu Thr Ile Arg Lys Phe Ala
145                 150                 155                 160

Ala Val Pro Leu Thr Val Gly Asp Leu Leu Gln Tyr Gly Thr Leu Thr
                165                 170                 175

Arg Gln Ala Ala Glu Phe Leu Asp Ala Cys Val Arg Gly Arg Arg Thr
            180                 185                 190

Ile Leu Val Ser Gly Gly Thr Gly Ser Gly Lys Thr Thr Ile Leu Asn
        195                 200                 205

Val Leu Ser Ser Phe Val Pro Ala Asp Glu Arg Ile Val Thr Ile Glu
210                 215                 220

Asp Ala Ala Glu Leu Gln Leu Val Gln Asp His Val Val Arg Leu Glu
225                 230                 235                 240

Ser Arg Pro Pro Asn Ser Glu Gly Arg Gly Thr Ile Thr Thr Arg Asp
                245                 250                 255

Leu Val Arg Asn Ala Leu Arg Met Arg Pro Asp Arg Ile Val Val Gly
            260                 265                 270

Glu Val Arg Asp Ala Ala Ala Leu Asp Met Leu Gln Ala Met Asn Thr
        275                 280                 285

Gly His Asp Gly Ser Leu Thr Thr Leu His Ala Asn Thr Pro Arg Asp
290                 295                 300

Ala Leu Ser Arg Leu Glu Thr Met Val Leu Met Ala Gly Met Asp Leu
305                 310                 315                 320

Pro Ile Arg Ala Ile Arg Asp Gln Ile Ser Ser Ala Val Asp
                325                 330

<210> SEQ ID NO 202
<211> LENGTH: 358
<212> TYPE: PRT
<213> ORGANISM: Actinoplanes liguriae

<400> SEQUENCE: 202

Met Ser Glu Leu Glu Ser Tyr Leu Pro Arg Tyr Pro Glu Thr Leu Leu
1               5                   10                  15

Val Val Ile Gly Ala Val Val Asp Leu Asp Glu Ala Leu Met Phe Thr
            20                  25                  30

Ala Tyr Gln Arg Leu Gln Arg Pro Val Ile Gly Val Val Leu Ile Arg
        35                  40                  45

His Ala Ile Glu Ala Gly Val Val Leu Arg Cys Leu Gln Ser Gly Ile
    50                  55                  60

Arg Asp Leu Val Ala Glu Glu Asp Glu Glu Gly Ile Arg Ser Ala Thr
65                  70                  75                  80

Val Arg Ser Val Asp Leu Ser Lys Ala Leu Ser Thr Thr Met Arg Gly
                85                  90                  95

Thr Gly Asp Asn Ala Pro Tyr Ala Ser Val Val Thr Val Phe Ala Gly
            100                 105                 110

Lys Gly Gly Cys Gly Arg Ser Val Val Ala Val Asn Leu Ala Val Ala
        115                 120                 125

Leu Ala Gly Ala Gly Arg Arg Val Leu Leu Met Asp Leu Asp Leu Gln
    130                 135                 140

Phe Gly Asp Val Ala Ile Met Met Lys Leu Ser Pro Glu Arg Asn Ile
145                 150                 155                 160

Ala Gly Gly Leu Gln Met Ala Gly Arg Leu Asp Glu Pro Gly Leu Arg
                165                 170                 175

Ser Ile Val Thr Thr Tyr Arg Gln Ser Leu Asp Ala Leu Leu Ala Pro
            180                 185                 190

Ala Ser Pro Ala Glu Gly Glu Gln Val Arg Arg Glu Phe Val Val Glu
        195                 200                 205

Leu Leu Asp Val Ala Arg Pro Leu Tyr Asp Phe Ile Val Val Asp Thr
210                 215                 220

Pro Ser Val Val Thr Asp Gln Val Leu Ala Ala Leu Asp Met Ser Asp
225                 230                 235                 240

Trp Phe Ile Pro Ile Val Thr Pro Asp Leu Pro Ala Leu Lys Ser Val
                245                 250                 255

Arg Leu Thr Ala Glu Met Phe Asp Leu Leu Asp Tyr Pro Lys Asp Lys
            260                 265                 270

Arg Leu Leu Val Phe Asn Arg Ala Gly Ala Gln Val Gly Leu Ser Pro
        275                 280                 285

Ser Glu Val Glu Val Ala Ala Gly Met Pro Phe Ala Val Gln Val Pro
    290                 295                 300

Ala Ser Arg Asp Val Thr Val Ser Val Asn His Gly Glu Pro Ile Ala
305                 310                 315                 320

Val Thr Asp Pro Leu His Pro Val Ser Arg Ala Ile Arg Glu Leu Gly
                325                 330                 335

Asp Arg Ile Ala Gly Val Gly Thr Thr Pro Gln Arg Arg Arg Gly Phe
            340                 345                 350

Leu Gly Arg Leu Phe Pro
        355

<210> SEQ ID NO 203
<211> LENGTH: 266
<212> TYPE: PRT
<213> ORGANISM: Actinoplanes liguriae

<400> SEQUENCE: 203

Met Arg Arg Arg Ile Leu Ile Leu Leu Ala Ala Leu Val Leu Ala Gly
1               5                   10                  15

Ile Ser Gly Ala Ala Val Leu Ser Tyr Ala Arg Ser Ala Asp Arg Arg
            20                  25                  30

Ala Leu Ser Gly Arg Glu Gly Thr Trp Ile Leu Val Ala Gly Gln His
        35                  40                  45

Ile Pro Ser Gly Thr Ser Gly Ala Glu Ile Arg Ala Arg Gly Leu Thr
    50                  55                  60

Glu Arg Leu Leu Val Pro Thr Val Thr Val Pro Ala Gly Ala Leu Thr
65                  70                  75                  80

```
Thr Trp Asp Ser Ala Leu Asp Pro Leu Arg Leu Gly Gly Asp Leu Gln
                85                  90                  95

Pro Arg Gln Leu Leu Met Arg Thr Leu Phe Val Pro Ala Ser Pro Ala
            100                 105                 110

Pro Ser His Thr Gly Arg Ile Pro Val Pro Arg Arg Ser Leu Ala Val
        115                 120                 125

Ser Val Ala Leu Asn Val Ala Pro Gln Val Ala Gly Asn Ile Thr Pro
130                 135                 140

Gly Asp Gln Val Ala Val Tyr Tyr Thr Tyr Gln Ala Lys Val Leu Met
145                 150                 155                 160

Ala Glu Asp His Glu Thr Ile Pro Met Thr Leu Leu Leu Pro Lys
                165                 170                 175

Ala Arg Val Ile Thr Ile Gly Glu Ala Glu Pro Gly Gln Ala Pro Val
            180                 185                 190

Thr Pro Ser Pro Ser Pro Thr Pro Gly Pro Ser Ala Ser Ala Gly Asp
        195                 200                 205

Ser Thr Ala Ala Val Lys Glu Ile Gln Arg Tyr Val Val Thr Leu Ala
210                 215                 220

Val Gly Asp Thr Asp Ala Leu Arg Leu Val His Ala Ala Gln Ser Gly
225                 230                 235                 240

Ser Leu Tyr Leu Ala Leu Leu Gly Pro Asn Ala Thr Ala Ser Thr Gly
                245                 250                 255

Pro Ala Ile Asp Thr Ser Trp Val Val Arg
            260                 265

<210> SEQ ID NO 204
<211> LENGTH: 432
<212> TYPE: PRT
<213> ORGANISM: Actinoplanes liguriae

<400> SEQUENCE: 204

Met Arg Arg Leu Ile His Ala Leu Phe Pro Pro Arg Gly Glu His Gly
1               5                   10                  15

Val Ile Thr Ala Leu Val Ala Val Leu Ala Gly Ala Gly Val Leu Leu
            20                  25                  30

Gly Met Ala Ala Leu Val Ile Asp Ile Gly Ala Leu Tyr Ala Glu Arg
        35                  40                  45

Glu Gln Leu Gln Ser Gly Ala Asp Ala Ala Ser Trp Lys Val Ala Gln
50                  55                  60

Ala Cys Ala Gly Thr Ala Gly Arg Asp Leu Thr Ser Ala Thr Cys Thr
65                  70                  75                  80

Val Ala Ala Gln Arg Asp Asn Ala Gln Arg Tyr Ala Asp Arg Asn Ala
                85                  90                  95

Lys Asp Leu Val Ser Asp Val Gln Phe Cys Ile Thr Val Ser Ala
            100                 105                 110

Ala Gly Val Thr Thr Ala Asp Ala Gly Cys Pro Ser Ser Trp Asn Thr
        115                 120                 125

Pro Val Thr Cys Pro Ala Pro Ser Ala Ser Gly Pro Tyr Arg Tyr
130                 135                 140

Val Glu Val Arg Thr Ser Thr Arg Asn Ser Asp Asn Thr Ser Val Val
145                 150                 155                 160

Pro Pro Leu Phe Gly Arg Gly Leu Ala Gly Ser Ala Tyr His Gly Ala
                165                 170                 175

Lys Met Gly Ala Cys Gly Arg Val Ala Trp Gly Ala Pro Ala Val Thr
            180                 185                 190
```

-continued

Asp Val Leu Ala Leu Gly Val Ser Arg Cys Asp Phe Leu Arg Leu Thr
            195                 200                 205

Gly Asp Tyr Thr Arg Phe Phe Ala Pro Pro Pro Thr Gly Pro Asn
    210                 215                 220

Pro Gln Thr Gly Val His Pro Leu Leu Gly Leu Ser Asp Pro Thr Ala
225                 230                 235                 240

Gly Tyr Ile Pro Ile Ser Asp Gly Ile Leu Ala Thr Ser Cys Pro Ala
                245                 250                 255

Asp Ala Gly Glu Thr Val Ala Gly Tyr Thr Trp Leu Gly Gln Pro Asp
            260                 265                 270

Gly Pro Pro Ala Leu Pro Gly Leu Leu Pro Val Ser Ala Pro Asp Ala
        275                 280                 285

Ser Cys Glu Leu Thr Gly Ile Pro Ala Thr Asp Gly Pro Ala Asp Ser
    290                 295                 300

Trp Val Gly Gly Phe Thr Ile Gly Pro Gly Asn Ala Ser Ala Ala Thr
305                 310                 315                 320

Ala Cys Leu Asp Arg Leu Asn Val Leu Ile Thr Ser Gly Gln Pro Val
                325                 330                 335

Leu Val Pro Ile Phe Asp Arg Gln Val Ala Val Ile Gly Thr Leu Pro
            340                 345                 350

Ser Tyr Tyr Arg Ile Ala Gly Phe Ala Pro Leu Val Leu Thr Gly Tyr
        355                 360                 365

Glu Ser Pro Val Ser Gly Pro Val Ser Gly Ser Ala Val Pro Ser
    370                 375                 380

Leu Val Pro Gly Ala Gln Arg Ala Leu Cys Ala Ala Gln Ser Cys Leu
385                 390                 395                 400

Tyr Gly Tyr Phe Thr Arg Ala Leu Val Thr Asp His Val Pro Thr Arg
                405                 410                 415

Phe Ala Thr Ser Arg Tyr Tyr Gly Ala Met Val Ile Gly Arg Thr Gly
            420                 425                 430

<210> SEQ ID NO 205
<211> LENGTH: 136
<212> TYPE: PRT
<213> ORGANISM: Actinoplanes liguriae

<400> SEQUENCE: 205

Met Trp Lys Ala Thr Glu Arg Gln Gly Pro Val Val Leu Leu Val Glu
1               5                   10                  15

Asp Asp Glu Asp Leu Arg Glu Leu Ala Ala Gln Met Leu Glu Met Arg
            20                  25                  30

Gly Phe Val Val Leu Val Ala Lys Asp Pro Val Ser Ala Ile Met Thr
        35                  40                  45

Cys Arg Val His Ser Gly Ala Ile Asp Val Leu Leu Thr Asp Leu Gly
    50                  55                  60

Leu Pro Gly Val Ser Gly Gly Leu Ala Arg Ser Ala Ser Glu Val
65                  70                  75                  80

Arg Pro Gly Met Lys Ile Val Tyr Val Ser Gly Val Pro Glu Glu Ile
                85                  90                  95

Ala Ile Lys Lys Gly Leu Ile Arg Ala Gly Ser Pro Phe Val Ala Lys
            100                 105                 110

Pro Tyr Thr Ala Asp Arg Leu Ala Gly Met Leu Arg Thr Val Leu Ala
        115                 120                 125

Gln Gly Ala Glu Ser Ser Ala Arg
    130                 135

<210> SEQ ID NO 206
<211> LENGTH: 363
<212> TYPE: PRT
<213> ORGANISM: Actinoplanes liguriae

<400> SEQUENCE: 206

```
Met Phe Asn Tyr Val Ser Phe Val Arg Pro Lys Thr Phe Ala Ala Thr
1               5                   10                  15

Phe Ala Ala Ala Leu Leu Leu Gly Ser Gly Ala Cys Ala Lys Ser
            20                  25                  30

Glu Asp Ser Gly Asp Thr Val Ala Ala Gly Pro Ala Pro Ser Ala Ala
            35                  40                  45

Gln Val Val Gln Ser Ala Ser Ala Gly Ser Ala Thr Cys Ala Leu Asp
        50                  55                  60

Gln Tyr Gly Ala Ser Lys Leu Asp Leu Lys Thr Ala Ser Val Gly Phe
65                  70                  75                  80

Ser Gln Ser Glu Lys Glu Ala Asn Pro Phe Arg Ile Ala Glu Thr Lys
                85                  90                  95

Ser Ile Lys Asp Glu Ala Ala Lys Leu Gly Ile Thr Asn Leu Lys Thr
            100                 105                 110

Ser Asn Ala Asn Ser Gln Phe Asn Lys Gln Ile Ala Asp Val Glu Gln
        115                 120                 125

Met Ile Asp Ala Gly Val Gln Leu Leu Val Ile Ala Pro Leu Asn Ser
    130                 135                 140

Asp Gly Trp Asp Ser Val Phe Ala Lys Ala Thr Ala Lys His Ile Pro
145                 150                 155                 160

Ile Ile Thr Ile Asp Arg Lys Ile Asn Ala Thr Ala Cys Lys Asp Tyr
                165                 170                 175

Leu Thr Phe Ile Gly Ser Asp Phe Ala Glu Gln Gly Lys Arg Ala Ala
            180                 185                 190

Asp Ala Leu Ala Lys Ser Leu Gly Asn Lys Gly Glu Val Ala Ile Leu
        195                 200                 205

Leu Gly Ala Pro Gly Asn Asn Val Thr Thr Leu Arg Thr Ser Gly Phe
    210                 215                 220

Lys Asp Glu Ile Ala Lys Val Ala Pro Asp Ile Lys Ile Thr Phe Glu
225                 230                 235                 240

Gln Thr Gly Asn Phe Ser Arg Glu Asp Gly Lys Val Ala Glu Gln
                245                 250                 255

Leu Leu Gln Ser Lys Pro Asn Ile Asn Gly Ile Tyr Gly Glu Asn Asp
            260                 265                 270

Glu Met Ala Leu Gly Ala Ile Thr Ala Leu Lys Gly Ala Gly Lys Lys
        275                 280                 285

Ala Gly Asp Val Lys Ile Val Ser Ile Asp Gly Thr Lys Gly Ala Val
    290                 295                 300

Gln Gly Ile Val Asp Gly Trp Val Ser Ala Val Ile Glu Ser Asn Pro
305                 310                 315                 320

Arg Phe Gly Pro Leu Ala Phe Asp Thr Ala Thr Lys Phe Phe Gly Gly
                325                 330                 335

Glu Pro Val Gly Gln Asp Ile Val Ile Gln Asp Arg Ala Tyr Asp Glu
            340                 345                 350

Ser Asn Ala Lys Thr Asp Ile Gly Ser Ala Tyr
        355                 360
```

<210> SEQ ID NO 207
<211> LENGTH: 501

<212> TYPE: PRT
<213> ORGANISM: Actinoplanes liguriae

<400> SEQUENCE: 207

```
Met Leu Leu Glu Val Ser Gly Val Ser Lys Thr Phe Pro Gly Val Arg
1               5                   10                  15

Ala Leu Asp Gly Val Ser Phe Thr Leu Asn Pro Gly Glu Val His Ala
            20                  25                  30

Leu Val Gly Glu Asn Gly Ala Gly Lys Ser Thr Leu Ile Lys Val Leu
        35                  40                  45

Thr Gly Val Tyr Gln Pro Asp Ser Gly Glu Leu Arg Tyr Arg Gly Glu
    50                  55                  60

Pro Ala Arg Phe Ala Thr Pro Leu Asp Ala Gln Arg Ala Gly Ile Ser
65                  70                  75                  80

Thr Ile Tyr Gln Glu Val Asn Leu Val Pro Leu Met Ser Val Ala His
                85                  90                  95

Asn Leu Phe Leu Gly Arg Glu Pro Arg Asn Arg Phe Gly Leu Leu Asp
            100                 105                 110

Glu Ala Arg Met Val Ala Glu Ala Thr Glu Ile Leu Ala Gly Tyr Gly
        115                 120                 125

Val Arg Thr Asp Val Arg Arg Leu Gly Thr Leu Ala Leu Gly Ala
    130                 135                 140

Gln Gln Met Val Ala Leu Ala Arg Ala Val Met Val Asp Ala Arg Val
145                 150                 155                 160

Val Val Met Asp Glu Pro Thr Ser Ser Leu Glu Pro Arg Glu Val Glu
                165                 170                 175

Thr Leu Phe Gly Val Ile Arg Glu Leu His Thr Ala Gly Ile Gly Ile
            180                 185                 190

Val Tyr Val Ser His Arg Leu Asp Glu Leu Tyr Arg Val Cys Asp Ala
        195                 200                 205

Val Thr Ile Leu Arg Asp Gly Lys Leu Val His Thr Gly Arg Met Ala
    210                 215                 220

Asp Leu Asp Arg Arg Thr Leu Val Ser Leu Met Leu Gly Arg Glu Phe
225                 230                 235                 240

Gly Ala Asp Phe Thr Ser Phe Ser Glu Ser Pro Gln Ser Thr Pro Glu
                245                 250                 255

Gly Glu Pro Val Leu Arg Val Ser Gly Leu Thr Ser Arg Pro Arg Leu
            260                 265                 270

Asp Asp Ile Ser Phe Asp Val Arg Pro Gly Glu Val Val Gly Leu Gly
        275                 280                 285

Gly Leu Leu Gly Ala Gly Arg Ser Glu Thr Ile Lys Ala Ile Gly Gly
    290                 295                 300

Ala Tyr Pro Ile Asp Ser Gly Val Ile Glu Val Gly Gly Val Arg Leu
305                 310                 315                 320

Gly Arg Pro Ser Thr Val Arg Ala Val Arg Ala Gly Val Ala Thr Gln
                325                 330                 335

Pro Glu Asp Arg Lys Ala Glu Gly Ile Val Pro Gly Leu Ser Ile Arg
            340                 345                 350

Asp Asn Ile Ala Leu Ala Ile Leu Pro Arg Met Ala Arg Phe Gly Leu
        355                 360                 365

Val Ser Asp Lys Arg Ile Asp Ser Ile Val Ala Thr Tyr Met Ser Arg
    370                 375                 380

Leu Arg Ile Lys Ala Ser Gly Pro Asp Gln Ala Val Gly Asp Leu Ser
385                 390                 395                 400
```

```
Gly Gly Asn Gln Gln Lys Val Leu Leu Ala Arg Leu Leu Ala Thr Gly
                405                 410                 415
Pro Lys Val Leu Leu Asp Glu Pro Thr Arg Gly Ile Asp Val Gly
        420                 425                 430
Ala Lys Ala Glu Val Gln Ala Leu Ile Asp Glu Leu Ala Lys Glu Gly
            435                 440                 445
Leu Gly Val Val Leu Val Ser Ser Asp Ala Glu Leu Val Glu Gly
    450                 455                 460
Ala Asp Arg Val Val Leu Arg Asp Gly Ala Val Val Gly Thr Leu
465                 470                 475                 480
Thr Gly Asp Arg Val Thr Thr Glu Ala Leu Met Ala Thr Ile Ala Glu
            485                 490                 495
Ala Ala Asp Glu His
            500
```

<210> SEQ ID NO 208
<211> LENGTH: 319
<212> TYPE: PRT
<213> ORGANISM: Actinoplanes liguriae

<400> SEQUENCE: 208

```
Met Ser Thr Glu Thr Leu Thr Arg Pro Arg Met Thr Phe Asn Pro Ala
1               5                   10                  15
Trp Ala Ala Arg Tyr Gly Val Tyr Ala Ala Ile Val Leu Leu Ile Val
                20                  25                  30
Val Asn Ile Ala Phe Thr Pro Tyr Phe Leu Thr Leu Ser Asn Leu Arg
            35                  40                  45
Ile Gln Leu Ile Gln Ala Ala Pro Val Val Ile Val Ala Leu Gly Met
        50                  55                  60
Ala Leu Val Ile Gly Thr Glu Gly Ile Asp Leu Ser Val Gly Ser Val
65                  70                  75                  80
Met Ala Leu Ala Ala Ala Phe Ile Pro Leu Tyr Leu Gly Tyr Gly Val
                85                  90                  95
Thr Ala Ala Ile Leu Val Ser Leu Leu Ala Gly Val Ala Val Gly Leu
            100                 105                 110
Ile Asn Gly Val Leu Val Ala Lys Ala Gly Leu Gln Pro Ile Val Ala
        115                 120                 125
Thr Leu Ala Leu Phe Val Gly Gly Arg Gly Leu Ala Val Val Ile Ser
    130                 135                 140
Gly Gly Gln Leu Lys Asp Val Arg Asn Ala Asp Leu Leu Tyr Leu Gly
145                 150                 155                 160
Ser Gly Asp Leu Leu Gly Val Pro Val Leu Val Trp Ile Ala Ala Leu
                165                 170                 175
Leu Val Leu Val Val Ala Phe Val Val Arg Arg Thr Val Phe Gly Arg
            180                 185                 190
Arg Leu Leu Ala Val Gly Gly Asn Arg Pro Ala Ala Glu Leu Ala Gly
        195                 200                 205
Leu Pro Val Lys Arg Val Leu Ile Gly Val Tyr Val Phe Cys Ala Val
    210                 215                 220
Leu Ala Ser Ile Ala Gly Leu Leu Ser Val Ala Arg Ile Gln Ser Ser
225                 230                 235                 240
Asp Ala Ser Ala Val Gly Leu Leu Ile Glu Leu Ser Ala Ile Thr Ala
                245                 250                 255
Val Val Val Gly Gly Thr Pro Leu Thr Gly Gly Arg Val Arg Val Leu
            260                 265                 270
```

```
Gly Thr Val Ala Gly Ala Leu Leu Met Gln Leu Val Ala Thr Met
        275                 280                 285

Ile Lys His Asp Leu Pro Pro Ser Thr Thr Glu Met Val Gln Ala Val
290                 295                 300

Ile Ile Leu Val Ala Val Tyr Val Ala Arg Glu Arg Arg Thr Arg
305                 310                 315

<210> SEQ ID NO 209
<211> LENGTH: 320
<212> TYPE: PRT
<213> ORGANISM: Actinoplanes liguriae

<400> SEQUENCE: 209

Met Ser Ile Pro Val Pro Ala Phe Arg Asn Gly Gly Phe Val Gln Arg
1               5                   10                  15

Gln Gly Ala Leu Ala Val Leu Val Thr Val Val Ala Ile Ser Leu Ala
            20                  25                  30

Ala Phe Pro Gly Phe Arg Ser Ala Asp Asn Ala Gly Thr Ile Leu Val
        35                  40                  45

Ala Ala Ala Pro Pro Met Leu Ile Ala Leu Gly Met Thr Phe Val Ile
50                  55                  60

Ile Thr Gly Gly Ile Asp Leu Ser Val Gly Ser Leu Tyr Val Leu Gly
65                  70                  75                  80

Gly Val Ala Ala Trp Ala Ser Gln Trp Gly Val Val Ala Ala Leu
                85                  90                  95

Ala Ala Pro Leu Leu Leu Cys Gly Ala Ile Gly Val Leu Asn Gly Ile
            100                 105                 110

Leu Ile Ser Arg Thr Gly Met Ala Pro Phe Ile Val Thr Leu Ala Ala
        115                 120                 125

Leu Leu Gly Ala Arg Gly Leu Met Arg Ser Ile Ser Asp Glu Gly Ser
130                 135                 140

Thr Thr Tyr Leu Val Arg Ser Asp Val Phe His Glu Leu Gly Thr Gly
145                 150                 155                 160

Ser Leu Leu Gly Val Gly Leu Pro Val Trp Leu Ala Ala Val Leu Val
                165                 170                 175

Gly Ala Gly Ile Leu Val Leu Asn Arg Thr Arg Phe Gly His Ala Val
            180                 185                 190

His Ala Ile Gly Gly Ser Glu Asp Ala Ala Ala Leu Met Gly Leu Pro
        195                 200                 205

Val Arg Arg Ile Lys Val Trp Val Tyr Leu Leu Ser Gly Leu Leu Ala
210                 215                 220

Gly Leu Ala Gly Ala Ile Asn Ala Ala Lys Leu Gly Ser Gly Val Thr
225                 230                 235                 240

Val Leu Gly Ser Gly Met Glu Leu Asp Ala Ile Ala Ala Val Val Ile
                245                 250                 255

Gly Gly Thr Leu Leu Thr Gly Gly Ser Gly Ser Ile Ala Gly Thr Val
            260                 265                 270

Ala Gly Val Leu Leu Leu Gly Val Ile Gln Asn Leu Ile Asn Gln Val
        275                 280                 285

Gly Asn Val Asn Ser Asn Trp Gln Gln Val Ile Ser Gly Gly Phe Leu
290                 295                 300

Ala Ala Val Val Val Ala Gln Thr Thr Leu Val Arg Ala Arg Arg Ser
305                 310                 315                 320

<210> SEQ ID NO 210
<211> LENGTH: 486
```

```
<212> TYPE: PRT
<213> ORGANISM: Actinoplanes liguriae

<400> SEQUENCE: 210

Met Arg Thr Ser Ala Gly Thr Arg Val Leu Thr Val Gly Ala Thr Val
1               5                   10                  15

Val Leu Ala Leu Ala Ala Ala Ala Pro Ala Gln Ala Gly Pro Ser
            20                  25                  30

Pro Ser Pro Gly Ser Ala Gly Leu Gly Asp Arg Leu Tyr Pro Leu Leu
            35                  40                  45

Gly Asn Gly Gly Tyr Asp Val Leu Asp Tyr Asp Leu Arg Leu Arg Tyr
    50                  55                  60

Pro Glu Lys Asp Pro Lys Gln Val Val Ser Gly Asp Val Thr Ile Thr
65              70                  75                  80

Ala Val Ala Gly Gln Ser Leu Ser Arg Phe Asp Leu Asp Phe Gly Gly
                85                  90                  95

Ala Ser Ile Gly Arg Val Ser Val Asp Gly Gln Pro Arg Ala Ala
            100                 105                 110

Arg Asp Gly Asp Glu Leu Thr Val Ile Pro Arg Arg Pro Leu Pro Arg
            115                 120                 125

Gly Arg Leu Phe Arg Val Thr Val Ala Asn Phe Thr Ala Ala Pro Ala
    130                 135                 140

Ala Leu Val Ala Thr Pro Asp Gly Thr Val Leu Ala Ala Gln Pro Gly
145             150                 155                 160

Ser Ala His Leu Leu Phe Pro Gly Asn Asp His Pro Arg Asp Lys Ala
                165                 170                 175

Thr Phe Thr Ile Thr Leu Thr Val Pro Ala Gly Trp Thr Gly Thr Ala
            180                 185                 190

Asn Gly Thr Leu Val Ser Thr Thr Glu His Asp Gly His Val Ser Ser
    195                 200                 205

Val Tyr Arg Glu Ser Ala Pro Met Ala Thr Glu Leu Val Gln Thr Ala
210                 215                 220

Val Gly Asp Phe Val Val Glu Arg Arg Pro Ala Ala Gly Gly Thr Pro
225             230                 235                 240

Ile Arg Asp Val Val Pro Arg Arg Leu Ala Gly Thr Leu Pro Ala
            245                 250                 255

Ile Ala Gly Glu Arg Glu Gln Leu Ala Trp Met Glu Lys Gln Ala Gly
            260                 265                 270

Pro Tyr Pro Phe Glu Asp Tyr Gly Ser Leu Val Ile Asp Asp Asp Leu
    275                 280                 285

Gly Tyr Ala Leu Glu Thr Gln Thr Leu Ser Leu Tyr Gly Ala Ala Leu
    290                 295                 300

Phe Thr Gly Pro Glu Thr Thr Arg Gly Pro Ser Met Thr His Glu Leu
305             310                 315                 320

Ala His Gln Trp Phe Gly Asp Ser Val Ser Pro Phe Ser Trp Ser Asp
                325                 330                 335

Val Trp Leu Asn Glu Gly His Ala Thr Trp Tyr Glu Met Leu Trp Ser
            340                 345                 350

Glu Glu Thr Gly Gly Phe Pro Gln Tyr Thr Gly Leu Ala Asp Arg Glu
        355                 360                 365

Ala Phe Phe Lys Ala Val Tyr Ala Ala Gly Asp Ile Phe Arg Ala Arg
    370                 375                 380

Tyr Gly Pro Val Ala Ala Pro Leu Asp Ala Ala Thr Thr Trp Asp Val
385                 390                 395                 400
```

```
Phe Asn Pro Asn Val Tyr Ala Gly Gly Ala Leu Val Leu Tyr Ala Leu
                405                 410                 415

Arg Gln Lys Ile Gly Ala Ala Thr Phe Gln Arg Val Glu Arg Ala Trp
            420                 425                 430

Leu Thr Thr Tyr Arg Gly Arg Ser Ala Ser Thr Gly Asp Phe Ile Thr
        435                 440                 445

Leu Ala Ser Arg Val Ala Arg Gln Asp Leu Arg Pro Phe Leu Thr Ser
    450                 455                 460

Trp Leu Leu Gly Val Thr Thr Pro Pro Met Pro Asn His Pro Asp Trp
465                 470                 475                 480

Val Val Thr Pro Gly Ser
                485

<210> SEQ ID NO 211
<211> LENGTH: 286
<212> TYPE: PRT
<213> ORGANISM: Actinoplanes liguriae

<400> SEQUENCE: 211

Met Asp Ser Pro Arg Leu Asn Gly Glu Asp Pro Arg His Thr Glu Val
1               5                   10                  15

Leu Ala Gly Phe Gly Ala Glu Leu Pro Pro Ile Val Val His Arg Ala
            20                  25                  30

Thr Met Arg Val Ile Asp Gly Ala His Arg Leu Ser Ala Ala Arg Leu
        35                  40                  45

Arg Gly Asp Asp Arg Ile Arg Ala Val Leu Phe Asp Gly Thr Glu Gln
    50                  55                  60

Glu Ala Tyr Val Leu Ser Val Lys Ala Asn Val Thr His Gly Leu Pro
65                  70                  75                  80

Leu Ser Ala Ala Glu Arg Thr Arg Ala Ala Glu Arg Ile Ile Thr Met
                85                  90                  95

His Pro Asp Trp Ser Asp Arg Met Ile Ala Ala Ser Ser Gly Leu Gly
            100                 105                 110

Ala Arg Thr Val Gly Gly Leu Arg Arg Arg Ala Ala Ser Gly Glu
        115                 120                 125

Ser Pro Ala Gly Leu Arg Ser Arg Ala Gly Arg Asp Ser Arg Val Arg
    130                 135                 140

Pro Ala Gly Ser Thr Ala Gly Arg Leu Lys Ala Val Asp Tyr Leu Gln
145                 150                 155                 160

Asp Arg Pro Asp Ala Ser Leu Arg Glu Ile Ala Arg His Ala Gly Val
                165                 170                 175

Ser Pro Ser Thr Ala Arg Asp Val Arg Asp Arg Leu His Arg Gly Glu
            180                 185                 190

Asp Pro Ile Pro Ala Thr Gln Arg Ala Ala Ala Arg Pro Gly Asn Asp
        195                 200                 205

Ser Pro Pro Leu Arg Ser Leu Val Gln Gly Leu Ala Ser Asp Pro Ser
    210                 215                 220

Leu Arg Phe Ser Glu Ser Gly Arg Asp Leu Leu Arg Trp Leu Ile Ala
225                 230                 235                 240

His Ala Val Gln Asp Gly Glu Trp Lys Gly Leu Val Asp Thr Ile Pro
                245                 250                 255

Ala His Ser Ala Gln Ala Leu Ala Lys Ile Ala Arg His Cys Ser Arg
            260                 265                 270

Glu Trp Arg Glu Phe Ala Asp Ile Leu Glu Lys Asp Ala Ala
        275                 280                 285
```

<210> SEQ ID NO 212
<211> LENGTH: 64
<212> TYPE: PRT
<213> ORGANISM: Actinoplanes liguriae

<400> SEQUENCE: 212

Met Ser Ala Ile Thr Val Glu Thr Thr Trp Lys Asn Thr Asp Leu Arg
1               5                   10                  15

Glu Asp Leu Thr Ala His Pro Ala Gly Leu Gly Phe Gly Glu Leu Ser
            20                  25                  30

Phe Glu Asp Leu Arg Glu Asp Arg Thr Ile Tyr Ala Ala Ser Ser Gly
        35                  40                  45

Trp Val Cys Thr Leu Thr Ile Glu Cys Gly Thr Leu Val Cys Ala Cys
    50                  55                  60

<210> SEQ ID NO 213
<211> LENGTH: 1046
<212> TYPE: PRT
<213> ORGANISM: Actinoplanes liguriae

<400> SEQUENCE: 213

Met Ser Ser Phe Ala Ile Ala Ala Ser Pro Ala Ser Ala Tyr Leu His
1               5                   10                  15

Glu Arg Ser Ala Gly Pro Gly Gly Asp Pro Val Ala Glu His Glu Arg
            20                  25                  30

Val Glu Ser Trp Arg Glu Ser Ala Phe Leu Asp Asp Pro Val Leu Asp
        35                  40                  45

Ile Arg Leu Arg Glu Leu Gly Leu Ser Arg Ala Glu Phe Gly Arg Leu
    50                  55                  60

Leu Thr Asp Gly Ala Tyr Asp Ala Gly Ser Thr Ala Leu Asp Trp Ala
65                  70                  75                  80

Gly Glu Leu Ala Ala Val Leu Ala Thr Gly Thr Gly Ala Val Thr Gly
                85                  90                  95

Leu Ala Arg Ser Thr Lys Leu Trp Ala Gln Gly Phe Asp Arg Leu Pro
            100                 105                 110

Phe Ala Gly Leu Ile Glu Arg Phe Leu Ala Tyr Tyr Glu Pro Arg Val
        115                 120                 125

Pro Arg Thr Ala Gly Thr Val Arg Val Ser Leu Leu Glu Ser Leu Ala
    130                 135                 140

Asn Arg Leu Leu Thr Val Ala Thr Arg Thr Leu Leu Leu Glu Leu Asn
145                 150                 155                 160

Val Ala Arg Val His Gly Arg Leu Thr Gly Ala Thr Pro Gly Glu Arg
                165                 170                 175

Tyr Asp His Tyr Asp Arg Val Leu Leu Thr Asp Pro Asp Tyr Leu Arg
            180                 185                 190

Ser Leu Phe Gly Glu Tyr Pro Val Leu Gly Arg Ala Met Val Glu Cys
        195                 200                 205

Gly Arg Arg Trp Ala Ser Ala Met Ala Glu Leu Phe Gln Arg Leu Asp
    210                 215                 220

Ala Asp Arg Pro Ala Leu His Ala Gly Leu Leu Pro Ala Gly Ala
225                 230                 235                 240

Gly Glu Val Thr Ala Leu Arg Pro Asp Leu Gly Asp Pro His Asn Ser
                245                 250                 255

Gly Arg Ala Val Ala Ile Leu Thr Phe Arg Ser Gly Ala Gln Leu Val
            260                 265                 270

Tyr Lys Pro Arg Pro Val Gly Pro Glu Arg Ala Tyr Ala Glu Thr Ala

```
                275                 280                 285
Ala Ala Leu Asn Arg His Gly Leu Ser Leu Pro Leu Thr Ala Val Asp
290                 295                 300

Val Leu Asp Arg Gly Ala Tyr Gly Trp Cys Glu Leu Val Arg His Glu
305                 310                 315                 320

Pro Cys Ala Asp Arg Ala Asp Leu Asp Arg Phe Tyr Arg Arg Thr Gly
                325                 330                 335

Ala Val Leu Ala Thr Thr Leu Leu Leu Gly Ala Val Asp Val His Met
                340                 345                 350

Glu Asn Val Ile Ala Ala Gly Ser Ser Cys Met Pro Ile Asp Leu Glu
                355                 360                 365

Thr Leu Leu Gln Pro Gly Val Pro Ser Gly Asp Ala Thr Asp Ala Tyr
370                 375                 380

Thr Arg Ala Leu Asp Leu Leu Asn Gln Ser Val Leu Ala Ile Gly Ile
385                 390                 395                 400

Leu Pro Ala Arg Ala Phe Gly Gly Arg Glu Arg Lys Ser Val Asp Val
                405                 410                 415

Ser Ala Ile Gly Gly Gly Glu Ala Gln Thr Ala Pro Arg Pro Val Pro
                420                 425                 430

Met Val Val Glu Pro Phe Thr Asp Val Ala Arg Ile Glu Ala Val Glu
                435                 440                 445

Ala Thr Met Leu Gly Ala Gln Asn Arg Pro Val Leu Val Gly Ala Glu
                450                 455                 460

Val Arg Pro Glu Glu His Thr Glu Ala Val Val Ala Gly Phe Thr Glu
465                 470                 475                 480

Ala Tyr Asp Leu Ile Val Arg His Arg Glu Asp Phe Ala Asp Leu Leu
                485                 490                 495

Ala Gly Phe Gly Asp Val Glu Val Arg Tyr Leu Pro Arg Pro Thr Arg
                500                 505                 510

Arg Tyr Ser Met Phe Leu Thr Glu Ser Tyr His Pro Asp Tyr Leu Arg
                515                 520                 525

Asp Ala Arg Asp Arg Asp Arg Leu Leu Asp Lys Leu Trp Thr Ala Ala
530                 535                 540

Gly Ala Arg Pro Asp Leu Ile Pro Ile Ile Glu Ser Glu Lys Arg Gln
545                 550                 555                 560

Leu Leu Ala Gly Asp Ile Pro Cys Phe Arg Ala Leu Ala Gly Asp Arg
                565                 570                 575

Ala Ile Arg Thr Ala Ser Ala Pro Val Ala Pro Asp Phe Phe Asp Ala
                580                 585                 590

Pro Gly Ile Glu Val Leu Ala Gly Arg Leu Arg Gln Phe Gly Pro Val
                595                 600                 605

His Arg Ala Ala Gln Leu Arg Ile Ile Arg Glu Ser Met Gly Thr Met
                610                 615                 620

Pro Ala Pro Gly Pro Ile Ala Gly Thr Pro Ala Pro Ser Ser Glu Arg
625                 630                 635                 640

Arg Gly Gly Leu Asp Pro Arg Glu Ala Ala Thr Leu Gly Asp Arg Leu
                645                 650                 655

Val Arg Glu Leu Ala Asp Glu Ala Ile Leu Gly Ala Asp Asp Ala Gly
                660                 665                 670

Trp Ile Gly Val Ser Ile Glu Gly Leu Asp Gln Glu Thr Phe Ser Tyr
                675                 680                 685

Lys Pro Met Ala Thr Gly Leu Tyr Asp Gly Ile Ala Gly Met Ala Leu
690                 695                 700
```

Thr Tyr Ala Tyr Ala Ala Arg Thr Leu Gly Asp Glu Arg Tyr Leu Asp
705                 710                 715                 720

Leu Thr Arg Arg Thr Val Lys Leu Val Ser Gly Tyr Leu Arg Tyr Leu
                725                 730                 735

Ala Glu His Arg Ile Val Glu Thr Val Gly Ala Tyr Ser Gly Met Ala
            740                 745                 750

Gly Leu Leu Tyr Thr Leu Asp His Val Ala His Ala Thr Gly Asp Ala
        755                 760                 765

Ser Leu Leu Gly Glu Ile Glu Ala Ala Leu Pro Trp Leu Arg Glu Cys
770                 775                 780

Ala Thr Arg Glu Glu Cys Pro Asp Leu Ile Ala Gly Leu Ala Gly Cys
785                 790                 795                 800

Ala Val Val Ala Leu Ser Leu Tyr Arg Arg His Gly Ile Ala Gly Tyr
                805                 810                 815

Arg Glu Val Ala Glu Ile Cys Gly Arg Leu Ala Gly Thr Ala Val
            820                 825                 830

Asp Val Glu Gly Ala Ala Gly Trp Ala Ala Thr Arg Thr Gly Val Ile
            835                 840                 845

Leu Gly Gly Phe Ser His Gly Ser Ala Gly Ile Ala Trp Ala Leu His
850                 855                 860

Glu Leu Ala Ala Glu Phe Gly Asp Arg Asp Leu Arg Glu Leu Ala Asp
865                 870                 875                 880

Arg Ala Val Glu Phe Asp Arg Arg Leu Tyr Val Pro Ala Ala Gly Ala
                885                 890                 895

Trp Arg Asp Leu Arg Pro Glu Met Ala Gly Thr Asp Gly Tyr Pro Ala
            900                 905                 910

Leu Trp Cys His Gly Ala Ala Gly Ile Gly Leu Ser Arg Leu Leu Ile
        915                 920                 925

His Arg Ile Arg Pro Asp Glu Arg Leu Ala Glu Glu Ala Arg Ala Ala
    930                 935                 940

Val Ala Leu Val Arg Arg His Gly Phe Gly His Asn His Ser Leu Cys
945                 950                 955                 960

His Gly Asp Phe Gly Ala Leu Ala Leu Leu Gly Leu Ala Asp Arg Ala
                965                 970                 975

Trp Pro Gly Ser Gly His Asp Glu Arg Ala Gly Ala Val Val Arg
            980                 985                 990

Asp Ile Gly Glu Thr Gly Leu Arg  Cys Gly Leu Gly Asn  Gly Ile Arg
            995                 1000                 1005

Met Pro  Gly Leu Met Leu Gly  Ala Ala Gly Ala Gly  Leu Ser Leu
    1010                 1015                 1020

Leu Arg  Leu Ala Ala Pro Ala  Asp Val Pro Ala Val  Thr Trp Leu
    1025                 1030                 1035

Glu Pro  Pro Arg Gly Thr His  Val
    1040                 1045

<210> SEQ ID NO 214
<211> LENGTH: 575
<212> TYPE: PRT
<213> ORGANISM: Actinoplanes liguriae

<400> SEQUENCE: 214

Met Ser Glu Thr Ala Gly Leu Leu Arg Arg Ser Leu Leu Asp His Arg
1               5                   10                  15

Gly Lys Leu Ala Ala Val Ala Gly Leu Ala Val Ala Gly Val Gly Cys
            20                  25                  30

```
Gln Leu Gly Gln Pro Phe Leu Ile Arg Arg Val Leu Thr Ala Val Gln
        35                  40                  45

Ser Ala Gln Pro Tyr Arg Gln Leu Ala Leu Ala Val Leu Ala Val Met
 50                  55                  60

Val Val Gly Ala Leu Gly Ala Val Gln Gln Phe Leu Leu Gln Arg
 65                  70                  75                  80

Thr Gly Glu Ala Met Val Phe Thr Val Arg Arg Thr Leu Val Ala His
                 85                  90                  95

Leu Leu Arg Leu Pro Val Ala Ala Tyr Asp Glu Arg Gln Ser Gly Asp
                100                 105                 110

Leu Val Ser Arg Val Gly Ala Asp Thr Ala Gln Val Arg Ser Val Ile
                115                 120                 125

Thr Ser Gly Val Val Asp Leu Ala Gly Gly Val Leu Leu Val Gly Gly
        130                 135                 140

Ser Ile Ala Gly Met Ile Ile Asp Pro Val Leu Leu Gly Val Ser
145                 150                 155                 160

Leu Ala Pro Val Leu Cys Gly Ala Ala Gly Val Arg Leu Val Gly Arg
                165                 170                 175

Arg Leu Arg Pro Leu Ser Ser Ala Val Gln Glu Ser Ile Gly Ala Leu
                180                 185                 190

Thr Ala Ser Thr Thr Arg Ala Leu Gly Ala Ile Arg Thr Ile Arg Val
                195                 200                 205

Ala Gly Ala Thr Glu Arg Glu Thr Ala Leu Ile Val Ala Glu Ala Asp
                210                 215                 220

Arg Ala Arg Ala Ala Gly Val Arg Leu Ala Leu Val Ala Ala Gln Ala
225                 230                 235                 240

Gly Pro Ile Val Arg Leu Ala Leu Gln Gly Ala Phe Val Ala Val Ile
                245                 250                 255

Gly Phe Gly Gly Tyr Arg Val Ala Asn Gly Ala Val Ser Val Gly Asp
                260                 265                 270

Leu Val Ala Phe Thr Leu Leu Phe Thr Leu Ala Leu Pro Leu Ala
                275                 280                 285

Gln Leu Ala Glu Ala Ala Thr Arg Ile Gln Thr Gly Leu Gly Ala Leu
                290                 295                 300

Thr Arg Ile Glu Glu Ile Leu Ala Leu Pro Asp Glu Asp Ser Ala Leu
305                 310                 315                 320

Gly Val Arg Ala Arg Thr Pro Ala Thr Val Arg His Asp Pro Val Leu
                325                 330                 335

Leu Glu Phe Asp His Val Ser Phe Arg Tyr Pro Thr Gly Gly Glu Ile
                340                 345                 350

Leu Arg Asp Val Ser Phe Arg Val Pro Ala Gly Ser Thr Thr Ala Leu
                355                 360                 365

Val Gly Pro Ser Gly Ala Gly Lys Ser Thr Ile Leu Ala Leu Ile Ala
        370                 375                 380

Arg Leu Tyr Glu Val His Gly Gly Arg Ile Leu Leu His Gly Arg Asp
385                 390                 395                 400

Ile Arg Asp Tyr Pro Leu Ala Glu Leu Arg Ala Ala Leu Gly Tyr Val
                405                 410                 415

Glu Gln Glu Ala Pro Val Leu Ala Gly Thr Val Arg Asp Asn Leu Thr
                420                 425                 430

Leu Ala Ala Pro Asp Val Ala Glu His Ala Ile Arg His Val Thr Ala
                435                 440                 445

Ser Val Asn Leu Asp Asp Leu Leu Ala Arg Asp Pro Ala Gly Leu Asp
450                 455                 460
```

```
Ala Pro Val Gly Asp Gly Val Leu Phe Ser Gly Gly Glu Arg Gln
465                 470                 475                 480

Arg Leu Ala Val Ala Arg Thr Leu Leu Ala Pro Gly Glu Leu Leu Leu
            485                 490                 495

Phe Asp Glu Pro Thr Ala His Leu Asp Ala Arg Asn Glu Gln Ala Leu
                500                 505                 510

Gln His Gly Leu Thr Ala His Ala Ala Gly Arg Thr Leu Val Val Val
            515                 520                 525

Ala His Arg Leu Ala Thr Val Ala His Ala Asp Gln Ile Leu Val Ile
        530                 535                 540

Asp Asp Gly Arg Ser Val Ala Ala Gly Arg His Glu Glu Leu Leu Val
545                 550                 555                 560

Arg Asp Pro Thr Tyr Arg Glu Phe Ala Thr Arg Gln Leu Leu Thr
                565                 570                 575

<210> SEQ ID NO 215
<211> LENGTH: 347
<212> TYPE: PRT
<213> ORGANISM: Actinoplanes liguriae

<400> SEQUENCE: 215

Met Leu Ser Val Leu Asp Gln Val Pro Val Phe Arg Gly Asp Asp Pro
1               5                   10                  15

Ala Glu Ala Val Arg Glu Ala Val Gly Leu Ala Arg Ala Ala Glu Ser
                20                  25                  30

Leu Gly Tyr His Arg Phe Trp Ile Ala Glu His His Gly Ser Ala Ala
            35                  40                  45

Asn Ala Cys Ala Ala Pro Glu Ile Val Ala Ala Val Ala Gly Ala
        50                  55                  60

Thr Glu Arg Ile Arg Val Gly Thr Gly Val Leu Leu Pro Tyr Tyr
65                  70                  75                  80

Ser Pro Leu Lys Val Ala Glu Ala Phe Arg Val Leu Ala Ala Leu Tyr
                85                  90                  95

Pro Gly Arg Ile Asp Leu Gly Phe Gly Arg Gly Arg Gly Pro Ala
            100                 105                 110

Val Met Ala Glu Leu Leu Asn Pro Tyr Ala Ile Ala Thr Glu Glu Ala
            115                 120                 125

Tyr Ala Glu Gln Val Gly Arg Leu Leu Ala Phe Leu Gly Asp Ala Arg
130                 135                 140

Thr Val Ser Arg Val Ser Val Thr Pro Ala Val Gln Asp Pro Pro Leu
145                 150                 155                 160

Pro Trp Leu Leu Gly Ser Gly Val Gly Ser Ala Arg Leu Ala Gly Met
                165                 170                 175

Leu Gly Val Pro Phe Cys Phe Ala Gln Phe Ile Ala Thr Glu Glu Cys
            180                 185                 190

Pro Glu Ala Ile Ala Ala Tyr Gln Glu Ser Phe Arg Ser Ser Pro Trp
        195                 200                 205

Leu Asp Glu Pro Gln Ala Met Leu Ala Leu Arg Val Leu Ala Ala Gly
    210                 215                 220

Thr Ala Glu Asp Ala Glu Glu Leu Ala Thr Gly Phe Trp Met Ser Cys
225                 230                 235                 240

Thr Thr Gly Trp Arg Ala Gln Val Arg Pro Asp Asp Tyr Arg Gly
                245                 250                 255

Gly Val Pro Asn Leu Ala Asp Ala Gln Arg Tyr Thr Leu Thr Glu Glu
            260                 265                 270
```

```
Asp Leu Ala Met Arg Ala Ser Arg Pro Tyr Leu Gln Ile Ser Gly Thr
        275                 280                 285

Ala Glu Thr Val Gly Glu Glu Ile Arg Arg Leu Arg Lys Val Tyr Asp
        290                 295                 300

Val Ala Glu Val Met Leu Thr Thr Asn Cys Pro Gly Ala Ala Ala Pro
305                 310                 315                 320

Ala Pro Val Leu Arg Ala Ala Gly Arg Ala Arg Asp Arg Ala
                325                 330                 335

Gly Val Thr Arg Val Arg Pro Ala Arg Arg Trp
        340                 345
```

<210> SEQ ID NO 216
<211> LENGTH: 217
<212> TYPE: PRT
<213> ORGANISM: Actinoplanes liguriae

<400> SEQUENCE: 216

```
Met Ala Asp Val Leu Val Ala Glu Glu Ala Leu Val Ser Ile Gly
1               5                   10                  15

Ile Lys Met Ile Leu Glu Thr Met Gly Gly Phe Ser Val Ala Ala
            20                  25                  30

Asp Arg Asp Ser Ala Leu Ala Ala Val Ser Glu His Arg Pro Ala Val
        35                  40                  45

Val Leu Leu Asp Ala His Ala Thr Leu Pro Glu Ser Val Pro Leu Leu
    50                  55                  60

Thr Arg Leu Arg Asp Leu Glu Ser Gly Pro Ala Leu Ala Val Leu Ala
65                  70                  75                  80

Thr Leu Ala Ala Ser Ser Thr Val Leu Glu Ser Leu Arg Gly Gly Ala
                85                  90                  95

Cys Gly Phe Leu Leu Lys Asp Ser Gln Pro Glu Gln Leu Val Ala Ala
            100                 105                 110

Val Arg Ala Leu Ala Ser Gly Val Thr Val Leu Ala Pro Glu Ala Ser
        115                 120                 125

Ser Ile Met Leu Gly Ala Ala Cys Arg Gly Thr Pro Ala Ala Glu Asn
    130                 135                 140

Ala Val Asp Glu Val Lys Gln Leu Ser Asp Arg Glu Gln Ala Val Leu
145                 150                 155                 160

Gly Leu Ile Gly Gln Gly Leu Thr Asn Ala Glu Ile Ala Gly Arg Leu
                165                 170                 175

Phe Ile Ser Asp Ser Thr Val Lys Glu Tyr Val Ser Val Ile Leu Arg
            180                 185                 190

Lys Leu Gly Val Ala Asn Arg Val Gln Ala Ala Val Leu Ala Tyr Ala
        195                 200                 205

Ala Gly Leu Thr Thr Asp Glu Leu Ala
    210                 215
```

<210> SEQ ID NO 217
<211> LENGTH: 814
<212> TYPE: PRT
<213> ORGANISM: Actinoplanes liguriae

<400> SEQUENCE: 217

```
Met Ile Phe Thr Leu Ala Trp Ser Gln Val Arg Ser His Pro Gly Arg
1               5                   10                  15

Leu Leu Ala Ile Val Ala Val Val Leu Ala Thr Gly Phe Leu Ala
            20                  25                  30
```

-continued

Ala Thr Ala Thr Phe Ala Ser Thr Ser Asp Glu Gly Leu Arg Leu Thr
            35                  40                  45

Ala Ala Ala Pro Leu Thr Thr Ala Asp Ile Val Leu Asp Ala Asp Asp
        50                  55                  60

Thr Val His Asp Pro Gln Trp Tyr Gln Ala Ala Gly Val Arg Gly
65                  70                  75                  80

Val Arg Ser Val Asp Pro Gln Tyr Ala Arg Thr Val Ser Val Phe Gly
                85                  90                  95

Gly Asp Arg Arg Gly Ser Ala Asn Val Gln Ser Ile Pro Ala Thr Ala
            100                 105                 110

Ser Val Arg Trp Phe Thr Val Asp Glu Gly Thr Trp Pro Ser Ala Ala
            115                 120                 125

Gly Gln Val Val Ala Asp Arg Arg Thr Leu Thr Asp Leu Gly Val Gly
        130                 135                 140

Val Gly Ala His Leu Asp Phe Arg Gln Gly Thr Ala Ala Pro Val Pro
145                 150                 155                 160

Val Thr Val Val Gly Ser Ala Asp Leu Gly Phe Arg Pro Leu Thr Gly
                165                 170                 175

Ser Asp Tyr Arg Phe Tyr Ala Ala Ala Ser Phe Phe Ala Gly Asp Thr
            180                 185                 190

Pro Pro Ala Ala Leu Leu Thr Val Thr Asp Arg Asp Arg Leu Ala Glu
        195                 200                 205

Thr Val Asp Ala Val Gly Arg Ala Leu Pro Pro Gly Ala Thr Ala Thr
210                 215                 220

Asp Ala Ser Ala Ala Asp Ala Ala Gly Arg Phe Ala Gly Gly
225                 230                 235                 240

Asn Thr Gln Leu Val Val Leu Met Leu Ala Phe Ala Ala Val Ala Leu
                245                 250                 255

Leu Ala Ser Ile Leu Val Ile Ala Asn Thr Phe Gln Val Ile Val Ser
            260                 265                 270

Gln Arg Val Arg Gln Val Ala Leu Leu Arg Leu Val Gly His Arg
        275                 280                 285

Arg Gln Val Ser Arg Val Val Leu Ala Glu Ala Ala Ile Ala Gly Ser
290                 295                 300

Ile Gly Ala Val Ile Gly Ala Ala Gly Val Gly Leu Gly Tyr Leu
305                 310                 315                 320

Gly Ala Gly Leu Leu Asp Ile Asn Gly Gly Leu Ala Val Asn Pro
                325                 330                 335

Ile Val Leu Ala Leu Cys Val Leu Thr Gly Val Gly Ala Thr Val Val
            340                 345                 350

Ala Ala Trp Ala Pro Ala Arg Arg Ala Thr Arg Val Pro Pro Val Arg
        355                 360                 365

Ala Leu Gln Glu Val Pro Asp Ala Leu Pro Ala Gln Val Arg Gly Gly
370                 375                 380

Arg Arg Leu Val Ala Gly Leu Ile Leu Ile Gly Leu Ala Val Gly Val
385                 390                 395                 400

Leu Gly Leu Ala Ala Ile Gly Thr Ser Leu Pro Leu Ala Leu Val Gly
                405                 410                 415

Gly Val Leu Leu Ala Ala Gly Leu Leu Thr Ala Leu Pro Leu Gly Ile
            420                 425                 430

Ala Leu Leu Leu Pro Pro Ala Ala Arg Gly Leu Glu Arg Phe Gly Val
        435                 440                 445

Ala Ala Ser Leu Ala Gly Ser Asn Leu Arg Gln Asn Ala Arg Arg Thr
450                 455                 460

```
Ala Ser Ala Thr Met Ala Val Val Gly Ala Ala Leu Ile Thr Gly
465                 470                 475                 480

Leu Ala Val Ala Ser Ala Ser Gly Arg Ala Thr Val Glu Ala Asp Leu
            485                 490                 495

Glu Ala Arg Tyr Pro Val Ala Val Ser Val His Thr Asp Gly Ala Ala
        500                 505                 510

Ile Asp Asp Arg Thr Val Arg Ala Leu Ser Gly Ile Thr Gly Leu Thr
    515                 520                 525

Thr Ala Thr Val Ala Thr Ser Ala Ala Thr Phe Pro Ala Ala Gly Lys
530                 535                 540

Pro Thr Pro Ala Arg Ile Ala Ala Leu Pro Thr Asp Val Ala Gly Arg
545                 550                 555                 560

Leu Ala Pro Glu Leu Ser Ala Ser Thr Gly Asp Pro Val Leu Leu Val
            565                 570                 575

Pro Ala Ser Tyr Leu Thr Ala Arg Gly Leu Thr Asp Gly Ala Pro Leu
        580                 585                 590

Thr Val Thr Ala Gly Gly Arg Asp Leu Arg Phe Thr Ala Arg Gly Ser
    595                 600                 605

Arg Leu Ala Asp Thr Thr Gly Gln Leu Leu Gly Val Thr Thr Gly Asp
610                 615                 620

Val Leu Thr Ala Ala Gly Val Arg Thr Val Pro Thr Thr Val Trp Gly
625                 630                 635                 640

Thr Ala Pro Gly Gly Phe Asp Arg Glu Thr Leu Ala Ala Asp Val Asn
            645                 650                 655

Ala Val Ala Ala Arg Asp Ala Gly Val Glu Val Gly Gly Val Thr
        660                 665                 670

Glu Gly Gly Asp Ile Met Asn Val Leu Ser Ile Leu Leu Gly Leu Ser
    675                 680                 685

Leu Gly Met Leu Ala Val Thr Val Val Ile Ala Leu Leu Gly Ile Ala
690                 695                 700

Asn Leu Leu Gly Leu Ser Val Ile Glu Arg Thr Arg Glu Met Ala Leu
705                 710                 715                 720

Leu Arg Ala Leu Gly Thr Arg Ser Arg Leu Arg Ala Met Val Ala
            725                 730                 735

Val Glu Ala Val Thr Ile Thr Leu Val Gly Thr Val Ala Gly Ile Val
        740                 745                 750

Ile Gly Val Pro Val Gly Leu Val Gly Val Ile Ala Ala Val Gly Arg
    755                 760                 765

Gln Ala Glu Pro Val Ile Met Leu Ala Trp Pro Gln Leu Gly Leu Val
770                 775                 780

Leu Val Ala Ala Ala Val Thr Gly Val Leu Ala Ser Leu Ala Pro Ala
785                 790                 795                 800

Arg Arg Ala Thr Arg Ile Ala Pro Ala Glu Gly Leu Val Arg
            805                 810

<210> SEQ ID NO 218
<211> LENGTH: 240
<212> TYPE: PRT
<213> ORGANISM: Actinoplanes liguriae

<400> SEQUENCE: 218

Met Val Ser Cys Arg Asn Leu Arg Lys Arg Tyr Gly Thr Gly Asp Ala
1               5                   10                  15

Ala Val Val Ala Val Asp Gly Val Ser Thr Ser Phe Ala Ala Gly Glu
            20                  25                  30
```

```
Phe Thr Ala Ile Met Gly Pro Ser Gly Ser Gly Lys Thr Thr Leu Met
             35                  40                  45

His Leu Leu Ala Gly Leu Asp Thr Pro Thr Glu Gly Glu Val Ser Leu
 50                  55                  60

Ala Gly Thr Ala Leu Ala Gly Leu Asp Asp Arg Ala Leu Thr Asp Leu
 65                  70                  75                  80

Arg Arg Asp Arg Val Gly Phe Ile Phe Gln Ala Phe Asn Leu Leu Pro
                 85                  90                  95

Thr Leu Thr Ala Glu Gln Asn Ile Val Leu Pro Leu Arg Leu Ala Gly
             100                 105                 110

Arg Pro Val Asp Arg Asp Arg Leu Gln Arg Ile Ala Ala Ser Leu Gln
             115                 120                 125

Ile Gly Asp Arg Leu Gly His Arg Pro Ala Glu Leu Ser Gly Gly Gln
 130                 135                 140

Gln Gln Arg Val Ala Val Ala Arg Ala Leu Leu Thr Glu Pro Ser Val
145                 150                 155                 160

Val Phe Ala Asp Glu Pro Thr Gly Ala Leu Asp Ile Ala Thr Gly Arg
                 165                 170                 175

Ala Leu Leu Ala Gly Leu Gln Asn Ala Ala Arg Gln Ala Ser Gln Thr
             180                 185                 190

Ile Ile Met Val Thr His Asp Ala Ala Ala Thr Tyr Ala Asp Arg
             195                 200                 205

Val Leu Ile Met Ala Asp Gly Arg Leu Trp Asp Glu Leu Arg Ala Pro
 210                 215                 220

Thr Leu Glu Ser Ile Met Ser Val Met Ala Ser Val Thr Val Thr Ser
225                 230                 235                 240

<210> SEQ ID NO 219
<211> LENGTH: 362
<212> TYPE: PRT
<213> ORGANISM: Actinoplanes liguriae

<400> SEQUENCE: 219

Val Ile Ala Gly Ala Ala Val Met Val Cys Leu Leu Gly Leu Ala
 1               5                  10                  15

Gly Leu Asp Glu Trp Tyr Trp Ser Ala Ala Leu Cys Val Pro Leu Val
             20                  25                  30

Ile Arg Arg Ser Ala Pro Val Val Phe Leu Ala Leu Val Ala Val Leu
             35                  40                  45

Ser Gly Ile His Met Ile Tyr Ser Gly Ser Phe Ala Phe Pro Gly Asp
 50                  55                  60

Leu Val Asp Leu Val Ala Val His Ala Val Ala Gly Tyr Gly Pro Ala
 65                  70                  75                  80

Arg Val Arg His Leu Gly Leu Leu Gly Val Ala Gly Ser Leu Val
                 85                  90                  95

Val Thr Ala Arg Ala Leu His Asp Gly Leu Pro Ser Ser Ala Thr Leu
             100                 105                 110

Pro Ala Ala Leu Ile Val Ala Thr Leu Ala Ala Trp Ser Thr Gly
             115                 120                 125

Leu Met Gln Arg Arg Gln Arg Ala Asp Val Ile Glu Ala Asp His Arg
 130                 135                 140

Arg Arg Leu Ala Glu Gln Asp Ser Ala Met Arg Ala Arg Leu Ala Ala
145                 150                 155                 160

Ile Glu Glu Arg Thr Arg Ile Ser Gln Glu Met His Asp Ile Ile Ala
                 165                 170                 175
```

His Ser Leu Ala Ser Val Ile Ala Gln Ala Glu Gly Gly Arg Val Ala
            180                 185                 190

Ala Arg Ala Asp Ala Val Val Ala Gly Pro Leu Phe Asp Arg Ile Ala
        195                 200                 205

Gln Ile Gly Arg Glu Ala Leu Asn Asp Val Lys Arg Leu Leu Asn Ser
    210                 215                 220

Ile Asp Gly Asp Thr Pro Asp Asp Phe Ala Gln Gly Leu Pro Asp Leu
225                 230                 235                 240

Pro Gly Leu Leu Ala Gly Val Ser Ala Ala Gly Leu Asp Val Thr Phe
                245                 250                 255

Glu Val Ala Gly Pro Glu Gln Pro Leu Ala Ser Gly Met Asp Leu Ala
            260                 265                 270

Val Tyr Arg Val Ile Gln Glu Ser Leu Thr Asn Val Leu Lys His Ala
        275                 280                 285

Thr Gln Arg Gln Ala Arg Leu Ser Leu Val Trp Thr Pro Ala Trp Leu
    290                 295                 300

Glu Val Ser Val Thr Ser Pro Leu Thr Phe Ala Gly Ala Leu Arg Glu
305                 310                 315                 320

Gly Arg Gly Leu Ser Gly Ile Arg Gln Arg Cys Ser Leu Phe Asn Gly
                325                 330                 335

Asp Cys Glu Ile Val Ala Gly Gln Thr Phe Ser Val Ile Thr Arg Trp
            340                 345                 350

Pro Leu Ala Arg Pro Glu Val Ala Val Pro
        355                 360

<210> SEQ ID NO 220
<211> LENGTH: 218
<212> TYPE: PRT
<213> ORGANISM: Actinoplanes liguriae

<400> SEQUENCE: 220

Met Thr Glu Pro Gln Ile Asp Val Val Ile Ala Asp Gln Asp Leu
1               5                   10                  15

Val Arg Thr Gly Phe Ala Leu Val Asp Ser Ala Pro Asp Met Arg
            20                  25                  30

Val Val Ala Thr Ala Ala Asp Gly Ala Glu Val Val Arg Leu Ala Ala
        35                  40                  45

Glu Phe Arg Pro Asp Val Val Leu Met Asp Ile Arg Met Pro Arg Val
    50                  55                  60

Asp Gly Ile Thr Ala Ala Arg Ala Ile Leu Glu Gly Asn Ala Gln Pro
65                  70                  75                  80

Pro Lys Ile Val Ala Leu Thr Thr Tyr Asp Asn Asp Glu Tyr Ala Ser
                85                  90                  95

Arg Ile Leu Ala Ala Gly Ala Ser Gly Tyr Leu Leu Lys Asp Thr Thr
            100                 105                 110

Ala Glu Gly Leu Thr Ala Ala Ile Arg Thr Val His Arg Gly Gly Ser
        115                 120                 125

Val Leu Ala Pro Ser Thr Thr His Arg Leu Val Thr Ala His Arg Gln
    130                 135                 140

His Pro Ala Arg Pro Ser Ala Leu Leu Asp Ser Phe Thr Thr Arg Glu
145                 150                 155                 160

Arg Glu Val Phe Asp Leu Ile Val Ala Gly Ala Ser Asn Ala Glu Ile
                165                 170                 175

Ala Asp Arg Leu Asn Leu Ala Glu Val Thr Ile Lys Thr His Val Gly
            180                 185                 190

```
Arg Val Leu Ala Lys Ile Gly Val Arg Asp Arg Val Asn Val Ile
        195                 200                 205

Trp Ala Tyr Arg Asn Gly Ala Gly Pro Ser
    210                 215

<210> SEQ ID NO 221
<211> LENGTH: 301
<212> TYPE: PRT
<213> ORGANISM: Actinoplanes liguriae

<400> SEQUENCE: 221

Met Pro Ile Leu Trp Thr Ala Val Leu Ala Gly Ala Val Ile Leu Gly
1               5                   10                  15

His Arg Leu Val Pro Asn Ala Val Gly Asn Ala Gly Ser Leu Ile Glu
            20                  25                  30

Ala Phe Leu Pro Trp Phe Gly Leu Ala Val Pro Val Leu Leu Leu Leu
        35                  40                  45

Ala Leu Met Arg Arg Ser Leu Thr Gly Leu Ala Ala Val Leu Leu Pro
    50                  55                  60

Leu Gly Ala Trp Leu Ile His Phe Gly Gly Tyr Val Val Asp Arg Asp
65                  70                  75                  80

Thr Gly Thr Pro Asp Leu Ile Val Val Gln His Asn Val Ser Asp Glu
                85                  90                  95

Asn Pro Asp Pro Ala Gly Thr Ala Arg Ala Leu Leu Ala Ala His Pro
            100                 105                 110

Asp Leu Val Gly Leu Glu Glu Val Leu Pro Glu Ala Val Ala Ala Tyr
        115                 120                 125

Arg Gly Val Leu Asp Ala Glu Leu Pro Phe His Thr Val Gln Gly Thr
    130                 135                 140

Val Ala Leu Trp Ser Arg Tyr Pro Leu Thr Gly Ala Glu Ala Ile Asp
145                 150                 155                 160

Ile Arg Pro His Asp Leu Gly Glu Asp Trp Asn Arg Gly Leu Arg Ala
                165                 170                 175

Val Ala Arg Thr Pro Gly Gly Asp Thr Ala Val Tyr Val Ala His Leu
            180                 185                 190

Pro Ser Val Arg Val Thr Ala Ala Gly Leu Thr Ser Ala Arg Arg Asp
        195                 200                 205

Glu Ser Ala Arg Lys Leu Gly Ala Leu Leu Ala Asp Pro Val Pro
    210                 215                 220

Arg Leu Val Val Ile Gly Asp Leu Asn Thr Ser Val Asp Arg Gly
225                 230                 235                 240

Leu Arg Pro Ile Arg Gln Val Met Ile Asp Ser Pro Ala Asp Phe Ala
                245                 250                 255

Phe Thr Trp Pro Ala Arg Thr Pro Val Ala Arg Ile Asp Gln Val Leu
            260                 265                 270

Ala Arg Ser Met Thr Val Thr Arg Leu Thr Ala Leu Pro Arg Thr Gly
        275                 280                 285

Ser Asp His Leu Pro Leu Ala Ala Glu Ile Arg Phe Pro
    290                 295                 300

<210> SEQ ID NO 222
<211> LENGTH: 290
<212> TYPE: PRT
<213> ORGANISM: Actinoplanes liguriae

<400> SEQUENCE: 222
```

```
Met Arg Asn Asn Glu Thr Val Arg Ile Pro Val Ala Thr Gly Gly Ala
1               5                   10                  15

Val Thr Ala Thr Leu Phe Ala Pro Glu Ser Ala Arg Ala Val Leu Val
            20                  25                  30

Val His Pro Ala Thr Ala Thr Pro Gln Gly Phe Tyr Ala Ser Phe Ala
            35                  40                  45

Thr Tyr Leu Ala Glu Asn Gly Ile Ala Thr Val Thr Tyr Asp Tyr Arg
        50                  55                  60

Gly Thr Gly Arg Ser Gly Ser Pro Arg Asp His Arg Asp Leu Gly Met
65                  70                  75                  80

Arg Asp Trp Ile Gly Ala Asp Ala Pro Ala Val Ala Trp Ala Ala
                85                  90                  95

Asp Arg Phe Pro Gly Leu Pro Arg Leu Ala Ala Gly His Ser Leu Gly
                100                 105                 110

Gly His Val Ile Ala Leu Gly Ala Ala Gly Pro Asp Leu Ala Ala Ser
            115                 120                 125

Val Ile Val Ala Ser His Ile Ala Ala Leu Arg Thr Ile Pro Ser Arg
130                 135                 140

Leu Glu Arg Phe Arg Val Arg Ile Met Leu His Ile Leu Gly Pro Ala
145                 150                 155                 160

Leu Gly Arg Leu Leu Gly Tyr Val Pro Ala Arg Ser Leu Gly Leu Gly
                165                 170                 175

Glu Asp Leu Pro Ala Ala Ala Met Leu Glu Trp Gly Trp Ala Arg
                180                 185                 190

Arg Asp Asn Tyr Phe Phe Asp Asp Pro Ser Met Arg Ala Ala Glu Arg
                195                 200                 205

Ala Ala Thr Leu Thr Gly Pro Val Leu Ala Val Gly Thr Thr Asp Asp
210                 215                 220

Pro Trp Ser Thr Pro Arg Gln Met Asp Ala Leu Thr Val His Leu Thr
225                 230                 235                 240

Ser Ala Ser Val Glu Arg Arg Thr Tyr Ser Pro Ala Ala Ala Gly Val
                245                 250                 255

Pro Val Ile Gly His His Gly Leu Phe Arg Arg Ala Val Arg Asp Thr
                260                 265                 270

Val Trp Pro Glu Leu Leu Ala Trp Leu His Ala His Ser Glu Lys Ala
                275                 280                 285

Ser Arg
    290

<210> SEQ ID NO 223
<211> LENGTH: 145
<212> TYPE: PRT
<213> ORGANISM: Actinoplanes liguriae

<400> SEQUENCE: 223

Val Arg Leu Pro Arg Leu Ile Phe Leu Leu Phe Asn Ala Asp Arg Ala
1               5                   10                  15

Val Arg Arg Trp Ile Asp Ala Arg Ser Gly Asp Thr Gly Ile Gly Ala
            20                  25                  30

Ser Gly Ala Gly Val Leu Phe Tyr Leu Ala Gly His Glu Asn Ala Leu
            35                  40                  45

Ile Gly Asp Val Thr Ala Ala Leu Gly Ala Ser Pro Ser Gly Met Ser
        50                  55                  60

Gly Leu Val Asn Arg Leu Glu Arg Gly Gly Cys Leu Thr Arg Ser Gln
65                  70                  75                  80
```

```
Asp Pro Ala Asp Ala Arg Ala Val Arg Leu Ala Leu Thr Pro Arg Gly
                85                  90                  95

His Gln Val Val Ile His Ala Arg Gly Leu Val Asp Asp Leu Asn Glu
            100                 105                 110

Gln Leu Thr Ala Gly Phe Asp Asp Ala Glu Ile Ala Val Val Gln Arg
        115                 120                 125

Trp Leu Glu His Val Thr Arg Val Ser Val Gln Arg Glu Glu Arg Leu
    130                 135                 140

Gly
145

<210> SEQ ID NO 224
<211> LENGTH: 175
<212> TYPE: PRT
<213> ORGANISM: Actinoplanes liguriae

<400> SEQUENCE: 224

Met Ala Asp Ser Val Val Phe Asp Gln Ile Pro Val Val Arg Ala Ile
1               5                   10                  15

Gly Arg Gly Thr Thr Ser Leu Ser Ala Phe His Asp Ala Leu Val Thr
            20                  25                  30

Met Glu Cys Gly Phe Tyr Asn Leu Val Arg Leu Ser Ser Val Ile Pro
        35                  40                  45

Pro Gly Thr Ala Val Asp Pro Ser Gly Lys Ala Pro Val Pro Val Gly
    50                  55                  60

Ala Trp Gly Asp Lys Leu Tyr Cys Val Tyr Ala Glu Gln His Ala Ser
65                  70                  75                  80

Gln Pro Gly Glu Glu Ala Trp Ala Gly Ile Gly Trp Val Gln Arg Arg
                85                  90                  95

Asp Gly Gln Gly Gly Leu Phe Val Glu His Glu Gly Thr Ser Glu Ser
            100                 105                 110

Phe Val Arg Glu Ala Ile Lys Ala Ser Leu Arg Asp Leu Val Lys Gly
        115                 120                 125

His Glu Asp Asp Phe Asp Gly Pro Asp Phe Val His Gly Val Val
    130                 135                 140

Ser Asp Gly Glu Pro Val Cys Ala Met Val Leu Ala Pro Tyr Glu Thr
145                 150                 155                 160

Ala Pro Trp Arg Gly Val Arg Ala Thr Asp Pro Pro Gly Met Asn
                165                 170                 175

<210> SEQ ID NO 225
<211> LENGTH: 406
<212> TYPE: PRT
<213> ORGANISM: Actinoplanes liguriae

<400> SEQUENCE: 225

Met Thr Leu Ser Glu Ile Leu Pro Ser Leu Gly Ala Ser Leu Arg Pro
1               5                   10                  15

Arg Leu Asp Pro Ala Asn Trp Pro Leu Thr Ala Arg Trp Thr Glu Pro
            20                  25                  30

Gly Asp Leu Thr Val Gly Val Pro Val Thr Arg Ile Ala Ala Ala
        35                  40                  45

His Gly Thr Pro Val His Val Ile Asp Glu Thr Asp Val His Ser Arg
    50                  55                  60

Cys Ala Glu Tyr Val Ala Ala Phe Gly Pro Gly Ala Val Cys Cys Ser
65                  70                  75                  80

Ala Lys Gly Gly Leu Leu Arg Gly Ala Ala Arg Trp Ile Ala Arg Asp
```

```
                    85                  90                  95
Gly Leu Gly Cys Tyr Cys Arg Ser Ala Glu Leu Arg Thr Ala Leu
            100                 105                 110
Asp Ala Gly Ile Arg Pro Glu Ser Leu Ala Leu Phe Gly Ser Gly Lys
            115                 120                 125
Ser Val Ala Asp Leu Glu Ala Ala Leu Ser Cys Gly Ala Ala Val Val
            130                 135                 140
Ile Gly Ser Ala Ser Glu Ala Glu Val Val Ala Arg Ser Arg Pro
145                 150                 155                 160
Gly Gln Arg Val Leu Leu Arg Val Arg Pro Gly Ser Ala Gln Arg Gly
                165                 170                 175
Tyr Gly Val Arg Leu Asn Ser Ser Ala Ala Leu Ala Ala Val Ala Thr
                180                 185                 190
Val Thr Arg Ser Arg Arg Leu Val Leu Ala Gly Leu Asp Cys Ser Leu
                195                 200                 205
Gly His Arg Leu Asn Arg Phe Gly Thr Tyr Glu Ser Cys Leu Arg Glu
            210                 215                 220
Ala Ile Gly Phe Val Ala Arg Leu Arg Thr Thr Val Pro Val Leu Asn
225                 230                 235                 240
Leu Gly Gly Gly His Ala Ala Asp Leu Pro Val Gly Ile Phe Ala Ala
                245                 250                 255
Arg Leu Arg Ala Val Ala Gln Val Thr Ser Glu Gly Tyr Gly Ile Glu
                260                 265                 270
Pro Pro Glu Val His Val Ser Pro Gly Arg Ala Leu Leu Gly Arg Ala
                275                 280                 285
Gly Ile Thr Val His Arg Val Val Ala Ala Gly Asp Gly Val Ile Glu
            290                 295                 300
Leu Asp Gly Asp Val Pro Asp Cys Leu Pro Gly Ala Asp Cys Ala Gly
305                 310                 315                 320
Leu His Thr Ala Ala Leu Ile Gly Arg Ala Ser Pro Ala Pro Gly Arg
                325                 330                 335
Ser Ile Thr Val Arg Cys Gly Asp Ala Thr Val Ala Val Ala Glu Leu
                340                 345                 350
Pro Gly Asp Met Ala Ala Gly Asp Leu Val Ala Leu Ser Gly Thr Gly
                355                 360                 365
Ala Tyr His Gln Arg Arg Asp Val Tyr Val Gly Arg Pro Ala Val Val
                370                 375                 380
Ala Val Cys Gly Gly Arg Ala Arg Thr Leu Leu Pro Arg Glu Thr Ile
385                 390                 395                 400
Asp Arg Ile Leu Tyr Ala
                405

<210> SEQ ID NO 226
<211> LENGTH: 309
<212> TYPE: PRT
<213> ORGANISM: Actinoplanes liguriae

<400> SEQUENCE: 226

Val Arg Ser Lys Arg Glu His Ser Ala Asp Ile Arg Arg Gly Arg Arg
1               5                   10                  15
Ala Val Leu Val Val Asn Thr Arg Ser Arg Arg Gly Arg Leu Leu Tyr
                20                  25                  30
Glu Glu Ala Arg Arg Arg Leu Val Glu Ala Gly Phe Glu Leu Leu Gly
            35                  40                  45
Thr Tyr Ala Leu Glu Gln Ser Gly Gly Leu Asp Gly Leu Ile Ser Glu
```

```
                50                  55                  60
Ala Leu Arg Lys Glu Pro Asp Leu Leu Ile Ala Gly Gly Asp Gly
 65                  70                  75                  80

Thr Ile Ser Thr Ala Gly Arg Met Leu Ala His Arg Asp Val Ala Leu
                 85                  90                  95

Gly Val Leu Pro Leu Gly Thr Thr Asn Asn Phe Ala Arg Thr Val Arg
                100                 105                 110

Ile Glu Pro Asp Leu Glu Ala Ala Ile Ala Thr Leu Val Asp Gly Lys
                115                 120                 125

Val Ile Asp Val Asp Leu Gly Val Ala Gly Asp Val Pro Phe Thr Asn
130                 135                 140

His Val Gly Ile Gly Leu Ser Gly Glu Val Met Ile Ser Ala Pro Pro
145                 150                 155                 160

Arg Leu Lys Arg Ala Val Gly Arg Leu Ala Tyr Pro Met Thr Ala Leu
                165                 170                 175

Gly Leu Leu Ala Arg His Arg Pro Val Arg Ala Val Ile Arg Ala Glu
                180                 185                 190

Gly Arg Glu Leu Arg Phe His Thr His Gln Val Tyr Val Ala Asn Gly
                195                 200                 205

Gly Phe His Ala Gly Arg Pro Ile Thr Ala Asp Ala His Ala Asp Asp
                210                 215                 220

Arg Leu Leu Val Ala Tyr Pro Val Gly Gly Ala Ser Arg Arg Glu Leu
225                 230                 235                 240

Leu Arg Glu Thr Ala Arg Asn Ala Ala Thr Gly His Arg Arg Thr Leu
                245                 250                 255

His Glu Arg Pro Phe Ile Ala Val Arg Glu Leu Trp Leu Glu Thr Asp
                260                 265                 270

Arg Pro Val Ala Val Glu Val Asp Gly Glu Pro Arg Gly Thr Thr Pro
                275                 280                 285

Met Arg Ile Ala Ile Asp Pro Asn Ala Leu Arg Ile Met Ala Pro Ala
                290                 295                 300

Asp Ser Pro Asp Leu
305

<210> SEQ ID NO 227
<211> LENGTH: 367
<212> TYPE: PRT
<213> ORGANISM: Actinoplanes liguriae

<400> SEQUENCE: 227

Val Val Phe Gly Ser Leu Leu Leu Val Gly Gly Gly Gly Ala Ile
 1               5                  10                  15

Gly Leu Asn Ala Thr Val Ala Ala Thr Ser Ser Val Gly Gln Glu
                 20                  25                  30

Ser Leu Leu Gly Ser Ala Lys Pro Ala Glu Glu Lys Lys Asn Ala Asn
                 35                  40                  45

Leu Asp Gly Ala Lys Asn Leu Leu Val Gly Ile Asp Gln Arg Pro
 50                  55                  60

Thr Gln Thr Asn Gly Glu Pro Leu Arg Ser Asp Ser Ile Ile Leu Leu
 65                  70                  75                  80

His Ile Asn Lys Asp His Ser Ser Gly Tyr Met Ile Ser Leu Pro Arg
                 85                  90                  95

Asp Ser Tyr Val Tyr Ile Pro Ala Tyr Asp Asn Gly Lys Gln Lys Trp
                100                 105                 110

Ala Gly Gly Lys Thr Lys Ile Asn Ala Ala Phe Ala Phe Gly Thr Arg
```

```
            115                 120                 125
Gly Leu Lys Gly Asn Glu Ala Leu Gln His Gly Phe Glu Leu Leu Thr
130                 135                 140

Met Thr Val Lys Glu Leu Thr Gly Ile Thr Pro Asp Ala Gly Ala Ile
145                 150                 155                 160

Ile Asp Phe Gln Gly Phe Arg Asp Val Val Asn Val Leu Gly Lys Val
                165                 170                 175

Cys Met Tyr Val Asp Thr Thr Lys Ser Ile His Leu Gly Lys Asp
                180                 185                 190

Gln Asn Gly Lys Thr Ala Lys Pro Phe Val Ile Asn Pro Asp Gly Thr
                195                 200                 205

Leu Lys Ser Lys Ile Ser Gly Val Thr Pro Asn Thr Tyr Thr Lys Gly
                210                 215                 220

Asp His Cys Phe Thr Pro Gly Gln Ala Leu Asp Phe Val Arg Gln Arg
225                 230                 235                 240

Asp Leu Leu Ala Asp Asn Ser Leu Asp Tyr Gly Arg Gln Arg His Gln
                245                 250                 255

Gln Gln Phe Phe Lys Ala Ile Ile Asn Gln Ala Leu Lys Asp Gly Leu
                260                 265                 270

Asp Ser Pro Thr Lys Leu Pro Lys Leu Leu Ser Ala Phe Gly Lys Ala
                275                 280                 285

Met Thr Val Asp Asp Gly Gly Ile Asp Leu Ala Asp Trp Ala Leu Ala
                290                 295                 300

Met Arg Ser Leu Lys Pro Asp Lys Leu Leu Thr Ile Lys Thr Asn Ala
305                 310                 315                 320

Gly Lys Leu Asn Ser Glu Asn Val Pro Gly Ser Gly Ser Val Glu Leu
                325                 330                 335

Leu Ser Asp Asp Ser Met Asp Leu Leu Lys Ser Ile Lys Lys Asp Gln
                340                 345                 350

Ile Asp Thr Phe Leu Leu Ser His Pro Ala Phe Ile Ala Asn Ser
                355                 360                 365

<210> SEQ ID NO 228
<211> LENGTH: 317
<212> TYPE: PRT
<213> ORGANISM: Actinoplanes liguriae

<400> SEQUENCE: 228

Met Pro Ser Glu Pro Asp Val Ser Val Ile Pro Thr Cys Asn Arg
1               5                   10                  15

Pro Glu Leu Ala Val Arg Ala Val Arg Ser Ala Leu Gly Gln Thr His
                20                  25                  30

Arg Asn Leu Glu Val Ile Val Val Asp Gly Pro Asp Glu Ala Thr
                35                  40                  45

Val Thr Ala Leu Gly Glu Val Gly Asp Pro Arg Leu Ser Val Ile Val
50                  55                  60

Leu Pro Glu Arg Gly Lys Ala Pro Asn Ala Arg Asn Thr Gly Ala Arg
65                  70                  75                  80

Ala Ala Arg Gly Arg Trp Thr Ala Met Leu Asp Asp Asp Glu Trp
                85                  90                  95

Leu Pro Thr Lys Ile Glu Arg Gln Leu Glu Thr Ala Ala Ala Thr
                100                 105                 110

Val Glu Arg Pro Val Val Ala Cys Arg Met Ile Ser Arg Thr Pro Arg
                115                 120                 125

Ala Asp Thr Ile Met Pro Arg Arg Leu Pro Glu Pro Gly Glu Pro Ile
```

```
                130                 135                 140
Ser Glu Tyr Leu Leu Val Arg Arg Gly Leu Phe Tyr Gly Asp Gly Phe
145                 150                 155                 160

Val Gln Thr Ser Cys Ile Met Ala Pro Thr Glu Leu Trp Arg Lys Val
                165                 170                 175

Pro Phe Thr Val Gly Leu Arg Arg Ala Gln Glu Leu Asp Trp Thr Leu
                180                 185                 190

Arg Ala Met Arg Glu Pro Gly Thr Ala Leu Ile Tyr Ala Glu Glu Pro
                195                 200                 205

Leu Val Leu Trp His Gln Asp Glu Asn Arg Asp Arg Ile Ser Leu Gln
                210                 215                 220

Asn Pro Trp Arg Glu Gln Leu Glu Trp Leu Arg Gly Asn Arg Glu Leu
225                 230                 235                 240

Phe Thr Pro Arg Ala Tyr Ala Ala Phe Thr Leu Ser Val Leu Ser Ser
                245                 250                 255

Met Ala Ala Pro Thr Arg Asp Thr Gly Leu Phe Arg Glu Leu Leu Ala
                260                 265                 270

Glu Ala Arg Thr His Gly Asp Pro Gly Thr Val Asp Tyr Leu Thr His
                275                 280                 285

Met Gln Ile Trp Ala Leu Pro Pro Ser Val Arg His Arg Leu Arg Asp
                290                 295                 300

Val Val Gly Arg Gly Lys Thr Ser Ser Asn Ala Gly
305                 310                 315

<210> SEQ ID NO 229
<211> LENGTH: 369
<212> TYPE: PRT
<213> ORGANISM: Actinoplanes liguriae

<400> SEQUENCE: 229

Met Pro Ala Glu Arg Arg Val Ala Ile Trp Arg Ser Ser Met Leu Pro
1               5                   10                  15

Gly Ser Glu Thr Phe Val Arg Asn Gln Ala Asp Ala Leu Thr Arg Trp
                20                  25                  30

Thr Pro Ala Tyr Val Gly Ala Val Arg His Glu Ser Val Leu Ser Arg
                35                  40                  45

Pro Asp Asp Val Ile Ala Phe Pro Gly Gly Lys Gly Phe Leu Arg Leu
50                  55                  60

Arg Leu Thr Gly Ala Ser Pro Gln Leu Gln Lys Thr Ile Ser Ala Val
65                  70                  75                  80

Arg Pro Asn Leu Val His Ala His Phe Gly Asp Gly Trp Leu Val
                85                  90                  95

Ser His Ser Ala Gln Gln Leu Gly Val Pro Leu Ala Val Thr Val His
                100                 105                 110

Gly His Asp Val Thr Arg Gln Pro Ser Ser Pro Gly Ala Lys Gly Val
                115                 120                 125

Arg Tyr Arg Arg Asn Leu Gln Thr Val Phe Thr Arg Ala Ser Leu Val
                130                 135                 140

Ile Ala Val Ser Glu Val Ile Arg Gly Gln Ala Ile Arg Trp Gly Ala
145                 150                 155                 160

Asp Pro Ala Lys Val Lys Val His Tyr Thr Gly Ile Ala Val Pro Pro
                165                 170                 175

Glu Gln Pro Glu Glu Val Pro Lys Arg Trp Asp Val Val Phe Ile Gly
                180                 185                 190

Arg Phe Val Ala Lys Lys Gly Val Asp Asp Leu Leu Thr Ala Leu Ala
```

```
                195                 200                 205
Ala Val Glu Ser Arg Pro Arg Ala Leu Leu Ile Gly Asp Gly Glu Leu
    210                 215                 220

Met Thr Ala Met Arg Ala Arg Ala Glu Gln Leu Gly Val Asp Val Thr
225                 230                 235                 240

Phe Ala Gly Ser Arg Thr Pro Glu Gln Val Arg Arg His Leu Leu Glu
                245                 250                 255

Ser Arg Leu Leu Ala Cys Pro Ser Lys Thr Ala Pro Asp Gly Asp Thr
            260                 265                 270

Glu Gly Leu Pro Thr Thr Ile Leu Glu Ala Ala Leu Gly Leu Pro
        275                 280                 285

Val Val Ala Thr Arg His Ser Gly Ile Pro Glu Ala Val Ile Asp Gly
    290                 295                 300

Glu Thr Gly Leu Leu Ser Pro Glu Ala Asp Pro Ala Ala Leu Ala Val
305                 310                 315                 320

Ser Leu Thr Arg Leu Leu Gly Asp Glu Asp Leu Gln Arg Arg Leu Gly
                325                 330                 335

Ala Arg Ala Arg Arg His Val Thr Ala His Phe Asp Leu Val Glu Gln
            340                 345                 350

Thr Arg Arg Leu Glu Asp Leu Tyr Asp Glu Val Val Ala Gly Ala Arg
        355                 360                 365

Val

<210> SEQ ID NO 230
<211> LENGTH: 459
<212> TYPE: PRT
<213> ORGANISM: Actinoplanes liguriae

<400> SEQUENCE: 230

Met Gly Glu His Phe Asp Leu Val Val Leu Gly Ala Gly Pro Gly Gly
1               5                   10                  15

Tyr Val Ala Ala Ile Arg Gly Ala Gln Leu Gly Leu Thr Thr Ala Ile
            20                  25                  30

Val Glu Asp Lys Tyr Trp Gly Gly Val Cys Leu Asn Val Gly Cys Ile
        35                  40                  45

Pro Ser Lys Ala Leu Leu Arg Asn Ala Glu Leu Ala His Ile Phe His
    50                  55                  60

His Gln Ala Gln Thr Phe Gly Ile Glu Gly Lys Val Thr Phe Asp Phe
65                  70                  75                  80

Ala Val Ala His Gln Arg Ser Arg Ser Val Ala Asp Gly Arg Val Lys
                85                  90                  95

Gly Val His Phe Leu Met Lys Lys Asn Gly Ile Thr Glu Ile Gln Gly
            100                 105                 110

Arg Gly Glu Phe Thr Asp Ala His Thr Leu Arg Val Gly Asp Arg Thr
        115                 120                 125

Val Thr Phe Asp Asn Cys Ile Leu Ala Thr Gly Ala Ser Thr Arg Met
    130                 135                 140

Ile Pro Gly Thr Ser Val Ser Lys Arg Val Val Thr Tyr Glu Glu Gln
145                 150                 155                 160

Ile Leu Asp Pro Asp Leu Pro Asp Ser Ile Val Ile Gly Ala Gly
                165                 170                 175

Ala Ile Gly Val Glu Phe Ala Tyr Val Leu Arg Asn Tyr Gly Val Asp
            180                 185                 190

Val Thr Ile Val Glu Phe Leu Asp Arg Met Leu Pro Leu Glu Asp Glu
        195                 200                 205
```

```
Glu Val Ser Lys Glu Leu Leu Arg Gln Tyr Arg Lys Leu Gly Val Asp
    210                 215                 220

Val Arg Val Gly Thr Arg Val Glu Gly Ile Glu Gly Ala Asp Ser
225                 230                 235                 240

Val Arg Val Thr Val Ser Lys Asn Gly Lys Thr Glu Val Leu Glu Ala
                245                 250                 255

Asp Lys Val Met Gln Ala Ile Gly Phe Lys Pro Asn Val Glu Gly Tyr
            260                 265                 270

Gly Leu Glu Thr Thr Gly Val Thr Val Ser Asp Arg Gly Ala Val Glu
        275                 280                 285

Ile Asp Asp Phe Cys Arg Thr Asn Val Pro Gly Ile Tyr Ala Ile Gly
    290                 295                 300

Asp Val Thr Ala Lys Leu Met Leu Ala His Ala Ala Glu Ala Met Gly
305                 310                 315                 320

Ile Val Ala Ala Glu Thr Ile Ala Gly Ala Glu Thr Met Ala Leu Asp
                325                 330                 335

Tyr Arg Met Ile Pro Arg Ala Thr Phe Cys Gln Pro Gln Val Ala Ser
            340                 345                 350

Phe Gly Trp Thr Glu Ala Gln Ala Arg Glu Gln Gly Phe Asp Val Lys
        355                 360                 365

Val Ala Lys Phe Pro Phe Thr Ala Asn Gly Lys Ala His Gly Leu Gly
    370                 375                 380

Asp Ala Thr Gly Phe Val Lys Ile Leu Ser Asp Ala Lys Tyr Gly Glu
385                 390                 395                 400

Leu Leu Gly Ala His Leu Ile Gly Pro Asp Val Thr Glu Leu Leu Pro
                405                 410                 415

Glu Leu Thr Leu Ala Gln Gln Trp Asp Leu Thr Val His Glu Val Gly
            420                 425                 430

Arg Asn Val His Ala His Pro Thr Leu Ala Glu Ala Val Lys Glu Ala
        435                 440                 445

Ile His Gly Leu Ala Gly His Met Ile Asn Phe
    450                 455

<210> SEQ ID NO 231
<211> LENGTH: 348
<212> TYPE: PRT
<213> ORGANISM: Actinoplanes liguriae

<400> SEQUENCE: 231

Met Thr Thr Pro Pro Arg Arg Ser Gly Thr Leu Ser Leu Val Thr Leu
1               5                   10                  15

Thr Val Glu Pro Pro Ile Ala Pro Ala Pro Ala Ala Pro Gly Arg
            20                  25                  30

Ser Arg Arg Arg Arg Leu Gly Tyr Leu Ala Phe Val Leu Val Ala Val
        35                  40                  45

Val Ala Val Val Thr Leu Arg Asp Arg Leu Pro Asp Pro Gly Glu Phe
    50                  55                  60

Leu Asp Ala Leu Arg Ala Ala Asp Trp Arg Trp Ala Ala Leu Ala Val
65                  70                  75                  80

Gly Ala Gly Val Leu Ser Gln Ile Ala Tyr Ala Glu Gln Gln Arg Arg
                85                  90                  95

Leu Leu Ala Ala Phe Gly Val Arg Val Pro Ala Arg Arg Ala Ile Ala
            100                 105                 110

Met Thr Tyr Val Arg Ser Ala Leu Ser Met Ala Leu Pro Ala Gly Ser
        115                 120                 125
```

Ala Ala Ser Ala Ala Tyr Ala Phe Gln Val Tyr Arg Arg His Gly Ala
            130                 135                 140

Thr Ala Ala Ile Ser Ala Thr Ala Thr Leu Ile Ser Thr Val Val Thr
145                 150                 155                 160

Val Met Ser Leu Gly Leu Leu Tyr Ala Ala Thr Trp Ser Leu Thr Ala
                165                 170                 175

Thr Val Val Ala Gly Leu Ala Val Leu Leu Leu Trp Ile Tyr Arg Thr
            180                 185                 190

Val Arg Gly Pro Val Pro Ala Arg Ala Gly Val Pro Arg Arg Leu Arg
            195                 200                 205

Val Ala Pro Ile Ala Arg Leu Leu Gln Arg Pro Ala Val Ala Gln Ala
        210                 215                 220

Leu Arg Gly Ala Arg Ser Val Pro Ala Arg Thr Trp Leu Thr Val Thr
225                 230                 235                 240

Leu Ala Gly Val Ile Asn Trp Leu Leu Asp Met Ala Cys Leu Leu Leu
                245                 250                 255

Ala Ala Asp Ala Leu His Ala Gly Leu Gly Trp Ser Arg Leu Ala Leu
            260                 265                 270

Ile Tyr Leu Ala Val Gln Val Arg Gln Ile Pro Leu Thr Pro Gly
        275                 280                 285

Gly Ile Gly Leu Ile Glu Thr Ser Met Leu Ala Gly Leu Ile Ala Ala
        290                 295                 300

Gly Ala Pro Gln Val Thr Ala Ala Gly Ile Val Leu Ile Tyr Arg Leu
305                 310                 315                 320

Ile Ser Phe Trp Leu Ile Leu Pro Ser Gly Leu Ala Ala His Leu Thr
                325                 330                 335

Leu Arg Arg Gly Thr Val Pro Pro Val Thr Pro Gly
            340                 345

<210> SEQ ID NO 232

<400> SEQUENCE: 232

000

<210> SEQ ID NO 233

<400> SEQUENCE: 233

000

<210> SEQ ID NO 234

<400> SEQUENCE: 234

000

<210> SEQ ID NO 235

<400> SEQUENCE: 235

000

<210> SEQ ID NO 236

<400> SEQUENCE: 236

000

<210> SEQ ID NO 237

```
<400> SEQUENCE: 237
000

<210> SEQ ID NO 238
<400> SEQUENCE: 238
000

<210> SEQ ID NO 239
<400> SEQUENCE: 239
000

<210> SEQ ID NO 240
<400> SEQUENCE: 240
000

<210> SEQ ID NO 241
<400> SEQUENCE: 241
000

<210> SEQ ID NO 242
<400> SEQUENCE: 242
000

<210> SEQ ID NO 243
<400> SEQUENCE: 243
000

<210> SEQ ID NO 244
<400> SEQUENCE: 244
000

<210> SEQ ID NO 245
<400> SEQUENCE: 245
000

<210> SEQ ID NO 246
<400> SEQUENCE: 246
000

<210> SEQ ID NO 247
<400> SEQUENCE: 247
000

<210> SEQ ID NO 248
<400> SEQUENCE: 248
```

000

<210> SEQ ID NO 249

<400> SEQUENCE: 249

000

<210> SEQ ID NO 250

<400> SEQUENCE: 250

000

<210> SEQ ID NO 251

<400> SEQUENCE: 251

000

<210> SEQ ID NO 252

<400> SEQUENCE: 252

000

<210> SEQ ID NO 253

<400> SEQUENCE: 253

000

<210> SEQ ID NO 254

<400> SEQUENCE: 254

000

<210> SEQ ID NO 255

<400> SEQUENCE: 255

000

<210> SEQ ID NO 256

<400> SEQUENCE: 256

000

<210> SEQ ID NO 257

<400> SEQUENCE: 257

000

<210> SEQ ID NO 258

<400> SEQUENCE: 258

000

<210> SEQ ID NO 259

<400> SEQUENCE: 259

000

<210> SEQ ID NO 260

<400> SEQUENCE: 260

000

<210> SEQ ID NO 261

<400> SEQUENCE: 261

000

<210> SEQ ID NO 262

<400> SEQUENCE: 262

000

<210> SEQ ID NO 263

<400> SEQUENCE: 263

000

<210> SEQ ID NO 264

<400> SEQUENCE: 264

000

<210> SEQ ID NO 265

<400> SEQUENCE: 265

000

<210> SEQ ID NO 266

<400> SEQUENCE: 266

000

<210> SEQ ID NO 267

<400> SEQUENCE: 267

000

<210> SEQ ID NO 268

<400> SEQUENCE: 268

000

<210> SEQ ID NO 269

<400> SEQUENCE: 269

000

<210> SEQ ID NO 270

<400> SEQUENCE: 270

000

<210> SEQ ID NO 271

<400> SEQUENCE: 271

000

<210> SEQ ID NO 272

<400> SEQUENCE: 272

000

<210> SEQ ID NO 273

<400> SEQUENCE: 273

000

<210> SEQ ID NO 274

<400> SEQUENCE: 274

000

<210> SEQ ID NO 275

<400> SEQUENCE: 275

000

<210> SEQ ID NO 276

<400> SEQUENCE: 276

000

<210> SEQ ID NO 277

<400> SEQUENCE: 277

000

<210> SEQ ID NO 278

<400> SEQUENCE: 278

000

<210> SEQ ID NO 279

<400> SEQUENCE: 279

000

<210> SEQ ID NO 280

<400> SEQUENCE: 280

000

<210> SEQ ID NO 281

<400> SEQUENCE: 281

000

<210> SEQ ID NO 282

<400> SEQUENCE: 282

000

<210> SEQ ID NO 283
<400> SEQUENCE: 283
000

<210> SEQ ID NO 284
<400> SEQUENCE: 284
000

<210> SEQ ID NO 285
<400> SEQUENCE: 285
000

<210> SEQ ID NO 286
<400> SEQUENCE: 286
000

<210> SEQ ID NO 287
<400> SEQUENCE: 287
000

<210> SEQ ID NO 288
<400> SEQUENCE: 288
000

<210> SEQ ID NO 289
<400> SEQUENCE: 289
000

<210> SEQ ID NO 290
<400> SEQUENCE: 290
000

<210> SEQ ID NO 291
<400> SEQUENCE: 291
000

<210> SEQ ID NO 292
<400> SEQUENCE: 292
000

<210> SEQ ID NO 293
<400> SEQUENCE: 293
000

<210> SEQ ID NO 294

```
<400> SEQUENCE: 294

000

<210> SEQ ID NO 295
<400> SEQUENCE: 295

000

<210> SEQ ID NO 296
<400> SEQUENCE: 296

000

<210> SEQ ID NO 297
<400> SEQUENCE: 297

000

<210> SEQ ID NO 298
<400> SEQUENCE: 298

000

<210> SEQ ID NO 299
<400> SEQUENCE: 299

000

<210> SEQ ID NO 300
<211> LENGTH: 48
<212> TYPE: DNA
<213> ORGANISM: Artificial sequence
<220> FEATURE:
<223> OTHER INFORMATION: Synthetic sequence: Primer O/SBDIG-1
<220> FEATURE:
<221> NAME/KEY: misc_feature
<222> LOCATION: (30)..(30)
<223> OTHER INFORMATION: n is a, c, g, or t

<400> SEQUENCE: 300
tgggtstgca csctsacsat cgartgcggn acsgtsatct gcgcstgc        48

<210> SEQ ID NO 301
<211> LENGTH: 16
<212> TYPE: DNA
<213> ORGANISM: Artificial sequence
<220> FEATURE:
<223> OTHER INFORMATION: Synthetic sequence: Primer O/ACT08F

<400> SEQUENCE: 301
tccagcacgc gcgggg                                            16

<210> SEQ ID NO 302
<211> LENGTH: 16
<212> TYPE: DNA
<213> ORGANISM: Artificial sequence
<220> FEATURE:
<223> OTHER INFORMATION: Synthetic sequence: Primer O/ACT09R

<400> SEQUENCE: 302
gttcgaccag ccgccc                                            16
```

```
<210> SEQ ID NO 303
<211> LENGTH: 27
<212> TYPE: DNA
<213> ORGANISM: Artificial sequence
<220> FEATURE:
<223> OTHER INFORMATION: Synthetic sequence: Primer O/AGvar01bF

<400> SEQUENCE: 303
ttctagacgt tgttctccca ttttcac                                          27

<210> SEQ ID NO 304
<211> LENGTH: 27
<212> TYPE: DNA
<213> ORGANISM: Artificial sequence
<220> FEATURE:
<223> OTHER INFORMATION: Synthetic sequence: Primer O/AGvar02bR

<400> SEQUENCE: 304
aagatcttcg aaggtgagct cgccgaa                                          27

<210> SEQ ID NO 305
<211> LENGTH: 94
<212> TYPE: DNA
<213> ORGANISM: Artificial sequence
<220> FEATURE:
<223> OTHER INFORMATION: Synthetic sequence: Primer O/AGvar03F

<400> SEQUENCE: 305
gatcttcgcg aggaccgcac catctacgcc gccagcagcg gctgggtgtg tacactgacg      60
atcgagtgcg gcaccgtgat ctgcgcctgc tgac                                  94

<210> SEQ ID NO 306
<211> LENGTH: 94
<212> TYPE: DNA
<213> ORGANISM: Artificial sequence
<220> FEATURE:
<223> OTHER INFORMATION: Synthetic sequence: Primer O/AGvar04R

<400> SEQUENCE: 306
ctaggtcagc aggcgcagat cacggtgccg cactcgatcg tcagtgtaca cacccagccg      60
ctgctggcgg cgtagatggt gcggtcctcg cgaa                                  94

<210> SEQ ID NO 307
<211> LENGTH: 26
<212> TYPE: DNA
<213> ORGANISM: Artificial sequence
<220> FEATURE:
<223> OTHER INFORMATION: Synthetic sequence: Primer O/AGvar05F

<400> SEQUENCE: 307
gcctgctgac ctaggtcgac gatcgt                                           26

<210> SEQ ID NO 308
<211> LENGTH: 27
<212> TYPE: DNA
<213> ORGANISM: Artificial sequence
<220> FEATURE:
<223> OTHER INFORMATION: Synthetic sequence: Primer O/AGvar06r

<400> SEQUENCE: 308
tgaattcggc tgctccccgc gcgaaat                                          27

<210> SEQ ID NO 309
<211> LENGTH: 59
<212> TYPE: DNA
<213> ORGANISM: Artificial sequence
```

```
<220> FEATURE:
<223> OTHER INFORMATION: Synthetic sequence: Primer O/SB50F

<400> SEQUENCE: 309
attcgcccgg gaagtccacc gaaaggaaga cacaccatga ttccggggat ccgtcgacc      59

<210> SEQ ID NO 310
<211> LENGTH: 58
<212> TYPE: DNA
<213> ORGANISM: Artificial sequence
<220> FEATURE:
<223> OTHER INFORMATION: Synthetic sequence: Primer O/SB51R

<400> SEQUENCE: 310
gggcgatgcc cgccccgggc cggaaacgat cgtcgatcat gtaggctgga gctgcttc       58

<210> SEQ ID NO 311
<211> LENGTH: 59
<212> TYPE: DNA
<213> ORGANISM: Artificial sequence
<220> FEATURE:
<223> OTHER INFORMATION: Synthetic sequence: Primer O/SB52F

<400> SEQUENCE: 311
aagtatatat gagtaaactt ggtctgacag ttaccaatga ttccggggat ccgtcgacc      59

<210> SEQ ID NO 312
<211> LENGTH: 58
<212> TYPE: DNA
<213> ORGANISM: Artificial sequence
<220> FEATURE:
<223> OTHER INFORMATION: Synthetic sequence: Primer O/SB53R

<400> SEQUENCE: 312
gcttcaataa tattgaaaaa ggaagagtat gagtattcat gtaggctgga gctgcttc       58

<210> SEQ ID NO 313
<211> LENGTH: 19
<212> TYPE: PRT
<213> ORGANISM: Artificial sequence
<220> FEATURE:
<223> OTHER INFORMATION: Synthetic sequence: Compound of Formula I
<220> FEATURE:
<221> NAME/KEY: MOD_RES
<222> LOCATION: (7, 9, 14)
<223> OTHER INFORMATION: Abu
<220> FEATURE:
<221> NAME/KEY: THIOETH
<222> LOCATION: (1)..(6)
<220> FEATURE:
<221> NAME/KEY: THIOETH
<222> LOCATION: (7)..(12)
<220> FEATURE:
<221> NAME/KEY: THIOETH
<222> LOCATION: (9)..(17)
<220> FEATURE:
<221> NAME/KEY: MISC_FEATURE
<222> LOCATION: (14)..(19)
<223> OTHER INFORMATION: Linked by Y, where Y is -S- or -S(O)-

<400> SEQUENCE: 313

Ala Ser Gly Trp Val Ala Xaa Leu Xaa Ile Glu Ala Gly Xaa Leu Val
1               5                   10                  15

Ala Ala Ala

<210> SEQ ID NO 314
<211> LENGTH: 19
<212> TYPE: PRT
<213> ORGANISM: Artificial sequence
```

```
<220> FEATURE:
<223> OTHER INFORMATION: Synthetic sequence: Compound of Formula I
<220> FEATURE:
<221> NAME/KEY: MOD_RES
<222> LOCATION: (7, 9, 14)
<223> OTHER INFORMATION: Abu
<220> FEATURE:
<221> NAME/KEY: THIOETH
<222> LOCATION: (1)..(6)
<220> FEATURE:
<221> NAME/KEY: THIOETH
<222> LOCATION: (7)..(12)
<220> FEATURE:
<221> NAME/KEY: THIOETH
<222> LOCATION: (9)..(17)
<220> FEATURE:
<221> NAME/KEY: MISC_FEATURE
<222> LOCATION: (14)..(19)
<223> OTHER INFORMATION: Linked by Y, where Y is -S- or -S(O)-

<400> SEQUENCE: 314

Ala Ser Gly Trp Val Ala Xaa Leu Xaa Ile Glu Ala Gly Xaa Val Val
1               5                   10                  15

Ala Ala Ala

<210> SEQ ID NO 315
<211> LENGTH: 19
<212> TYPE: PRT
<213> ORGANISM: Artificial sequence
<220> FEATURE:
<223> OTHER INFORMATION: Synthetic sequence: Compound of Formula I
<220> FEATURE:
<221> NAME/KEY: MOD_RES
<222> LOCATION: (7, 9, 14)
<223> OTHER INFORMATION: Abu
<220> FEATURE:
<221> NAME/KEY: THIOETH
<222> LOCATION: (1)..(6)
<220> FEATURE:
<221> NAME/KEY: THIOETH
<222> LOCATION: (7)..(12)
<220> FEATURE:
<221> NAME/KEY: THIOETH
<222> LOCATION: (9)..(17)
<220> FEATURE:
<221> NAME/KEY: MISC_FEATURE
<222> LOCATION: (14)..(19)
<223> OTHER INFORMATION: Linked by Y, where Y is -S- or -S(O)-

<400> SEQUENCE: 315

Ala Ser Gly Trp Val Ala Xaa Leu Xaa Ile Glu Ala Gly Xaa Leu Ile
1               5                   10                  15

Ala Ala Ala

<210> SEQ ID NO 316
<211> LENGTH: 20
<212> TYPE: PRT
<213> ORGANISM: Artificial sequence
<220> FEATURE:
<223> OTHER INFORMATION: Synthetic sequence: Compound of Formula I
<220> FEATURE:
<221> NAME/KEY: MOD_RES
<222> LOCATION: (8, 10, 15)
<223> OTHER INFORMATION: Abu
<220> FEATURE:
<221> NAME/KEY: THIOETH
<222> LOCATION: (2)..(7)
<220> FEATURE:
<221> NAME/KEY: THIOETH
<222> LOCATION: (8)..(13)
<220> FEATURE:
<221> NAME/KEY: THIOETH
<222> LOCATION: (10)..(18)
<220> FEATURE:
```

```
<221> NAME/KEY: MISC_FEATURE
<222> LOCATION: (15)..(20)
<223> OTHER INFORMATION: Linked by Y, where Y is -S- or -S(O)-

<400> SEQUENCE: 316

Ala Ala Ser Gly Trp Val Ala Xaa Leu Xaa Ile Glu Ala Gly Xaa Leu
1               5                   10                  15

Val Ala Ala Ala
            20

<210> SEQ ID NO 317
<211> LENGTH: 20
<212> TYPE: PRT
<213> ORGANISM: Artificial sequence
<220> FEATURE:
<223> OTHER INFORMATION: Synthetic sequence: Compound of Formula I
<220> FEATURE:
<221> NAME/KEY: MOD_RES
<222> LOCATION: (8, 10, 15)
<223> OTHER INFORMATION: Abu
<220> FEATURE:
<221> NAME/KEY: THIOETH
<222> LOCATION: (2)..(7)
<220> FEATURE:
<221> NAME/KEY: THIOETH
<222> LOCATION: (8)..(13)
<220> FEATURE:
<221> NAME/KEY: THIOETH
<222> LOCATION: (10)..(18)
<220> FEATURE:
<221> NAME/KEY: MISC_FEATURE
<222> LOCATION: (15)..(20)
<223> OTHER INFORMATION: Linked by Y, where Y is -S- or -S(O)-

<400> SEQUENCE: 317

Ala Ala Ser Gly Trp Val Ala Xaa Leu Xaa Ile Glu Ala Gly Xaa Val
1               5                   10                  15

Val Ala Ala Ala
            20

<210> SEQ ID NO 318
<211> LENGTH: 20
<212> TYPE: PRT
<213> ORGANISM: Artificial sequence
<220> FEATURE:
<223> OTHER INFORMATION: Synthetic sequence: Compound of Formula I
<220> FEATURE:
<221> NAME/KEY: MOD_RES
<222> LOCATION: (8, 10, 15)
<223> OTHER INFORMATION: Abu
<220> FEATURE:
<221> NAME/KEY: THIOETH
<222> LOCATION: (2)..(7)
<220> FEATURE:
<221> NAME/KEY: THIOETH
<222> LOCATION: (8)..(13)
<220> FEATURE:
<221> NAME/KEY: THIOETH
<222> LOCATION: (10)..(18)
<220> FEATURE:
<221> NAME/KEY: MISC_FEATURE
<222> LOCATION: (15)..(20)
<223> OTHER INFORMATION: Linked by Y, where Y is -S- or -S(O)-

<400> SEQUENCE: 318

Ala Ala Ser Gly Trp Val Ala Xaa Leu Xaa Ile Glu Ala Gly Xaa Leu
1               5                   10                  15

Ile Ala Ala Ala
            20
```

LANTIBIOTIC BIOSYNTHETIC GENE CLUSTERS FROM A. GARBADINENSIS AND A. LIGURIAE

RELATED APPLICATIONS

The present application is a U.S. National Phase Application of International Application No. PCT/GB2007/000138 (filed Jan. 17, 2007) which claims the benefit of Great Britain Patent Application No. 0600928.6 (filed Jan. 17, 2006), each of which is hereby incorporated by reference in their entirety.

FIELD OF THE INVENTION

This invention relates to characterisation of the biosynthetic gene cluster for the lantibiotic actagardine, identification of a novel variant of actagardine and its biosynthetic cluster, and methods of production and use of actagardine, a novel actagardine variant produced in a strain of *A. liguriae*, and variants of both of these produced according to this invention, utilizing genes from the characterised biosynthetic gene clusters.

BACKGROUND OF THE INVENTION

Lantibiotics are peptides having antibiotic and other activities, produced by Gram-positive bacteria. They contain, among other modified residues, the thioether amino acids lanthionine and methyllanthionine, which cross-link the peptide chain into a polycyclic structure. They have been classified into two classes, type-A and type-B, though such classification is not unproblematic. Type-A lantibiotics are generally elongate amphiphiles that are capable of forming pores in bacterial and other plasma membranes. Examples are nisin and subtilin. Type-B lantibiotics, by contrast, are globular, conformationally defined peptides that inhibit enzyme functions. Examples are cinnamycin and duramycin.

Activities ascribed to type-B lantibiotics such as cinnamycin include antimicrobial activity (providing potential application as antibiotics), inhibition of angiotensin-converting enzyme (providing a potential application in blood pressure regulation), immunomodulation via inhibition of phospholipase A2 (providing a potential application as anti-inflammatories), and interference with prostaglandin and leucotriene biosynthesis.

Type-B lantibiotics appear to exert their activity by interfering with enzyme activities by blocking the respective substrates. For example, type B lantibiotics such as mersacidin and actagardine have been found to inhibit biosynthesis of peptidoglycan; transglycosylation was identified as the target reaction. The substrate for this reaction is the lipid-bound cell wall precursor lipid II. While this is a target for the lantibiotic vancomycin, the site of action is different and is a new target binding site not used by any current antibacterial drug.

For the cinnamycin class of type B lantibiotics antibacterial activity has been observed, in particular with *Bacillus* strains, with effects described on membrane functions, ATP-dependent proton translocation and $Ca^{2+}$-uptake, and on ATPases. Also, the formation of defined pores in phosphatidylethanolamine-containing planar membranes has been reported. These effects can be attributed to the specific binding of these type-B lantibiotics to phosphatidylethanolamine.

Lantibiotics have been shown to have efficacy and utility as food additives and antibacterial agents against *Propionibacterium acnes* and problematic pathogens, e.g. methicillin-resistant *Staphylococcus aureus* (MRSA), which has or is developing resistance to many commonly used antibiotics, and *Streptococcus pneumoniae*. For reviews, see Sahl and Bierbaum (1998) Annual Rev. Microbiol. 52:41-79; Jack and Sahl (1995) TIBTECH 13:269 278; Gasson (1995) Chapter 10, Lantibiotics, in Vining and Stuttard (eds) Biotechnology Series: Genetics and Biochemistry of Antibiotic Production, Biotechnological I 30 Series 28, pages 283-306.

Within the field of antibiotics, there is a continuing need for the provision of new antibiotic compounds, to overcome issues such as resistance, bio-compatibility, toxicity and the like. Accordingly, methods of producing lantibiotics, and the production of variant forms of lantibiotics (which may have a different activity profile compared to native forms), are desirable.

Actagardine is a known type B tetracyclic lantibiotic, 19 amino acids in length (1890 Da). It has potent activity against important Gram positive pathogens such as *Staphylococcus aureus* and *Streptococcus pyogenes* both in vitro and in in vivo animal models. The structure of actagardine is shown in FIG. 4. The compound is produced from a pre-pro-peptide, the C-terminal portion of which has the polypeptide sequence of SSGWVCTLTIECGTVICAC (SEQ ID NO:4). The polypeptide of SEQ ID NO:4 is modified by the following crosslinks, creating secondary and tertiary structure: CROSSLINK 1-6, Lanthionine (Ser-Cys); CROSSLINK 7-12, Beta-methyllanthionine (Thr-Cys); CROSSLINK 9-17, Beta-methyllanthionine (Thr-Cys); CROSSLINK 14-19, Beta-methyllanthionine sulfoxide (Thr-Cys).

Actagardine has been reported to be produced by two species of *Actinoplanes*; *A. garbadinensis* and *A. liguriae*. Also co-produced is an analogue in which the CROSSLINK 14-19 is not oxidized i.e. it is a beta-methyllanthionine not betamethyllanthionine sulfoxide which is named herein deoxy-actagardine.

U.S. Pat. No. 6,022,851 describes the isolation of actagardine from isolated strains of *A. garbadinensis* and *A. liguriae*.

DISCLOSURE OF THE INVENTION

The present invention relates to the cloned, sequenced and elucidated structural and regulatory information relevant to the biosynthetic gene cluster for the type-B lantibiotic, actagardine, from *Actinoplanes garbadinensis* and *A. liguriae*.

We have also surprisingly found that in an isolate of *A. liguriae*, designated herein as *A. liguriae* NCIMB 41362, a novel form of actagardine is produced which we have termed actagardine B or, in the non-oxidised form, deoxy-actagardine B. These forms have similar anti-microbial activity to actagardine and are generated from the primary polypeptide sequence of SEQ ID NO:1, which undergoes similar cross-linking to actagardine. The variants provide new and useful alternatives to actagardine. In addition, the identification of residues in actagardine B which are different from actagardine leads to the provision of further lantibiotics based on these differences.

We have also isolated gene clusters from both actagardine-producing *A. garbadinensis* and *A. liguriae* NCIMB 41362 which comprise the genes for the production of actagardine and actagardine B.

In one aspect, the present invention provides the novel actagardine B and variants thereof, including variants based on the primary polypeptide sequences of SEQ ID NO:2 and SEQ ID NO:3, as well as variants thereof.

In a further aspect, the invention provides nucleic acids encoding actagardine B and its variants, sets of nucleic acids and variants thereof derived from the above-mentioned gene clusters, methods of making actagardine B and its variants, and methods of generating novel variants of actagardine B.

DESCRIPTION OF THE SEQUENCES

Figure 1:
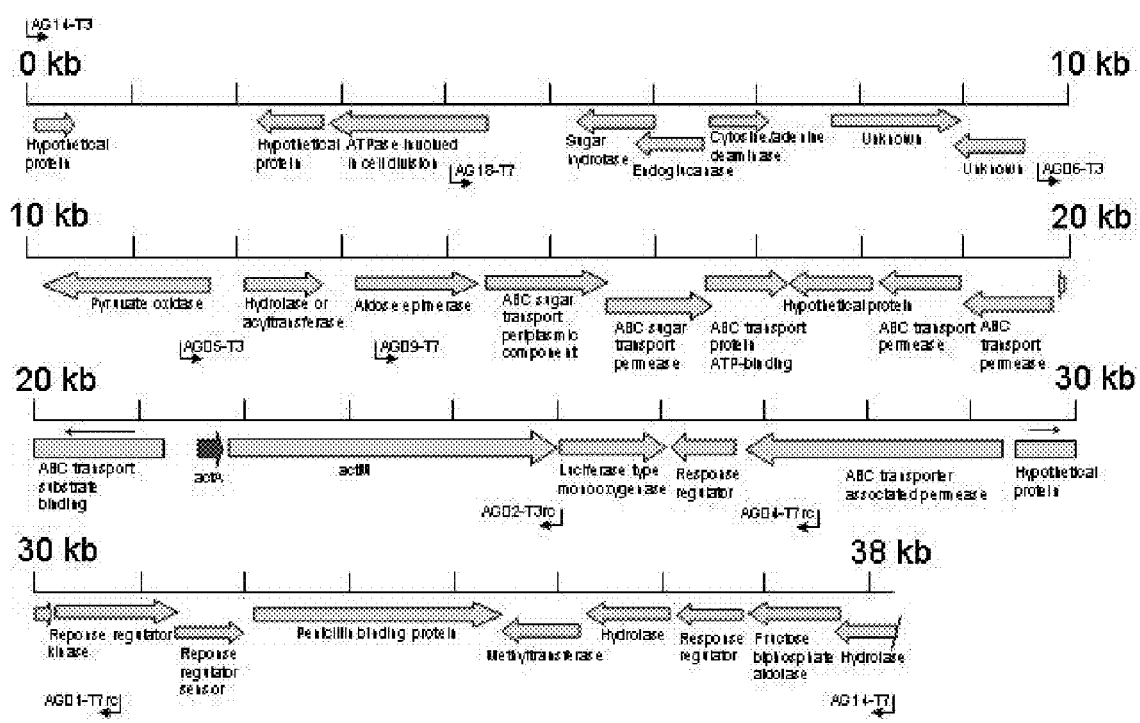
FIG. 1 provides a map of the actagardine encoding and regulatory gene cluster isolated from *A. garbadinensis*.
Figure 2:
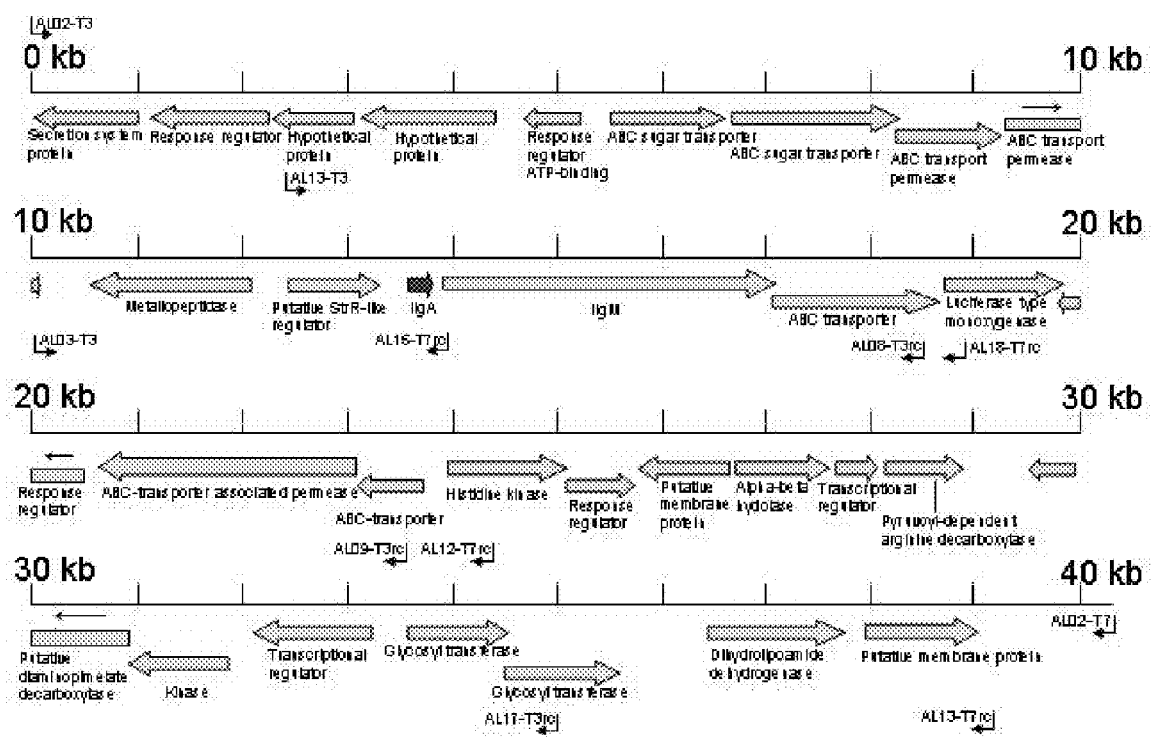
FIG. 2 provides a map of the encoding and regulatory gene cluster isolated from *A. liguriae* which encodes a novel variant of actagardine, herein referred to as actagardine B.
Figure 3:
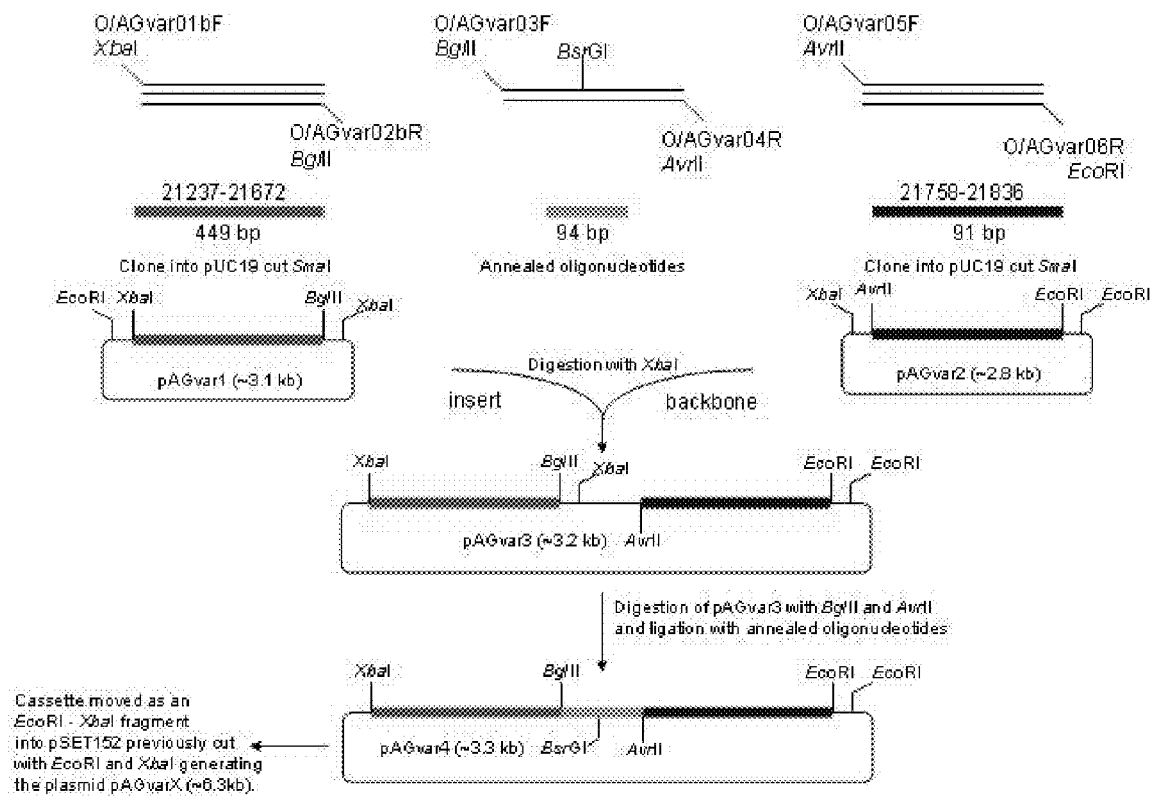
FIG. 3 provides a schematic showing a method disclosed herein for generation of actagardine variants utilizing nucleic acid sequences isolated from *A. garbadinensis* or from *A. liguriae*.

For the convenience of the reader, the sequences of the present application have been numbered non-contiguously as follows:

SEQ ID NO:1 is the primary polypeptide sequence of Actagardine B:
SSGWVCTLTIECGTLVCAC.

SEQ ID NO:2 is the primary polypeptide sequence of Actagardine B variant VV:
SSGWVCTLTIECGTVVCAC.

SEQ ID NO:3 is the primary polypeptide sequence of Actagardine B variant LI
SSGWVCTLTIECGTLICAC.

SEQ ID NO:4 is the primary polypeptide sequence of Actagardine:
SSGWVCTLTIECGTVICAC;

SEQ ID NO:11 is the primary polypeptide sequence of Ala-Actagardine B:
ASSGWVCTLTIECGTLVCAC.

SEQ ID NO:12 is the primary polypeptide sequence of Ala-Actagardine B variant VV:
ASSGWVCTLTIECGTVVCAC.

SEQ ID NO:13 is the primary polypeptide sequence of Ala-Actagardine B variant LI
ASSGWVCTLTIECGTLICAC.

SEQ ID NO:14 is the primary polypeptide sequence of Ala-Actagardine:
ASSGWVCTLTIECGTVICAC.

SEQ ID NO:212 is the primary polypeptide sequence of pre-pro-Actagardine B:
MSAITVETTWKNTDLREDLTAHPAGLGF-GELSFEDLREDRTIYAASSGWVCTLTIECG TLVCAC.

SEQ ID NO:22 is the primary polypeptide sequence of pre-pro-Actagardine B variant VV:
MSAITVETTWKNTDLREDLTAHPAGLGF-GELSFEDLREDRTIYAASSGWVCTLTIECG TVVCAC.

SEQ ID NO:23 is the primary polypeptide sequence of pre-pro-Actagardine B variant LI:
MSALAIEKSWKDVDLRDGATSHPAGLGF-GELTFEDLREDRTIYAASSGWVCTLTIECG TLICAC.

SEQ ID NO:119 is the primary polypeptide sequence of pre-pro-Actagardine:
MSALAIEKSWKDVDLRDGATSHPAGLGF-GELTFEDLREDRTIYAASSGWVCTLTIECG TVICAC.

SEQ ID NO:100 is the non-vector, *A. garbadinensis*-derived, nucleotide sequence of the cosmid CosAG14.

SEQ ID NOs:101-132 are the polypeptide sequences of the open reading frames orf1-orf32 of SEQ ID NO:100 respectively.

SEQ ID NO:200 is the non-vector, *A. liguriae*-derived, nucleotide sequence of the cosmid CosAL02.

SEQ ID NOs:201-231 are the polypeptide sequences of the open reading frames orf1-orf31 of SEQ ID NO:200 respectively.

SEQ ID NOs:300-312 are primer sequences described herein below.

DETAILED DESCRIPTION OF THE INVENTION

The present invention relates to the gene clusters of SEQ ID NO:100 and SEQ ID NO:200 and the polypeptides encoded by these clusters and variants thereof. The polypeptide of SEQ ID NO:119 is pre-pro-actagardine and the polypeptide of SEQ ID NO:212 is pre-pro-actagardine B. The remaining polypeptides and their variants (as defined herein) are referred to herein generically as "cluster polypeptides". Cluster polypeptides derived from SEQ ID NO:100 are referred to as "1xx polypeptides" and those derived from SEQ ID NO:200 are referred to as "2xx polypeptides". Polypeptides which are 100% identical in both sequence and length to a cluster polypeptide are referred to as "wild-type" polypeptides. A cluster polypeptide derived from SEQ ID NO:100 or SEQ ID NO:200 may be wild type or variant.

A polypeptide may be in substantially isolated form. Isolated polypeptides of the invention will be those as defined above in isolated form, free or substantially free of material with which it is naturally associated such as other polypeptides with which it is found in the cell. For example, the polypeptides may of course be formulated with diluents or adjuvants and still for practical purposes be isolated.

A polypeptide of the invention may also be in a substantially purified form, in which case it will generally comprise the polypeptide in a preparation in which more than 90%, e.g. 95%, 98% or 99% of the polypeptide in the preparation is a polypeptide of the invention.

Lantibiotic Polypeptide and LantibioticA Gene

In the present invention, reference to a lantibioticA or LanA polypeptide, the LantibioticA or LanA gene refers generically to a type B lantibiotic polypeptide or the gene encoding such a peptide. Thus reference to these includes reference to cinnamycin, mersacidin, actagardine and actagardine B and the genes encoding these products. Reference to a lantibiotic producing host cell refers to any host cell which in its native form produces a LanA polypeptide, as further defined herein below.

A LanA polypeptide is a polypeptide with anti-microbial activity. Anti-microbial activity may be examined by determining the MIC value against a reference organism, e.g. *Micrococcus luteus*. A LanA polypeptide is considered to exhibit anti-microbial activity if it has a MIC value of less than or equal to 16-fold higher than that of actagardine against the same strain of the reference microorganism. In the present invention, the *A. garbadinensis* LanA gene is referred to as actA and the *A. liguriae* LanA gene is referred to as LigA.

Other Lan Polypeptides

As used herein, reference to a "LanM" polypeptide is a polypeptide derived from a Lantibiotic gene cluster which is a modification factor required for the conversion of a precursor polypeptide to a lantibiotic compound. LanM polypeptides include those of SEQ ID NO:120 (ActM) or a variant thereof, SEQ ID NO:213 (LigM) or a variant thereof, a cinM polypeptide as defined in WO02/088367, a mrsM polypeptide as disclosed in Altena et al, 2000, or a homologous polypeptide from another gene cluster of a bacteria which produces a type B lantibiotic.

Reference to a "LanR" polypeptide is a polypeptide derived from a Lantibiotic gene cluster which is a regulatory factor required for the regulation of production of a precursor polypeptide. LanR polypeptides include those of SEQ ID NO:122 (ActR) or a variant thereof, SEQ ID NO:216 (LigR) or a variant thereof, a cinR1 polypeptide as defined in WO02/088367, a mrsR1 polypeptide as disclosed in Altena et al, 2000, or a homologous polypeptide from another gene cluster of a bacteria which produces a type B lantibiotic.

Reference to a "LanT" polypeptide is a polypeptide derived from a Lantibiotic gene cluster which is a transporter factor required for the production of a precursor polypeptide to a lantibiotic compound. LanT polypeptides include those of SEQ ID NO:123 (ActT) or a variant thereof, SEQ ID NO:214 (LigT) or a variant thereof, a cinT polypeptide as defined in WO02/088367, a mrsT polypeptide as disclosed in Altena et al, 2000, or a homologous polypeptide from another gene cluster of a bacteria which produces a type B lantibiotic.

Reference to a "LanO" polypeptide is a polypeptide derived from a Lantibiotic gene cluster which is a factor believed to be involved in the oxidation of the deoxy-form of actagardine and compounds of the invention to actagardine or to compounds of the invention in which Y is —S(O)—.

LanO polypeptides include those of SEQ ID NO:122 (ActO) or a variant thereof, SEQ ID NO:215 (LigO) or a variant thereof, or a homologous polypeptide from another gene cluster of a bacteria which produces a type B lantibiotic.

Cluster Polypeptides

In one aspect, the invention provides an isolated cluster polypeptide selected from any one of SEQ ID NOs: 101, 102, 103, 104, 105, 106, 107, 108, 109, 110, 111, 112, 113, 114, 115, 116, 117, 118, 120, 121, 122, 123, 124, 125, 126, 127, 128, 129, 130, 131, 132, 201, 202, 203, 204, 205, 206, 207, 208, 209, 210, 211, 213, 214, 215, 216, 217, 218, 219, 220, 221, 222, 223, 224, 225, 226, 227, 228, 229, 230 and 231. In another aspect, the invention provides a cluster polypeptide which is a variant of any of the above-mentioned sequences.

Cluster polypeptides of particular interest include 1xx and 2xx polypeptides which are LanM, LanR, LanT or LanO polypeptides.

A "variant", in relation to a cluster polypeptide, denotes: any polypeptide having an amino acid sequence which is different from, but which shows significant amino acid sequence identity with, the amino acid sequence of a reference polypeptide (in this case any wild type cluster polypeptide), or a fragment of that polypeptide.

Unless otherwise specified, significant amino acid sequence identity is preferably at least 80%, more preferably 85%, 90% or 95%, still more preferably 98% or 99%. A variant is preferably of a length which is the same as, or at least 70%, preferably at least 80%, more preferably at least 90% and most preferably at least 95% of the length of the wild type cluster polypeptide.

"Percent (%) amino acid sequence identity" is defined as the percentage of amino acid residues in a candidate sequence that are identical with the amino acid residues in the sequence with which it is being compared, after aligning the sequences and introducing gaps, if necessary, to achieve the maximum percent sequence identity, and not considering any conservative substitutions as part of the sequence identity. The % identity values used herein are generated by BLAST-2 which was obtained from Altschul et al. (1996). WU-BLAST-2 uses several search parameters, most of which are set to the default values. The adjustable parameters are set with the following values: overlap span=1, overlap fraction=0.125, word threshold (T)=11. The HSPS and HSPS2 parameters are dynamic values and are established by the program itself depending upon the composition of the particular sequence and composition of the particular database against which the sequence of interest is being searched; however, the values may be adjusted to increase sensitivity. A % amino acid sequence identity value is determined by the number of matching identical residues divided by the total number of residues of the "longer" sequence in the aligned region, multiplied by 100. The "longer" sequence is the one having the most actual residues in the aligned region (gaps introduced by WU BLAST-2 to maximize the alignment score are ignored).

Desirably, a variant will retain a biological function of the reference polypeptide. In the present invention, biological function is retained wherein the variant, when present in a host cell with the other members of its cluster, is capable of producing a lantibiotic. This may be determined, for example, by providing a host cell containing SEQ ID NO:100 in the case of a 1xx cluster polypeptide variant, or SEQ ID NO:200 in the case of a 2xx polypeptide variant, wherein the host cells produce actagardine or actagardine B respectively, modifying the sequence to encode the variant, and determining whether a lantibiotic polypeptide is still produced.

Precursor Polypeptides

In another aspect, the invention provides polypeptides, preferably in isolated form, which are precursors of the compounds of the present invention or of actagardine. The precursor polypeptides include the polypeptides of any one of SEQ ID NOs:1-4, SEQ ID NOs:11-14, SEQ ID NOs:212, 22, 23 and 119, as well as variants or derivatives thereof which can be converted to a lantibiotic polypeptide.

A variant of a precursor polypeptide of any one of SEQ ID NOs:1-4 is a polypeptide in which one or more, for example from 1 to 5, such as 1, 2, 3 or 4 amino acids are substituted by another amino acid. Preferably the amino acid is at a position selected from positions 2, 3, 4, 5, 8, 10, 11, 13 or 18 of any one of SEQ ID NOs:1-4.

A variant of a precursor polypeptide of any one of SEQ ID NOs:11-14 is a polypeptide in which one or more, for example from 1 to 5, such as 1, 2, 3 or 4 amino acids are substituted by another amino acid. Preferably the amino acid is at a position selected from positions 3, 4, 5, 6, 9, 11, 12, 14 or 19 of any one of SEQ ID NOs:11-14.

A variant of a precursor polypeptide of any one of SEQ ID NOs:212, 22, 23 and 119 is a polypeptide in which one or more, for example from 1 to 5, such as 1, 2, 3 or 4 amino acids of the C-terminal region (residues 46-64) corresponding to SEQ ID NOs:1-4 respectively are substituted by another amino acid. Preferably the amino acid is at a position selected from positions corresponding to positions 2, 3, 4, 5, 8, 10, 11, 13 or 18 of any one of SEQ ID NOs:1-4. Such variants may further include changes to the N-terminal region which retain at least 70%, for example at least 80%, preferably at least 90%, for example at least 95% of the N-terminal regions (residues 1-45). For example, a variant of the N-terminal region of SEQ ID NO:212 or SEQ ID NO:119 may comprise one or more substitutions (e.g. from 1 to 12, such as from 1 to 5, e.g. 1, 2 or 3 substitutions at positions 4, 5, 6, 8, 9, 12, 13, 17, 18, 19, 21 and 32 which our data shows are varied between SEQ ID NO:212 and 119.

Substitutions may be of one amino acid by another naturally occurring amino acid and may be conservative or nonconservative substitutions. Conservative substitutions include those set out in the following table, where amino acids on the same block in the second column and preferably in the same line in the third column may be substituted for each other:

| ALIPHATIC | Non-polar | G A |
| | | I L V |
| | Polar - uncharged | C S T M |
| | | N Q |
| | Polar - charged | D E |
| | | K R |
| AROMATIC | | H F W Y |

For SEQ ID NO:212, the substitutions may be of an amino acid which differs from the amino acid residue located in the corresponding location of SEQ ID NO:119, or vice versa. In either case, the substitution may be to introduce the SEQ ID NO:119 amino acid into SEQ ID NO:212, or vice versa (e.g. Ile at position 4 of SEQ ID NO:212 may be substituted by Leu, and so on).

A precursor polypeptide may be obtained by expression of a nucleic acid encoding the polypeptide in a cell which is a non-producer of a lantibiotic.

Compounds

In one aspect, the present invention provides a compound of the formula (I):

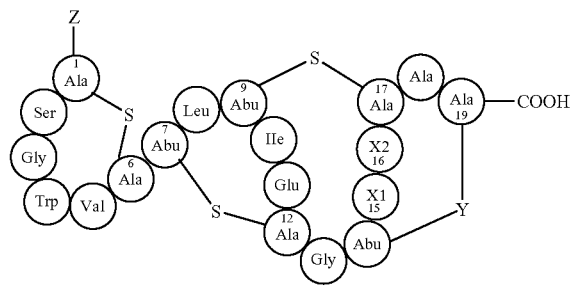

wherein:
-X1-X2- represent -Leu-Val-; -Val-Val- or -Leu-Ile-;
Y is —S— or —S(O)—; and
Z is either $H_2N$— or Ala-,
or a pharmaceutically acceptable salt thereof. In a further aspect, the invention provides variants and biologically active derivatives of these compounds.

Where -X1-X2- represent -Leu-Val-, Y is —S(O)— and Z is $NH_2$ the compound of the invention is also referred to as actagardine B.

Where -X1-X2- represent -Leu-Val-, Y is —S(O)— and Z is Ala- the compound of the invention is also referred to as ala-actagardine B.

Where -X1-X2- represent -Leu-Val-, Y is —S— and Z is $NH_2$ the compound of the invention is also referred to as deoxy-actagardine B.

Where -X1-X2- represent -Leu-Val-, Y is —S— and Z is Ala- the compound of the invention is also referred to as ala-deoxy-actagardine B.

It will be understood by reference to Z being a group $H_2N$—, that this moiety represents the N-terminus of the alanine residue at position 1 of the above compound. By reference to the group Z being Ala-, it will be understood that this moiety represents an alanine, conventionally referred to in the art as Ala(0), linked to the alanine at position 1 via an amide bond.

Variants

A variant of a compound of formula (I) is a compound which one or more, for example from 1 to 5, such as 1, 2, 3 or 4 amino acids are substituted by another amino acid. Preferably the amino acid is at a position selected from positions 2, 3, 4, 5, 8, 10, 11, 13 or 18 of the compound of formula (I).

A variant may also comprise a substitution at position 15 or 16, provided that when both positions 15 and 16 are substituted and none of the other positions are changes, 15 and 16 are not Val and Ile respectively.

Where Z is Ala-, variants of compounds of the invention include those in which Ala- is replaced by another amino acid (particularly a naturally occurring amino acid encoded by the genetic code or its D-isoform), more particularly an amino acid selected from the group Ile-, Lys-, Phe-, Val-, Glu-, Asp-, His-, Leu, Arg-, Ser- and Trp-. In one aspect, the amino acid may be selected from the group Ile-, Lys-, Phe-, Val-, Glu-, Asp-, His-, Leu-, Arg- and Ser-. Such variants may be produced by chemical addition of the residue to compounds where Z=$H_2N$, as described in U.S. Pat. No. 6,022,851. It will be appreciated that the chemical addition of an amino acid allows the amino acid to be in the L- or D-configuration. This includes D-Ala, in addition to the D-forms of other amino acids such as those mentioned above.

Derivatives

Derivatives of compounds of the invention (including variants) are those in which one or more amino acid side chain of the compound of the invention has been modified, for example by esterification, amidation or oxidation.

Derivatives of compounds of the invention may be monoamide derivatives at one of the carboxy functions of actagardine, particularly at the C-terminal. More particularly, a derivative may be a compound in which the C-terminal of the compound of the invention is of the formula —COR, in which R represents the group —$NR^1R^2$, wherein $R^1$ and $R^2$ independently represent:

(i) hydrogen;
(ii) a group of formula —$(CH_2)_n$—$NR^3R^4$, in which n represents an integer from 2 to 8 and $R^3$ and $R^4$ independently represent hydrogen or ($C_1$-$C_4$) alkyl or $R^3$ and $R^4$ taken together represent a group —$(CH_2)_3$—, —$(CH_2)_4$—, $(CH_2)_2$—O—$(CH_2)_2$—, —$(CH_2)_2$—S—$(CH_2)_2$— or —$(CH_2)_5$—;

or $R^1$ and $R^2$ taken together with the adjacent nitrogen atom represent a piperazine moiety which may be substituted in position 4 with a substituent selected from:
(a) ($C_1$-$C_4$)alkyl;
(b) ($C_5$-$C_7$)-cycloalkyl,
(c) pyridyl,
(d) —$(CH_2)_p$—$NR^5R^6$ in which p represents an integer from 1 to 8 and $R^5$ and $R^6$ independently represent hydrogen or ($C_1$-$C_4$) alkyl;
(e) piperidinyl;
(f) substituted piperidinyl, wherein the substituted piperidinyl bears a N-substituent which is ($C_{1-4}$)alkyl;
(g) benzyl; and
(h) substituted benzyl, wherein the phenyl moiety bears 1 or 2 substituents selected from chloro, bromo, nitro, ($C_1$-$C_4$)alkyl and ($C_1$-$C_4$)alkoxy.

In one embodiment, in the formula —COR, R represents the group —$NR^1R^2$, wherein $R^1$ and $R^2$ independently represent hydrogen, a group of formula —$(CH_2)_n$—$NR^3R^4$, in which n represents an integer from 2 to 8 and $R^3$ and $R^4$ independently represent hydrogen or ($C_1$-$C_4$) alkyl or $R^3$ and $R^4$ taken together represent a group —$(CH_2)_3$—, —$(CH_2)_4$—, $(CH_2)_2$—O—$(CH_2)_2$—, —$(CH_2)_2$—S—$(CH_2)_2$— or —$(CH_2)_5$—, or $R^1$ and $R^2$ taken together with the adjacent nitrogen atom represent a piperazine moiety which may be substituted in position 4 with a substituent selected from $(C_1-C_4)$alkyl, $(C_5-C_7)$-cycloalkyl, pyridyl, benzyl, and substituted benzyl wherein the phenyl moiety bears 1 or 2 substituents selected from chloro, bromo, nitro, $(C_1-C_4)$alkyl and $(C_1-C_4)$alkoxy.

Further, a derivative may include a compound in which the carboxy function of a side chain of an internal residue, e.g. that of the residue Glu11, is modified from —COOH to a group —COOR$^5$ in which R$^5$ represents hydrogen, $(C_1-C_4)$alkyl or $(C_1-C_4)$alkoxy$(C_2-C_4)$alkyl.

N-terminal derivatives of compounds of the invention may be those in which the N-terminal amino group —NH$_2$ is instead a group —NHR$^6$ wherein R$^6$ represents $C_{1-4}$alkyl.

The term "$(C_1-C_4)$alkyl" represents straight or branched alkyl chains of from 1 to 4 carbon atoms, such as: methyl, ethyl, propyl, 1-methylethyl, butyl, 1-methylpropyl or 1,1-dimethylethyl while the term "$(C_2-C_4)$alkyl" represents straight or branched alkyl chains of from 2 to 4 carbon atoms such as: ethyl, propyl, 1-methylethyl, butyl, 1-methylpropyl or 1,1-dimethylethyl. The term "$(C_5-C_7)$cycloalkyl" represents a cycloalkyl group selected from cyclopentyl, cyclohexyl and cycloheptyl.

The term "$(C_1-C_4)$alkoxy" represents a straight or branched alkoxy chain of 1 to 4 carbon atoms such as methoxy, ethoxy, propoxy, 1-methylethoxy, butoxy, 1-methylpropoxy and 1,1-dimethylethoxy.

Derivatives according to the present invention may be made according to the methods described for the manufacture of derivatives of actagardine in EP-0195359, the disclosure of which is incorporated herein by reference.

Further Embodiments

Where the derivative is a compound where the C-terminal is of the formula —COR, in which R represents the group —NR$^1$R$^2$, in some embodiments, R$^1$ is H and R$^2$ represents a group of formula —(CH$_2$)$_n$—NR$^3$R$^4$, in which n represents an integer from 2 to 8 and R$^3$ and R$^4$ independently represent hydrogen or $(C_1-C_4)$ alkyl or R$^3$ and R$^4$ taken together represent a group —(CH$_2$)$_3$—, —(CH$_2$)$_4$—, (CH$_2$)$_2$—O—(CH$_2$)$_2$—, —(CH$_2$)$_2$—S—(CH$_2$)$_2$— or —(CH$_2$)$_5$—. In these embodiments, R$^3$ and R$^4$ preferably represent hydrogen or $(C_1-C_4)$ alkyl. More preferably R$^3$ and R$^4$ represent $(C_1-C_2)$ alkyl, e.g. methyl. Integer n may be preferably from 2 to 5, and more preferably 2 to 4, e.g. 3.

In other embodiments, R$^1$ and R$^2$ taken together with the adjacent nitrogen atom represent a piperazine moiety. The N-substituent in the 4 position may preferably be selected from:
(a) $(C_1-C_4)$alkyl;
(b) $(C_5-C_7)$-cycloalkyl,
(d) —(CH$_2$)$_p$—NR$^5$R$^6$ in which p represents an integer from 1 to 8 and R$^5$ and R$^6$ independently represent hydrogen or $(C_1-C_4)$ alkyl;
(e) piperidinyl; and
(f) substituted piperidinyl, wherein the substituted piperidinyl bears a N-substituent which is $(C_{1-4})$alkyl.

The piperidinyl and substituted piperidinyl groups preferably have their nitrogen atom at the 4-position.

The N-substituent may more preferably be selected from:
(d) —(CH$_2$)$_p$—NR$^5$R$^6$ in which p represents an integer from 1 to 8 and R$^5$ and R$^6$ independently represent hydrogen or $(C_1-C_4)$ alkyl; and
(f) substituted piperidinyl, wherein the substituted piperidinyl bears a N-substituent which is $(C_{1-4})$alkyl.

If the N substituent is —(CH$_2$)$_p$—NR$^5$R$^6$, then R$^5$ and R$^6$ may be preferably $(C_1-C_4)$alkyl, more preferably $(C_1-C_2)$ alkyl, e.g. methyl. Integer p is preferably 1 to 4, e.g. 3.

If the N substituent is substituted piperidinyl, then the N-substituent is preferably $(C_1-C_2)$ alkyl, e.g. methyl. As mentioned above, the N is preferably in the 4-position.

Nucleic Acid

A nucleic acid of the invention may be a DNA or RNA, though preferably a DNA. A nucleic acid of the invention may be single- or double-stranded. In one aspect, the invention provides an isolated nucleic acid encoding a cluster polypeptide. In another aspect, the invention provides an isolated nucleic acid encoding a precursor polypeptide or variant or fragment thereof.

In a further aspect, the invention provides an isolated nucleic acid which may comprise all or a fragment of SEQ ID NO:100 or SEQ ID NO:200, including a fragment comprising an intergenic region disclosed herein. Such regions may include a promoter or other regulatory element for the expression of a cluster polypeptide or a precursor polypeptide of the present invention.

Twenty-five nucleotides is recognised by those skilled in the art as a sufficient number of nucleotides to be specific to the particular gene or gene cluster or sub-sequence thereof as disclosed herein. Thus fragments include fragments of SEQ ID NO:100 or SEQ ID NO:200, or variants thereof having significant sequence identity, which are at least 25, e.g. at least 30, e.g. at least 50, e.g. at least 100, e.g. at least 250 nucleotides in length.

Promoters that are variants of those intergenic sequences are also included and the specific intergenic sequences (or parts thereof) are preferred embodiments. In all cases, where a preferred embodiment of an orf, gene, nucleic acid, polypeptide or promoter is defined by reference to a specific sequence, the invention in its broader sense is intended to include embodiments having variants of that specific sequence.

The term "variant" as used herein in relation to a particular nucleic acid (the reference nucleic acid) denotes: any nucleic acid having a sequence which is different from that of the reference nucleic acid, but which is its complement or which shows significant nucleic acid sequence identity with, or hybridization under stringent conditions to, the reference nucleic acid or its complement or a fragment of the reference nucleic acid or its complement; or any nucleic acid which encodes an amino acid sequence having significant amino acid sequence identity with the amino acid sequence encoded by the reference nucleic acid, or a fragment of that nucleic acid. The term "variant" also refers to nucleic acids which differ from each other due only to the degeneracy of the genetic code, and which therefore encode identical deduced amino acid sequences. Variant nucleic acids of the invention are further defined as follows. If a variant nucleic acid of the invention is introduced into the gene clusters identified herein, in place of the sequence of which it is a variant, and the recombinant fragment is introduced into a suitable host cell under suitable conditions for lantibiotic production (e.g. as shown in the Examples), then production of a molecule having one or more activities of a lantibiotic (especially antibiotic activity) will result. Preferably production will be regulated to occur at high cell density.

Significant nucleic acid sequence identity is preferably at least 50%, more preferably 60%, 70%, 80% or 90%, still more preferably 95%, 98% or 99%. Significant nucleic acid sequence identity is preferably shown between the variant nucleic acid (or a portion thereof) and a fragment of at least 30 residues of the reference nucleic acid, more preferably a fragment of at least 60, 90 or 120 residues, still more preferably a fragment of 180, 240 or 300 residues, more preferably the entire reference nucleic acid.

"Percent (%) nucleic acid sequence identity" is defined as the percentage of nucleotide residues in a candidate sequence that are identical with the nucleotide residues in the sequence under comparison. The identity values used herein were generated by the BLASTN module of WU BLAST-2 set to the default parameters, with overlap span and overlap fraction set to 1 and 0.125, respectively.

In relation to variants of the promoters used in the present invention, nucleic acid sequence identity is preferably assessed over a sequence of at least 30 residues, more preferably 40 or 50 residues, still more preferably 60 residues.

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 g/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

When a nucleic acid of interest is said to be in "operative association" with a promoter or regulatory sequence, this means that the promoter/regulatory sequence is able to direct transcription of the nucleic acid of interest in an appropriate expression system, with the nucleic acid of interest in the correct reading frame for translation. Preferably when a nucleic acid of interest is in operative association with a promoter/regulatory sequence, the transcript of the nucleic acid of interest contains an appropriately located ribosome binding site for expression in an appropriate expression system of the polypeptide encoded by the nucleic acid of interest. See for example Sambrook et al. (1989) and Ausubel et al. (1995).

When a nucleic acid is referred to as "isolated", this may mean substantially or completely isolated from some or all other nucleic acid normally present in *A. garbadinensis* and/or *A. liguriae*, especially nucleic acid from outside the gene cluster segments identified herein.

In light of the foregoing disclosure, it will be appreciated that this invention provides nucleotide sequences or a set of nucleotide sequences encoding the actagardine or actagardine B biosynthetic gene cluster. Accordingly, the entire gene cluster or portions thereof of at least twenty-five contiguous nucleotides may be used for a wide variety of applications, including but not limited to: expression of actagardine or actagardine B; use as probes to screen other organisms for related molecules and the like; use to induce gene silencing and the like.

Expression Construct

In a further aspect of the invention, there is provided an expression construct comprising a nucleic acid encoding a cluster polypeptide or a lantibiotic polypeptide of the invention operably linked to a promoter.

In a further aspect, there is provided a set of expression constructs. A set of expression constructs comprises two or more polypeptide coding sequences of the present invention and at least one promoter suitable for the expression of said sequences. The promoter(s) may be a promoter with which the polypeptide gene is naturally associated with (or in the case of a variant, the promoter of the gene from which the variant is derived), or may be a constitutive or inducible promoter functional in the host cell. Promoters thus include intergenic regions of SEQ ID NO:100 or SEQ ID NO:200 upstream of any of the open reading frames listed in Tables 1 and 2.

The promoter(s) will be operably linked to the nucleic acids of the set of expression constructs. By "operably linked" it will be understood that the promoter will be able to direct transcription of the nucleic acid of interest in an appropriate expression system, with the nucleic acid of interest in the correct reading frame for translation. Preferably when a nucleic acid of interest is in operative association with a promoter/regulatory sequence, the transcript of the nucleic acid of interest contains an appropriately located ribosome binding site for expression in an appropriate expression system of the polypeptide encoded by the nucleic acid of interest. See for example Sambrook et al. (1989), Ausubel et al. (2002) and Kieser (2000).

Sets of expression constructs according to the invention include numerous permutations of genes encoding precursor and cluster polypeptides of the invention as defined above. In various aspects of the invention, the set will include at least a LanA gene. Examples of such sets are set out as "Set 1" to "Set 7" below, though these sets should be understood to be merely illustrative and not limiting.

Set 1: A LanA gene encoding a precursor polypeptide, preferably a precursor polypeptide capable of being converted to a compound of the invention, plus a LanM gene encoding a LanM polypeptide. The LanM polypeptide is preferably a LanM of SEQ ID NO:120 or a variant thereof, or SEQ ID NO:213 or a variant thereof.

Set 2: A LanA gene encoding a precursor polypeptide, preferably a precursor polypeptide capable of being converted to a compound of the invention, plus a LanR gene encoding a LanR polypeptide. The LanR polypeptide is preferably a LanR of SEQ ID NO:122 or a variant thereof, or SEQ ID NO:216 or a variant thereof.

Set 3: A LanA gene encoding a precursor polypeptide, preferably a precursor polypeptide capable of being converted to a compound of the invention, plus a LanM gene encoding a LanM polypeptide, plus a LanR gene encoding a LanR polypeptide. The LanM polypeptide is preferably a LanM of SEQ ID NO:120 or a variant thereof, or SEQ ID NO:213 or a variant thereof. The LanR polypeptide is preferably a LanR of SEQ ID NO:122 or a variant thereof, or SEQ ID NO:216 or a variant thereof.

Set 4: The genes of Set 3 together with a LanO gene encoding a LanO polypeptide. The LanO polypeptide is preferably SEQ ID NO:122 or a variant thereof, or SEQ ID NO:215 or a variant thereof.

Set 5: The genes of Set 3 or Set 4 together with a LanT gene encoding a LanT polypeptide. The LanT polypeptide is preferably SEQ ID NO:123 or a variant thereof, or SEQ ID NO:214 or a variant thereof.

Set 6: The genes of SEQ ID NOs:116 to 127 or variants thereof.

Set 7: The genes of SEQ ID NOs:206 to 220 or variants thereof.

In one aspect, a set will comprises sequences which all encode 1xx polypeptides or which all encode 2xx polypeptides. However sets which are made up of both 1xx and 2xx polypeptides are not excluded from the present invention.

Recombinant Expression Vector

In another aspect, there is provided a recombinant vector comprising one or more expression constructs of the invention. In an alternative aspect, there is provided a set of recombinant vectors which comprise a set of expression constructs of the invention. Suitable vectors comprising nucleic acid for introduction into bacteria can be chosen or constructed, containing appropriate additional regulatory elements if necessary, including additional promoters, terminator fragments, enhancer elements, marker genes and other elements as appropriate. Vectors may be plasmids, viral e.g. phage, or phagemid, as appropriate. For further details see, for example, Sambrook et al (1989) Molecular Cloning, A Laboratory Manual, 2nd ed., Cold Spring Harbor Laboratory Press, Cold Spring Harbor. Many known techniques and protocols for manipulation of nucleic acid, for example in preparation of nucleic acid constructs, mutagenesis, sequencing, introduction of DNA into cells and gene expression, and analysis of proteins, are described in detail in Ausubel et al. (1995) Current Protocols in Molecular Biology, Wiley Interscience Publishers, (1995). Many aspects of the employment of these techniques in the context of *Streptomyces* spp. are described in detail in Hopwood et al (1985) Genetic manipulation of *Streptomyces* a laboratory manual (Norwich: John Innes Foundation) and Practical *Streptomyces* Genetics (2000) Kieser T. et al., The John Innes Foundation p. 386. The disclosures of Sambrook et al, Ausubel et al, Hopwood et al and Kieser et al are all incorporated herein by reference for these and all other purposes.

Expression Cassettes

In another aspect, the inventors have developed a vector system useful for producing and screening lantibiotic derivatives of actagardine B. This is achieved by introducing one or more restriction endonuclease recognition sites into the LanA gene which encodes SEQ ID NO:1, 11 or 212 in order to produce an expression cassette system. Thus in another aspect, the invention provides a recombinant DNA cassette which comprises a nucleotide sequence encoding an actagardine B precursor polypeptide, wherein said sequence comprises a first restriction site at or adjacent the N-terminal encoding region of the encoding sequence;

optionally a second restriction site downstream of the first restriction site and within the encoding sequence; and a third restriction site at or adjacent the C-terminal encoding region of the encoding sequence, wherein at least one of said restriction sites does not occur within the LanA coding sequence shown as SEQ ID NO:200.

In a further aspect, there is provided a recombinant DNA cassette which comprises a nucleotide sequence encoding an actagardine precursor polypeptide, wherein said sequence comprises a first restriction site at or adjacent the N-terminal encoding region of the encoding sequence;

optionally a second restriction site downstream of the first restriction site and within the encoding sequence; and a third restriction site at or adjacent the C-terminal encoding region of the encoding sequence, wherein at least one of said restriction sites does not occur within the LanA coding sequence shown as SEQ ID NO:100.

Generally, all two or three sites will be different from each other. It is also desirable that when the cassette is carried by a vector, the sites are unique for that vector.

In a preferred aspect, the non-naturally occurring restriction enzyme site is the second restriction site and is located between codons 5 and 16, such as between 6 and 15, of the encoding sequence of SEQ ID NO:1 or SEQ ID NO:4.

The cassette will desirably also include a LanA leader sequence and a LanA promoter, and may include in addition one or more cluster genes, particularly where such a cluster gene is required to complement the loss of the equivalent host cell gene.

The cassette of the invention described above may be engineered in a variety of ways. For example, the fragment obtained by cleaving the cassette between the first and second, first and third, or second and third, restriction sites may be replaced with a variant coding sequence encoding a lantibiotic A variant. Thus the invention provides a variant of the cassette of the invention wherein said variant has from 1 to 15 nucleotide substitutions within the encoding region of the encoding sequence.

As an intermediate to the production of such a variant, the sequence of between the first and second, first and third, or second and third, restriction sites may be replaced by a larger stuffer fragment.

In another aspect, the cassette encoding a lantibiotic derivative may be used to transform a host cell to express the derivative, for example to assess its anti-bacterial properties.

In one aspect, a multiplicity of expression cassettes may be made to provide a library of different derivatives, which may then be screened for activity.

An expression cassette of the invention may be based on any cloning and expression vector used in the art for the expression of genes in host cells. Such vectors will include one or more origins of replication, which may be temperature sensitive. The vectors may include a selectable marker, such as the chloramphenicol acetyl transferase gene, the erythromycin resistance gene, the apramycin resistance gene or the tetracycline resistance gene. The vector may also contain a targeting region, this region being homologous to a genomic sequence present in the host cell outside the LanA gene cluster. Such a vector may be used to integrate the cassette into the genomic sequence homologous to the targeting region.

The expression cassette may also comprise one or more cluster genes in addition to the LanA gene or derivative thereof. Where the host cell is a ΔLanA host cell in which the LanA gene has been inactivated in a manner which also inactivates such a cluster gene (e.g. in the strain disclosed in Altena et al, 2000), it is desirable that this gene or an equivalent gene is provided on the expression cassette.

As used herein, by "at or adjacent the N-terminal encoding region" it is meant that the first base of the restriction site is located at a position from six residues upstream of the ATG codon of the LanA leader sequence to no more than six codons downstream of the first codon of the propeptide. Preferably the first base of the restriction site is located at a position from twelve, preferably six, residues upstream to six residues downstream of the first codon of the propeptide encoding sequence.

In one aspect, the first restriction site is a Bg/II site.

Similarly, by "at or adjacent the C-terminal encoding region" it is meant that the first base of the restriction site either includes at least one of the nucleotides of the termination codon of the propeptide or the 5' or 3' nucleotide of the restriction site is no more than twelve, preferably six, residues downstream or upstream respectively of the termination codon.

In one aspect, the third restriction site is a AvrII site.

The second restriction site, when present, will lie between the first and third restriction sites. Preferably the restriction site includes at least one nucleotide present from codon 5 to codon 16, preferably codon 8 to 16 of the propeptide-encoding sequence. In the accompanying examples, a BsrG1 site has been introduced by altering codons 6 and 7 of the ActA-encoding sequence. However, other changes are also contemplated by the present invention.

It is also possible to introduce more than one change such that the expression cassette includes two or more sites between the first and third restriction sites.

The cassette may include two or three non-naturally occurring restriction sites. In the accompanying example, all three sites do not normally occur in the ActA sequence encoded by of SEQ ID NO:100.

The expression cassette simplifies the rapid production of lantibiotic derivatives, as discussed further herein below.

In one aspect, the region between the first and second sites, the first and third, or the second and third sites, may be replaced by a stuffer fragment. Where two or more sites between the first and third sites are present, the region between any pair of such sites may also be replaced by a stuffer fragment. A stuffer fragment is a piece of DNA which is larger than the sequence which it replaces. The stuffer fragment may be from 50 to 5000 nucleotides in size, for example from about 500 to 2000 nucleotides in size. The value of introducing these stuffer DNA fragments is that when the region is replaced by a lantibiotic-encoding oligonucleotide there is a significant decrease in plasmid size. The resulting plasmid can thus be readily purified away from any minor population of unrestricted plasmid thus eliminating any background.

A cassette of the invention may be used to introduce specific changes to the ActA sequence in a vector which can then be introduced into a host cell for expression of a lantibiotic. To achieve this, the sequence is desirably operably linked to the LanA (e.g. ActA or LigA) leader sequence, which in turn is operably linked to the LanA promoter (e.g. ActA or LigA)

In addition or as an alternative, the vector comprising the cassette may also include a LanR gene. The LanR gene will be located downstream of, and in tandem with, the lantibiotic A coding sequence.

Expression Libraries

Expression cassettes of the invention may be used to provide libraries of lantibiotic-encoding genes. Such libraries may be made by introducing into the cassette, between the first and second restriction sites, the first and third restriction sites, or the second and third restriction sites, a multiplicity of sequences each of which corresponds to the corresponding ActA or LigA sequence apart from having from 1 to 15, for example from 1 to 10, preferably from 1 to 6, for example from 1 to 3 nucleotide changes compared to the propeptide portion of SEQ ID NOs: 100 or 200. Preferably such changes result in a change of the protein encoded by the sequence. However non-coding changes are not excluded.

Libraries form a further aspect of the invention. Such libraries may comprise from 10 to 100,000, such as from 10 to 10,000 for example from 10 to 1,000 different coding sequences which are variants of the lantibiotic A coding sequence of an expression cassette.

An expression cassette encoding a lantibiotic A derivative may be introduced into a host cell for expression of the lantibiotic.

In one embodiment, the library may be transformed into host cells, and colonies isolated and/or screened for antibacterial activity. The sequences of the lantibiotic A expressed by individual colonies showing such activity can be determined. Where the lantibiotic A shows activity, the invention further provides a lantibiotic obtained by the method of the invention.

Host Cell

Two main types of host cells are envisaged by the present invention. The first type of host cell is a lantibiotic producing host cell. Alternatively the host cell may be a non-producer cell, i.e. does not contain a LanA gene or its associated cluster genes required for producing a LanA polypeptide.

In one embodiment, the invention provides a host cell transformed with a set of expression constructs of the invention. The set of constructs may be any one of Sets 1 to 7 as defined above, or a set based upon any other combination of precursor and cluster polypeptide-encoding nucleic acids. In another embodiment, the host cell may be transformed with a expression cassette of the invention.

In a further embodiment, there is provided a library of host cells, each one comprising a different expression cassette of the invention.

A Lantibiotic-Producing Host Cell.

In one embodiment, the host cell may be a lantibiotic producing host cell. A lantibiotic producing host cell is one in which an expression construct comprising a LanA gene, if introduced into the cell in the absence of any cluster gene, would be expressed and a LanA polypeptide produced. Such cells include any type-B lantibiotic producing cell such as any strain of a bacillus, an actinomycete, or a streptomycete, (e.g. *S. lividans* or *S. coelicolor*) which produces a lantibiotic. Examples of such cells include a cinnamycin-producing host cell (*Streptomyces cinnamoneus cinnamoneus* DSM 40005), or an actagardine-producing *Actinoplanes garbadinensis* or *A. liguriae* NCIMB 41362.

Where the invention relates to the productions of compounds of the formula (I) in which -X1-X2- represent -Leu-Val-, the host cell may be *A. liguriae* NCIMB 41362 without any further modification.

In one aspect, a host cell of this class may comprise a mutation in its endogenous LantibioticA gene such that the gene is not expressed or the gene product is inactive. Such a host cell may be obtained by targeted homologous recombination to delete or mutate the LanA gene of the host cell. Methods to achieve this are known as such in the art and are illustrated in Altena et al, (2000) and WO2005/093069, the disclosures of which are incorporated herein by reference. The resulting host cell is referred to as a ΔLanA host cell. In one particular embodiment, the host cell is a ΔLigA *A. liguriae* NCIMB 41362 host cell in which the ligA gene has been inactivated, for example by mutation or deletion, e.g. deletion brought about by homologous recombination. In another embodiment, the host cell is a ΔActA *A. garbadinensis* host cell in which the ActA gene has been inactivated, for example by mutation or deletion, e.g. deletion brought about by homologous recombination.

The transformation of a host cell of this type with other cluster genes is also contemplated by the present invention, though where the host cell provides cluster genes necessary for the production of a lanA, the provision of such cluster genes is optional.

Non-Producer Cell

A non-producer cell may be any host cell in which expression of a LanA gene encoding a precursor polypeptide capable of being converted to actagardine or a variant thereof, or to a compound of the invention, can produce such a product provided the LanA gene is introduced into the cell as part of a set of expression constructs which are capable of converting a precursor polypeptide to actagardine or a variant thereof, or to a compound of the invention.

A non-producer host cell may be a bacterial host cell. Bacterial host cells include an actinomycete, or a streptomycete, e.g. *S. lividans, S. coelicolor* or *S. cinnamoneus*.

Host cells may be those in which the lanO gene is inactivated by mutation or deletion (or in the case of non-producer cells, not present), or those in which the expression of the lanO gene is increased, e.g. by provision of two or more copies of the gene or by linking the gene to a promoter which enhances expression in the host cell. Modulation of the lanO gene in this manner may be desirable to alter the relative levels of oxidized (Y═S(O)) and reduced (Y═S—) forms of compounds of the invention produced in the host cell.

Production of Compounds of the Invention

Compounds of the invention may be produced by expression of a nucleic acid, for example in the form of an expression construct encoding a precursor polypeptide carried in a recombinant expression vector, in a host cell which carries a LanA gene together with where necessary, associated cluster genes required for conversion of the precursor polypeptide to the product. As noted above, where the invention relates to the productions of compounds of the formula (I) in which -X1-X2- represent -Leu-Val-, the host cell may be *A. liguriae* NCIMB 41362 without any further modification.

The introduction of the expression cassette, or vector(s) into a host cell may (particularly for in vitro introduction) be generally referred to without limitation as "transformation". This may employ any available technique. For bacterial cells, suitable techniques may include calcium chloride transformation, polyethyleneglycol assisted transformation, electroporation, conjugation and transfection or transduction using bacteriophages.

In one aspect, the present invention provides a method of expressing nucleic acid of the invention, the method comprising providing a host cell (or other expression system) culturing the host cell, so as to express the nucleic acid of interest. The nucleic acid of interest will be in an expression cassette, such that culturing the host cell leads to the production of a product of the invention.

Preferably the nucleic acid of interest is expressed substantially only when the host cell culture reaches high cell density, more preferably at or close to the stationary phase of host cell culture. Cell cultures at or close to stationary phase may have OD650 values in the range of 1-20. Known methods of culturing cells are well known in the art, for example from Sambrook et al (1989), Ausubel et al (2002), and (in particular for *Streptomyces* spp.) Kieser et al (2000). The expression products of the expression systems may be collected and purified. Isolation methods may comprise capture from the fermentation medium using solvent extraction techniques, adsorption resin such as hydrophobic resins or precipitation methods such as ammonium sulfate precipitation. Purification methods may include chromatography techniques such as ion exchange, hydrophobic interaction, reverse phase, normal phase, solid phase extraction and HPLC, e.g. as described in U.S. Pat. No. 5,112,806 for the isolation of mersacidin Following culture of the cell, the compounds of the invention may be recovered from the host cell culture. The recovered compounds may be formulated in the form of a pharmaceutical composition, optionally in the form of a pharmaceutically acceptable salt.

Where host cells produce a mixture of compounds of the invention, e.g. those in which Y is —S— or —S(O)— or those in which Z is $NH_2$ or Ala-, or mixtures of all four types, the products may be isolated using standard separation techniques such as hplc, e.g. as described in U.S. Pat. No. 6,022,851 for the production of Actagardine and Ala-Actagardine.

The recovered compounds may be formulated in the form of a pharmaceutical composition, optionally in the form of a pharmaceutically acceptable salt.

Pharmaceutically Acceptable Salt

A "pharmaceutically acceptable salt", may be an acid addition salt in which the base retains the biological effectiveness and properties of the compound and which is physiologically acceptable. Such salts include those formed with inorganic acids such as hydrochloric acid, hydrobromic acid, sulphuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

Salts also include basic salts, such as an alkali or alkaline earth metal salt, e.g. a sodium, potassium, calcium or magnesium salt.

Pharmaceutical Compositions

The lantibiotics of the present invention may be formulated together with one or more other pharmaceutically acceptable ingredients well known to those skilled in the art, including, but not limited to, pharmaceutically acceptable carriers, adjuvants, excipients, diluents, fillers, buffers, preservatives, anti-oxidants, lubricants, stabilizers, solubilisers, surfactants (e.g., wetting agents), masking agents, colouring agents, flavouring agents, and sweetening agents. The formulation may further comprise other active agents, for example, other therapeutic or prophylactic agents. Thus, the present invention further provides pharmaceutical compositions, as defined above, and methods of making a pharmaceutical composition comprising admixing at least one active compound, as defined above, together with one or more other pharmaceutically acceptable ingredients well known to those skilled in the art, e.g., carriers, adjuvants, excipients, etc. If formulated as discrete units (e.g., tablets, etc.), each unit contains a predetermined amount (dosage) of the active compound.

The term "pharmaceutically acceptable" as used herein pertains to compounds, ingredients, materials, compositions, dosage forms, etc., which are, within the scope of sound medical judgement, suitable for use in contact with the tissues of the subject in question (e.g., human) without excessive toxicity, irritation, allergic response, or other problem or complication, commensurate with a reasonable benefit/risk ratio. Each carrier, adjuvant, excipient, etc. must also be "acceptable" in the sense of being compatible with the other ingredients of the formulation.

Compositions may be formulated for any suitable route and means of administration. Pharmaceutically acceptable carriers or diluents include those used in formulations suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

For solid compositions, conventional non-toxic solid carriers include, for example, pharmaceutical grades of mannitol, lactose, cellulose, cellulose derivatives, starch, magnesium stearate, sodium saccharin, talcum, glucose, sucrose, magnesium carbonate, and the like may be used. The active compound as defined above may be formulated as suppositories using, for example, polyalkylene glycols, acetylated triglycerides and the like, as the carrier. Liquid pharmaceutically administrable compositions can, for example, be prepared by dissolving, dispersing, etc., an active compound as defined above and optional pharmaceutical adjuvants in a carrier, such as, for example, water, saline aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. Actual methods of preparing such dosage forms are known, or will be apparent, to those skilled in this art; for example, see "Remington: The Science and Practice of Pharmacy", 20th Edition, 2000, pub. Lippincott, Williams & Wilkins. The composition or formulation to be administered will, in any event, contain a quantity of the active compound(s) in an amount effective to alleviate the symptoms of the subject being treated.

Dosage forms or compositions containing active ingredient in the range of 0.25 to 95% with the balance made up from non-toxic carrier may be prepared.

For oral administration, a pharmaceutically acceptable non-toxic composition is formed by the incorporation of any of the normally employed excipients, such as, for example, pharmaceutical grades of mannitol, lactose, cellulose, cellulose derivatives, sodium crosscarmellose, starch, magnesium stearate, sodium saccharin, talcum, glucose, sucrose, magnesium, carbonate, and the like. Such compositions take the form of solutions, suspensions, tablets, pills, capsules, powders, sustained release formulations and the like. Such compositions may contain 1%-95% active ingredient, more preferably 2-50%, most preferably 5-8%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, triethanolamine sodium acetate, etc.

For topical applications, the pharmaceutically acceptable compositions may be formulated in a suitable ointment or gel containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

The percentage of active compound contained in such parental or topical compositions is highly dependent on the specific nature thereof, as well as the activity of the compound and the needs of the subject. However, percentages of active ingredient of 0.1% to 10% w/w employable, and will be higher if the composition is a solid which will be subsequently diluted to the above percentages. Preferably, the composition will comprise 0.2-2% w/w of the active agent in solution.

Further teaching regarding suitable carriers, adjuvants, excipients, etc. can be found in standard pharmaceutical texts, for example, Remington: The Science and Practice of Pharmacy", 20th Edition, 2000, pub. Lippincott, Williams & Wilkins; and Handbook of Pharmaceutical Excipients, 2nd edition, 1994.

Administration of Compounds

Lantibiotic compounds and compositions of the invention may be administered to a subject in a method of medical treatment or prophylaxis. The subject may be a human or animal subject. The animal subject may be a mammal, or other vertebrate.

Thus there is provided a compound of the invention for use in a method of treatment or prophylaxis of a subject. There is also provided use of a compound of the invention for the manufacture of a medicament for use in a method of treatment or prophylaxis of a subject.

The method of treatment may be of a bacterial infection, including a skin, mucosal, enteric or systemic infection.

The variants and composition may be used for systemic treatment of bacteraemia (including catheter related bacteraemia), pneumonia, skin and skin structure infections (including surgical site infections), endocarditis and osteomyelitis. These and other such treatments may be directed against causative agents such as staphylococci, streptococci, enterococci. The compounds of the invention or compositions thereof may also be used for topical treatment of skin infections including acne ie. *Propionibacterium acnes*. The variants and compositions thereof may also be used in the treatment of eye infections, such as conjunctivitis, and for oral treatment for gut super-infection, such as that caused by *Clostridium difficile* including multiply-resistant *C. difficile* (pseudomembranous colitis), or gut infections associated with *Helicobacter pylori*.

The variants may also be used in the treatment or prevention of infection of the skin in wounds or burns. In addition, the variants and compositions thereof may be used in prophylactic methods, such as for the clearance of the nares to prevent transmission of MRSA. This may be practiced on subjects at risk of infection (e.g. patients entering a hospital) or on health professionals or other carers at risk of being carriers of such infections. Prophylactic clearance of gut flora ahead of abdominal surgery is also contemplated.

The compounds according to the invention can be administered enterally (orally), parenterally (intramuscularly or intravenously), rectally or locally (topically). They can be administered in the form of solutions, powders (tablets, capsules including microcapsules), ointments (creams or gel), or suppositories. Possible auxiliaries for formulations of this type are the pharmaceutically customary liquid or solid fillers and extenders, solvents, emulsifiers, lubricants, flavor corrigents, colorants and/or buffer substances. As an expedient dose, 0.1-1000, preferably 0.2-100, mg/kg of body weight are administered. They are expediently administered in dose units which contain at least the efficacious daily amount of the compounds according to the invention, e.g. 30-3000, preferably 50-1000, mg.

The experimental basis of the present invention, including its best mode, will now be further described in detail, by way of example only, with reference to the accompanying drawings.

EXAMPLE 1

Cloning of Gene Clusters

Identifying and cloning the actagardine biosynthetic gene clusters from *A. garbadinensis* and *A. liguriae*.

O/SBDIG-1 is a digoxigenin (DIG)-labelled degenerate oligonucleotide composed of 48 bases. It was designed by translating the known amino acid sequence of actagardine and considering codon usage for *Actinoplanes*. Southern hybridisation analysis of genomic DNA isolated from *A. garbadinensis* and digested using the restriction enzyme NcoI, identified a ~3 kb fragment which hybridised to O/SBDIG-1. The NcoI digest of the genomic DNA was repeated and DNA fragments of ~3 kb were isolated and cloned into NcoI cut pLITMUS28 (NEB). The resulting plasmids were introduced into *E. coli* DH10B cells and then analysed by Southern hybridisation using the probe O/SBDIG-1. A hybridising clone was identified and submitted for sequence analysis. Sequencing revealed that this plasmid designated pLITAG01 consists of DNA encoding the lanA structural gene for actagardine biosynthesis (actA) together with an upstream region believed to encode a portion of an ABC sugar transporter and a region downstream partially encoding lan M (actM).

The primers O/ACT08F and O/ACT09R were designed based upon sequence from pLITAG01. Using these primers in a PCR reaction together with DIG-labelled dNTPs (Roche) and pLITAG01 as a template, a 2296 bp DIG-labelled DNA fragment was generated and designated SBDIG-2.

Two cosmid libraries were generated by cloning Sau3AI digested genomic DNA from *A. garbadinensis* ATCC 31049 and *A. liguriae* NCIMB 41362, into the cosmid SuperCos1 (Stratagene) previously digested using BamHI. Each cosmid library was analysed by Southern hybridisation using SBDIG-1. Twenty-five cosmids from each library believed to hybridise to SBDIG-1 were selected and re-analysed via Southern hybridisation using the probes O/SBDIG-1 and SBDIG-2. Nine cosmids derived from genomic DNA from *A. garbadinensis* and eleven cosmids derived from genomic DNA from *A. liguriae* hybridised to both probes. DNA was isolated from each cosmid and sequenced using the primers T3 and T7. The cosmids CosAL02 and CosAG14 were subsequently fully sequenced (Sequencing facility, Department of Biochemistry, University of Cambridge).

Materials and Methods
  Strains
  Bacterial strains used in the present invention are summarised in Table 5.
  Vectors
  The cosmid SuperCos1 was obtained from Stratagene.
  The plasmid pLITMUS was obtained from New England Biolabs.
  Primers

| Primer name | SEQ. ID | Sequence 5'-3' |
| --- | --- | --- |
| O/SBDIG-1 | 300 | TGGGTSTGCACSCTSACSATCGARTGCGGNACSG TSATCTGCGCSTGC |
| O/ACT08F | 301 | TCCAGCACGCGCGGGG |
| O/ACT09R | 302 | GTTCGACCAGCCGCCC |

Southern Hybridisation
  Labelling of DNA Probe
  DNA hybridisation probes were prepared using the Digoxygenin (DIG) PCR DNA labeling and detection kit supplied by Roche, according to their instructions.
  Transfer of DNA to Nylon Membrane
  The DNA of interest was initially separated by agarose gel electrophoresis and transferred to a nylon membrane (Hybond-N, Amersham Int., UK) using a vacuum blotter (Q BIO gene). The time taken for depurination of the DNA using 0.5 M HCl was judged by the time taken for the bromophenol blue marker band to turn completely yellow (typically 15-20 min for a 0.7% agarose gel). The DNA was then systematically denatured with 1.5 M NaCl, 1.5 M NaOH and then neutralised using 0.5 M Tris, 1.5 M NaCl, pH 8.0 for a further 15-20 min each. Complete blotting of the DNA was facilitated by flooding with 20×SSC for a minimum of 60 min. After removing the blotted membrane from the vacuum it was left to air dry at room temperature. The DNA was cross-linked by placing the membrane (DNA face down) on a UV transilluminator (UVP) and exposing it to UV at a wavelength of 365 nm for 5 min.
  Colony Lifts and Hybridisation
  Colonies to be screened by hybridisation were transferred onto a nylon membrane (Roche diagnostics). This was achieved by placing the positively charged nylon membrane over the colonies and pressing firmly for 1 min to ensure effective transfer. Reference points were marked on the membrane to indicate its orientation with respect to the colonies. Following this, the membrane was removed and prepared for hybridisation as directed in the Roche user's manual (DIG Application manual for filter hybridisation).
  Hybridisation and Development of Membranes
  DNA was hybridised with the prepared probe overnight (~16 hr) at 68° C. in a HB-1000 hybridisation oven (UVP). Following hybridisation the membrane was washed for 2 periods of 5 min at room temperature using 2× salt sodium citrate (SSC)+0.1% sodium dodecyl sulphate (SDS). These washes were followed with a second series of 2×15 min washes at 68° C. using 1×SSC+0.1% SDS for the membrane hybridised in the presence of SBDIG-1 and 0.1×SSC+0.1% SDS for the membrane screened using SBDIG-2. Membranes were then developed as recommended in the Roche user's manual (DIG Application manual for filter hybridisation).

Software
  The consensus sequences were analysed using FramePlot version 2.3.2, BioEdit sequence alignment editor, ClustalW (EMBL-EBI) and the Basic Local Alignment Search Tool (BLAST, NCBI).

Results and Discussion
CosAG14
  The cosmid, CosAG14, contains a 38168 bp fragment of genomic DNA isolated from *A. garbadinensis*. Sequence analysis has identified DNA encoding the leader and actagardine prepeptide, this gene has been assigned the name actA. Two alanine residues lie immediately upstream of the actagardine prepeptide. These residues are believed to represent the recognition site for protease cleavage of the leader peptide from actagardine. Partial cleavage at this position resulting in the retention of an alanine is thought to result in the production of ala-actagardine routinely observed in fermentation broths of *A. garbadinensis*. Downstream of the actA gene lies a 3162 bp region of DNA with strong sequence similarity to several lanM proteins, for example, mrsM (30% identity) from the mersacidin gene cluster. This putative gene has been designated actM and is thought to be involved in the modification of the actagardine prepeptide, catalysing dehydration and thioether formation. An open reading frame designated actO, that is located 11 bp downstream of actM encodes a 341-amino-acid protein with sequence similarity (~39% identity) to several luciferase-type monooxygenases. The role of the monooxygenase, ActO, is believed to be to catalyse the incorporation of oxygen generating actagardine from deoxy-actagardine. In reverse orientation to actO and located 62 bp downstream is the open reading frame named actR. The protein product of this orf shows sequence similarity (~37% identity) to several two-component response regulators. Positioned 789 bp downstream and in the same orientation to actR lies a putative 812 amino-acid protein that shows sequence similarity (~25% identity) to ABC transporter permeases. This putative protein designated actT is potentially responsible for the export of the modified lantibiotic from the cell. The amino acid sequences of the second and fourth orf downstream of actT show similarity (~30% identity) to response regulator kinases and penicillin binding proteins respectively.

Recent work on the nisin biosynthetic gene cluster in *Listeria monocytogenes* (Gravesen et al., 2004) has demonstrated that a histidine kinase together with a penicillin-binding protein and protein of unknown function are involved in conferring nisin resistance. The presence of analogous genes within close proximity to the actA may indicate that these genes are involved in an actagardine resistance mechanism.

CosAL02

The cosmid CosAL02 contains a 40402 bp fragment of genomic DNA isolated from *Actinoplanes liguriae*. Sequence analysis has identified a lanA gene encoding a 64-amino-acid protein with strong sequence homology (50 identical residues) to the actA gene identified in the cosmid CosAG14. We have termed this species of lanA gene as ligA. The amino acid sequence of the prepeptide of this lanA differs from that of actagardine by two residues indicated in the alignment of the two genes shown below (SEQ. ID 119 and SEQ. ID 212):

```
AG  actA  MSALAIEKSWKDVDLRDGATSHPAGLGFGELTFEDLREDRTIYAASSGWVCTLTIECGTVICAC
64

AL  lanA  MSAITVETTWKNTDLREDLTAHPAGLGFGELSFEDLREDRTIYAASSGWVCTLTIECGTLVCAC
64

***:::*.:**:.***:. *:**********:***************************::***
```

The mutations V15L and I16V would generate a protein with an identical mass to actagardine and would therefore not be distinguished by mass spectroscopy (lc-ms) analysis. The potential product of the lanA gene identified in CosAL02 represents a novel lantibiotic. An open reading frame that lies 321 bp upstream of ligA encodes a putative 286-amino acid protein that shows sequence similarity (46% identity) to the StrR protein of *Streptomyces glaucescens*. The StrR protein is a pathway-specific DNA binding activator involved in the regulation of streptomycin gene expression. The sequence similarity (31% identity) of the orf lying downstream of ligA suggests that it encodes for a 1046-amino-acid lanM polypeptide (called "ligM" below) potentially involved in modification of the ligA prepeptide. The start codon of the following downstream open reading frame, lanT (ligT), overlaps the stop codon of ligM. LigT is a 575 amino-acid protein with sequence similarity to several ABC-transporters. LanT proteins are responsible for the secretion of either the final mature product or the posttranslationally modified product still attached to its leader sequence. As observed in the cosmid, CosAG14, the next orf downstream of ligT encodes for a 347 amino-acid protein with sequence similarity (~38% identity) to luciferase-type monooxygenases. This putative monooxygenase (ligO) is believed to be involved in the incorporation of oxygen and sulfoxide bond formation. Positioned downstream of ligO and in reverse orientation lies a putative 217 amino-acid protein that shows sequence similarity (~37%) to several two-component response regulators. This putative regulator has been designated ligR.

TABLE 1

Annotation of CosAG14 (38168bp fragment isolated from *A. garbadinensis*. The SuperCos1 vector backbone sequence is omitted)

| Gene | Description | Position (DNA) | Frame | Size AAs (bp) | Start-end (3AA) |
|---|---|---|---|---|---|
| orf1 | Hypothetical protein | 482-42 | −1 | 146 (441) | MPR-RCG |
| orf2 | Hypothetical protein | 2824-2375 | −2 | 149 (450) | VSV-ERA |
| orf3 | ATPase AAA involved in cell division | 4432-2876 | −2 | 518 (1557) | VER-TNR |
| orf4 | Sugar hydolase | 6002-5391 | −1 | 203 (612) | VGE-NYS |
| orf5 | Endoglucanase | 6484-5825 | −2 | 219 (660) | MRR-TVR |

TABLE 1-continued

Annotation of CosAG14 (38168bp fragment isolated from *A. garbadinensis*.
The SuperCos1 vector backbone sequence is omitted)

| Gene | Description | Position (DNA) | Frame | Size AAs (bp) | Start-end (3AA) |
|---|---|---|---|---|---|
| orf6 | Cytosine/adenine deaminase | 6627-7112 | +3 | 161 (486) | MTI-PAQ |
| orf7 | Unknown | 7756-8997 | +1 | 413 (1242) | VTT-YDK |
| orf8 | Unknown | 9586-8933 | −2 | 217 (654) | VGK-FRG |
| orf9 | Pyruvate oxidase | 11886-10108 | −3 | 592 (1779) | VSD-DPS |
| orf10 | Hydrolase or acyltransferase | 12066-12866 | +3 | 266 (801) | VSR-SGT |
| orf11 | Aldose epimerase | 13116-14306 | +3 | 396 (1191) | MTE-TAD |
| orf12 | ABC sugar transport periplasmic component | 14385-15521 | +3 | 378 (1137) | MPR-AHG |
| orf13 | ABC sugar transport permease | 15514-16572 | +1 | 352 (1059) | MDD-GRS |
| orf14 | ABC transport protein. ATP-binding | 16569-17330 | +3 | 253 (762) | MTA-RGR |
| orf15 | Hypothetical protein. Methyltransferase | 18102-17335 | −3 | 255 (768) | MES-RKR |
| orf16 | ABC transport permease | 18962-18120 | −1 | 280 (843) | MPP-RKG |
| orf17 | ABC transport permease | 19896-18991 | −3 | 301 (906) | MSA-ESE |
| orf18 | ABC transport substrate binding | 21236-19899 | −1 | 445 (1338) | MFI-SGR |
| orf19 | actA, structural gene | 21572-21766 | +2 | 64 (195) | MSA-CAC |
| orf20 | actM, modification gene | 21837-24998 | +3 | 1053 (3162) | MSP-PLT |
| orf21 | actO, monooxygenase | 25009-26034 | +1 | 341 (1026) | MPE-PAA |
| orf22 | actR, response regulator | 26791-26096 | −2 | 231 (696) | MRS-CLS |
| orf23 | actT, ABC transporter associated permease | 29323-26885 | −2 | 812 (2439bp) | MLA-LTR |
| orf24 | Hypothetical protein | 29462-30196 | +2 | 244 (735) | MIV-RNR |
| orf25 | Reponse regulator kinase | 30235-31338 | +1 | 367 (1104) | VLR-ARA |
| orf26 | Response regulator sensor | 31335-31997 | +3 | 220 (663) | MTR-AVG |
| orf27 | Penicillin binding protein | 32138-34486 | +2 | 782 (2349) | MLI-PPR |
| orf28 | Methyltransferase | 35209-34448 | −2 | 253 (762) | MAP-DRR |
| orf29 | Hydrolase | 36030-35245 | −3 | 261 (786) | VPR-PPP |
| orf30 | Response regulator | 36086-36820 | +2 | 244 (735) | VSP-TGS |
| orf31 | Fructose biphosphate aldolase | 36844-37689 | +1 | 281 (846) | MKD-RAW |
| orf32 | Hydrolase | 37590-38168 | +3 | 192 (579) | MGS-DPA |

TABLE 2

Annotation of CosAL02 (40402bp fragment isolated from *A. liguriae*. The SuperCos1 vector backbone sequence is omitted).

| Gene | Description | Position (DNA) | Frame | Size AAs (bp) | Start-end (3AA) |
|---|---|---|---|---|---|
| orf1 | Secretion system protein | 1008-1 | −2 | 335 (1008) | VRL-VDI |
| orf2 | Response regulator | 2198-1122 | −3 | 358 (1077) | MSE-LFP |
| orf3 | Hypothetical protein | 3088-2288 | −1 | 266 (801) | MRR-VVR |
| orf4 | Hypothetical protein | 4410-3112 | −2 | 432 (1299) | MRR-RTG |
| orf5 | Response regulator ATP-binding | 5205-4795 | −2 | 136 (411) | MWK-SAR |
| orf6 | ABC sugar transporter | 5516-6607 | +2 | 363 (1092) | MFN-SAY |
| orf7 | ABC sugar transporter ATP-binding | 6673-8178 | +1 | 501 (1506) | MLL-DEH |
| orf8 | ABC transport permease | 8168-9127 | +2 | 319 (960) | MST-RTR |
| orf9 | ABC transporter permease protein | 9130-10092 | +1 | 320 (963) | MSI-RRS |
| orf10 | Metallopeptidase | 12046-10586 | −1 | 486 (1461) | MRT-PGS |
| orf11 | Putative StrR-like regulator | 12460-13320 | +1 | 286 (861) | MDS-DAA |
| orf12 | ligA | 13641-13835 | +3 | 64 (195) | MSA-CAC |
| orf13 | ligM | 13907-17047 | +2 | 1046 (3141) | MSS-THV |
| orf14 | ligT, ABC transporter | 17040-18767 | +3 | 575 (1728) | MSE-LLT |
| orf15 | ligO, Luciferase type monooxygenase | 18785-19828 | +2 | 347 (1044) | MLS-RRW |
| orf16 | ligR, Response regulator | 20459-19806 | −3 | 217 (654) | MAD-ELA |
| orf17 | ABC-transporter associated permease | 23069-20625 | −3 | 814 (2445) | MIF-LVR |
| orf18 | ABC-transporter. ATP-binding protein | 23788-23066 | −1 | 240 (723) | MVS-VTS |
| orf19 | Histidine kinase | 23980-25068 | +1 | 362 (1089) | VIA-AVP |
| orf20 | Response regulator | 25065-25721 | +3 | 218 (657) | MTE-GPS |

TABLE 2-continued

Annotation of CosAL02 (40402bp fragment isolated from *A. liguriae*. The SuperCos1 vector backbone sequence is omitted).

| Gene | Description | Position (DNA) | Frame | Size AAs (bp) | Start-end (3AA) |
|------|-------------|----------------|-------|---------------|-----------------|
| orf21 | Putative membrane protein | 26673-25768 | -2 | 301 (906) | MPI-RFP |
| orf22 | alpha-beta hydolase | 26697-27569 | +3 | 290 (873) | MRN-ASR |
| orf23 | Transcriptional regulator | 27574-28011 | +1 | 145 (438) | VRL-RLG |
| orf24 | Pyruvoyl-dependent arginine decarboxylase | 28102-28629 | +1 | 175 (528) | MAD-GMN |
| orf25 | Putative diaminopimelate decarboxylase | 30946-29626 | -2 | 406 (1221) | MTL-LYA |
| orf26 | Kinase | 31860-30931 | -2 | 309 (930) | VRS-PDL |
| orf27 | Transcriptional regulator | 33248-32145 | -3 | 367 (1104) | VVF-ANS |
| orf28 | Glycosyl transferase | 33600-34553 | +3 | 317 (954) | MPS-NAG |
| orf29 | Glycosyl transferase | 34543-35652 | +1 | 369 (1110) | MPA-ARV |
| orf30 | Dihydrolipoamide dehydrogenase | 36432-37811 | +3 | 459 (1380) | MGE-INF |
| orf31 | Putative membrane protein | 37973-39019 | +2 | 348 (1047) | MTT-TPG |

EXAMPLE 2

Expression Cassette

Generation of an Expression Cassette

This example illustrates the production of an expression cassette according to the present invention. This expression cassette, plasmid pAGvarX has been designed for the efficient generation of variant lanA genes of the present invention which can then be introduced into a host cell, such as a strain of *A. garbadinensis* in which the wild-type actA has been removed (*A. garbadinensis* Δ actA). This plasmid, a derivative of the vector pSET152 (Bierman et al., 1992) will integrate into the host's chromosome via the attP attachment site. Expression of the mutated actA gene by the host organism together with the remaining wild-type genes of the actagardine biosynthetic gene cluster should generate actagardine variants.

Construction of the Plasmid pAGvarX

Unless stated otherwise all quoted positions relate to SEQ ID NO:100. The scheme for the construction of plasmid pAGvarX is shown in FIG. 3. The base adjacent to the orf lying upstream of the actA at position 21237 to the leucine residue within the actA encoding region at position 21672 was amplified by PCR using the primers O/AGvar01bF and O/AGvar02bR (primer table) and pLITAG01 as a template. The primers were designed to introduce a flanking XbaI site at the 5' end and a Bg/II site via a silent mutation at the 3' leucine region encoding the actA. This fragment was introduced into dephosphorylated pUC19 previously digested using SmaI to yield pAGvar1.

The region of DNA spanning from the C-terminus of the actA to the adjacent downstream orf (21758-21836 inclusive) was amplified by PCR using the primers O/AGvar05F and O/AGvar06R and pLITAG01 as a template. The primers were designed to introduce a flanking AvrII site at the 5' position and an EcoRI site at the 3' end. The resulting PCR product was cloned into dephosphorylated pUC19 previously digested using SmaI to yield pAGvar2. The plasmids pAGvar1 and pAGvar2 were then digested using XbaI and the PCR fragment from pAGvar1 recovered and cloned into dephosphorylated XbaI digested pAGvar2, the correct orientation of the incoming fragment was determined by restriction analysis. The resulting plasmid pAGvar3 was subsequently digested using Bg/II and AvrII and ligated to the annealed oligonucleotides O/AGvar03F and O/AGvar04R generating pAGvar4. The plasmid pAGvar4 was subsequently digested using EcoRI and XbaI and the resulting ~620 bp fragment including the annealed oligonucleotides introduced into pSET152 previously digested using EcoRI and XbaI yielding the vector pAGvarX.

The region of pAGvarX constructed by annealing the respective oligonucleotides, introduce a BsrGI site via a silent mutation at the amino acids 6 and 7 (C and T respectively) with respect to the actagardine peptide. This site can be used in conjunction with either the upstream Bg/II site or downstream AvrII site to introduce DNA encoding targeted mutations to any of the amino acids encoded within the actA peptide.

EXAMPLE 3

Host Cell

This example illustrates the production of a lantibiotic-producing host cell in which the lanA gene has been inactivated. In this example, the host cell is *A. garbadinensis* in which the actA gene has been deleted.

Construction of the Strain *A. garbadinensis* Δ actA

The strain *A. garbadinensis* Δ actA is utilized as a host for expressing variants of the actagardine structural gene actA. This strain was generated from wild-type *A. garbadinensis* using the Redirect technology developed by Gust et al., 2002. Firstly, the region of DNA from the cosmid CosAG14 encoding actA was replaced with the cassette SBdel-1. SBdel-1 consists of the apramycin resistance gene (aac(3)IV) and oriT flanked by FLP recognition target (FRT) sites and was amplified by PCR using the plasmid pIJ773 as the template together with the primers O/SB50F and O/SB51R which bind at 21536 and 21802 of SEQ ID NO:100 respectively. Following the Redirect protocol (Gust et al., 2004), actA of CosAG14 was replaced with SBdel-1 generating the cosmid CosAG14ΔA. The central part of the SBdel-1 cassette was subsequently removed from CosAG14ΔA by FLP-mediated excision following step 7 of the Redirect protocol generating CosAG14ΔB. Removal of this region allows the generation of non-polar, unmarked in-frame deletions as well as repeated use of the same resistance marker (Gust et al., 2003).

The second stage of construction was to engineer the cosmid so that it could be introduced into *A. garbadinensis* via conjugation. This began by first inserting CosAG14ΔB into the *E. coli* strain BW25113/pIJ790 by transformation.

The ampicillin gene of CosAG14ΔB was then replaced with SBdel-2 following the Redirect protocol (Gust et al., 2004) generating the cosmid CosAG14ΔC. The cassette SBdel-2, like SBdel-1, houses the apramycin resistance gene (aac(3) IV) and oriT flanked by FRT sites but was generated using the primers O/SB52F and O/SB53R together with the template pIJ773.

CosAG14ΔC was used to transform electrocompetent cells of *E. coli* ET12567/pUZ8002 before being conjugated with *A. garbadinensis* following the Redirect protocol (Gust et al., 2004; see also following paragraph). The resulting strain in which the actA gene has been removed from the chromosome of the wild-type producer is *A. garbadinensis* Δ actA.

In more detail, to obtain the *A. garbadinensis* Δ actA strain above, CosAG14ΔC was used to transform electrocompetent cells of *E. coli* ET12567/pUZ8002 before being conjugated with *A. garbadinensis*. Apramycin resistant exconjugants were obtained and sub-cultured through six successive rounds of growth in TSB without apramycin. Cells from culture 6 were plated onto medium 65 and incubated at 30° C. After 5 days colonies were transferred and patched out over an area of approximately 1 cm$^2$ onto medium 65. After 3 days incubation at 30° C. the patched cells were transferred to medium 65 containing apramycin at a final concentration of 50 μg/ml. Following 72 h incubation at 30° C., cells sensitive to apramycin were selected and the respective patches used to inoculate 50 ml flasks containing 10 ml TSB and grown at 30° C., 250 rpm for 4 days. Genomic DNA was prepared from each culture and analysed by PCR using oligonucleotides O/AGvar01bF and O/AGvar06r. PCR products of a size consistent with the deletion of the actA gene were generated. In parallel, analysis of fermentation broths by hplc demonstrated that these same samples did not produce actagardine.

EXAMPLE 4

Heterologous Expression

This example illustrates the expression of actagardine from the SEQ ID NO:100 gene cluster in a host cell which is a non-producer cell, *S. lividans*. Such host cells provide an alternative means of generating active variants of these two peptides.

The cosmids CosAG14 and CosAL02 containing the biosynthetic gene clusters encoding the production of actagardine and deoxy-actagardine B do not possess an origin of transfer (oriT) necessary to facilitate conjugal transfer to a heterologous host. Using Redirect technology (Gust et al., 2002) an oriT together with a phage attachment site attP and integrase (int) can be introduced into the SuperCos1 backbone of CosAG14 and CosAL02 replacing the neomycin resistance gene, neo.

Construction of Vectors for Heterologous Expression.

The cosmid pMJCOS1 (supplied by the JIC, Norwich) is a derivative of SuperCos1 (Stratagene) in which the gene encoding for neomycin resistance has been replaced by a cassette (HEapra) which includes DNA encoding an oriT, attP, integrase (int) and apramycin resistance gene (aac(3) IV). The cassette HEapra was isolated by digesting pMJ-COS1 with SspI and recovering the DNA from an agarose gel. This cassette together with CosAG14 and CosAL02 were used to generate the cosmids CosAG14HEapra and CosAL02HEapra respectively following the Redirect protocol as described by Gust et al., 2004.

The cosmid CosAG14HEapra was subsequently introduced into *S. lividans* via conjugation. Apramycin resistant exconjugants of *S. lividans*/CosAG14HEapra were isolated. Three exconjugants were used to inoculate TSB seed media. *S. lividans*, *A. garbadinensis* and *A. liguriae* were grown in parallel to provide controls. Following 48 h incubation the seed cultures were used to inoculate a range of four different production media namely, AAS1, GM1, GM3 and TSB. These cultures were incubated for a total of nine days at 30° C. with 1.5 ml aliquots being removed from each flask after 5, 7 and 9 days incubation. The aliquots were centrifuged at 14000 rpm (IEC micromax benchtop centrifuge) for 10 minutes and the supernatants then decanted and used undiluted for bioassays and HPLC-MS analysis.

Zones of inhibition (haloes) indicative of the presence of a biological active compound(s) were observed around all of the wells loaded with supernatants of *S. lividans* containing the cosmid CosAG14HEapra (*S. lividans*/CosAG14HEapra) except for wells loaded with supernatant from fermentations in TSB where no haloes were generated. No biological activity was observed around wells loaded with supernatant from fermentations of *S. lividans* grown in any of the four media. Haloes were evident around all wells loaded with supernatants from cultures of *A. liguriae* and *A. garbadinensis* where growth was supported. All haloes were consistently generated from the first day of sampling on day 5 through to day 9 although a general reduction in the diameter of the haloes was evident.

HPLC-MS analysis of the supernatants from the fermentations of *S. lividans*/CosAG14HEapra confirm the presence of peaks with retention times and masses corresponding to ala(O)actagardine. These same peaks were absent from supernatants of *S. lividans* only. Table 3 summarises the HPLC-MS analyses of supernatants from fermentation of *S. lividans*, *S. lividans*/CosAG14HEapra, *A. garbadinensis* and *A. liguriae* following incubation for 5 days.

TABLE 3

| Sample | Fermentation medium | Concentration of product (μg/ml) | Retention Time (min) | Molecular ion (m/z) | Identity |
|---|---|---|---|---|---|
| *S. lividans*/ CosAG14HEapra | GM1 | 83 | 6.75 | 981 | Ala(0)Actagardine (M + 2H)$^{+2}$ |
| | | | | 991 | Ala(0)Actagardine (M + H + Na)$^{+2}$ |
| *S. lividans*/ CosAG14HEapra | GM3 | 33 | 6.75 | 981 | Ala(0)Actagardine (M + 2H)$^{+2}$ |
| | | | | 991 | Ala(0)Actagardine (M + H + Na)$^{+2}$ |

TABLE 3-continued

| Sample | Fermentation medium | Concentration of product (µg/ml) | Retention Time (min) | Molecular ion (m/z) | Identity |
|---|---|---|---|---|---|
| S. lividans | GM1 | Not Detected | Not Detected | Not Detected | Not Detected |
| S. lividans | GM3 | Not Detected | Not Detected | Not Detected | Not Detected |
| A. garbadinensis | GM1 | 58 | 6.9 | 945 | Actagardine $(M + 2H)^{+2}$ |
| A. garbadinensis | GM3 | 24 | 6.8 | 981 | Ala(0)Actagardine $(M + 2H)^{+2}$ |
|  |  |  |  | 991 | Ala(0)Actagardine $(M + H + Na)^{+2}$ |
| A. liguriae | GM1 | Not detected | 7.06 | 937 | Deoxy-actagardineB $(M + 2H)^{+2}$ |
| A. liguriae | GM3 | Not detected | 7.06 | 937 | Deoxy-actagardineB $(M + 2H)^{+2}$ |

EXAMPLE 5

Antibacterial Activities

MIC Determination

A selection of the variants produced as disclosed herein above were tested further for activity against a range of bacteria. Minimum inhibitory concentrations (MICs) for all organisms with the exception of Streptococcus pneumoniae were determined by two-fold serial antibiotic dilutions in Mueller-Hinton broth (MHB) supplemented with calcium chloride dehydrate to a final calcium concentration of 400 µg/ml. Minimum inhibitory concentrations (MICs) for S. pneumoniae were determined by two-fold serial antibiotic dilutions in Brain Heart Infusion (BHI) broth supplemented with 400 µg/ml calcium chloride dihydrate. Antimicrobial agent stock solutions were prepared and stored according to NCCLS standard M7-A6.

Actively growing broth cultures were diluted to contain 105 to 106 CFU/ml by adjusting to an absorbance of 0.2-0.3 at 600 nm, equivalent to the McFarland 0.5 standard. They were then diluted a further 1:100 in broth. The assays were performed in duplicate in sterile 96-well microtitre plates in a total volume of 200 µl (160 µl broth, 20 µl antibiotic, 20 µl inoculum) in a concentration range from 64 µg/ml to 0.06 µg/ml. The 12th well of the microtitre plate contained no antimicrobial agent. Vancomycin was used as a reference antibiotic for quality control. Plates were incubated aerobically, shaking, for 18-20 hours at 37° C. with the MIC defined as the lowest concentration of drug that produced no visible growth.

EXAMPLE 6

NMR Analysis

NMR Studies on Actagardine and Deoxy-actagardine

Figure 4:
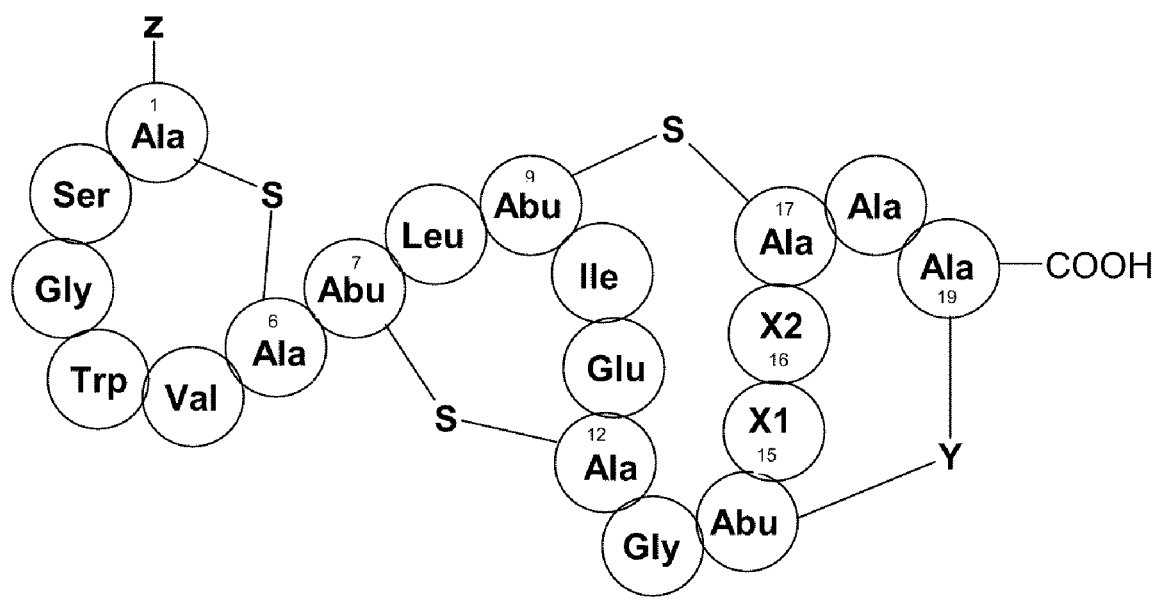
FIG. 4 is a representation of the primary structure of mature actagardine where X1-X2 represent Val-Ile, Y is —S(O)— and Z is NH$_2$. "Deoxy-actagardine B" is the Val15Leu Ile16Val variant with a non-oxidised methyllanthionine bridge between AbuS14 and AlaS19.

NMR spectroscopy (COSY, TOCSY, HSQC and NOESY) was successfully used to confirm the sequencing results obtained from producers of actagardine (A. garbadinensis) and deoxy-actagardine B (A. liguriae). Whilst the data obtained did not permit a completely unambiguous assignment of all residues, it was consistent with the structures shown in FIG. 4 and sufficient to confirm that deoxy-actagardine B from A. liguriae has at positions 15 and 16 the residues Leu and Val respectively.

EXAMPLE 7

Synthesis of Derivatives

The following derivatives of deoxy-actagardine B were made, in which the groups Z and the C-terminal amide were as follows:

| Compound Structures | | |
|---|---|---|
| Compound | Z | C-terminal amide |
| I | H | HN~~~N~ |

|  | E. faecium 19579 | E. faecalis 29212 | S. aureus R33 | S. aureus SH1000 | S. epidermidis 11047 | S. pneumoniae R6 |
|---|---|---|---|---|---|---|
| Actagardine | 4, 4 | <4, <4 | 16, 8 | 8, 8 | 8, 8 | <4, <4 |
| Actagardine | 4, 4 | <4, <4 | 16, 16 | 8, 8 | 8, 8 | <4, <4 |
| Ala(0)Actagardine | 8, 8 | 4, 4 | 8, 8 | 8, 8 | 8, 4 | <4, <4 |
| Ala(0)Actagardine | 32, 16 | 8, 8 | <4, <4 | 8, 8 | 8, 8 | <4, <4 |
| Deoxyactardine B | 16, 16 | 4, 4 | 16, 16 | 16, 16 | 16, 16 | 8, 8 |
| Deoxyactardine B | 16, 16 | <4, <4 | 16, 16 | 16, 16 | 16, 16 | <4, <4 |

-continued

Compound Structures

| Compound | Z | C-terminal amide |
|---|---|---|
| II | H | (piperazine-piperidine-N structure) |
| III | H | (HN-piperazine-propyl-N structure) |
| IV | D-Ala | H |
| V | L-Ile | H |
| VI | L-Val | H |
| VII | L-Phe | H |
| VIII | L-Lys | H |
| IX | L-Tryp | H |

The synthesis of the compounds I-XI was as follows:

General Procedure 1. Preparation of Compounds I-III

To a solution of deoxy-actagardine B (20 mg, 11 nmol), the appropriate amine (11 nmol) and diisopropylethylamine (7.2 μl, 70 nmol) in dry dimethylformamide (0.8 ml) were added 200 μl of a solution of benzotriazole-1-yl-oxy-tris-pyrrolidino-phosphonium hexafluorophosphate (PyBop) (70 mg, 134 nmol) in dry dimethylformamide (1.0 ml). The mixture was analysed by HPLC to follow the progress of the reaction, adding further aliquots of the Pybop solution until all the starting material had been consumed. HPLC analysis at this stage also showed variable amounts (5-20%) of the diamide. After completion of the reaction, the mixture was diluted with 30% acetonitrile in 20 mM Kpi aqueous phosphate buffer, pH 7 (10 ml) and the monoamide was purified by preparative HPLC using the conditions described in Table 4. The appropriate fractions were concentrated to 25% of their original volume and desalted by loading on to a preconditioned C18 Bond Elut column (500 mg) which was subsequently washed by sequential elution with two column volumes of 30, 40, 70 and 90% aqueous methanol. Evaporation of the appropriate fractions gave the desired products as white solids.

Compound I: Deoxy-Actagardine B N-[3-dimethylaminopropyl]monocarboxamide

Was obtained from coupling of deoxyactagardine B and 3-(dimethylamino)propylamine according to General Procedure 1. Yield 18 mg, 85% yield. [M+2H $2^+$] calculated 979.0; found 980.2.

Compound II: Deoxy-Actagardine B N-[1-(1-methyl-4-piperidinyl)piperazine]monocarboxamide Was obtained from the coupling of deoxyactagardine B and 4-(piperidino)piperazine according to General Procedure 1. Yield 8 mg, 37% yield. [M+2H $2^+$] calculated 1019.5; found 1020.0. [M+3H $3^+$] calculated 680.0; found 680.0.

Compound III: Deoxy-Actagardine B [1-(3-dimethylaminopropyl)piperazine]monocarboxamide Was obtained from the coupling of Deoxy-actagardine B and 1-(3-dimethylaminopropyl)piperazine according to general procedure 1. Yield 10 mg, 46% [M+2H $2^+$] calculated 1013.5; found 1014.0.

General Procedure 2. Preparation of Compounds IV-IX

A solution of the appropriate Fmoc protected amino acid (34 nmol) in dry dimethylformamide (0.4 ml) was treated with a solution of benzotriazole-1-yl-oxy-tris-pyrrolidino-phosphonium hexafluorophosphate (PyBop) (11.4 mg, 22 nmol) and diisopropylethylamine (11 μl, 68 nmol) in dry dimethylformamide (0.4 ml). The mixture was then added to a solution of Deoxy-Actagardine B (2 mg, 11 nmol) in dry dimethylformamide (0.5 ml) The mixture was left at room temperature for 1 h, after which time analytical HPLC (30-65% acetonitrile in 20 mM Kpi aqueous phosphate buffer, pH 7) showed complete conversion of the starting material. The reaction mixture was diluted with 40% aqueous methanol (20 ml) and the mixture was passed through a C18 Bond Elute column (500 mg) that had been preconditioned by washing with two column volumes of 100% methanol followed by two column volumes of water. The column was eluted sequentially with two column volumes of 40, 50, 60, 70, 80, 90 and 100% aqueous methanol. The fractions were analysed by HPLC and the fractions containing the Fmoc-protected coupling product were evaporated to dryness. The residue was taken up in dimethylformamide (1 ml) and piperidine (50 μl) was added to remove the Fmoc protecting group. Progress of the reaction was monitored by HPLC and after complete consumption of the starting material the solution was diluted into 30% aqueous methanol (20 ml). The mixture was then eluted through a C18 Bond Elut cartridge (500 mg) as previously described and the product obtained after evaporation of the appropriate fractions was further purified by preparative HPLC using the conditions described in Table 4. The appropriate fractions were concentrated to 25% of their original volume and desalted by loading on to a preconditioned C18 Bond Elut column (500 mg) which was subsequently washed by sequential elution with two column volumes of 30, 40, 70 and 90% aqueous methanol. Evaporation of the appropriate fractions gave the desired products as white solids.

Compound IV: D-Ala (0)deoxy-actagardine B

Was prepared according to general procedure 2 from Deoxy-actagardine B and Fmoc-D-alanine in 74% yield. [M+2H $2^+$] calculated 972.5; found 973.0.
043/188

Compound V: L-Ile(0)deoxy-actagardine B

Was prepared according to general procedure 2 from Deoxy-actagardine B and Fmoc-L-isoleucine in 27% yield. [M+2H $2^+$] calculated 993.5; found 993.8.

Compound VI: L-Val(0)deoxyactagardine B

Was prepared according to general procedure 2 from Deoxy-actagardine B and Fmoc-L-valine in 55% yield. [M+2H $2^+$] calculated 986.5; found 985.9.

Compound VII: L-Phe(0)deoxyactagardine B

Was prepared according to general procedure 2 from Deoxy-actagardine B and Fmoc-L-phenylalanine in 22% yield. [M+2H $2^+$] calculated 1010.5; found 1010.9.

Compound VIII: L-Lys(0)deoxyactagardine B

Was prepared according to general procedure 2 from Deoxy-actagardine B and Bis(Fmoc)-L-lysine in 45% yield. [M+2H $2^+$] calculated 1001.0; found 1001.6.

Compound IX: L-Tryp(0)deoxyactagardine B

Was prepared according to general procedure 2 from Deoxy-actagardine B and Fmoc-L-tryptophan in 55% yield. [M+2H 2$^+$] calculated 1030.0; found 1029.9.

EXAMPLE 8

Further Antibacterial Data

MIC Determination

*Staphylococcus, Streptococcus, Enterococcus* spp.

Minimum inhibitory concentrations (MICs) were determined and antimicrobial agent stock solutions were prepared and stored according to the NCCLS reference microdilution broth method for aerobic bacteria (M7-A6, 2003). MICs were determined by two-fold serial antibiotic dilutions in Mueller-Hinton broth (MHB) or Brain Heart Infusion (BHI) broth (*S. pneumoniae*). Actively growing broth cultures were adjusted in sterile broth or by direct colony suspension (*S. pneumoniae*) to a turbidity equivalent to the McFarland 0.5 standard ($1 \times 10^8$ CFU/ml), then further diluted in sterile broth for a final inoculum in sterile 96-well microtitre plates of approximately $5 \times 10^5$ CFU/ml. The assays were performed in duplicate with *Enterococcus faecalis* ATCC 29212 included as a reference control strain and Vancomycin as a reference antibiotic for quality control. Plates were incubated aerobically, shaking, for 18-20 hours at 37° C. with the MIC defined as the lowest concentration of drug that produced no visible growth.

*Clostridium difficile*

Minimum inhibitory concentrations (MICs) for *C. difficile* were determined and antimicrobial agent stock solutions were prepared and stored according to the NCCLS reference agar dilution method for anaerobic bacteria (M11-A5, 2001). Two-fold serial antibiotic dilutions were prepared in Wilkens-Chalgren agar (WCA). Test organisms were selected from 48 hour growth on Braziers (C.C.E.Y.) agar, subcultured in Schaedler broth to a density equivalent to a McFarland 0.5 standard ($1 \times 10^8$ CFU/ml), with a final inoculum onto WCA plates of approximately $10^5$ CFU/spot. *Bacteroides fragilis* ATCC 25285 was included as a reference control strain and Metronidazole was used as a reference antibiotic for quality control. All manipulations were performed in duplicate in ambient atmosphere in pre-reduced media with only brief exposure to oxygen. Plates were incubated anaerobically for 48 hours at 37° C. with the MIC defined as the concentration of drug where a marked reduction occurred in the appearance of growth on the test plate compared to growth on the anaerobic control plate.

*Propionibacterium acnes*

Test organisms were selected from 3-7 day growth on Wilkens-Chalgren agar (WCA) supplemented with furazolidone (1-2 µg/ml). Fresh Wilkens-Chalgren broth (WCB) was inoculated by direct colony suspension with single colonies of *P. acnes* and adjusted to a density equivalent to the McFarland 0.5 standard ($1 \times 10^8$ CFU/ml), then further diluted in sterile WCB for a final inoculum in sterile 96-well microtitre plates of approximately $10^5$ CFU/ml. Two-fold serial antibiotic dilutions were performed in sterile water with stock solutions prepared and stored according to NCCLS standards (M11-A5, 2001). The assays were performed in duplicate with Vancomycin and Clindamycin used as reference antibiotics for quality control. Plates were incubated anaerobically for 48-72 hours at 37° C. with the MIC defined as the concentration of drug where a marked reduction occurred in the appearance of growth on the test plate compared to growth on the anaerobic control plate. All manipulations were performed in duplicate in ambient atmosphere in pre-reduced media with only brief exposure to oxygen.

Culture media were supplemented with calcium ions (as calcium chloride) at 50 µg/ml except where higher concentrations are indicated. MIC values in µg/ml are shown in the following Tables:

TABLE 6

MIC values against *Enterococci, Streptococci* and *Staphylococci*

| Organism | Ala(O)-deoxyactagardine-B | Deoxyactagardine-B |
|---|---|---|
| *M. luteus* 4698 + 200 µg/ml Ca2+ | 4 | 8 |
| *E. faecalis* 29212 | 16 | 16 |
| *E. faecalis* 29212 + 200 µg/ml Ca$^{2+}$ | 4 | 8 |
| *E. faecalis* 29212 + 400 µg/ml Ca$^{2+}$ |  | 4 |
| *E. faecium* 7131121 (VRE) | >64 | >64 |
| *E. faecium* 7131121 (VRE) + 200 µg/ml Ca$^{2+}$ | >64 | >64 |
| *E. faecium* 7131121 (VRE) + 400 µg/ml Ca$^{2+}$ |  | 32 |
| *E. faecium* 19579 | >64 | >64 |
| *E. faecium* 19579 + 200 µg/ml Ca2+ | >64 | >64 |
| *E. faecium* 19579 + 400 µg/ml Ca$^{2+}$ |  | 16 |
| *S. aureus* R33 (MRSA) | 32 | 32 |
| *S. aureus* R33 (MRSA) + 200 µg/ml Ca$^{2+}$ | 16 | 8 |
| *S. aureus* R33 (MRSA) + 400 µg/ml Ca$^{2+}$ |  | 16 |
| *S. aureus* SH1000 | 16 | 16 |
| *S. aureus* SH1000 + 200 µg/ml Ca$^{2+}$ | 8 | 8 |
| *S. aureus* SH1000 + 400 µg/ml Ca$^{2+}$ |  | 16 |
| *S. epidermidis* 11047 | 16 | 32 |
| *S. epidermidis* 11047 + 200 µg/ml Ca$^{2+}$ | 8 | 16 |
| *S. epidermidis* 11047 + 400 µg/ml Ca$^{2+}$ |  | 16 |
| *S. pnuemoniae* R6 | 16 | 16 |
| *S. pnuemoniae* R6 + 200 µg/ml Ca2+ | 32 | 6 |
| *S. pnuemoniae* R6 + 400 µg/ml Ca$^{2+}$ |  | 4 |
| *S. aureus* 12232 MRSA |  | 16 |
| *S. aureus* R36 (MRSA) |  | 16 |
| *S. aureus* R34 (MRSA) |  | 16 |
| *S. aureus* R39 (MRSA) |  | >32 |
| *S. aureus* R40 (MRSA) |  | >32 |
| *S. aureus* W71 (MRSA) |  | >32 |

TABLE 6-continued

MIC values against Enterococci, Streptococci and Staphylococci

| Organism | Ala(O)-deoxyactagardine-B | Deoxyactagardine-B |
|---|---|---|
| S. aureus W74 (MRSA) | | >32 |
| S. aureus W96 (MRSA) | | >32 |
| S. aureus W97 (MRSA) | | >32 |
| S. aureus W98 (MRSA) | | >32 |
| S. aureus W99 (MRSA) | | >32 |
| S. epidermidis 7755298 (MRSE) | | >32 |
| S. epidermidis 7865688 (MRSE) | | >32 |
| S. epidermidis 7753921 (MRSE) | | >32 |
| S. epidermidis GRL05011 (MRSE) | | >32 |

TABLE 7

MIC values against fusidic acid-resistant Staphylococcus aureus

| Organism | Deoxy-Actagardine B |
|---|---|
| Fusidic acid-res S. aureus 8325-4 | 8, 8 |
| Fusidic acid-res S. aureus CS1116 | 32, 32 |
| Fusidic acid-res S. aureus CS957 | 32, 32 |
| Fusidic acid-res S. aureus CS767 | 32, 32 |
| Fusidic acid-res S. aureus CS858 | 32, 32 |
| Fusidic acid-res S. aureus CS741 | 32, 32 |
| Fusidic acid-res S. aureus CS1145 | 16, 16 |
| Fusidic acid-res S. aureus CS872 | 16, 16 |
| Fusidic acid-res S. aureus CS866 | 32, 32 |
| Fusidic acid-res S. aureus CS607 | 64, 64 |
| Fusidic acid-res S. aureus CS22 | 16, 16 |
| Fusidic acid-res S. aureus 8325-4 + 200 µg/ml Ca2+ | 4, 4 |
| Fusidic acid-res S. aureus CS1116 + 200 µg/ml Ca2+ | 16, 16 |
| Fusidic acid-res S. aureus CS957 + 200 µg/ml Ca2+ | 16, 16 |
| Fusidic acid-res S. aureus CS767 + 200 µg/ml Ca2+ | 16, 16 |
| Fusidic acid-res S. aureus CS858 + 200 µg/ml Ca2+ | 16, 16 |
| Fusidic acid-res S. aureus CS741 + 200 µg/ml Ca2+ | 16, 16 |
| Fusidic acid-res S. aureus CS1145 + 200 µg/ml Ca2+ | 8, 8 |
| Fusidic acid-res S. aureus CS872 + 200 µg/ml Ca2+ | 8, 8 |
| Fusidic acid-res S. aureus CS866 200 µg/ml Ca2+ | 8, 8 |
| Fusidic acid-res S. aureus CS607 + 200 µg/ml Ca2+ | 32, 32 |
| Fusidic acid-res S. aureus CS22 + 200 µg/ml Ca2+ | 4, 4 |

TABLE 8

MIC values against mupirocin-resistant Staphylococcus. aureus

| Organism | Deoxy-actagardine B |
|---|---|
| 8325-4 | 8, 8 |
| GISA-2 | 8, 8 |
| LZ6 | 16, 16 |
| LZ8 | 16, 16 |
| LZ9 | 16, 16 |
| LZ10 | 8, 8 |
| 420 | 4, 4 |
| 1205 | 16, 16 |
| 1120 | 16, 16 |
| 1454 | 16, 16 |
| 1086 | 8, 8 |

TABLE 9

MIC values against Propionibacterium acnes

| Organism | Deoxy-Actagardine B |
|---|---|
| Propionibacterium acnes P37 (lab strain) | 4, 4 |
| P. acnes AT1 | 4, 4 |
| P. acnes AT26 | 2, 2 |
| P. acnes 101897d | 2, 2 |
| P. acnes PF284 (tet res) | 2, 2 |
| P. acnes PF286 (erythro & clin res) | 2, 2 |
| P. acnes PF289 (clin and co-trimazole res) | 4, 8 |

TABLE 10

MIC values against C. difficile

| Organism | Ala(O)-deoxyactagardine-B | Deoxyactagardine-B |
|---|---|---|
| C. difficile 37779 | 4 | 4 |
| C. difficile 19126 | 2 | 4 |
| MIC$_{50}$ 10 C. difficile strains | | 2 |
| MIC$_{90}$ 10 C. difficile strains | | 4 |

TABLE 11

MIC values against C. difficile

| Organism | I | II | III | IV | V | VI | VII | VIII | IX |
|---|---|---|---|---|---|---|---|---|---|
| C. difficile 37779 | | | >8 | 4 | 4 | 8 | 1 | 4 | 1 |
| C. difficile 19126 | | | >8 | 4 | 4 | 8 | 2 | 4 | 2 |
| MIC$_{50}$ C. difficile | 2 | 2 | | | | | 2 | | |
| MIC$_{90}$ C. difficile | 4 | 4 | | | | | 2 | | |

Materials & Methods

The materials and methods used in Examples 2-7 above are as follows:

Media

All buffers, solutions and media were made up using reverse osmosis (RO) water and contained per liter the following ingredients:

| AAS1 | |
|---|---|
| Soluble starch | 10 g |
| Glucose | 10 g |
| Peptone | 5 g |
| Dry corn steep liquor | 1 g |
| Yeast extract | 2 g |
| Adjust pH to 6.0 | |

-continued

GM1

| | |
|---|---|
| Lablemco meat extract | 4 g |
| Peptone | 4 g |
| NaCl | 2.5 g |
| Yeast extract | 1 g |
| Soy flour | 10 g |
| Glucose | 25 g |
| CaCO$_3$ | 5 g |
| Adjust pH to 7.6 | |

Mueller Hinton

| | |
|---|---|
| Mueller Hinton broth | 21 g |
| For agar plates add; | 10 g |
| Agar | |

ABB13

| | |
|---|---|
| Soytone peptone | 5 g |
| Soluble starch | 5 g |
| CaCO$_3$ | 3 g |
| MOPS | 2.1 g |
| Agar | 20 g |
| Adjust pH to 7.0 | |

BHI

| | |
|---|---|
| Brain Heart Infusion | 37 g |

GM3

| | |
|---|---|
| Arkasoy soyflour | 20 g |
| Mannitol | 20 g |
| Adjust pH to 7.0 | |

LA

| | |
|---|---|
| Luria agar | 40 g |

LB

| | |
|---|---|
| Luria broth | 25 g |

SFM

| | |
|---|---|
| Soya Flour | 20 g |
| D-mannitol | 20 g |
| Agar | 16 g |

TAE buffer

| | |
|---|---|
| Tris | 48.44 g |
| EDTA | 3.72 g |
| Adjust pH to 8.3 | |

2TY

| | |
|---|---|
| Tryptone | 16 g |
| Yeast extract | 10 g |
| NaCl | 5 g |
| Adjust pH to 6.5-7.0 | |

SV2

| | |
|---|---|
| Glucose | 15 g |
| Glycerol | 15 g |
| Peptone | 15 g |
| NaCl | 3 g |
| CaCO$_3$ | 1 g |
| Adjust pH to 7.0 | |

TSB

| | |
|---|---|
| Tryptic soy broth | 30 g |
| Adjust pH to 7.0 | |

'65'

| | |
|---|---|
| Glucose | 4 g |
| Yeast extract | 4 g |
| Malt extract | 10 g |
| CaCO$_3$ | 2 g |
| Agar | 12 g |
| Adjust pH to 7.2 | |

Bioassays

*Micrococcus luteus* was inoculated from frozen stock into 10 ml Mueller-Hinton broth and grown overnight at 30° C. with shaking at 200 rpm. 1 ml of this culture was used to inoculate 300 ml of Mueller-Hinton agar which was then poured into petri dishes. Wells (6 mm diameter) placed equidistant apart were made using a cork-borer and subsequently loaded with 50 µl of the respective sample. The bioassay plate was placed into a laminar air flow until the loaded samples had diffused, at which point the plates were transferred to a 30° C. incubator and left overnight.

Endonuclease Restriction Digestions

Digestions of DNA with restriction enzymes were carried out in the supplied buffers and in accordance with the manufacturer's guidelines. Typically, for preparative digests 5 µg of DNA was digested with 12 units of enzyme for 3 h at the recommended temperature. For analytical digests, 0.5 µg of DNA was digested with 2 units of enzyme for 2-3 h again at the recommended temperature. The digested DNA was analysed by agarose gel electrophoresis.

Sub-Culturing Exconjugants

Agar plugs of patched exconjugants were used to inoculate 50 ml flasks containing 8 ml TSB and 2 glass beads. The cultures were incubated at 30° C., 250 rpm for 10 days then 100 µl were removed and added to 10 ml TSB in a 50 ml flask containing 2 glass beads. The flasks were incubated for 2 days then 1 ml was removed and used to inoculate a 50 ml flask containing 10 ml TSB. Using 1 ml inoculum a total of six successive rounds of growth were carried out each incubated for 2 days at 30° C., 250 rpm. Cells from the sixth round of sub-culturing were pelleted by centrifuging at 4000 rpm for 20 minutes (Heraeus Sepatech Megafuge) then sonicated (MSE Sanyo Soniprep 150, amplitude 10-15 microns) for 30 seconds in TSB to disrupt the mycelium. Serial dilutions ($10^{-1}$ to $10^{-5}$ in TSB) of the sonicated cells were plated onto medium 65 and incubated at 30° C.

Fermentation for Heterologous Expression 50 ml conical flasks each containing 2 glass beads and either 8 ml TSB or AAS1 media supplemented with nalidixic acid and the appropriate selective antibiotic were inoculated using agar plugs or 250 µl of a −80° C. glycerol stock. Following 2-4 days incubation at 30° C., 200 rpm, 1.2 ml (3%) per seed culture was used to inoculate 40 ml of the respective production media in 250 ml conical flasks containing 2 glass beads. These cultures were incubated at 30° C., 200 rpm for 9 days. 1.5 ml whole broth aliquots were removed periodically from each culture for analysis by bioassay and/or HPLC-MS analysis.

Fermentation of *A. liguriae* for the Isolation of deoxy-actagardine B 250 ml conical flasks each containing 2 glass beads and 50 ml SV2 media were inoculated with 500 µl (1%) of *A. liguriae* cells from a glycerol stock. Following 4 days incubation at 30° C., 250 rpm, 12 ml (3%) per seed culture was used to inoculate 400 ml of GM3 in 2 L conical flasks. These cultures were incubated at 30° C., 225 rpm for nine days. The culture broth was harvested by centrifugation at 4000 rpm (Heraeus Sepatech Megafuge) for 30 minutes after which the supernatant was decanted from the pellet of cells.

Fermentation of *A. garbadinensis* for the Isolation of Actagardine and Ala(O)-actagardine 250 ml conical flasks each containing 2 glass beads and 50 ml AAS media were inoculated with 500 µl (1%) of *A. garbadinensis* cells from a glycerol stock. Following 9 days incubation at 30° C., 250 rpm, 12 ml (3%) per seed culture was used to inoculate 400 ml of AAS in 2 L conical flasks. These cultures were incubated at 30° C., 200 rpm for eight days. The culture broth was harvested by centrifugation at 4000 rpm (Heraeus Sepatech Megafuge) for 30 minutes after which the supernatant was decanted from the pellet of cells.

Isolation of Deoxy-actagardine B for MIC Studies

Diaion HP-20 resin (50 g/L) was added and mixed with supernatant isolated from a fermentation of *A. liguriae* and left overnight at 4° C. The suspension was aliquoted into Bond Elut columns (60 ml) and the resin washed sequentially with four bed volumes of water followed by three bed volumes of 25, 50, 75 and 100% methanol. HPLC analysis confirmed the presence of Deoxy-actagardine B in the 50, 75 and 100% methanol fractions. These fractions were combined then concentrated to approximately a quarter of the volume of the starting pool. The concentrate from 1 L of broth was loaded onto two C18 Bond Elut columns (5 g) that had been pre-conditioned by washing with two column volumes of 100% methanol followed by two column volumes of water. The columns were eluted sequentially with two column volumes of 50, 60, 70, 80, 90% methanol followed by two column volumes of 100% methanol. HPLC analysis confirmed the presence of Deoxy-actagardine B in the 80, 90 and 100% methanol fractions, these fractions were pooled and concentrated to a third of the starting volume. An equal volume of 40 mM potassium phosphate pH 2.5 in 50% methanol was added and the concentrate then loaded evenly onto three pre-equilibrated SCX Bond Elut columns (1 g). The SCX columns were initially washed with 40 mM potassium phosphate pH 2.5 in 50% methanol and then eluted using 1.5 column volumes of 250 mM potassium phosphate pH 7.0 in 50% methanol. The eluent was desalted by loading onto a C18 Bond Elut column (5 g) that had been pre-conditioned with two column volumes of methanol followed by two column volumes of water. The column was washed with two column volumes of 50% and then 60% methanol. Deoxy-actagardine B was eluted following the addition of two column volumes each of 70, 80, 90 and 100% methanol. Fractions containing purified Deoxy-actagardine B as confirmed by HPLC and LC-MS analyses were pooled and evaporated to dryness.

Isolation of Ala(0)-Deoxyactagardine B from Fermentation of *A. liguriae*

Diaion HP-20 resin (50 g/L) was mixed with supernatant from a four liter fermentation of *A. liguriae* and left overnight at 4° C. The suspension was collected into a glass sinter funnel and the resin was washed sequentially with four bed volumes of water followed by four bed volumes of 50% Methanol. Deoxy-actagardineB and Ala(0)-deoxyactagardine B were eluted from the resin by washing with five bed volumes of 100% Methanol. The 100% Methanol fraction was concentrated to a third of the original volume and was then diluted by addition of water to a final concentration of 60% Methanol. The resulting solution was loaded onto four 10 g C18 Bond Elut columns prior to washing with two column volumes of 50% Methanol. Deoxy-actagardine B-related components were eluted from the column using two column volumes of Methanol/0.5% Formic Acid. The resulting eluent was concentrated by evaporation to 40 ml and Ala(0)-deoxy-actagardine B was separated from Deoxy-actagardine B by preparative HPLC using the conditions described in the table below.

| | |
|---|---|
| Column | Capitol HPLC Ltd C18-BDS-HL5-26052 15 cm × 20 mm |
| Solvent A | 30% ACN in 20 mM Potassium Phosphate pH 5.0 |
| Solvent B | 65% ACN in 20 mM Potassium Phosphate pH 5.0 |
| Detection | 210 nm |
| Flow Rate | 10 ml/min |
| Time (T) = 0 min | 100% A |
| T = 1 min | 100% A |
| T = 29 min | 35% B |
| T = 30 min | 100% B |
| T = 33 min | 100% B |
| T = 34 min | 100% A |
| T = 35 min | 100% A |
| Collection | Start 10 min; End 30 min; 0.5 or 0.25 minute fractions |

Fractions containing Ala(0)-deoxy-actagardine B (as confirmed by HPLC and LC-MS analyses) were desalted using C18 Bond Elut columns as described above before being evaporated to dryness.

Ala(0)-deoxy-actagardine B was eluted from the column at Retention Time=5.04 minutes. MS analysis confirmed a species of 972.2 m/z $(M+2H)^{+2}$.

Isolation of Actagardine and Ala(O)-actagardine for MIC Studies

Actagardine and Ala(0)-actagardine were purified using the method described for the purification of Deoxy-actagardine B from *A. liguriae* with the exception that preparative HPLC was required to resolve Ala(0)actagardine and Actagardine following the SCX Bond Elut step. Eluent from the SCX Bond Elut column was concentrated by rotary evaporation from 70 to 18 ml and the resulting concentrate was purified by preparative HPLC using the conditions described in Table 4 The respective fractions containing Actagardine and Ala(0)actagardine (as confirmed by HPLC and LC-MS analyses) were desalted using C18 Bond Elut columns as described previously before being evaporated to dryness.

TABLE 4

Preparative HPLC conditions for the separation of Actagardine and Ala(0)actagardine.

| | |
|---|---|
| Column | Capitol HPLC Ltd C18-BDS-HL5-26052 15 cm × 20 mm |
| Solvent A | 30% Acetonitrile in 20 mM Potassium Phosphate pH 7.0 |
| Solvent B | 65% Acetonitrile in 20 mM Potassium Phosphate pH 7.0 |
| Detection | 268 nm |
| Flow Rate | 10 ml/min |
| Time (T) = 0 min | 100% A |
| T = 1 min | 100% A |
| T = 19 min | 25% B |
| T = 20 min | 100% B |
| T = 25 min | 100% B |
| T = 26 min | 100% A |
| T = 30 min | 100% A |
| Collection | Start 8 min; End 20 min; 1 minute fractions |

Agarose Gel Electrophoresis

Electrophoresis of DNA was carried out as described by Sambrook et al., 1989. Agarose gels (0.7-1%) were prepared in TAE buffer containing a final concentration of 0.1 µg/ml ethidium bromide to allow visualisation of the DNA by UV light. 0.1 volumes of 10× agarose gel loading solution was mixed with the samples. Samples were loaded onto the gel alongside a 100 bp, 1 kb, or lambda DNA-HindIII digest ladders (NEB) and run at 1-5 V/cm. The gel was visualised at λ=300 nm and photographed using a UVP video camera.

Recovery of DNA from Agarose Gels

DNA was excised from agarose gels and recovered using a Qiaquick gel extraction kit (Qiagen) and eluted in either sterile reverse osmosis purified water, Tris-HCl (10 mM, pH 8.5) or TE buffer.

End-Filling

Filling the recessed 3' termini created by digestion of DNA with restriction enzymes was done using *E. coli* DNA polymerase Klenow fragment. In a typical reaction 1 unit of enzyme was added per µg DNA along with 250 µM each dNTP. The reaction was incubated at 25° C. for 15-30 min and stopped by adding EDTA to a final concentration of 10 mM.

Phosphorylation of DNA

PCR products were treated with T4 polynucleotide kinase at 37° C. for 30 min, following the method described by Sambrook et al., 1989. The enzyme was inactivated by incubating at 65° C. for 20 min.

Dephosphorylation of Linearised Vectors

To avoid self-ligation of linearised vectors, 5'-phosphate groups were removed using shrimp alkaline phosphatase (SAP) following the manufacturer's guidelines. In a typical reaction 1 unit of SAP was added to the restriction mixture for the last hour of the DNA restriction reaction. The enzyme was inactivated by incubating at 65° C. for 20 min.

Ligations

DNA ligations were performed as described by Sambrook et al., (1989) using 1 unit (U) of T4 DNA ligase in a total volume of 15 μl and incubating for 12-16 h at 16° C.

Maintenance of Bacterial Cultures

Viable cells were stored as glycerol suspensions by freezing 0.5 ml of the respective culture at −80° C. with glycerol at a final concentration of 10%. Single colonies of *A. garbadinensis* and *A. liguriae* were obtained by streaking 50 μl from a fermentation broth or glycerol stock onto either medium 65 or ABB13 plates.

Polymerase Chain Reaction

Polymerase chain reactions (PCRs) were performed on a Stratagene Robocycler Gradient96. In a typical reaction 100-200 ng template DNA was mixed with 20 pmol of each oligonucleotide primer and dNTP's at 250 μM each. Thermophilic DNA polymerase buffer as supplied by the manufacturer and DMSO made up 10% (v/v) each of a final volume of 50 or 100 μl reaction mixture. A typical reaction began with an initial cycle of 1 min denaturation (94° C.), 1 min, Y° C. (annealing) and 30 seconds-3 min extension (72° C.), at which point 5 units of thermophilic DNA polymerase was added. This was followed by 30 cycles of 94° C. for 1 min, Y° C. (annealing) for 1 min and 72° C. for X min and a final cycle of 72° C. for 2X min. The extension time X, was 1 min per kb of product when Taq polymerase was used and 2 min per kb of product when Pfu polymerase was used. The annealing temperature Y was 55° C. and 49° C. in the generation of pAGvar1 and pAGvar2 respectively. The conditions used for the generation of SBdel-1 and SBdel-2 were as described in the Redirect protocol (Gust et al., 2004).

Primers

| Primer name | SEQ ID NO: | Sequence 5'-3' |
|---|---|---|
| O/AGvar01bF | 303 | TTCTAGACGTTGTTCTCCCATTTTCAC |
| O/AGvar02bR | 304 | AAGATCTTCGAAGGTGAGCTCGCCGAA |
| O/AGvar03F | 305 | GATCTTCGCGAGGACCGCACCATCTACGCCGCCAGCA GCGGCTGGGTGTGTACACTGACGATCGAGTGCGGCAC CGTGATCTGCGCCTGCTGAC |
| O/AGvar04R | 306 | CTAGGTCAGCAGGCGCAGATCACGGTGCCGCACTCGA TCGTCAGTGTACACACCCAGCCGCTGCTGGCGGCGTA GATGGTGCGGTCCTCGCGAA |
| O/AGvar05F | 307 | GCCTGCTGACCTAGGTCGACGATCGT |
| O/AGvar06r | 308 | TGAATTCGGCTGCTCCCCGCGCGAAAT |
| O/SB50F | 309 | ATTCGCCCGGGAAGTCCACCGAAAGGAAGACACACCAT GATTCCGGGGATCCGTCGACC |
| O/SB51R | 310 | GGGCGATGCCCGCCCCGGGCCGGAAACGATCGTCGAT CATGTAGGCTGGAGCTGCTTC |
| O/SB52F | 311 | AAGTATATATGAGTAAACTTGGTCTGACAGTTACCAATG ATTCCGGGGATCCGTCGACC |
| O/SB53R | 312 | GCTTCAATAATATTGAAAAAGGAAGAGTATGAGTATTCA TGTAGGCTGGAGCTGCTTC |

Preparation of Plasmid DNA

Plasmid DNA was prepared on a small scale (less than 20 μg preparation) by inoculating 3 ml of sterile 2TY or LB containing the appropriate antibiotic with single colonies picked from 2TY (or LA) agar plates. The cultures were incubated overnight (12-16 h) at 37° C. and 250 rpm. The cells were collected by centrifugation at 12,000×g for 1 min and plasmid DNA obtained using Wizard (Promega) Miniprep kits according to the manufacturer's guidelines. In the case of larger preparations of up to 100 μg of plasmid DNA, 30 ml of 2TY cultures were grown and plasmid DNA extracted using a Qiagen Midi-prep kit, following the manufacturer's instructions. All plasmid preparations were checked by a combination of restriction analysis and/or sequence analysis.

Preparation of Cosmid DNA

Cosmid DNA was prepared by inoculating 50 ml of sterile 2TY or LB containing the appropriate antibiotic with single colonies picked from 2TY (or LA) agar plates. The cultures were incubated overnight (12-16 h) at 37° C. and 250 rpm. The cells were collected by centrifugation at 4,000 rpm (Heraeus sepatech Megafuge 2.0R) for 20 min and Cosmid DNA isolated using a Qiagen Midi-prep kit according to the manufacturer's guidelines.

Preparation and Transformation of Electrocompetent *E. coli* Cells.

Electrocompetent *E. coli* DH10B were prepared by the method of Dower et al. (1988). Aliquots (60 μl) of competent cells were thawed on ice and 1.8 µl of ligation mixture or plasmid DNA added. The mixture was placed into an electroporation cuvette (Sigma 0.1 cm) and transferred to the electroporator (Stratagene electroporator-1000). A potential difference of 1.8 kV/mm (25 µF, 200Ω) was applied and 0.5 ml of 2TY or LB medium subsequently added. The cells were then incubated at 37° C. for 45-60 min to allow expression of the antibiotic resistance genes, prior to plating on the appropriate selective medium.

Preparation of Genomic DNA

Genomic DNA templates were prepared using the procedure described by Kieser et al. (2000).

Conjugation Procedure for *Actinoplanes* sp.

Intergeneric conjugation between *E. coli* and *Actinoplanes* sp. was performed following the procedure described by Heinzelmann et al. (2003), except, the strain *E. coli* ET12567/pUB8002 (Kieser et al., 2000) was used in place of the strain *E. coli* ET12567/pUB307 (Flett et al., 1997). Exconjugants were transferred and patched out over an area approximately 1 cm² onto medium 65 or ABB13 containing 50 µg/ml nalidixic acid and the relevant selective antibiotic. These plates were incubated at 30° C. for 4-7 days prior to being used as inoculum for broth cultures.

Conjugation Procedure for *Streptomyces* sp.

Intergeneric conjugation between *E. coli* and *Streptomyces* sp. was performed following the procedure described by Kieser et al., 2000. Exconjugants were transferred and patched out over an area approximately 1 cm² onto SFM containing 50 µg/ml nalidixic acid and the relevant selective antibiotic. These plates were incubated at 30° C. for 4-7 days prior to being used as inoculum for broth cultures.

TABLE 5

Bacterial Strains

| Name | Description/Use |
| --- | --- |
| *Actinoplanes garbadinensis* ATCC31049 | Isolation of the biosynthetic gene cluster for the production of actagardine. |
| *Actinoplanes garbadinensis* Δ actA | *Actinoplanes garbadinensis* ATCC31049 in which the actA gene has been removed. Expression of variant actA genes |
| *Actinoplanes liguriae* NCIMB 41362 | Isolation of the biosynthetic gene cluster for the production of deoxy-actagardine B. Expression of variant ligA genes. |

TABLE 5-continued

Bacterial Strains

| Name | Description/Use |
| --- | --- |
| *Escherichia coli* XL1-Blue MR | Generation of a cosmid library. |
| *Escherichia coli* DH10B | Routine cloning. |
| *Escherichia coli* ET12567 | Isolation of non-methylated DNA. |
| *Escherichia coli* ET12567/pUZ8002 | Intergenic transfer of DNA via conjugation. |
| *Escherichia coli* BW25115/pIJ790 | Strain containing the lambda red recombination plasmid pIJ790. Facilitates the targetted recombination of a cassette flanked by FLP recognition sites. |
| *Escherichia coli* DH5α/BT340 | Strain containing the plasmid BT340 facilitating FLP-mediated excision of disruption cassettes. |
| *Micrococcus luteus* ATCC4698 | Bioassay test organism. |
| *Streptomyces lividans* 1326 | Host organism for the heterologous expression. |
| *Streptomyces coelicolor* B757 | Host organism for the heterologous expression |
| *Streptomyces cinnamoneus* DSM 40005 | Host organism for the heterologous expression |

Antibiotics

Antibiotic stock solutions were prepared in water (unless stated otherwise) and filter sterilised by passing through a 0.22 µm Millipore filter. Solutions dissolved in ethanol were not sterilised (Sambrook et al., 1989). All antibiotics were stored at −20° C. In media where apramycin was used, MgCl$_2$ was added to a final concentration of 10 mM (from a stock of 2.5 M).

| | Stock solution | Working concentration |
| --- | --- | --- |
| Ampicillin (amp) | 100 mg/ml | 100 µg/ml |
| Apramycin (apra) | 100 mg/ml | 50 µg/ml |
| Carbenicillin (car) | 100 mg/ml | 100 µg/ml |
| Chloramphenicol (cm) | 25 mg/ml in ethanol | 25 µg/ml |
| Kanamycin (kan) | 50 mg/ml | 50 µg/ml |
| Nalidixic acid (na) | 25 mg/ml | 25 µg/ml |

Cassettes

| Name | Size (bp) | Source | Description/Use |
| --- | --- | --- | --- |
| SBdel-1 | 1462 | PCR using the primers O/SB50F and O/SB51R and pIJ773 as a template. | Contains an origin of transfer (oriT) and apramycin resistance gene flanked by FLP recognition target sites. The 5' and 3' regions are homologous to DNA flanking the actA gene from *A. garbadinensis*. |
| SBdel-2 | 1462 | PCR using the primers O/SB52F and O/SB53R and pIJ773 as a template. | Contains an origin of transfer (oriT) and apramycin resistance gene flanked by FLP recognition target sites. The 5' and 3' regions are homologous to DNA flanking the ampicillin resistance gene from SuperCos1. |
| HEapra | 5247 | pMJCOS1 | SspI fragment isolated from pMJCOS1. Cassette consists of an apramycin resistance gene, origin of transfer (oriT), attachment site (attP) and øC31 integrase. |

Vectors

| Name | Size (kb) | Resistance marker | Source | Description/Use |
|---|---|---|---|---|
| pAGvar1 | 3.1 | amp | This study. | 449 bp PCR fragment generated using the primers O/AGvar01bF and O/AGvar02bR and template pLITAG01 cloned into pUC19 previously digested using SmaI. |
| pAGvar2 | 2.8 | amp | This study. | 91 bp PCR fragment generated using the primers O/AGvar05F and O/AGvar06R and template pLITAG01 cloned into pUC19 previously digested using SmaI. |
| pAGvar3 | 3.2 | amp | This study. | XbaI fragment (~450 bp) cloned into pAGvar2 previously digested using XbaI. |
| pAGvar4 | 3.3 | amp | This study. | Annealed oligonucleotides O/AGvar03F, O/AGvar04R ligated to pAGvar3 previously digested using BgII and AvrII. |
| pAGvarX | 6.3 | apra | This study. | XbaI-EcoRI fragment (~650 bp) from pAGvar4 ligated to pSET152 previously digested using EcoRI/XbaI. Variant actagardine genes can be assembled and introduced into the hosts chromosome via the attachment site attP. |
| CosAL02 | 47.2 | amp and neo. | This study. | 40402 bp Sau3AI DNA fragment from A. liguriae cloned into SuperCos1 previously digested using BamHI. |
| CosAL02HEapra | 49.1 | amp and apra. | This study. | CosAL02 in which the gene encoding neomycin has been replaced with the HEapra cassette. |
| CosAG14 | 45 | amp and neo. | This study. | 38168 bp Sau3AI DNA fragment from A. garbadinensis cloned into SuperCos1 previously digested using BamHI. |
| CosAG14ΔA | 46.3 | amp, neo and ampra. | This study. | CosAG14 in which the actA gene has been replaced by the cassette SBdel-1. |
| CosAG14ΔB | 44.9 | amp and neo. | This study. | CosAG14ΔA in which the cassette SBdel-1 has been removed by FLP-recombinase leaving an 81 bp scar. |
| CosAG14ΔC | 45.5 | neo and apra. | This study | CosAG14ΔB in which the ampicillin resistance gene has been replaced with the cassette SBdel-2. |
| CosAG14HEapra | 46.9 | amp and apra. | This study. | CosAG14 in which the gene encoding neomycin has been replaced with the HEapra cassette. |
| pIJ773 | 4.3 | amp and apra. | John Innes Centre (JIC), Norwich. | Redirect template (Gust et al., 2003) used to generate the cassettes SBdel-1 and SBdel-2. |
| pLITAG01 | 6.1 | amp. | This study. | 3263 bp NcoI fragment isolated from A. garbadinensis (19955-23217 CosAG14rc) cloned into pLITMUS28 previously digested using NcoI. |
| pLITMUS28 | 2.8 | amp. | New England Biolabs (NEB). | Routine cloning |
| pMJCOS1 | 9.8 | amp and apra. | JIC, Norwich. | SuperCos1 in which the gene encoding neomycin has been replaced by an SspI fragment consisting of an apramycin resistance gene, oriT, attP and øC31 integrase. Source of HEapra cassette. |

-continued

| Name | Size (kb) | Resistance marker | Source | Description/Use |
|---|---|---|---|---|
| pSET152 | 5.7 | apra. | NRRL B14792 | Conjugative plasmid which can facilitate introduction of DNA into the host's chromosome via the attP site. |
| SuperCos1 | 7.9 | amp and neo. | Stratagene. | T3 and T7 promoter regions flanking a unique cloning site. |
| pUC19 | 2.7 | amp. | NEB. | Routine cloning |

High Performance Liquid Chromatography

HPLC analyses were performed using a Hewlett Packard 1050 series HPLC system with the parameters as described below:

| | |
|---|---|
| Column: | Zorbax SB-C18, 4.6 × 150 mm, 5µ |
| Mobile Phase A: | 30% Acetonitrile in 20 mM potassium phosphate buffer pH 7.0 |
| Mobile Phase B: | 65% Acetonitrile in 20 mM potassium phosphate buffer pH 7.0 |
| Flow rate: | 1 ml/min |
| Gradient: | Time    0 min    100% A    0% B |
| Time 10 min | 0%    A    100% B |
| Time 11 min | 0%    A    100% B |
| Time 11.2 min | 100%    A    0% B |
| Cycle time 15 min | |
| Injection volume: | 10 µl |
| Detection: | 210 nm |

High Performance Liquid Chromatography-Mass Spectrometry (HPLC-MS)

HPLC-MS analyses were performed on a Hewlett Packard 1050 series HPLC system linked to a Micromass Platform LC (operated with MassLynx version 3.5 software) with the following parameters:

Column: Agilent Zorbax SB-C18 150×4.6 mm 5µ

Flow rate: 1 ml/min

Mobile phase: A 10% acetonitrile, 0.1% formic acid 90% water.

B 90% acetonitrile, 0.1% formic acid, 90% water.

Linear gradient A to B over 10 minutes, hold 1 min, B-A

Wavelength: 200-400 nm

Injection volume: 10 µl

Post column split: 1:10

Mass spectrometer: Micromass Platform LC

Mode: Electrospray positive

Nitrogen flow: 380 l/hr

Capillary voltage: 40V

Skimmer lens offset: 5V

Deposit

NCIMB 41362 was deposited under the Budapest Treaty on 7 Dec. 2005 at NCIMB Ltd, Aberdeen, AB21 9YA, Scotland, UK, by Novacta Biosystems Limited.

REFERENCES

Altena, K., Guder, A., Cramer, C. and Bierbaum, G. (2000). Biosynthesis of the lantibiotic mersacidin: organization of a type B lantibiotic gene cluster. Applied Environmental Microbiology 66(6): 2565-71.'

Ausubel, F. M., Brent, R., Kingston, R. E., Moore, D. D., Seidman, J. G., Smith, J. A. and Struhl, K. (2002). Current Protocols in Molecular Biology ($5^{th}$ edition). Wiley Interscience Publishers.

Bierman, M., Logan, R., O'Brien, K., Seno, E. T., Nagaraja Rao, R. and Schoner, B. E. (1992). Plasmid cloning vectors for the conjugal transfer of DNA from *Escherichia coli* to *Streptomyces* spp. Gene 116(1): 43-49.

Chatterjee, S., Chatterjee, S., Ganguli, B. N., Chatterjee, D. K., Jani, R. K. H., Rupp, R. H., Fehlhaber, H-W., Kogler, H., Siebert, G. and Teetz, V. (1992) Antibiotic, mersacidin, a process for the preparation thereof and the use thereof as a pharmaceutical. U.S. Pat. No. 5,112,806.

Dower, W. J., Miller, J. F. and Ragsdale, C. W. (1988). High efficiency transformation of *E. coli* by high voltage electroporation. Nucleic Acids Research 16(13): 6127-6145.

Flett, F., Mersinias, V. and Smith, C. P. (1997). High efficiency intergeneric conjugal transfer of plasmid DNA from *Escherichia coli* to methyl DNA-restricting Streptomycetes. FEMS Microbiology Letters 155(2): 223-229.

Gravesen, A., Kallipolitis, B., Holmstrøm, K., Høiby, P. E., Ramnath, M. and Knøchel, S. (2004) pbp2229-Mediated nisin resistance mechanism in *Listeria monocytogenes* confers cross-protection to class IIa bacteriocins and affects virulence gene expression. Applied and Environmental Microbiology 70(3): 1669-1679.

Gust, B., Challis, G. L., Fowler, K., Kieser, T. and Chater, K. F. (2003). PCR-targeted *Streptomyces* gene replacement identifies a protein domain needed for biosynthesis of the sesquiterpene soil odor geosmin. PNAS 100(4): 1541-1546.

Gust, B., Chandra, G., Jakimowicz, D., Yuqing, T., Bruton, C. J. and Chater, K. F. (2004). λ Red-mediated genetic manipulation of antibiotic-producing *Streptomyces*. Advances in applied microbiology 54: 107-128.

Gust, B., Chater, K. F. and Kieser, T. E. (2002). Methods and materials for targeted gene disruption in actinomycete bacteria. Patent Application WO 02/103010 A1.

Heinzelmann, E., Berger, S., Puk, O., Reichenstein, B., Wohlleben, W. and Schwartz, D. (2002). A glutamate mutase is involved in the biosynthesis of the lipopeptide antibiotic friulimicin in *Actinoplanes friuliensis*. Antimicrobial Agents and Chemotherapy 47(2): 447-457.

Kieser, T., Bibb, M. J., Buttner, M. J., Chater, K. F. and Hopwood, D. A. (2000). Practical *Streptomyces* Genetics. Norwich, John Innes Foundation.

Sambrook, J., Fritsch, E. F. and Maniatis, T. (1989). Molecular Cloning: A laboratory manual. New York, Cold Spring Harbor Laboratory Press.

Vertesy, L., Herbert, K., Schiell, M. and Wink, J. (2000). Lantibiotic related to actagardine, and processes for the preparation and use thereof. U.S. Pat. No. 6,022,851.

The invention claimed is:
1. A compound of the formula:

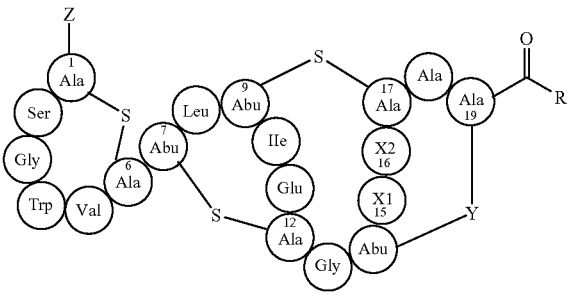

wherein:
-X1-X2- represent -Leu-Val-, -Val-Val- or -Leu-Ile-;
Y is —S— or —S(O)—;
Z is either —NH$_2$ or an amino acid; and
R represents the group —OH or —NR$^1$R$^2$, wherein R$^1$ and R$^2$ independently represent:
(i) hydrogen;
(ii) a group of formula —(CH$_2$)$_n$—NR$^3$R$^4$, in which n represents an integer from 2 to 8 and R$^3$ and R$^4$ independently represent hydrogen or (C$_1$-C$_4$) alkyl, or R$^3$ and R$^4$ taken together represent —(CH$_2$)$_3$—, —(CH$_2$)$_4$—, (CH$_2$)$_2$—O—(CH$_2$)$_2$—, —(CH$_2$)$_2$—S—(CH$_2$)$_2$— or —(CH$_2$)$_5$—;
or R$^1$ and R$^2$ taken together with the adjacent nitrogen atom represent a piperazine which may be substituted in position 4 with a substituent selected from:
(a) (C$_1$-C$_4$)alkyl;
(b) (C$_5$-C$_7$)-cycloalkyl,
(c) pyridyl,
(d) —(CH$_2$)$_p$—NR$^5$R$^6$ in which p represents an integer from 1 to 8 and R$^5$ and R$^6$ independently represent hydrogen or (C$_1$-C$_4$) alkyl,
(e) piperidinyl,
(f) substituted piperidinyl, wherein the substituted piperidinyl bears a N-substituent which is (C$_{1-4}$)alkyl,
(g) benzyl, and
(h) substituted benzyl, wherein a phenyl therein bears 1 or 2 substituents selected from chloro, bromo, nitro, (C$_1$-C$_4$)alkyl and (C$_1$-C$_4$)alkoxy;
or a biologically active variant thereof wherein 1, 2, 3 or 4 amino acids at positions 2, 3, 4, 5, 8, 10, 11, 13 or 18 are substituted by another amino acid, and the another amino acid is a naturally occurring amino acid or its D-isoform, or a pharmaceutically acceptable salt of said compound or variant.

2. The compound according to claim 1 wherein Z is an amino acid.

3. The compound according to claim 2 wherein Z is an amino acid selected from the group Ala, Ile-, Lys-, Phe-, Val-, Glu-, Asp-, His-, Leu-, Arg-, Ser- and Trp, and said amino acids are in the D- or L-configuration.

4. The compound according to claim 2 wherein Z is an amino acid selected from the group Ile-, Lys-, Phe-, Val-, Glu-, Asp-, His-, Leu-, Arg- and Ser-.

5. The compound according to claim 2 wherein the amino acid is Ala.

6. The compound according to claim 1 wherein R represents the group —NR$^1$R$^2$.

7. The compound according to claim 1 wherein R represents the group —NR$^1$R$^2$, wherein R$^1$ and R$^2$ independently represent hydrogen, a group of formula —(CH$_2$)$_n$—NR$^3$R$^4$, in which n represents an integer from 2 to 8 and R$^3$ and R$^4$ independently represent hydrogen or (C$_1$-C$_4$) alkyl, or R$^3$ and R$^4$ taken together represent —(CH$_2$)$_3$—, —(CH$_2$)$_4$—, (CH$_2$)$_2$—O—(CH$_2$)$_2$—, —(CH$_2$)$_2$—S—(CH$_2$)$_2$— or —(CH$_2$)$_5$—, or R$^1$ and R$^2$ taken together with the adjacent nitrogen atom represent a piperazine which may be substituted in position 4 with a substituent selected from (C$_1$-C$_4$) alkyl, (C$_5$-C$_7$)-cycloalkyl, pyridyl, benzyl, and substituted benzyl wherein a phenyl therein bears 1 or 2 substituents selected from chloro, bromo, nitro, (C$_1$-C$_4$)alkyl and (C$_1$-C$_4$) alkoxy.

8. The compound according to claim 1 in which the compound comprises a modification to a carboxy function of a side chain of an internal residue such that said function is modified from —COOH to a group —COOR$^5$ in which R$^5$ represents hydrogen, (C$_1$-C$_4$)alkyl or (C$_1$-C$_4$)alkoxy(C$_2$-C$_4$) alkyl.

9. The compound according to claim 1 in which the compound comprises a modification to the N-terminal amino group such that this group —NH$_2$ is instead a group —NHR$^6$ wherein R$^6$ represents C$_{1-4}$alkyl.

10. A variant of a compound as described in claim 1, wherein 1, 2, 3 or 4 amino acids are substituted by another amino acid, provided that when both positions 15 and 16 are substituted and none of the other positions are changed, 15 and 16 are not Val and Ile respectively.

11. A pharmaceutical composition comprising a compound according to claim 1 together with a pharmaceutically acceptable carrier or diluent.

12. A method of treatment of a bacterial infection selected from the group consisting of *Staphylococcus, Streptococcus, Enterococcus, Clostridium*, and *Propionibacterium*, comprising administering to a subject an effective amount of the compound according to claim 1.

13. The method of treatment of a bacterial infection according to claim 12 wherein said infection is a gut superinfection caused by *Clostridium difficile*.

14. A method of treatment of a bacterial infection selected from the group consisting of *Staphylococcus, Streptococcus, Enterococcus, Clostridium*, and *Propionibacterium*, comprising administering to a subject an effective amount of the compound according to claim 10.

15. The method of treatment of a bacterial infection according to claim 12 wherein said infection is a gut superinfection caused by *Clostridium difficile*.

* * * * *